US012263351B2

(12) United States Patent
Tian et al.

(10) Patent No.: US 12,263,351 B2
(45) Date of Patent: Apr. 1, 2025

(54) METHODS AND SYSTEMS FOR MODULATING CELLULAR ACTIVATION

(71) Applicant: The University of Chicago, Chicago, IL (US)

(72) Inventors: Bozhi Tian, Chicago, IL (US); Francisco Bezanilla, Chicago, IL (US); Erin Adams, Chicago, IL (US); Ramya Parameswaran, Chicago, IL (US); Yuanwen Jiang, Chicago, IL (US); João L. Carvalho-de-Souza, Chicago, IL (US); Kelliann C. Koehler, Chicago, IL (US); Michael G. Burke, Bordentown, NJ (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1253 days.

(21) Appl. No.: 16/975,034

(22) PCT Filed: Feb. 19, 2019

(86) PCT No.: PCT/US2019/018620
§ 371 (c)(1),
(2) Date: Aug. 21, 2020

(87) PCT Pub. No.: WO2019/168714
PCT Pub. Date: Sep. 6, 2019

(65) Prior Publication Data
US 2020/0390803 A1 Dec. 17, 2020

Related U.S. Application Data

(60) Provisional application No. 62/674,713, filed on May 22, 2018, provisional application No. 62/675,059, (Continued)

(51) Int. Cl.
*A61N 5/06* (2006.01)
*C12N 5/0783* (2010.01)
(Continued)

(52) U.S. Cl.
CPC ......... *A61N 5/0622* (2013.01); *A61N 5/0601* (2013.01); *C12N 5/0619* (2013.01);
(Continued)

(58) Field of Classification Search
CPC .... A61N 5/0622; A61N 5/062; C12N 5/0619; A61B 2018/00125
See application file for complete search history.

(56) References Cited

U.S. PATENT DOCUMENTS 9,592,292 B1 * 3/2017 Beckman ............... A61N 5/062
10,663,450 B2 5/2020 Tian et al.
(Continued)

FOREIGN PATENT DOCUMENTS

WO 2021/076981 A1 4/2021
WO 2021/138089 A1 7/2021
(Continued)

OTHER PUBLICATIONS

Tian et al., Coaxial silicon nanowires as solar cells and nanoelectronic power sources, Oct. 18, 2007, Nature Publishing Group, vol. 449, pp. 885-890 (Year: 2007).*
(Continued)

*Primary Examiner* — Catherine M Voorhees
(74) *Attorney, Agent, or Firm* — McDonnell Boehnen Hulbert & Berghoff LLP

(57) ABSTRACT

This disclosure relates to methods for modulating activity of a cell capable of being activated by light and treating diseases with such methods. The disclosure also provides
(Continued)

systems suitable for use in such methods, particularly systems having silicon nanostructures.

12 Claims, 74 Drawing Sheets

Related U.S. Application Data filed on May 22, 2018, provisional application No. 62/635,969, filed on Feb. 27, 2018, provisional application No. 62/635,852, filed on Feb. 27, 2018.

(51) Int. Cl.
| | |
|---|---|
| C12N 5/0793 | (2010.01) |
| A61B 18/00 | (2006.01) |
| C12N 13/00 | (2006.01) |

(52) U.S. Cl.
CPC ............... *C12N 5/0636* (2013.01); *A61B 2018/00125* (2013.01); *A61N 5/062* (2013.01); *A61N 2005/0659* (2013.01); *A61N 2005/0662* (2013.01); *A61N 2005/0663* (2013.01); *C12N 13/00* (2013.01)

(56) References Cited

U.S. PATENT DOCUMENTS

| | | | |
|---|---|---|---|
| 2007/0282247 A1* | 12/2007 | Desai | A61L 27/54 604/19 |
| 2009/0054954 A1 | 2/2009 | Foley et al. | |
| 2009/0088680 A1 | 4/2009 | Aravanis et al. | |
| 2010/0298895 A1 | 11/2010 | Ghaffari et al. | |
| 2011/0125078 A1 | 5/2011 | Denison et al. | |
| 2011/0270153 A1* | 11/2011 | Olson | A61N 1/36046 604/20 |
| 2012/0034622 A1* | 2/2012 | Ignatius | B82Y 5/00 435/7.2 |
| 2012/0136296 A1 | 5/2012 | Peyman | |
| 2012/0301446 A1* | 11/2012 | Zhu | C12N 5/0636 435/7.1 |
| 2013/0274838 A1 | 10/2013 | Entcheva et al. | |
| 2014/0236267 A1 | 8/2014 | Parker | |
| 2017/0326381 A1 | 11/2017 | Kozai et al. | |
| 2018/0311508 A1* | 11/2018 | Ellingwood | A61M 25/00 |
| 2019/0030190 A1* | 1/2019 | Peyman | A61K 9/51 |
| 2021/0033559 A1* | 2/2021 | Panat | H05K 3/0085 |
| 2023/0048814 A1 | 2/2023 | Tian et al. | |
| 2023/0183075 A1 | 6/2023 | Tian et al. | |
| 2024/0009630 A1 | 1/2024 | Tian et al. | |
| 2024/0100354 A1 | 3/2024 | Tian et al. | |
| 2024/0101997 A1 | 3/2024 | Tian et al. | |

FOREIGN PATENT DOCUMENTS

| | | |
|---|---|---|
| WO | 2021/242425 A2 | 12/2021 |
| WO | 2022/125328 A2 | 6/2022 |
| WO | 2024/076353 A2 | 4/2024 |

OTHER PUBLICATIONS

Jiang, Y., et al., "Rational Design of Silicon Structures for Optically Controlled Multiscale Biointerfaces", Nature Biomedical Engineering, Jul. 2018, vol. 2(7), pp. 508-521.
Thess, et al., "Crystalline Ropes of Metallic Carbon Nanotubes," Science, Jul. 26, 1996, vol. 273(5274), pp. 483-487.
International Search Report from the European Patent Office, mailing date of Feb. 5, 2021, for International Application No. PCT/US2020/056106, pp. 1-6.
Written Opinion from the International Searching Authority, mailing date of Feb. 5, 2021, for International Application No. PCT/US2020/056106, pp. 1-7.
Extended European Search Report from the European Patent Office, dated Nov. 2, 2021, for European Patent Application No. 19759936.8, pp. 1-8.
Dalby, M.J., et al., "Harnessing Nanotopography and Integrin-Matrix Interactions to Influence Stem Cell Fate", Nature Materials, May 21, 2014, vol. 13, pp. 558-569.
Gentemann, L., et al., "Modulation of Cardiomyocyte Activity Using Pulsed Laser Irradiated Gold Nanoparticles", Biomedical Optics Express, Dec. 8, 2016, vol. 8(1), pp. 177-192.
Jiang, et al., "Rational Design of Silicon Structures for Optically Controlled Multiscale Biointerfaces", Nature Biomedical Engineering, Jul. 2018, vol. 2(7), pp. 508-521.
Kabat, et al., "Sequences of Proteins of Immunological Interest U.S. Department of Health and Human Services, Bethesda" Nakamaya, K. and Eckstein, F., Nuc. Acids Res., 1991, vol. 14, pp. 9679-9698.
Parameswaran, R., et al., "Photoelectrochemical Modulation of Neuronal Activity with Free-Standing Coaxial Silicon Nanowires", Nat. Nanotechnol., Feb. 19, 2018, vol. 13(3), pp. 260-266.
Parameswaran, R., et al., "Optical Stimulation of Cardiac Cells with a Polymer-Supported Silicon Nanowire Matrix", PNAS, Dec. 11, 2018, vol. 116(2), pp. 413-421.
Thess, et al., "Crystalline Ropes of Metallic Carbon Nanotubes," Science, Jul. 26, 1996, vol. 273, Issue 5274, pp. 483-486.
Tian, B., et al., "Three-Dimensional, Flexible Nanoscale Field-Effect Transistors as Localized Bioprobes", Science, Aug. 13, 2010, vol. 329, pp. 830-834.
International Search Report, for International Application No. PCT/US2019/018620, date of mailing Apr. 22, 2019, pp. 1-3.
Written Opinion, for International Application No. PCT/US2019/018620, date of mailing Apr. 22, 2019, pp. 1-7.
Tian, B., et al., "Roadmap on Semiconductor-Cell Biointerfaces", Phys. Biol., Mar. 9, 2018, vol. 15, 031002, pp. 1-33.
Shuai Xu and John A. Rogers, "Transient Electronics and the Future of Medicine", Phys. Biol., Mar. 9, 2018, vol. 15, 031002, pp. 3-5.
Stefano Cestellos-Blanco and Peidong Yang, "Semiconductor-Microorganism Catalytic Biohybrid Systems for Artificial Photosynthesis", Phys. Biol., Mar. 9, 2018, vol. 15, 031002, pp. 6-8.
João L. Carvalho-de-Souza and Francisco Bezanilla, "Optocapacitance: Photostimulation without Cell Modification", Phys. Biol., Mar. 9, 2018, vol. 15, 031002, pp. 9-10.
Jia Liu and Zhenan Bao, "Roadmap of Polymer Bioelectronics-Cell Interface", Phys. Biol., Mar. 9, 2018, vol. 15, 031002, pp. 11-12.
Martin Hjort, Yuhong Cao and Nicholas Melosh, "Engineering Cell Access", Phys. Biol., Mar. 9, 2018, vol. 15, 031002, pp. 13-14.
Guglielmo Lanzani and Fabio Benfenati, "Organic Opto-Biointerfaces", Phys. Biol., Mar. 9, 2018, vol. 15, 031002, pp. 15-16.
Giulia Galli and Francois Gygi, "Predicting Interfacial Properties from First Principles Simulations: Semiconductors in Aqueous Media", Phys. Biol., Mar. 9, 2018, vol. 15, 031002, pp. 17-18.
Rylan Kautz and Alon A. Gorodetsky, "Revisiting a Classic Inspiration Source: Cephalopod-Derived Materials for Bioelectronics", Phys. Biol., Mar. 9, 2018, vol. 15, 031002, pp. 19-20.
Samuel S. Kim and Timothy K. Lu, "Accelerating Synthetic Biology with Approaches and Technologies from Semiconductor Engineering", Phys. Biol., Mar. 9, 2018, vol. 15, 031002, pp. 21-22.
Polina Anikeeva, "Addressing Signaling Complexity of the Nervous System", Phys. Biol., Mar. 9, 2018, vol. 15, 031002, pp. 23-24.
Michal Cifra, Ondrej Krivosudsky and Daniel Havelka, "High-Frequency Nanoscale Semiconductor Devices for Electric Sensing and Control of Proteins", Phys. Biol., Mar. 9, 2018, vol. 15, 031002, pp. 25-26.
Yuanwen Jiang and Bozhi Tian, "Silicon-Based Intracellular Biointerfaces", Phys. Biol., Mar. 9, 2018, vol. 15, 031002, pp. 27-32.
Jung, S.W., et al., "Neuron Stimulation Device Integrated with Silicon Nanowire-Based Photodetection Circuit on a Flexible Substrate", Sensors, 2016, vol. 16, Issue 2035, pp. 1-15.
Kwak, M., et al., "Interfacing Inorganic Nanowire Arrays and Living Cells for Cellular Function Analysis", Small, Sep. 9, 2015, vol. 11(42), pp. 5600-5610.

(56) References Cited

OTHER PUBLICATIONS

Parameswaran, R., et al., "Flexible Semiconductor-Polymer Hybrid Constructs for Optical Pacing of Cardiomyocyte", Materials Research Society Poster Presentation, Dec. 1, 2015.
Parameswaran, R., et al., "Silicon Nanowire Scaffold for Optical Pacing of Cardiomyocytes", Materials Research Society Poster Presentation, Nov. 28, 2016.
Koehler, K., et al., "Silicon Nanowire Based Scaffold for Optical Pacing of Cardiomyocytes", Materials Research Society Poster Presentation, Nov. 29, 2017.
Lee, C.H., et al., "Fabricating Nanowire Devices on Diverse Substrates by Simple Transfer-Printing Methods", PNAS, Jun. 1, 2010, vol. 107(22), pp. 9950-9955.
Wu, L., et al., "Automatic Release of Silicon Nanowire Arrays with a High Integrity for Flexible Electronic Devices", Scientific Reports, Feb. 3, 2014, vol. 4, Issue 3940, pp. 1-7.
Katherine Bourzac, Nanowires that Behave Like Cells, Aug. 11, 2019, MIT Technology Review.
Parameswaran, R. et al. "Flexible Semiconductor-Polymer Hybrid Constructs for Optical Pacing of Cardiomyocytes," Materials Research Society Poster Abstract (Dec. 1, 2015).
Koehler, K., et al. "Silicon Nanowire Based Scaffold for Optical Pacing of Cariomyocytes," Materials Research Society Poster Abstract (Nov. 29, 2017).
U.S. Appl. No. 18/712,154, filed May 21, 2024.
U.S. Appl. No. 18/612,387, filed Mar. 21, 2024.

* cited by examiner

METHODS AND SYSTEMS FOR MODULATING CELLULAR ACTIVATION

CROSS-REFERENCE TO RELATED APPLICATIONS

This application is a section 371 national phase of PCT/2019/018620, filed Feb. 19, 2019, which claims the benefit of priority of U.S. Provisional Patent Application No. 62/635,852, filed Feb. 27, 2018, U.S. Provisional Patent Application No. 62/635,969, filed Feb. 27, 2018, U.S. Provisional application No. 62/674,713, filed May 22, 2018, and U.S. Provisional application No. 62/675,059, filed May 22, 2018, all of which are incorporated by reference in their entirety.

STATEMENT REGARDING FEDERALLY SPONSORED RESEARCH OR DEVELOPMENT

This invention was made with government support under GM030376, Al138156, NS101488, NS061963 and GM007281 awarded by National Institutes of Health, FA9550-14-1-0175 and FA9550-15-1-0285 awarded by the United States Air Force, Air Force Office of Scientific Research, and DMR1254637 and DMR1420709 awarded by the National Science Foundation. The government has certain rights in the invention.

BACKGROUND OF DISCLOSURE

Field of Disclosure

This disclosure relates to methods for modulating activity of a cell capable of being activated by light and treating diseases with such methods. The disclosure also provides systems suitable for use in such methods, particularly systems having silicon nanostructures.

Technical Background

Extracellular electrical stimulation of excitable cells is the basis for many implantable devices that treat a variety of diseases. While these devices have been efficacious, they are often limited by their bulkiness, mechanical invasiveness, and inability to target single cells. Thus, researchers have looked to optical stimulation techniques, where organic or inorganic photodiode substrates are used for photovoltaic neuronal stimulation; however, these tools cannot be easily administered in a drug-like fashion. While some photothermally-modulating materials meet these criteria, chronic cellular effects due to heat from such devices are unknown. Optogenetics has been promising for addressing these issues, but fundamentally requires genetic modifications, which can be difficult to implement in vivo. As a result, there is still a need for exploring a non-genetic approach that can be administered in a drug-like fashion.

Silicon (Si) nanomaterials are promising to address these concerns as they have been widely used for many biophysical or biomedical applications due to their highly tunable electrical and chemical properties, ability to absorb a broad range of wavelengths of light, and biocompatibility. Dopant modulated and kinked Si nanowires, as well as bendable integrated circuits based on Si nanoscale membranes have been used before. Although the electrically registered device components have yielded impressive results, remotely-controlled and freestanding systems are rarely employed in biointerface studies. This is largely due to the limited understanding of the physicochemical processes at the free-standing material surfaces under physiological conditions.

Therefore, there exists a need for optical methods for modulating cellular behavior using Si that are not mechanically invasive and do not require genetic manipulation of target cells, yet provide sub-cellular specificity.

SUMMARY OF THE DISCLOSURE

The inventors have found that Si-based "bio-tronic" structures with dimension (e.g., length) scales from nanometer to centimeter can establish intra-, inter- and extracellular biointerfaces. The inventors have also found that the optical cellular-modulation can mimic naturally occurring extracellular signals, i.e., random, fast and multisite input signals, and that such modulation can modulate the activity of a cell.

Thus, one aspect of the disclosure provides methods for modulating activity of a cell capable of being activated by light. Such methods include contacting a membrane of the cell with a silicon nanostructure to form a structure-cell membrane interface; and exposing the interface to light under conditions to depolarize the cell membrane thereby increase a threshold for activation of the cell.

In certain embodiments, the cell is a neuron or an immune cell.

Another aspect of the disclosure provides methods of treating a disease in a subject by modulating activation of a cell. Such methods include (i) administering a therapeutically effective amount of a composition comprising silicon nanostructures to the subject; and (ii) exposing the subject to light under conditions sufficient to increase a threshold for activation of the cell and treat the disease.

In certain embodiments, methods of the disclosure treat an autoimmune disease, cancer, allergy, asthma, neuronal disease, cardiovascular disease, or a combination thereof.

In certain embodiments, the disclosure provides a method for treating a cardiovascular disease. In certain embodiments, such method includes optically training myocardium to beat at a target frequency. Thus, one aspect of the disclosure provides a method for optically training myocardium to beat at a target frequency. This method includes (i) contacting the myocardium with the composition comprising silicon nanostructures; and (ii) operating a light emitter to provide, during a training period of time, a plurality of pulses of light at a stimulation wavelength to the myocardium, wherein the plurality of pulses of light are provided at the target frequency. In certain embodiments, the composition comprising silicon nanostructures is a flexible silicon nanostructure that includes a flexible substrate on which silicon nanostructure or a plurality of silicon nanostructures are distributed and the flexible silicon nanostructure is configured to be placed in contact with cells of the myocardium such that the silicon nanostructures are in contact with cells of the myocardium. The silicon nanostructures provide, to cells of the myocardium that they are in contact with, excitatory stimulus in response to receiving light at the stimulation wavelength.

The disclosure also provides systems suitable for use in the methods of the disclosure.

Thus, in one aspect, the disclosure provides a system for treating a disease in a subject by modulating activation of a cell. Such system includes (i) a composition comprising silicon nanostructures of the disclosure as described herein; (ii) a light emitter configured to emit light at a stimulation wavelength; and (iii) a controller that is operably coupled to the light emitter. In such systems, the silicon nanostructures provide, to the cell they are in contact with, excitatory stimulus in response to receiving light at the stimulation wavelength. The controller includes one or more processors, wherein the controller is programmed to perform controller operations including: operating the light emitter to provide the light to the cell.

In certain embodiments, the disclosure provides a system for optically training myocardium to beat at a target frequency. As provided herein, such system includes: (i) a composition comprising silicon nanostructures of the disclosure as described herein; (ii) a light emitter configured to emit light at a stimulation wavelength; and (iii) a controller that is operably coupled to the light emitter. In certain embodiments, the composition comprising silicon nanostructures is a flexible silicon nanostructure that includes a flexible substrate on which silicon nanostructure or a plurality of silicon nanostructures are distributed and the flexible silicon nanostructure is configured to be placed in contact with a surface of the myocardium such that the silicon nanostructures are in contact with cells of the myocardium. The silicon nanostructures provide, to cells of the myocardium that they are in contact with, excitatory stimulus in response to receiving light at the stimulation wavelength. The controller includes one or more processors and is programmed to perform controller operations including: operating the light emitter to provide, during a training period of time, a plurality of pulses of light to the myocardium, wherein the plurality of pulses of light are provided at the target frequency.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the invention will become apparent to those skilled in the art from this detailed description.

BRIEF DESCRIPTION OF THE DRAWINGS

The accompanying drawings are included to provide a further understanding of the methods and materials of the disclosure, and are incorporated in and constitute a part of this specification. The drawings illustrate one or more embodiment(s) of the disclosure and, together with the description, serve to explain the principles and operation of the disclosure.

DETAILED DESCRIPTION

Figure 1:
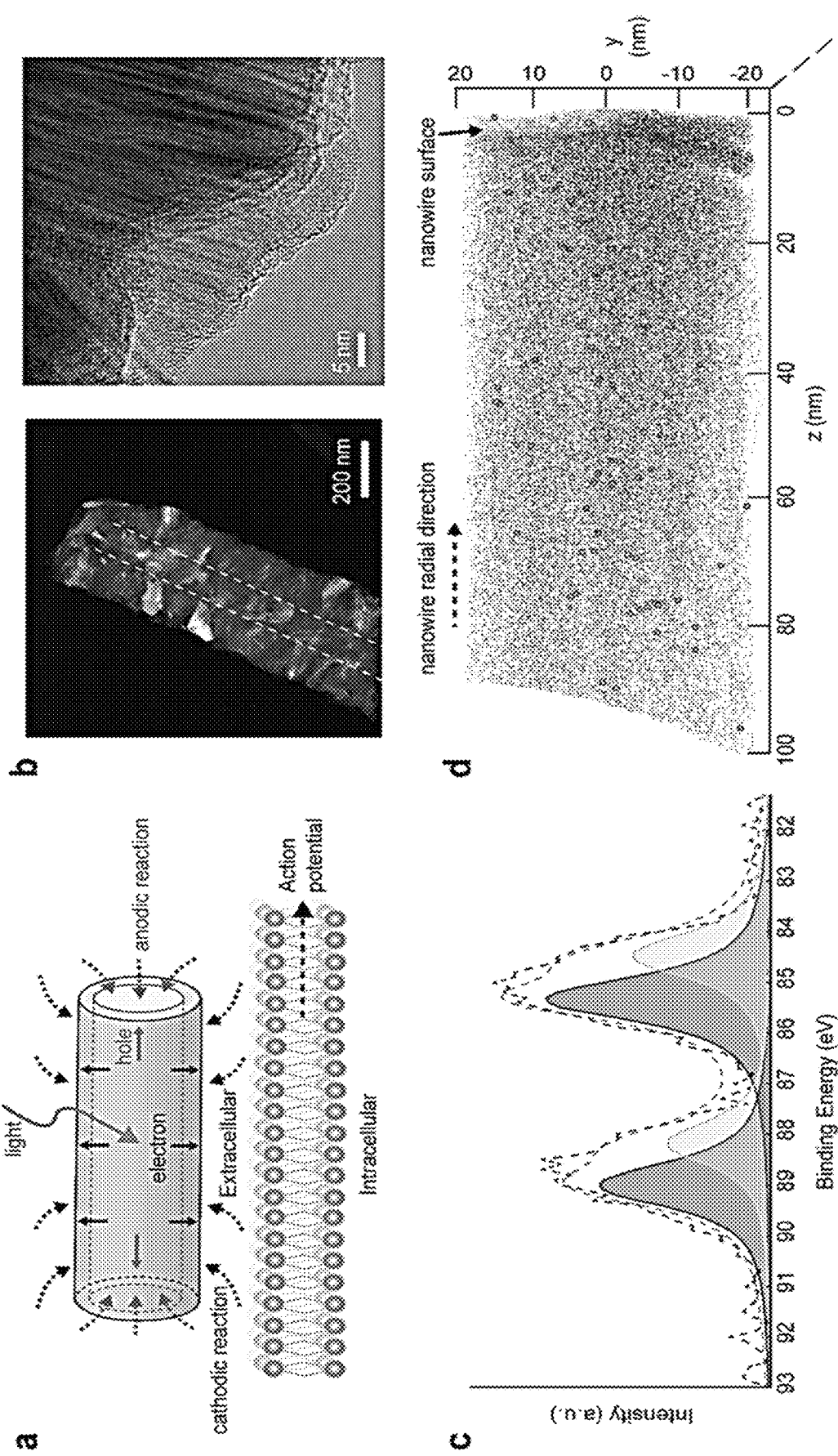
FIG. 1 illustrates atomic Au on coaxial nanowire surfaces by X-ray photoelectron spectroscopy and atom probe tomography. (A) shows a schematic of the Faradaic current produced by a PIN-SiNW at the neuronal cell membrane upon light stimulation, inducing action potential generation in the neuron via membrane depolarization. Solid arrows represent movement of electrons and holes towards n-type and p-type Si respectively upon light stimulation. Dotted lines represent the cathodic and anodic reactions, respectively. (B) shows a HAADF STEM image of PIN-SiNW (left) with p-type core outlined by white dotted line. This is a representative image from one of a total of 64 PIN-SiNWs imaged from 2 independent experiments. A TEM image of PIN-SiNW is also shown (right). This is a representative image from one of a total of 8 PIN-SiNWs imaged from 3 independent experiments. (C) illustrates an XPS spectrum (black dotted line) and the fitted curve of Au 4f signals from the PIN-SiNWs. Deconvoluted peaks of Au 4f 7/2 and Au 4f 5/2 at 84.46 eV and 88.13 eV represent nanoclustered Au species. Au 4f 7/2 and Au 4f 5/2 peaks at 85.4 eV and 89 eV represent atomic-like Au species. (D) shows 3D chemical reconstruction of local electrode APT data from a single PIN-SiNW displaying Si atoms (, 10% of all Si atoms displayed), O atoms (100% of all O atoms displayed), and Au atoms (100% of all Au atoms displayed). This is representative data from one of 3 independent probes that were prepared for APT analysis.

Before the disclosed methods and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting.

In view of the present disclosure, the methods and systems described herein can be configured by the person of ordinary skill in the art to meet the desired need. As provided above, the inventors have found that Si-based "bio-tronic" structures with dimension (e.g., length) scales from nanometer to centimeter can establish intra-, inter- and extracellular biointerfaces. The inventors have also found that the optical cellular-modulation can mimic naturally occurring extracellular signals, i.e., random, fast and multisite input signals, and that such modulation can modulate the activity of a cell.

As provided above, one aspect of the disclosure provides methods for modulating activity of a cell capable of being activated by light. Such methods include contacting a membrane of the cell with a silicon nanostructure to form a structure-cell membrane interface. In certain embodiments, the structure-cell interface is a direct interface between the silicon nanostructure and the cell membrane (i.e., there are no intervening structures between the silicon nanostructure and the cell membrane). In certain embodiments of the methods of the disclosure, the silicon nanostructure contacts the membrane without penetrating the membrane. For example, the silicon nanostructure may rest on the surface of the cell membrane.

The methods of the disclosure modulate activity of a cell capable of being activated by light. Thus, in certain embodiments, any cell capable of being activated by light may be used in the methods of the disclosure. In some embodiments, the cell is a neuron, an immune cell, or a cancer cell. In some embodiments, the cell is a neuron or an immune cell.

In some embodiments of the methods as described herein, the cell is a neuron.

In some embodiments of the methods as described herein, the cell is an immune cell. The immune cell, for example, may be selected from T cells, B cells, basophils, neutrophils, Natural Killer cells, mast cells, eisonophils, and macrophages. In some embodiments of the methods as described herein, the cell is a T cell selected from regulatory T cells and CD4+ T cells.

As noted above, the methods and systems of the disclosure generally require silicon nanostructures. The nanostructures of the disclosure include any nanoscale object that can be used in any of the embodiments described herein unless otherwise specified. Nanostructures include nanowires, nanotubes, nanoscaffolds such as mesh and membrane, nanorods, nanowhiskers, and other suitable geometries. "Nanowire" (also "NW," "SiNW," or "silicon NW") as used herein is a nanoscopic wire that is generally a solid wire, and may be elongated in some cases. "Nanotube" is generally nanoscopic wire that is hollow, or that has a hollowed-out core. "Nanoscaffold" is generally a free-standing porous scaffolds such as mesh and membrane. The silicon mesh can be made by photolithography and have a random or regular network of 3D features that can, for example, mimic the size scale and morphology of submicron bioactive extracellular matrices (ECMs). The nanostructures (e.g., nanowires), in some embodiments, may be formed having dimensions of at least about 1 micrometer, at least about 3 micrometers, at least about 5 micrometers, or at least about 10 micrometers or about 20 micrometers in length, and can be less than about 100 nm, less than about 80 nm, less than about 60 nm, less than about 40 nm, less than about 20 nm, less than about 10 nm, or less than about 5 nm in diameter or thickness (height and width). The nanowires may have an aspect ratio (length to thickness) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

In certain embodiments, the silicon nanostructure is a silicon nanowire. In some embodiments, the nanowire is cylindrical. In other embodiments, however, the nanowire can be faceted, i.e., the nanowire may have a polygonal cross-section. Where nanowires are described having, for example, a core and a shell, the above dimensions generally relate to those of the core. The cross-section of a nanowire may be of any arbitrary shape, including, but not limited to, circular, square, rectangular, annular, polygonal, or elliptical, and may be a regular or an irregular shape.

Many suitable silicon nanostructures are known in the art. In some embodiments, at least a portion of a nanostructure may be a doped. As used herein, a "doped" nanostructures is a nanostructures for which a dopant is incorporated substantially throughout the crystalline lattice of the nanostructure, as opposed to a nanostructure in which a dopant is only incorporated in particular regions of the crystal lattice at the atomic scale, for example, only on the surface or exterior. Heavily doped" and "lightly doped" are terms the meanings of which are clearly understood by those of ordinary skill in the art. In some cases, one or more regions may comprise a single monolayer of atoms ("delta-doping"). In certain cases, the region may be less than a single monolayer thick (for example, if some of the atoms within the monolayer are absent). As a specific example, the regions may be arranged in a layered structure within the nanoscale wire, and one or more of the regions may be delta-doped or partially delta-doped.

In certain embodiments, the silicon nanostructure contains n-doped, instrinsic and p-doped regions. Such structures are often referred to as "PIN" or "p-i-n." In certain embodiments, the silicon nanostructure is undoped, n-doped, or p-doped. In certain embodiments, the silicon nanostructure further comprises gold, silver, or platinum. In certain embodiments, the silicon nanostructure further comprises gold, silver, or platinum on the structure surface. These might be in the form of particles.

The silicon nanostructure may be freestanding. As used herein, "freestanding" nanowire means a nanowire free of contact with another nanowire (but not excluding contact of a type that may be desired between individual nanowires, e.g., as in a crossbar array). For example, a "freestanding" structure may, at some point in its life, not be attached to another structure, for example, with another nanowire, or the free-standing article maybe in solution. This is in contrast to nanotubes produced primarily by laser vaporization techniques that produce materials formed as ropes having diameters of about 2 nm to about 50 nm or more and containing many individual nanotubes (see, for example, Thess, et al., "Crystalline Ropes of Metallic Carbon Nanotubes," *Science*, 273:483-486 (1996)). This is also in contrast to conductive portions of structure which differ from surrounding material only by having been altered chemically or physically, in situ, i.e., where a portion of a uniform article is made different from its surroundings by selective doping, etching, etc. A "freestanding" structure is one that can be (but need not be) removed from the location where it is made, as an individual structure, and transported to a different location and combined with different components to make a functional device such as those described herein and those that would be contemplated by those of ordinary skill in the art upon reading this disclosure.

In certain embodiments, the silicon nanostructure may be freestanding and suspended in a pharmaceutically acceptable solution, paste, or a gel. For example, the solution or a gel may have an average concentration of silicon nanostructures in a range of 10,000 to 10,000,000 structures/mL (e.g., nanowires/mL). In certain embodiments, the solution or a gel may have an average concentration of silicon nanostructures in a range of 10,000 to 100,000, or 10,000 to 1,000,000, or 100,000 to 1,000,000, or 100,000 to 10,000,000, or 1,000,000 to 10,000,000 structures/mL (e.g., nanowires/mL).

The silicon nanostructure may be distributed in a flexible substrate comprising one or more of polymers. Distributed silicon nanostructures may be partially embedded or on the surface (e.g., bound to the surface) of the flexible substrate. In certain embodiments, partially embedded includes 10%, or 20%, or 30%, or 40%, or 50%, or 60%, or 70%, or even 80% of the total weight of silicon nanostructure is embedded into the flexible substrate. For example, when the structure is distributed on the flexible substrate, the surface average density is in a range of 10,000 to 1,000,000 structures/mm$^2$ (e.g., nanowires/mm$^2$). In certain embodiments, the surface average density of the structures when distributed on the flexible substrate is in a range of 10,000 to 100,000, or 10,000 to 1,000,000, or 100,000 to 1,000,000, or 100,000 to 10,000,000, or 1,000,000 to 10,000,000 structures/mm$^2$ (e.g., nanowires/mm$^2$).

Many suitable flexible substrates are known in the art. In certain embodiments, the flexible substrate is a polymer. In some embodiments, the polymer is selected from a photo-resist polymer, a biocompatible polymer, a biodegradable polymer, an extracellular matrix protein, and a combination thereof. In some embodiments, the flexible substrate comprises SU-8 photoresist. In some embodiments, the flexible substrate comprises polydimethylsiloxane. In certain embodiments, the flexible substrate comprises SU-8 photoresist and polydimethylsiloxane.

In certain embodiments, the flexible substrate has an open porosity of at least about 30%. For example, the flexible substrate has an open porosity of at least about 40%, or 45%, or 50%, or 55%, or even 60%.

Although the Si-based materials are composed primarily of silicon, they can include measurable amounts of other elements. In embodiments, the silicon nanostructures include oxygen. The oxygen may form bonds with silicon such that the oxygen (and some of the silicon) is in the form of an oxide, SiOx.

In certain other embodiments, the silicon nanostructures are free or substantially free of oxygen, and silicon oxide, SiOx.

In an example embodiment, a silicon nanostructure comprises a mesh of coaxial p-type/intrinsic/n-type silicon nanowires (PIN-SiNWs) and SU-8 as the flexible substrate. These nanowires may have a geometry, layer thickness, composition, or other configuration specified such that the nanowires provide electrical stimulation when they receive light within a specified range of stimulation wavelengths, e.g., between 900 nanometers and 400 nanometers or between 740 nanometers and 530 nanometers.

In certain embodiments of the disclosure, the silicon nanostructure may further comprise a targeting moiety for targeting the cell. Suitable targeting moiety may comprise a member of a binding pair, such as antibody-antigen, receptor-ligand, and the like. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991). The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. As used herein, "receptor" and "ligand" refer to two members of a specific binding pair and, hence, are binding partners. A receptor is that member of the pair that is typically localized on the surface of a cell; the ligand is the member of the pair that forms a complex with the receptor to serve a biological purpose. In receptor-ligand binding, the ligand is usually a molecule which produces a signal by binding to a site on a target receptor.

The methods of the disclosure require exposing the interface to light under conditions to depolarize the cell membrane. The depolarization of the cell membrane thereby increases a threshold for activation of the cell. The amount of light needs to be sufficient to accomplish polarization, yet low enough to not harm the cell. Thus, suitable exposing time, wavelength, and power of the light will be selected so to provide the desired activity without the toxicity to the cell. The exposing time may be for a time ranging from 0.5 ms to 15 ms. For example, in certain embodiments, the interface may be exposed for 0.5 ms to 10 ms, or 0.5 ms to 7 ms, or 0.5 ms to 5 ms, or 0.5 ms to 2 ms, or 0.5 ms to 1 ms, or 1 ms to 15 ms, or 1 ms to 10 ms, or 1 ms to 7 ms, or 1 ms to 5 ms, or 1 ms to 2 ms, or 2 ms to 15 ms, or 2 ms to 10 ms, or 2 ms to 7 ms, or 2 ms to 5 ms, or 5 ms to 15 ms, or 5 ms to 10 ms, or 5 ms to 7 ms, or 10 ms to 15 ms. In certain embodiments, the cell is a neuron cell and the exposure time is or 0.5 ms to 7 ms, or 0.5 ms to 5 ms, or 1 ms to 7 ms, or 1 ms to 5 ms.

In certain embodiments, a single pulse is sufficient to modulate activity of a cell. In certain embodiments, two or more pulses are sufficient to modulate activity of a cell. In certain embodiments, 5 or more, or 10 or more, or 25 or more, or 50 or more pulses are sufficient to modulate activity of a cell. In certain embodiments, 1 to 5, or 1 to 10, or 1 to 25, or 1 to 50, or 1 to 100, or 2 to 5, or 2 to 10, or 2 to 25, or 2 to 50, or 2 to 100, or 5 to 10, or 5 to 25, or 5 to 50, or 5 to 100 pulses are sufficient to modulate activity of a cell.

The selection of the wavelength may be determined on the type of silicon nanostructure and the amount of light energy required to deactivate the membrane without toxicity to the cell. The light may be provided at an excitation wavelength ranging from 400 to 900 nm. For example, in certain embodiments, the light may be provided at an excitation wavelength ranging from 400 to 800 nm, or 400 to 750 nm, or 400 to 600 nm, or 400 to 550 nm, or 500 to 900 nm, or 500 to 800 nm, or 500 to 750 nm, or 500 to 600 nm, or 600 to 900 nm, or 600 to 800 nm, or 600 to 750 nm. The light may be provided at a power in a range of 1 mW to 1 W. For example, in certain embodiments, the light may be provided at a power in a range of 10 mW to 1 W, or 100 mW to 1 W, or 500 mW to 1 W, or 1 mW to 500 mW, or 10 mW to 500 mW, or 100 mW to 500 mW.

Another aspect of the disclosure provides methods of treating a disease in a subject by modulating activation of a cell. Such methods include (i) administering a therapeutically effective amount of a composition comprising silicon nanostructures of the disclosure as described herein to the subject; and (ii) exposing the subject to light under conditions sufficient to increase a threshold for activation of the cell and treat the disease.

In certain embodiments, methods of the disclosure treat an autoimmune disease, cancer, allergy, asthma, neuronal disease, cardiovascular disease, or a combination thereof. In certain embodiments, methods of the disclosure treat an autoimmune disease. In certain embodiments, methods of the disclosure treat a cardiovascular disease.

Many suitable administration routes are known in the art. For example, the therapeutically effective amount of a composition comprising silicon nanostructures of the disclosure as described herein can be administered parenterally. In certain embodiments, the administration is intravenous. Other routes of administration include, but are not limited to, epidural, intraocular, intramuscular, transdermal, subcutaneous, intracardiac, intracerebral, etc.

The methods of the disclosure require exposing the subject to light under conditions sufficient to increase a threshold for activation of the cell and treat the disease. Suitable conditions for light exposure are as described above with respect to the modulating activity of a cell.

In certain embodiments, the disclosure provides a method for treating a cardiovascular disease. In certain embodiments, such method includes optically training myocardium to beat at a target frequency. Thus, one aspect of the disclosure provides a method for optically training myocardium to beat at a target frequency. This method includes (i)

contacting the myocardium with the composition comprising silicon nanostructures; and (ii) operating a light emitter to provide, during a training period of time, a plurality of pulses of light at a stimulation wavelength to the myocardium, wherein the plurality of pulses of light are provided at the target frequency. In certain embodiments, the composition comprising silicon nanostructures is a flexible silicon nanostructure that includes a flexible substrate on which silicon nanostructure or a plurality of silicon nanostructures are distributed and the flexible silicon nanostructure is configured to be placed in contact with cells of the myocardium such that the silicon nanostructures are in contact with cells of the myocardium. The silicon nanostructures provide, to cells of the myocardium that they are in contact with, excitatory stimulus in response to receiving light at the stimulation wavelength.

The disclosure also provides systems suitable for use in the methods of the disclosure.

Thus, in one aspect, the disclosure provides a system for treating a disease in a subject by modulating activation of a cell. Such system includes (i) a composition comprising silicon nanostructures of the disclosure as described herein; (ii) a light emitter configured to emit light at a stimulation wavelength; and (iii) a controller that is operably coupled to the light emitter. In such systems, the silicon nanostructures provide, to the cell they are in contact with, excitatory stimulus in response to receiving light at the stimulation wavelength. The controller includes one or more processors, wherein the controller is programmed to perform controller operations including: operating the light emitter to provide the light to the cell.

In certain embodiments, the disclosure provides a system for optically training myocardium to beat at a target frequency. As provided herein, such system includes: (i) a composition comprising silicon nanostructures of the disclosure as described herein; (ii) a light emitter configured to emit light at a stimulation wavelength; and (iii) a controller that is operably coupled to the light emitter. In certain embodiments, the composition comprising silicon nanostructures includes a flexible substrate on which silicon nanostructure or a plurality of silicon nanostructures are distributed and the flexible substrate is configured to be placed in contact with a surface of the myocardium such that the silicon nanostructures are in contact with cells of the myocardium. The silicon nanostructures provide, to cells of the myocardium that they are in contact with, excitatory stimulus in response to receiving light at the stimulation wavelength. The controller includes one or more processors and is programmed to perform controller operations including: operating the light emitter to provide, during a training period of time, a plurality of pulses of light to the myocardium, wherein the plurality of pulses of light are provided at the target frequency.

As noted above, it can be beneficial in a variety of applications to apply the silicon nanostructures (e.g., nanowires) as described herein to the stimulation and control of the activity of myocardium (e.g., myocardium of a heart of a person or animal). These structures can be used to efficiently control the pacing of a heart and/or to correct some other deleterious electrical and/or pacing condition of the heart (e.g., bradycardia, tachycardia, ventrical or atrial fibrillation). These structures may additionally or alternatively be used to "retrain" the electrical behavior of the myocardium of the heart, e.g., to train the heart tissue to beat at a more appropriate target rate, to change a pattern of electrical connection or conduction of the heart, or to train the myocardium of the heart in some other manner. The use of these nanowire-containing structures may provide a variety of benefits relative to the use of electrodes to pace or otherwise manipulate the heart, e.g., by providing a more energy-efficient interface that has a mechanical compliance that is better matched to the heart tissue.

In order to use the nanostructures described herein to facilitate optical control or manipulation of the electrical and/or physiological properties of myocardium, the silicon nanowires (or other nanostructures) can be distributed on or within a flexible substrate (e.g., a grid-shaped substrate formed of SU-8 or some other polymer). The flexible substrate material can provide a base for the nanowires, facilitating their organization and implantation within a body (e.g., by contacting with a surface of a heart or some other surface of a myocardial tissue) such that, when the nanowires receive light at an appropriate wavelength, nearby cardiac cells receive electrical or other stimulus.

The silicon nanostructures can be used to provide pulses of optical stimulation in order to cause, manipulate, alter, or otherwise affect the electrical activity of cells of the myocardium. Such pulses of stimulation can provide an entraining stimulus, causing the myocardium to beat or otherwise become electrically active in time with the pulses of stimulation. However, it can be difficult to determine the location, pulse width, pulse amplitude, pulse waveform, or other parameters of stimulation sufficient to excite the cells of the myocardium while reducing the total energy required to elicit the excitation. Such a reduction may be desirable in order to reduce the power requirements of a stimulator device, to reduce phototoxicity in the myocardium, to reduce an amount of localized heating of the myocardium, or to provide some other benefits.

In practice, it can be beneficial to quickly scan the illumination in a point, line, or other shape across the tissue to be stimulated. For example, a spot of illumination can be scanned across the tissue in a plurality of lines or according to some other scan pattern such that the entirety of the tissue surface is briefly illuminated respective periods of time across the scan period. This method was found to provide excellent stimulation of myocardium, especially for "training" the myocardium to pulse at a specified rate, while reducing the overall amount of illumination (e.g., the overall amount of illumination power) required to effect the stimulation. This may be due to the plurality of nanowires acting to waveguide and spread the illumination across the surface of the myocardium. Accordingly, each cell of the myocardium may receive a plurality of pulses of illumination during a particular scan, as the point (or line, or other shape) of illumination passes over and/or near the cell.

In certain embodiments, a point, line, or other shape of illumination can be scanned across an area of myocardium by operating a galvanometer to scan the output of a laser or other light-emitting element(s). Such a setup could be implemented in an implanted device setting, e.g., by providing a cowling over the nanowire substrate, by using mirrors, lenses, optical fiber(s), or other elements to direct the output of the galvanometer to the flexible nanowire substrate, or in some other manner. Additionally or alternatively, such scanning of illumination across the surface of the myocardium could be accomplished by activating individual light-emitting elements (e.g., LEDs, VCSELs) of an array of light-emitting elements according to a scan pattern. Such light-emitting elements could be disposed on or otherwise directly associated with the flexible nanowire substrate (e.g., by disposed on the substrate on which the nanowires are distributed, by being disposed on a flexible PCB or other substrate that is, in turn, adhered to the nanowire substrate).

Alternatively, the light-emitting elements could be coupled to respective different locations across the area of the flexible nanowire substrate, e.g., via respective optical fibers.

In order to stimulate the myocardium to pulse at a target frequency and/or to train the myocardium to pulse at such a target frequency independent of continued stimulation, pulses of illumination may be applied to the myocardium as described above. Each pulse of stimulation could include one or more scans of the illumination across the tissue. For example, a single pulse of illumination could include two or more scans of a point of illumination across the tissue, with the scans repeated at a specified frequency (e.g., 1 kHz). Multiple pulses may be provide during a training period, e.g., at a frequency corresponding to the target myocardial beat frequency (e.g., between 0.5 and 3 Hz). In order to train the myocardium to continue pulsing at the trained frequency, multiple periods of training pulses may be provided, each period of training pulses being separated from the others by a "break period" during which illumination is not provided. The duration of such a break period may be optimized, e.g., to have a two minute duration.

Note that the above methods used the fluorescent and/or electrical detection of cardiomyocyte pulse rate to assess the efficacy of the methods described herein to entrain the electrical activity of myocardium and/or of cardiac cells in culture. However, such detection may also be employed in an implant or other system used to effect training of myocardium in a clinical setting. Such a detected pulse rate may be used to determine that training pulses should be applied to the myocardium, e.g., by determining that the detected pulse rate has deviated from a target frequency by more than a threshold amount. Additionally or alternatively, the detected pulse rate could be used to determine whether sufficient training has been provided, and if not, to provide additional training pulses. For example, a first set of training pulses could be provided and the pulse rate following the training pulses could be detected. If the detected pulse rate deviated from a target by more than a threshold amount, additional training pulses could be provided.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

EXAMPLES

Certain aspects of the disclosure are illustrated further by the following examples, which are not to be construed as limiting the disclosure in scope or spirit to the specific methods and materials described in them.

Materials and Methods

Nanowire Synthesis. Coaxial pin silicon nanowires (PIN-SiNWs) were synthesized using a gold (Au) nanocluster-catalyzed chemical vapor deposition (CVD) process. Citrate-stabilized Au colloidal nanoparticles (Ted Pella Inc. 50 nm diameter) were deposited onto silicon (Si) <100> substrates (Nova Electronic Materials, n-type, 0.001-0.005 Ωcm) and used as catalysts. During the nanowire growth, silane ($SiH_4$) was used as the Si reactant, diboron ($B_2H_6$, 100 ppm in $H_2$) as the p-type dopant, phosphine ($PH_3$, 1000 ppm in $H_2$) as the n-type dopant, and hydrogen ($H_2$) as the carrier gas. For the p-type core nanowire growth, $SiH_4$, $B_2H_6$, and $H_2$ were delivered at flow rates of 2, 10, and 60 standard cubic centimeters per minute (sccm), respectively. For the intrinsic Si shell (i-shell) deposition, $SiH_4$ and $H_2$ were delivered at 0.3 and 60 sccm, respectively. Flow of $PH_3$ gas was then added for the n-type outer shell deposition at a flow rate of 1.5 sccm. The core growth was carried out at 470° C. at a pressure of 40 torr for 30 min. Prior to i-shell deposition, growth was paused in a vacuum for 20 minutes until the CVD furnace temperature was stabilized at 750° C. in preparation for shell deposition. The shell depositions were performed at 750° C. at a pressure of 20 torr for 15 min per shell.

P-doped Si nanowires (p-type SiNWs) were synthesized also using 250 nm Au nanocluster-catalyzed CVD. $SiH_4$, $B_2H_6$, and $H_2$ were delivered at flow rates of 2, 10, and 60 sccm, respectively, at 470° C. at a pressure of 40 torr for 30 min.

Undoped Si nanowires were synthesized also using 250 nm Au nanocluster-catalyzed CVD. $SiH_4$ and $H_2$ were delivered at flow rates of 2 and 60 sccm, respectively, at 475° C. at a pressure of 40 torr for 30 min.

P-doped Au diffused Si nanowires were synthesized also using 250 nm Au nanocluster-catalyzed CVD. $SiH_4$, $B_2H_6$, and $H_2$ were delivered at flow rates of 2, 10, and 60 sccm, respectively, at 470° C. at a pressure of 40 torr for 30 min. Au catalyst was allowed to diffuse down the synthesized nanowires in a vacuum at 750° C. for 30 min.

X-Ray Photoelectron Spectroscopy. PIN-SiNWs still attached to their growth substrate were cleaned in 10% HF for 90 sec, rinsed in DI $H_2O$ for 30 sec, and dried with $N_2$ gas. X-ray photoelectron spectroscopy (XPS) was performed on the nanowire samples using a monochromatic Al Kα X-ray source (AXIS Nova Kratos Analytical) that probes elemental composition 7-10 nm from the surface of the sample. The Al anode was powered at 10 mA and 15 kV. The instrument work function was calibrated to give an Au $4f_{7/2}$ metallic gold binding energy (BE) of 83.95 eV. Instrument base pressure was ca. $1 \times 10^{-9}$ Torr. The analysis area size was 0.3×0.7 $mm^2$. For calibration purposes, the binding energies were referenced to Si 2p peak at 99.8 eV and/or C 1s peak at 285.5 eV. To improve reliability of the calibration, Pt metal was also introduced to the surface of some samples and Pt 4f signal 71.0 eV was used for cross-checking the calibration. Survey spectra were collected with a step size of 1 eV and 160 eV pass energy. The high-resolution spectra of Si 2p and Au 4f were collected with a pass energy of 20 eV and 0.1 eV step size using 3 and 20 sweeps of 120 s for each sweep, respectively. XPS peaks were fitted with an asymmetric Gaussian/Lorentzian peak shape with linear background correction. Initial peak approximation model was based on the Au 4f peak modeling of the pure gold sample in order to better evaluate the asymmetric nature of the peak profile and the fit envelope.

Transmission Electron Microscopy. PIN-SiNWs synthesized from 50 nm AuNPs were sonicated off of their growth substrate in IPA, and then dropcasted onto copper grids (Ted Pella Inc., USA, Lacey Formvar/Carbon, 200 mesh) for TEM (JEOL, Japan, JEM-3010) energy dispersive x-ray spectroscopy (EDS) (Thermo Fisher Scientific, USA, Thermo Noran Vantage XEDS). 840 second EDS measurements were taken for each nanowire and elemental peaks were assigned.

Energy Dispersive X-ray Spectroscopy. PIN-SiNWs synthesized from 50 nm AuNPs were sonicated off of their growth substrate in IPA, and then dropcasted onto copper grids (Ted Pella Inc., USA, Lacey Formvar/Carbon, 200 mesh) for TEM (JEOL, Japan, JEM-3010) energy dispersive x-ray spectroscopy (EDS) (Thermo Fisher Scientific, USA, Thermo Noran Vantage XEDS). 840 second EDS measurements were taken for each nanowire and elemental peaks were assigned.

Atom probe tomography (APT). 200-350 nm PIN-SiNW were synthesized from 50 nm AuNPs and coated with 50 nm of Ni layers using an e-beam evaporator (AJA International, USA). The Ni-protected SiNWs were transferred onto Si microposts using a micromanipulator inside a focused ion beam (FIB) system (FEI, USA, Nova 600 NanoLab). Samples were then milled and sharpened into needle-like microtip specimens for APT characterization. The APT was run in an ultraviolet (UV) laser-assisted local-electrode atom-probe instrument (Cameca, USA, LEAP 400XSi). The surface atoms from each microtip were evaporated with an applied voltage of 1-6 kV and 20 pJ of 355 nm UV laser pulsing at a frequency of 250 kHz. The mass-to-charge (m/z) ratios of individual evaporated ions and their corresponding (x, y, z) coordinates in space were recorded with a position sensitive detector. The samples were held at 30 K and $2\times10^{-11}$ Torr during APT experiments. The 3D reconstructions and data analyses were performed using Cameca's Integrated Visualization and Analysis Software (IVAS) 3.6 code. The proximity histogram was created with respect to the 80% Si isoconcentration surface.

Cell culture protocol. Dorsal root ganglia (DRG) were excised from P1-P3 neonatal rats into DMEM-F12 on ice. They were then digested in 2.5 mg/mL trypsin (Worthington) in EBSS for 20 min in a 37° C. shaker. Following trypsinization, digested DRGs were resuspended into EBSS+10% FBS in order to inhibit further digestion by any remaining trypsin. Digested ganglia were then mechanically triturated via three glass pipettes decreasing in size. The resulting dispersed DRG cells were then resuspended into DMEM+5% FBS+100 U/mL penicillin+100 µg/mL streptomycin and seeded onto glass bottom dishes previously treated with 0.01% poly L lysine.

Neuron electrophysiology experiments. DRG neurons were patch clamped in whole cell current clamp configuration using an Axopatch 200B amplifier (Molecular Devices). The output voltage signal was digitized at 16-bit resolution by an Innovative Integration SBC-6711-A4D4 data acquisition board. The digital analogue converter (DAC) of the data acquisition board supplied the command voltage to the amplifier. DRG neurons were mounted onto a Zeiss IM 35 microscope (Carl Ziess Microscopy) and visualized through a 40× (0.55 NA) microscope objective lens. Si nanowires were sonicated for 10 seconds off of the growth substrate into a modified Tyrode's bath solution (NaCl 132 mM, KCl 4 mM, $MgCl_2$ 1.2 mM, $CaCl_2$) 1.8 mM, HEPES 10 mM, glucose 5.5 mM, pH 7.4). These wires were then drop casted on top of the cultured neurons and allowed to settle for 20 minutes. Cells visually interacting directly with a single nanowire were then chosen to be tested for the generation of action potentials by laser pulses. Borosilicate glass pipettes pulled on a $CO_2$ laser micropipette puller (Sutter Instruments P-2000) and flame polished using a custom microforge to produce 2 MΩ resistances when filled with internal pipette solution (NaCl 10 mM, KF 130 mM, $MgCl_2$ 4.5 mM, HEPES 10 mM, EGTA 9 mM, ATP 2 mM, pH 7.3) were used as patch pipettes. The 40× objective lens was used to focus a 532 nm DPSS laser (UltraLasers) spot (spot size: ~5 µm) onto the cell nanowire interface. This laser beam was modulated with an acousto-optic modulator (NEOS Technologies, Gooch & Housego, PLC) and power adjusted via a series of neutral density filters. Current injections were performed with amplitudes varying from 500 to 1000 pA depending on the current amplitude necessary to generate an action potential in each cell at a duration of 1 ms. Laser pulse durations at the neuron-SiNW interface were varied from 0.1 to 10 ms and powers varied from 1 to 85 mW as described in the results. The University of Chicago Animal Care and Use Committee approved all animal protocols used in this work.

Scanning Electron Microscopy. DRG neurons were cultured onto a glass coverslip. PIN-SiNWs were sonicated into culture medium, drop casted onto the cells, and left to be co-cultured with the cells for 24 hours. The cell/NW co-culture was then fixed with 4% paraformaldehyde and then stained with 4% osmium tetroxide for 1 hour at room temperature. The culture was then dehydrated with ethanol and critical point dried before being sputter coated with 8 nm of Platinum/Palladium metal. Images were taken on a Carl Zeiss Merlin FE-SEM.

Fluorescent Microscopy. DRG neurons were cultured onto a glass coverslip. PIN-SiNWs were sonicated into culture medium, drop casted onto the cells, and left to be co-cultured with the cells for 24 hours. Neurons were fixed in 4% paraformaldehyde and stained with a rabbit anti-rat anti-β tubulin III primary antibody (Abcam ab18207) and a goat anti-rabbit Texas Red secondary antibody (Abcam ab6719). Cells were visualized on an inverted fluorescent microscope under a Texas Red filter and nanowires visualized via SEPC as demonstrated previously.

Temperature Measurements. Thermometer pipettes with resistances of 2 MΩ were filled with bath solution and placed 2 µm away from the neuron/SiNW interface being tested. Pipette resistance was monitored as part of a tension divider using a voltage amplifier during action potential generation in the nearby cell. Conversion of pipette resistance to temperature was achieved by using a calibration curve produced individually for each pipette by pairing resistance values with a broad range of temperatures as a solution starting at 40° C. was cooled down passively to room temperature. The temperature was simultaneously recorded by a thermocouple placed very close to the pipette tip during the calibration procedure.

Photocurrent measurements. Si nanowires were synthesized as described above using a gold (Au) nanocluster-catalyzed chemical vapor deposition (CVD) process. Citrate-stabilized Au colloidal nanoparticles (Ted Pella Inc. 50 nm diameter) were deposited into quartz glass capillary tubes (Sutter Instruments) and used as catalysts. Nanowire growth was performed under the same conditions as described above. Quartz capillary tubes containing silicon nanowires were pulled to produce pipettes with 14-20 MΩ resistances (pipette tip diameter, ~1 µm) and filled with bath solution. These pipettes were then mounted onto the aforementioned electrophysiology setup and current recordings were performed in voltage-clamp mode at 0 mV with the 532 nm laser focused onto single nanowires positioned ~10-30 µm from the tip of the pipettes, thus minimizing any changes in pipette resistance due to increases in temperature produced by light absorption. Laser pulses between 0.5 and 10 ms durations and 1 to 20 mW powers were used. Raw traces were filtered by averaging every 10 points of data.

Cell Viability Assay. DRG neurons were cultured onto glass bottom petri dishes. PIN-SiNWs were sonicated into culture medium, drop casted onto the cells, and left to be co-cultured with the cells for 24 hours. For experiments without light stimulation, cells were stained with a LIVE/DEAD cell viability assay kit (ThermoFisher Scientific) and the numbers of live cells in culture with and without nanowires were counted. For experiments with light stimulation, cells were stimulated via the 592 nm depletion laser on an SP5 laser scanning confocal microscope (Leica, USA, SP5 II STED-CW) under a 40× objective (Leica, USA, HCX PL APO) at various frequencies for various durations at a total energy density of 0.31 µJ/µm$^2$ for each pulse. After stimulation, cells were stained with a LIVE/DEAD cell viability assay kit (ThermoFisher Scientific) and the numbers of live stimulated neurons, neurons neighboring the stimulated neurons, and unstimulated neurons were counted.

Example 1: Photoelectrochemical Behavior of Free-Standing Coaxial Silicon Nanowires Characterization of coaxial nanowire surfaces. The PIN-SiNWs were synthesized via a combination of gold (Au) nanoparticle (NP)-catalyzed vapor-liquid-solid growth of p-type SiNW cores, vacuum annealing, and a final vapor-solid growth of Si shells (as described in Materials and Methods above). High-angle annular dark field (HAADF) scanning transmission electron microscope (STEM) and transmission electron microscopy (TEM) show a final nanowire diameter of 200-250 nm with polycrystalline surfaces (FIG. 1B). NW shell synthesis of this kind at high temperatures and low pressures favors diffusion of the gold catalyst down the sidewalls of the NWs, resulting in atomic gold accumulation around the shells. X-ray photoelectron spectroscopy (XPS) of PIN-SiNWs attached to their growth substrate indicates the presence of two types of Au within 7-10 nm from the surface of the NWs (FIG. 1C; Table 1).

TABLE 1

| | XPS peaks with binding energies | | | | | |
|---|---|---|---|---|---|---|
| Sample | atomic-like 5/2 peak | atomic-like 7/2 peak | nanoclustered 5/2 peak | nanoclustered 7/2 peak | metallic 5/2 peak | metallic 7/2 peak |
| Metallic Au | | | | | 87.5 | 83.4 |
| p type SiNW | 89.1 | 85.4 | 88.6 | 84.9 | 87.7 | 84 |
| PIN-SiNW1 | 88.8 | 85.1 | 88.3 | 84.6 | | |
| PIN-SiNW2 | 88.9 | 85.2 | 88 | 84.4 | | |
| PIN-SiNW3 | 88.9 | 85.2 | 87.9 | 84.3 | | |
| PIN-SiNW4 | 89 | 85.4 | 88.1 | 84.4 | | |
| PIN-SiNW5 | 89 | 85.4 | 88.1 | 84.5 | | |
| PIN-SiNW6 | 89 | 85.3 | 88.2 | 84.5 | | |

Figure 2:
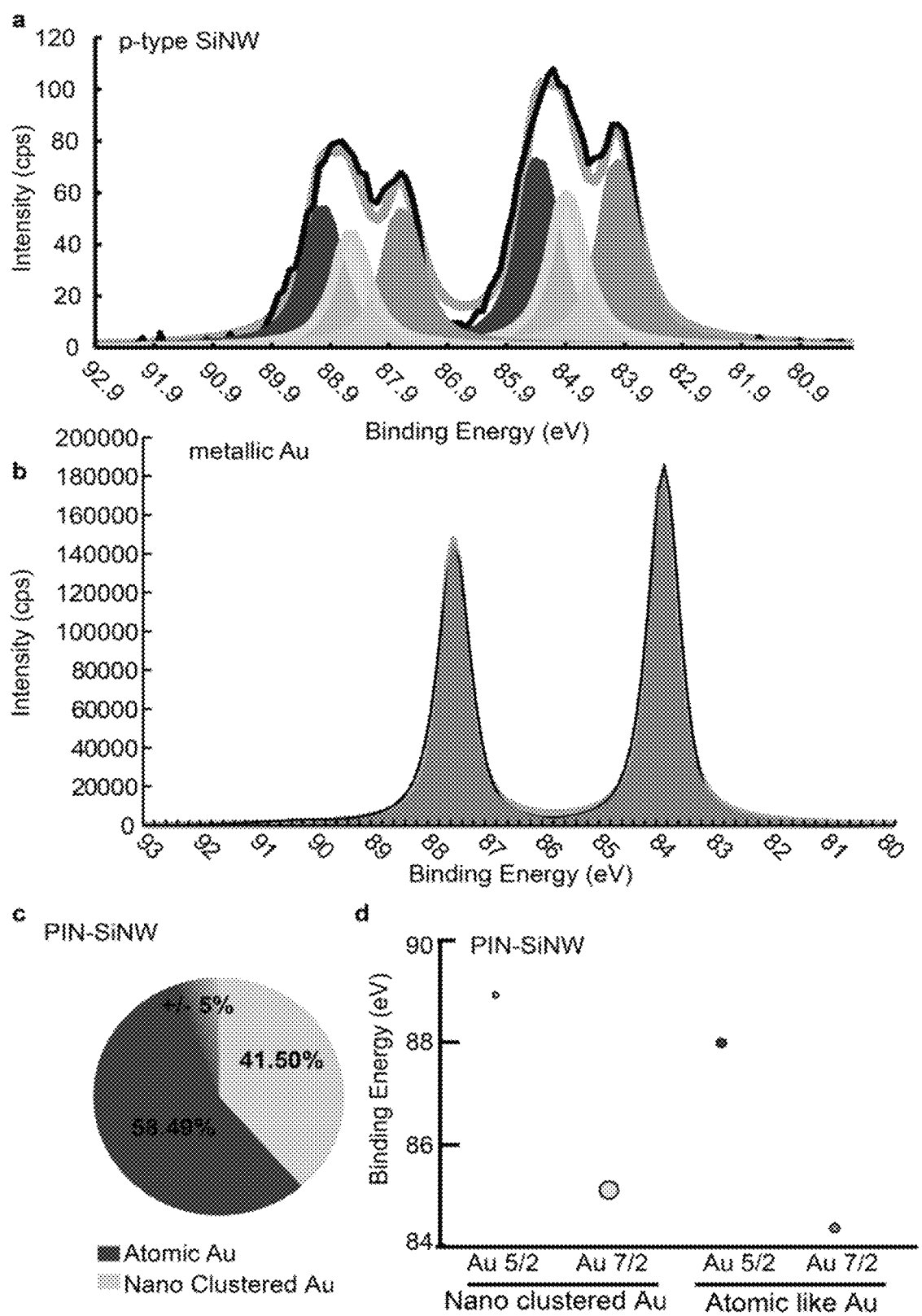
FIG. 2 illustrates a comparison of XPS Au 4f spectra from PIN-SiNW, p-type SiNW, and metallic Au samples, showing atomic and nanoclustered Au on PIN-SiNW surfaces. (A) shows an Au 4f XPS spectrum of control p-type SiNWs (black line) and a model thereof. Deconvoluted peaks of Au 4f 7/2 and Au 4f 5/2 at 84.9 eV and 88.6 eV represent nanoclustered Au species. Au 4f 7/2 and Au 4f 5/2 peaks at 85.4 eV and 89.1 eV represent atomic-like Au species. (B) shows an XPS spectrum of metallic Au sample displaying Au 4f peaks. (C) shows a pie chart representing the average percentage of atomic-like Au and nanoclustered Au species from 6 independent PIN-SiNW samples. (D) illustrates the average binding energies for Au 5/2 and Au 7/2 nanoclustered Au and atom-like Au peaks from 6 independent PIN-SiNW samples. Size of the circle represents the standard error about the average.
Figure 3:
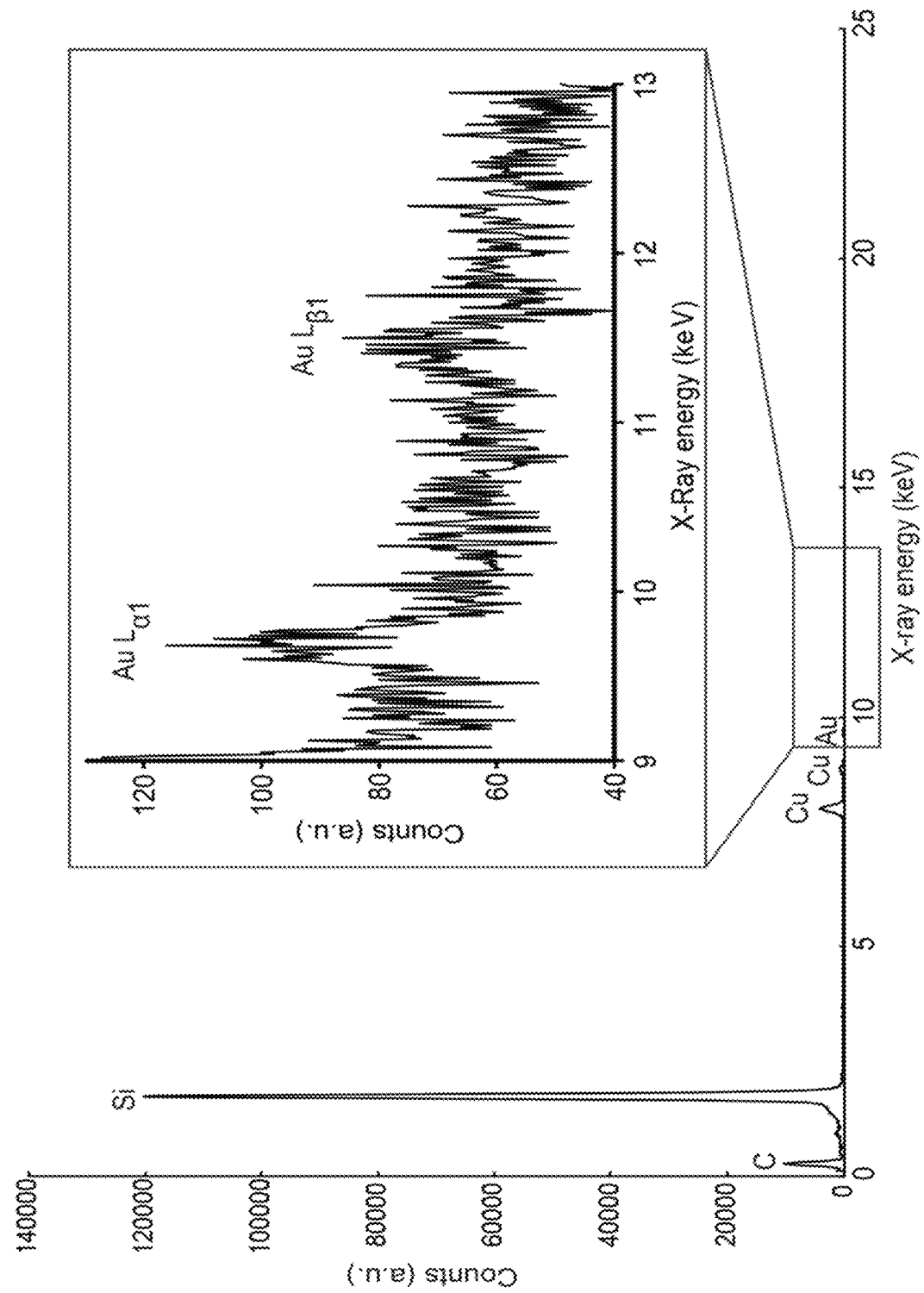
FIG. 3 illustrates the energy dispersive x-ray spectrum for a single PIN-SiNW displaying Au peaks. Energy dispersive x-ray spectroscopy (EDS) was performed on 6 independent PINSiNWs and characteristic Au elemental peaks were measured. Specifically, both Au Lα1 and Lβ1 peaks were detected above baseline at 9.7 and 11.4 keV X-ray energies (boxed inset).

XPS peaks with binding energies of 84.5 eV and 88.1 eV represent Au nanoclusters, while those with binding energies of 85.4 eV and 89.0 eV highlight the presence of atomic Au species (FIG. 1C, Table 1, FIG. 2). On average, 58.5% of the Au present is represented by the atomic Au and 41.5% is represented by the nanoclustered Au (FIG. 2), and no metallic Au is identified. Energy dispersive x-ray spectroscopy (EDS) further confirms this result in single PIN-SiNWs. Spectra acquired displayed characteristic Au Lα1 and Lβ1 peaks at 9.7 and 11.4 keV X-ray energies respectively, thus confirming the presence of Au atoms in single PIN-SiNW nanowires (FIG. 3).

Figure 4:
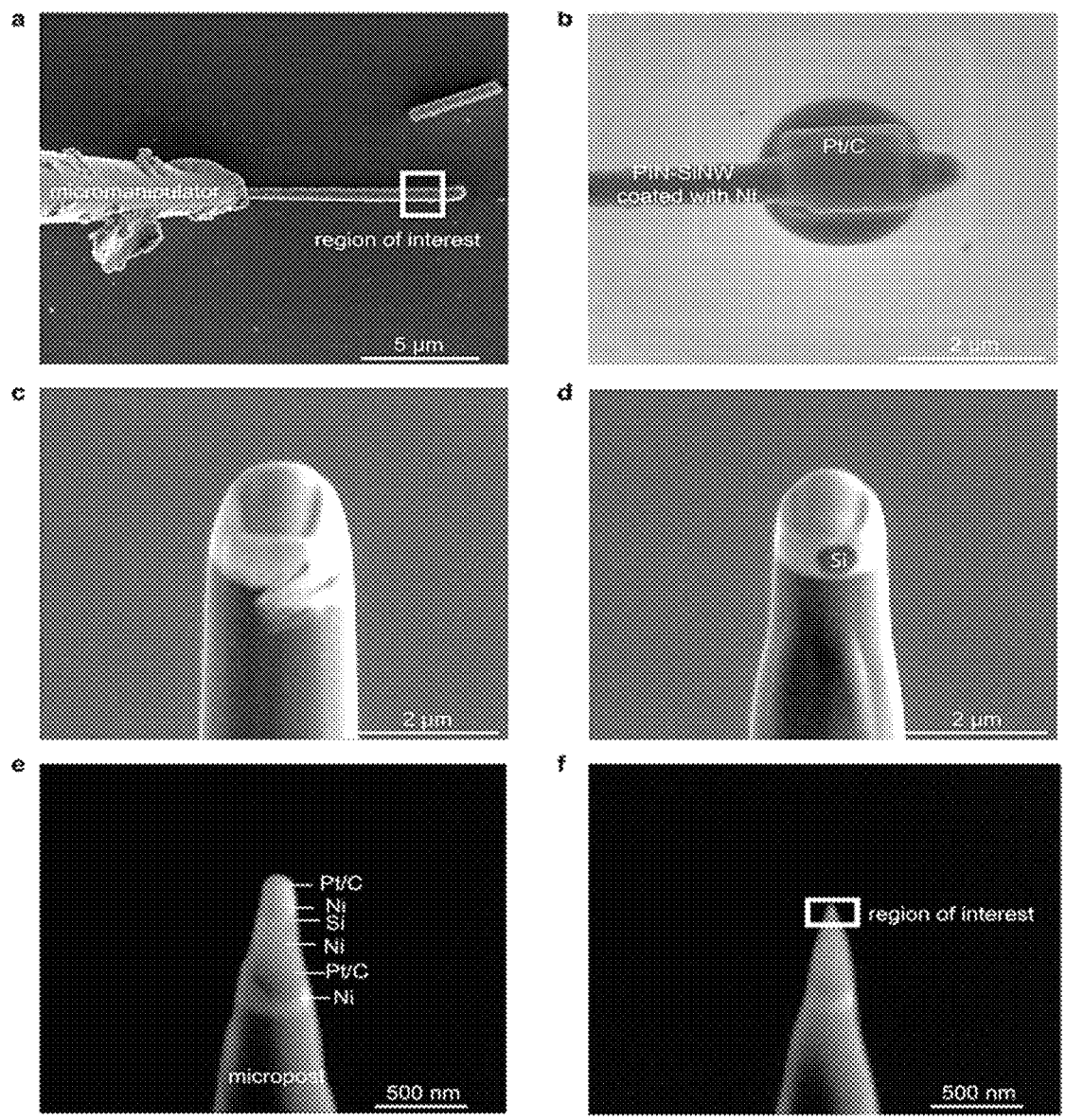
FIG. 4 shows representative SEM images of the APT tip preparation process from one of 3 independent APT probes prepared. (A) illustrates a micromanipulator picking up a single Ni coated PIN-SiNW of interest from Si wafer substrate. (B) shows PIN-SiNW bound to the Si micropost with Pt/C composite at the region of interest near the tip of the NW. (C) shows a sample pre-cut with a 30 kV Ga+ ion beam. (D) illustrates a sample milled with a 30 kV Ga+ ion beam. (E) shows a sample tip sharpened with a 5 kV Ga+ ion beam, with various material layers indicated. (F) shows a sample tip cleaned and region of interest for APT indicated.

To more definitively characterize the amount and spatial distribution of atomic Au in the NWs, local electrode atom probe tomography (APT) was performed on a single PIN-SiNW (FIG. 4). The APT data demonstrate the existence of atomic Au in band-like domains with additional accumulation at the surface (FIG. 1D). Without being bound by a particular theory, it is believed that the high temperature and low pressure conditions used for annealing and subsequent shell depositions allow for complete Au catalyst diffusion down the sidewalls of the nanowire cores and the subsequent Au migration into the shells through grain boundaries or gettering effect. Despite the dominant argument that atomic Au generates deep traps in Si, the Au at the Si surface may also confer properties that can be useful in a photoelectrochemical processes during cellular excitability modulation. Specifically, surface atomic Au may alter the surface states of the Si in such a way that is beneficial for reducing NW impedance in aqueous solutions, thus favoring the production of faradaic, not capacitive currents, as in traditional photoelectrochemical cells.

Figure 5:
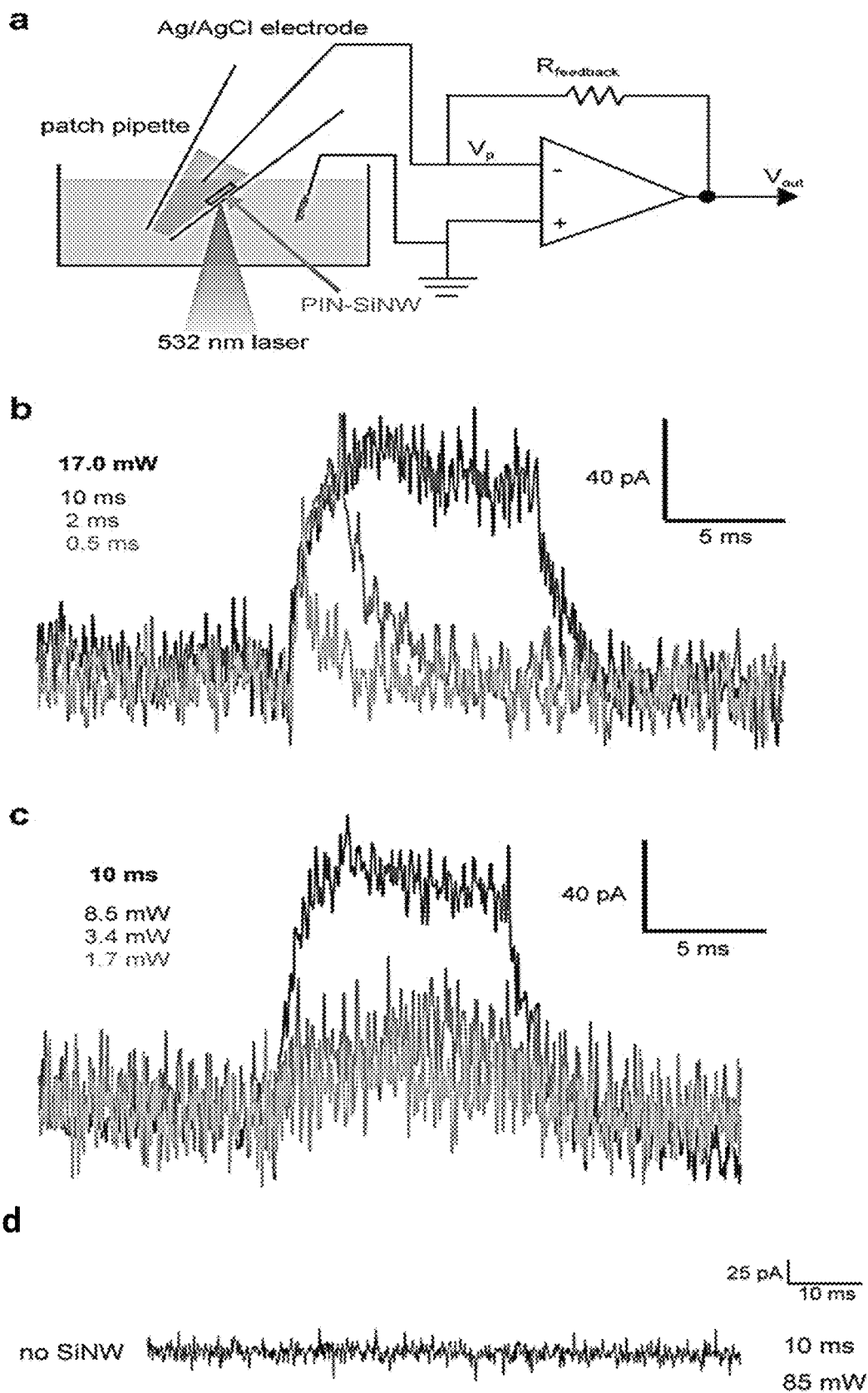
FIG. 5 provides single nanowire recordings showing photoelectrochemical current measured from coaxial Si nanowires. (A) shows a schematic of photocurrent measurement set-up. (B) illustrates a representative photocurrent trace from a single PIN-SiNW illuminated with a 532 nm laser at 17 mW for durations of 0.5 ms, 2 ms, or 10 ms. (C) illustrates a representative photocurrent trace from a single PIN-SiNW illuminated with a 532 nm laser at 8.5 mW, 3.4 mW, or 1.7 mW for a duration of 10 ms. (D) illustrates a representative photocurrent trace showing laser stimulation in the absence of a SiNW. When a photocurrent trace from pipette glass with no SiNW illuminated with a 532 nm laser at 85 mW for a duration of 10 ms, a measurable photocurrent may not be produced.

Estimation of the single nanowire photoelectrochemical behavior. Next a method to measure the photocurrents from single PIN-SiNWs in an interconnect free configuration was developed, using a patch clamp setup under physiological conditions (modified Tyrode's solution), in response to a 532 nm light illumination, which was chosen according to previously measured action spectra for PIN-SiNWs. PIN-SiNWs were grown with final diameters inside of quartz capillary tubes, pulled into patch pipettes, and mounted onto a patch clamp set-up. The laser was shone onto single NWs positioned so as to minimize any changes in pipette resistance due to increases in temperature produced by light absorption (FIG. 5A). All measurements were performed in voltage clamp mode, holding the voltage at zero in order to function as virtual ground. Keeping the power constant at 17 mW, the laser pulse duration was first altered (FIG. 5B). Measured pipette currents were characterized by a sharp and fast initial rise in current, likely limited by the system bandwidth, to peaks of 50.7 pA, 83.5 pA, and 101 pA for 0.5, 2, and 10 ms pulses, respectively (FIG. 5B). While the observed currents do not represent absolute values of photocurrents produced by single PIN-SiNWs, as some current will be inevitably shunted by the surrounding solution, much can still be garnered from the relative amplitudes and durations of the photocurrents measured. Notably, the current resulting from the 10 ms pulse was sustained at 101 pA for the whole illumination duration (FIG. 5B). This production of a sustained current is not characteristic of a capacitive current given that the NW-associated electrical capacitance is below the pF range, and instead is suggestive of a faradaic process. This observed faradaic process, characterized by electron transfer between the NW and the electrolyte, may be particularly favorable in the context of biological systems as it mimicks basic cellular processes that inherently utilize redox reactions. Additionally, light intensity-dependent current generation was observed in another PIN-SiNW (FIG. 5C). For a laser pulse duration of 10 ms, the photocurrent peaks were measured to be 120 pA, 43.1 pA, and 22.3 pA for laser powers of 8.5 mW, 3.4 mW, and 1.7 mW, respectively. The polarity of the current suggests a photocathodic reaction over the PIN-SiNW surface. When the laser spot was moved off the nanowire onto plain glass, no current was recorded (FIG. 5D). The observed unipolar photoelectrochemical current, for up to 10 ms (i.e., a time scale relevant to neural excitation), suggests that the solution reaction kinetics for light-generated hole carriers is much slower than that for electrons, partially due to the much smaller exposed surface area for p-type Si core. Without being bound by a particular theory, it is hypothesized that the surface atomic gold may also affect the observed non-equilibrium photoelectrochemical current production.

Figure 6:
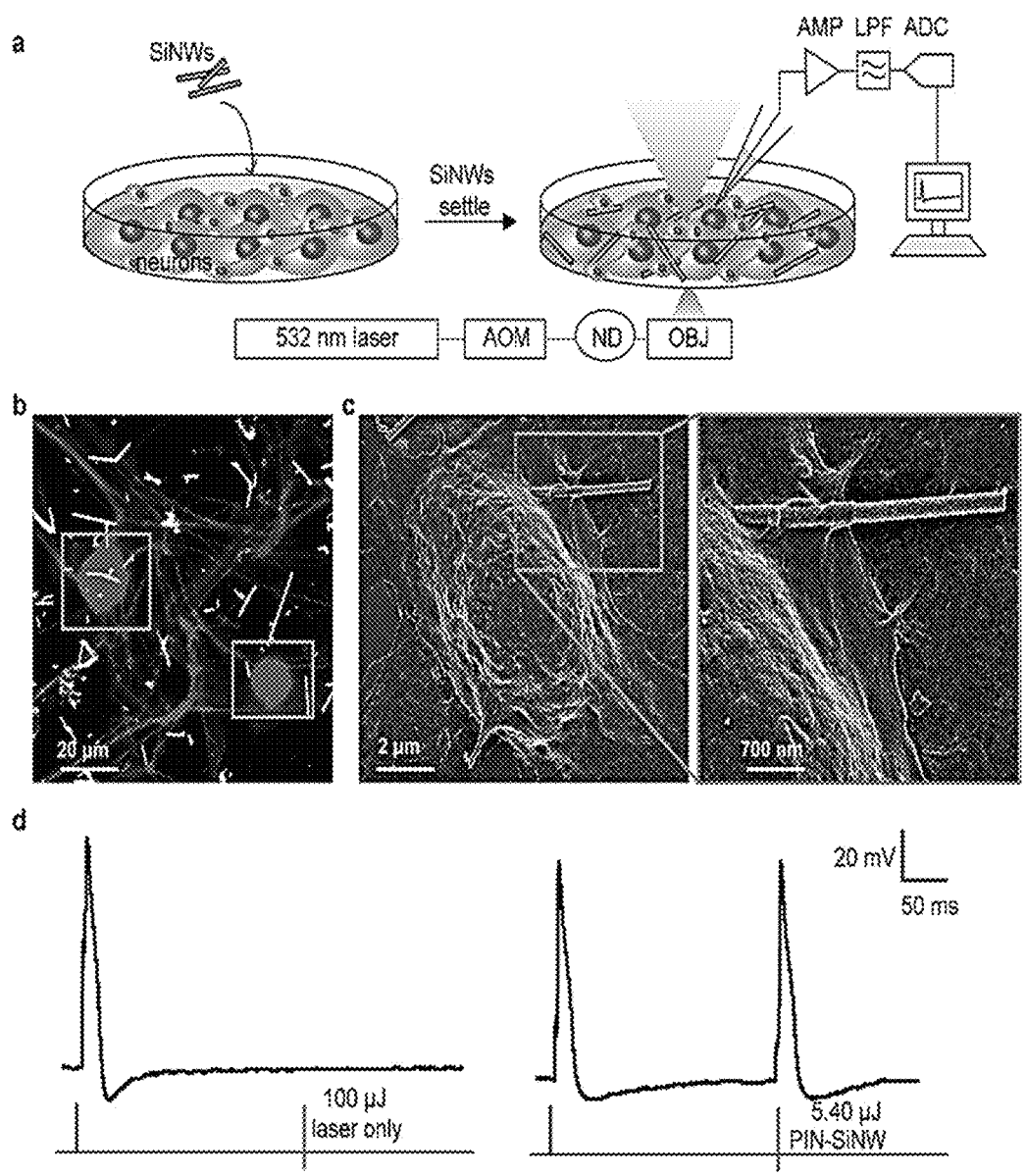
FIG. 6 illustrates basic silicon nanowire-based neural interfaces. (A) shows a schematic of a set-up used to record DRG neuron APs in response to a 532 nm laser stimulation at a single neuron/SiNW interface. This set-up includes an ordinary electrophysiology capability for patch clamp experiments, with an amplifier (AMP), used in current clamp mode, a low pass filter (LPF), and an analog to digital converter (ADC). In addition the setup was implemented with a 532 nm laser beam controlled by an acoustic modulator (AOM) and various neutral density (ND) filters (to attenuate the power). The laser beam is aligned to the optical central axis of the objective lens (OBJ) of an inverted microscope. SiNWs were sonicated off of their growth substrate and drop casted onto the primary neuron culture. After 20 min of settling, the experiments were performed. (B) provides a confocal microscopy image of primary neonatal rat dorsal root ganglion (DRG) neurons stained with anti-β-tubulin III co-cultured with PIN-SiNWs (white). This is a representative image from one of a total of 10 images taken from 2 independent experiments. (C) provides scanning electron microscopy images of a single DRG neuron interacting with a single PIN-SiNW (left); zoomed in image displaying neuron-PIN-SiNW interface (right). This is a representative image from one of a total of 63 images taken from 4 independent experiments. (D) illustrates a patch clamp electrophysiology current clamp trace of membrane voltage in DRG neuron stimulated or a laser pulse of various energies as labeled at the neuron/SiNW interface. Two conditions are displayed: laser only with no SiNW (left) and PIN-SiNW (right). These are representative traces from one of 173 total action potential traces measured from 30 neurons with PIN-SiNWs, and one of 27 total traces from 2 neurons with PIN-SiNWs.
Figure 7:
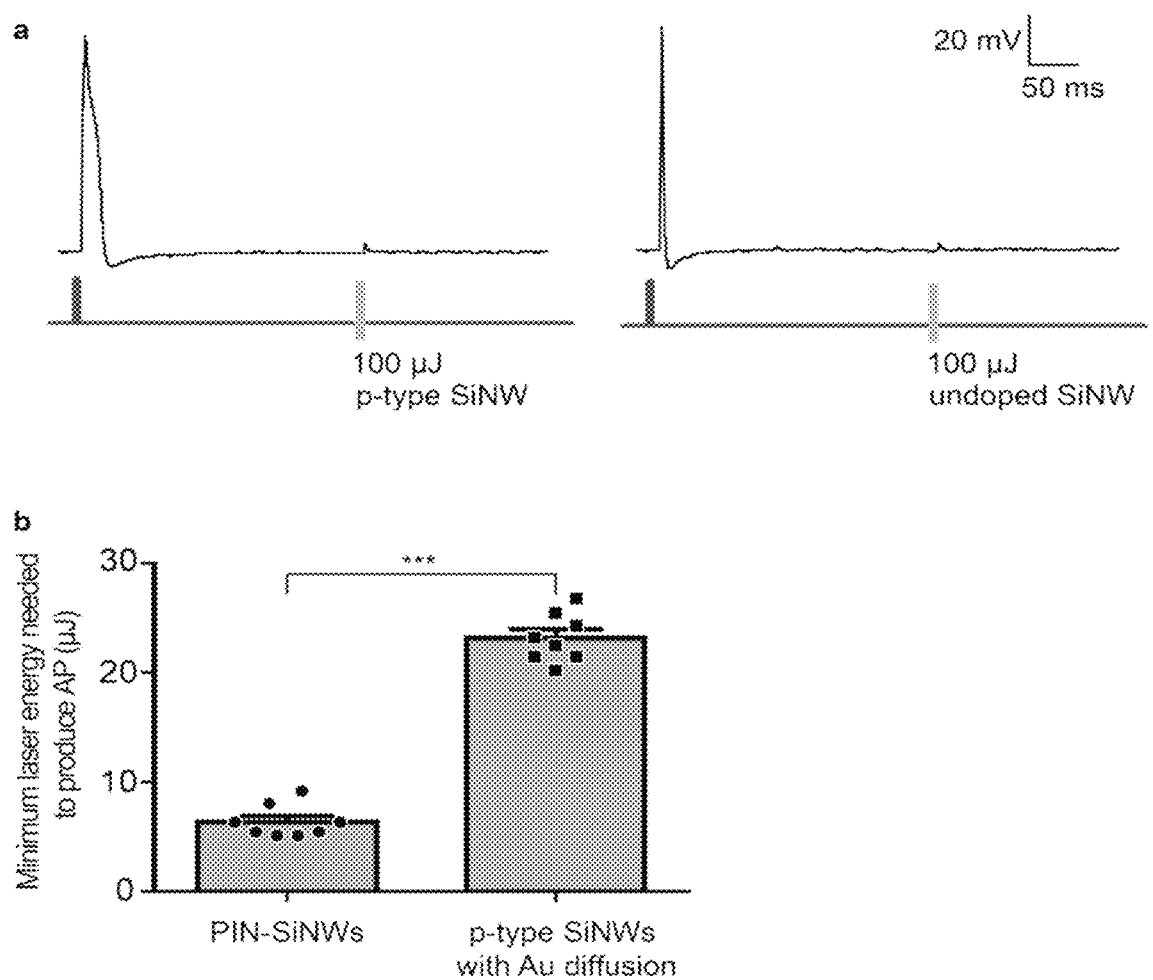
FIG. 7 provides a comparison of optical modulation of neuronal cell excitability with PIN-SiNWs, undoped SiNWs, p-type SiNWs, and p-type SiNWs with Au diffusion. (A) illustrates a patch clamp electrophysiology current clamp trace of membrane voltage in DRG neuron stimulated or a laser pulse of various energies as labeled at the neuron-SiNW interface. These are representative traces from one of 151 traces from 3 independent neurons for the p-type SiNW and of 691 traces from 4 independent neurons for the undoped SiNW. (B) shows an average minimum laser energy for PIN-SiNWs and p-type SiNWs with Au diffusion to generate APs in DRG neurons (N=6 biological replicates for each condition with a total of 8 technical replicates for each). Individual data points are indicated by the black circles (PINSiNWs) or black squares (p-type SiNWs with Au diffusion). Paired 2-tailed t-test performed to determine statistical significance. Error bars represent the standard error about the mean. p value: ***, 5.72E-11.
Figure 8:
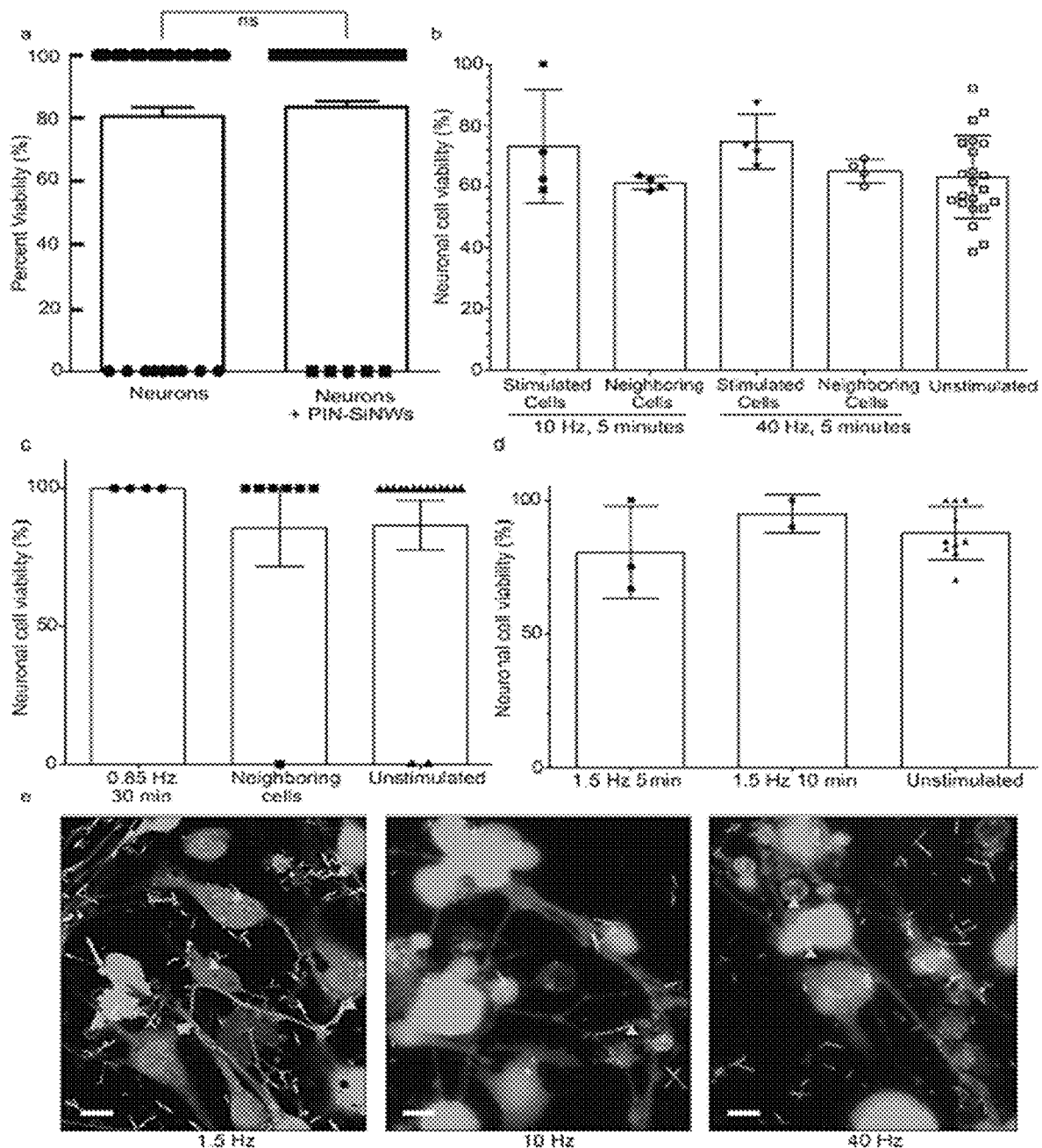
FIG. 8 shows images and graphical representations of neuronal cell viability, as measured by treating each cell assayed as a data point with the option of either being live (100% viability) or dead (0% viability), as indicated by staining in the live/dead assay. (A) shows a percentage of viable neurons 24 hours after initial culture with and without PIN-SiNWs (N=42 neurons for each condition). Each circle (neurons) and square (neurons+PIN-SiNWs) represents one data point. Paired 2-tailed t-test was performed to determine statistical significance. ns=not significant. (B) Neuronal cell viability was measured by calculating the percentage of viable neurons in each of several experiments performed. Each data point depicted represents the percentage of neuronal viability from each experiment performed. Percentage of viable neurons after 40 Hz (N=41 stimulated neurons and N=75 neighboring neurons from 4 experiments performed (black triangles and open circles, respectively)) and 10 Hz (N=43 stimulated neurons and N=77 neighboring neurons from four experiments performed (black squares and black circles, respectively)) 592 nm laser illumination at PIN-SiNW-neuron interfaces for 5 min durations. Viability of stimulated neurons, neighboring neurons, and completely unstimulated neurons (N=498 unstimulated neurons from 23 experiments performed (open squares)) were assessed. Paired 2-tailed t-test was performed to determine statistical significance in comparisons between all pairs of samples here. None were significant. (C) Neuronal cell viability was measured by treating each cell assayed as a data point with the option of either being live (100% viability) or dead (0% viability), as indicated by staining in the live/dead assay. Percentage of viable neurons after 0.85 Hz (N=4 stimulated neurons, 7 neighboring neurons, and N=16 unstimulated neurons) 592 nm laser illumination at PIN-SiNW neuron interfaces for 30 min durations. Individual data points for the 0.85 Hz stimulated neurons (black circles), neighboring neurons (black squares), and unstimulated neurons (black triangles) are indicated. Viability of stimulated neurons, neighboring neurons, and completely unstimulated neurons were assessed. Paired 2-tailed t-test was performed to determine statistical significance in comparisons between all pairs of samples here. None were significant. (D) Neuronal cell viability was measured by calculating the percentage of viable neurons in each of several experiments performed. Each data point depicted represents the percentage of neuronal viability from each experiment performed. Percentage of viable neurons after 1.5 Hz 592 nm laser illumination at PIN-SiNW-neuron interfaces for 5 (N=16 stimulated neurons from 3 experiments performed (black squares)), and 10 min (N=15 stimulated neurons from 2 experiments performed (black circles)) durations. Viability of stimulated neurons, and completely unstimulated neurons (N=28 unstimulated neurons from 10 experiments performed (black triangles)) were assessed. All error bars in this figure represent the standard error about the average. Paired 2-tailed t-test was performed to determine statistical significance in comparisons between all pairs of samples here. None were significant. (E) provides live/dead images taken on the SP5 Leica confocal microscope after 592 nm laser stimulation for 5 min at 1.5 Hz, 10 Hz, and 40 Hz (left to right). Live cells; Dead cells; PIN-SiNWs; laser stimulated neuron-PIN-SiNW interfaces. Scale bars, 10 μm. These are representative images from the live/dead experiments performed in (B) and (D).

Example 2: Photoelectrochemical Modulation of Neuronal Activity with Free-Standing Coaxial Silicon Nanowires Basic coaxial nanowire/neuron interfaces. PIN-SiNWs were drop-casted onto primary dorsal root ganglion (DRG) neurons cultured from neonatal rats (FIG. 6A-B). Scanning electron microscopy (SEM) shows that PIN-SiNWs form close interactions with neuronal membranes without being internalized into cells (FIG. 6C). Without being bound by a particular theory, it is hypothesized that the photocathodic electrochemical effect produced from a single nanowire could cause membrane depolarization (by reducing the potential in a local extracellular region) and trigger action potentials (APs). A neuron/PIN-SiNW interface was aligned to a 532 nm laser spot, and used a whole cell current clamp set-up to record the neuronal membrane voltage before, during and after laser stimulation (FIG. 6A). It was found that laser stimulation at the neuron/PIN-SiNW interface can elicit APs in neurons at an average minimum laser energy of 6.44 µJ for laser pulse durations ranging from 0.5 ms to 5 ms (FIG. 6D and FIG. 7). This laser energy is similar to or less than that required for other photothermally stimulating materials to elicit APs in neurons, even though the direct cell contact area is at least 10 times smaller in the present case. Additionally, the same minimal energy necessary to trigger APs at several stimulating pulse durations suggests that the PIN-SiNW mimicks a classic external stimulation electrode without the mechanical invasiveness and bulkiness inherent to physical electrodes. Control experiments using pure p-type and undoped SiNWs were unable to elicit APs, and only produced sub-threshold depolarizations upon laser stimulation, even at high energies of 100 µJ and 1 ms durations (FIG. 7). In the absence of a NW, laser stimulation with an energy of up to 100 µJ at 1 ms laser pulse durations cannot depolarize the cell's membrane (FIG. 6D). The presence of PIN-SiNWs in the neuron culture had a negligible effect on cell viability and that laser stimulation on the time scales explored here also had a negligible effect on cell viability (FIG. 8).

Figure 9:
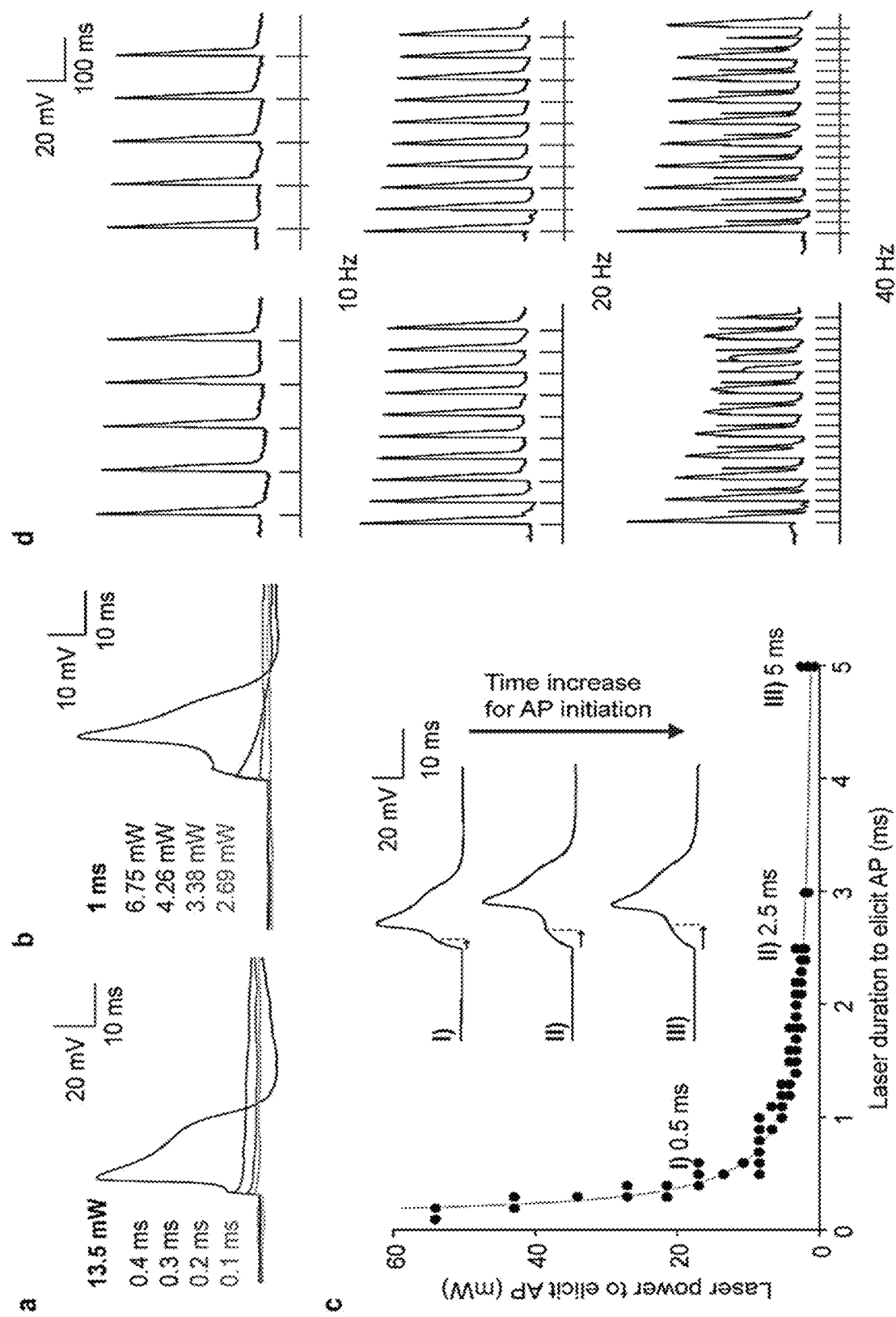
FIG. 9 illustrates action potentials in primary rat dorsal root ganglion neurons elicited by photocurrent generated by coaxial nanowires. (A) and (B) patch clamp electrophysiology current clamp traces of membrane voltage in DRG neurons illuminated by a 532 nm laser pulse at the neuron/PIN-SiNW interface at (A) 13.5 mW with durations of 0.1 ms, 0.2 ms, 0.3 ms, and 0.4 ms and (B) 2.69 mW, 3.38 mW, 4.26 mW, and 6.75 mW for 1 ms. These traces are representative traces from one of a total of 1398 traces from 30 independent neurons, many of which are sub-threshold depolarizations at various laser powers and durations. 173 traces out of the 1398 represent action potentials. (C) illustrates an excitability curve displaying 532 nm laser power and duration combinations that produce APs in neurons (N=6 neurons; total of N=78 replicates) interacting with a single PIN-SiNWs with specific traces and time to peak response for each of those traces at I) 0.5 ms, II) 2.5 ms, and III) 5 ms durations highlighted. Error bars represent the standard error about the average. Some of the data points are overlaid. (D) shows AP traces from neurons interacting with single PIN-SiNWs pulsed at 10, 20 and 40 Hz with light and injected current from patch amplifier. These are representative traces from a total of 6 pulse train traces for each frequency taken from 3 independent neurons.
Figure 10:
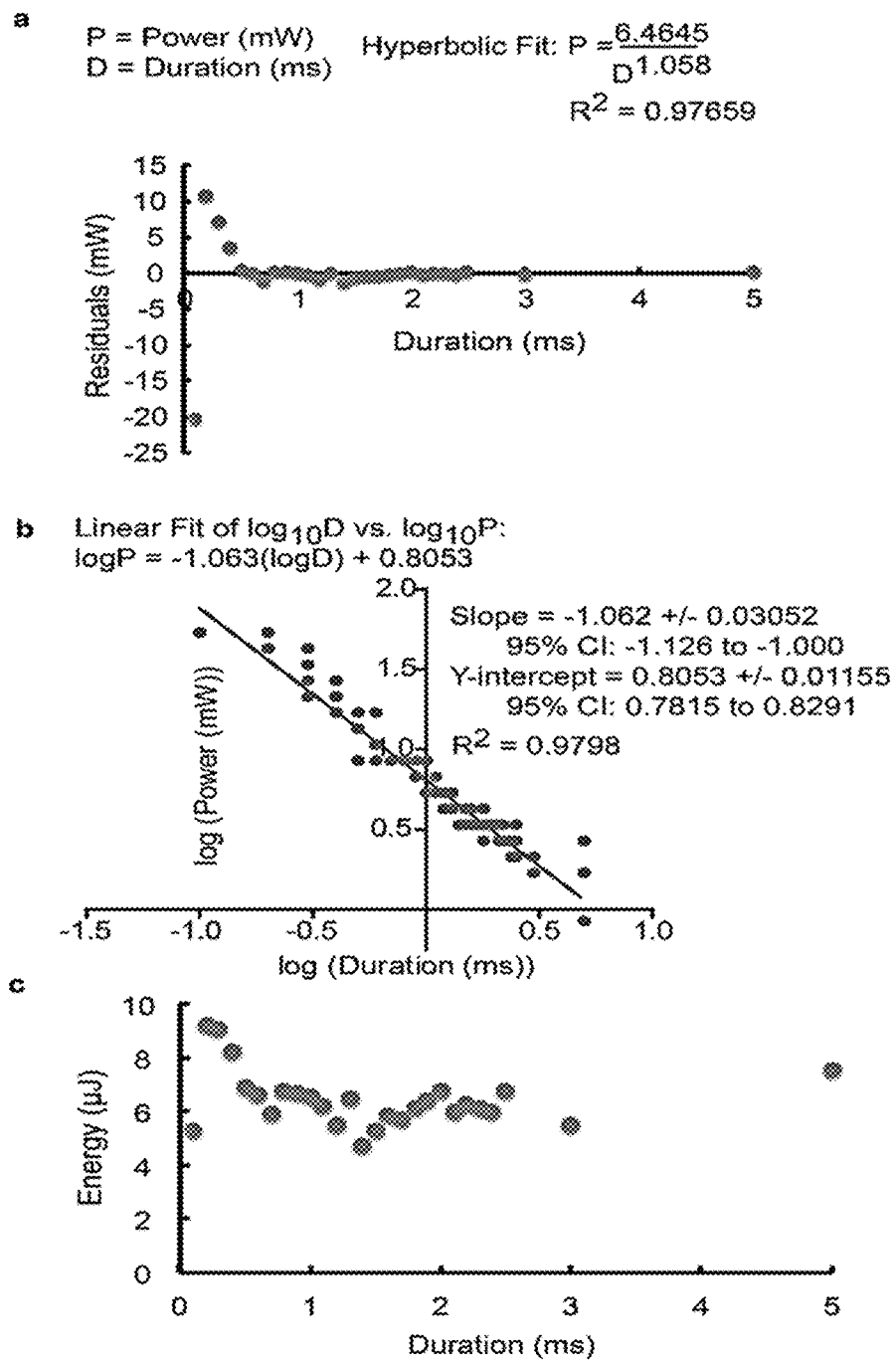
FIG. 10 provides plots demonstrating a hyperbolic excitability curve, with a minimal total energy to trigger APs that is independent of pulse duration. (A) shows a residual plot illustrating the goodness of fit of the hyperbolic fit curve (equation displayed above) to the data (N=27 average laser powers for each laser duration used from 6 independent neurons and a total of 78 replicates). (B) illustrates a Logarithmic excitability curve. Log D vs Log P plot with linear fit (N=6 neurons; total of N=78 replicates). Some of the data points are overlaid. (C) illustrates a minimum laser pulse energy necessary to trigger an AP using a PIN-SiNW plotted as a function of laser pulse duration (N=27 average laser powers for each laser duration used from 6 independent neurons and a total of 78 replicates).

Systematic neuromodulation studies. Next, the laser power and pulse duration was altered. At a laser power of 13.5 mW, sub-threshold depolarizations were observed at increasing durations of 0.1, 0.2, and 0.3 ms, respectively (FIG. 9A). At a laser duration of 0.4 ms and energy of 5.4 J, an AP was generated (FIG. 9A). Keeping the stimulus duration constant at 1 ms, the membrane was passively depolarized at increasing laser powers until reaching 6.75 mW and a total energy of 5.95 µJ, at which an AP was generated in the cell (FIG. 9B). An excitability curve that generated that indicated that as the duration of the laser stimulus increased, the amount of laser power required to generate an AP decreased (FIG. 9C). The data was fit to a hyperbolic function and found that the minimum total energy required to trigger an AP is independent of the pulse duration, as would be expected for current injecting electrodes (FIG. 10). This phenomenon can both be seen by directly plotting minimum total energy as a function of the laser pulse duration, as well as by the exponent in the denominator of the hyperbolic function, which is close to 1 (FIG. 10). The rheobase of the fitted curve is 1.178 mW and chronaxie 2.597 ms, which compares well to literature chronaxie values for DRG neurons (FIG. 9C). With increasing laser pulse durations, the time to AP initiation was increased (FIG. 9C). These results together demonstrate that PIN-SiNWs can elicit APs in a manner that is physiologically indistinguishable from those induced by classical external current injecting electrodes.

Figure 11:
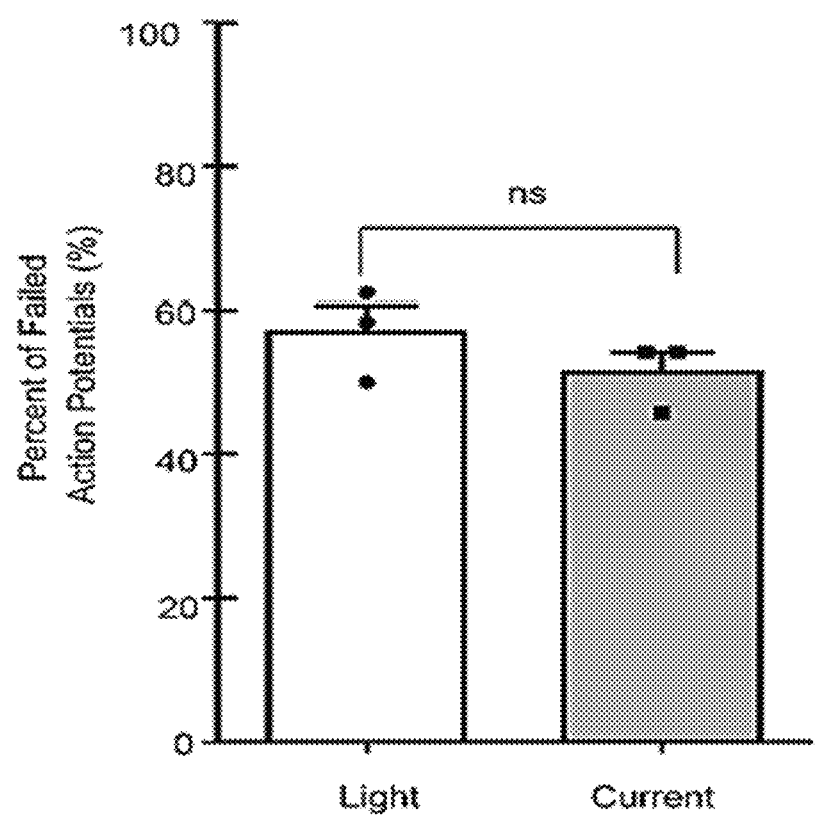
FIG. 11 provides a graph comparing the percentage of failed APs at the lowest frequency that the neuron begins to fail to generate 1 AP per pulse of current or light from 3 independent neurons. APs from pulse train stimulations fail at the same rate upon light stimulation of the PIN-SiNW interface and injected current. Individual data points are indicated with black circles (Light) and squares (Current). A paired two-tailed t-test was used to determine statistical significance. ns=not significant. Error bars represent the standard error about the mean.

The laser was also pulsed at varying frequencies at the neuron/PIN-SiNW interface and assessed for the cellular response. Neurons are able to generate trains of APs at 10 and 20 Hz both with injected current and laser stimulation (FIG. 9D). At 40 Hz, the cell depicted failed to produce APs in response to every pulse of laser light or injected current (FIG. 9D). This neuron produced 10 APs in the case of the light stimulation and 9 in the case of the injected current out of 20 pulses at 40 Hz (FIG. 9D). At the lowest frequency that neurons begin to fail to generate one AP for every pulse of current or light, the percentage of failed APs tended to be the same when comparing the two stimuli (FIG. 11). These results indicate that APs produced in neurons through PIN-SiNW-enabled optical stimulation are physiologically representative and follow the intrinsic limitation of the cell to fire trains of APs above a specific frequency.

Figure 12:
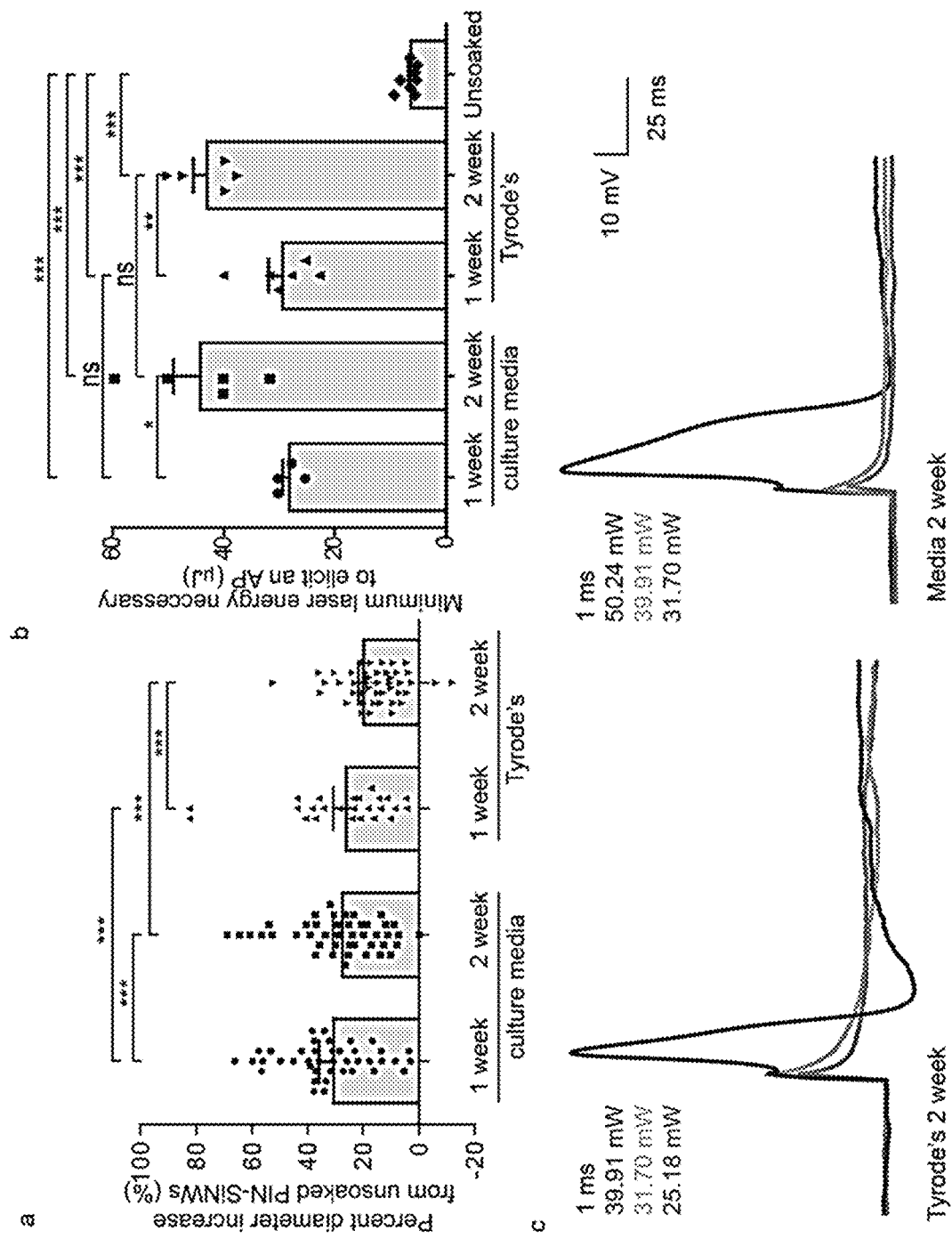
FIG. 12 illustrates the efficiency of PIN-SiNWs soaked in Tyrode's buffer or culture media for 1-2 weeks in triggering APs in neurons. (A) shows a graph comparing the percent increase in diameter of PIN-SiNWs under the various soaking conditions. NWs were observed via SEM and it was found that PIN-SiNWs soaked in media for 1 and 2 weeks experienced a 32.36%+/−3.85% and 28.37%+/−3.58% increase in diameter, respectively, as compared to an average diameter from 109 unsoaked NWs (N=41, 1 week (circles); N=44, 2 week (squares)). Those NWs soaked in Tyrode's buffer for 1 and 2 weeks experienced a 28.02%+/−4.44% and 15.76%+/−1.51% increase in diameter, respectively, as compared to unsoaked NWs (N=25, 1 week (triangles); N=45, 2 week (inverted triangles)). It is possible that this increase in diameter in the first week is a result of oxidization/hydration-induced swelling and formation of a protein corona around NWs in media. The 2-week time point for both conditions showed a decrease in diameter from that of the 1-week, indicating a subsequent degradation process. Paired two-tailed t-tests were used to determine statistical significance between the distributions of raw nanowire diameters represented by each data point for various conditions. All error bars in this figure represent the standard error about the mean. P values: 3.734E-6 (1 week media vs. 2 week media); 6.737E-27 (1 week Tyrode's vs. 2 week Tyrode's); 8.451E-5 (1 week Tyrode's vs. 1 week media); 6.218E-38 (2 week media vs. 2 week Tyrode's). (B) shows a graph comparing the minimum laser energy threshold necessary for PIN-SiNWs under various conditions to elicit APs in neurons. Individual data points are indicated with black circles (N=4, 1 week media), squares (N=5, 2 week media), triangles (N=6, 1 week Tyrode's), inverted triangles (N=5, 2 week Tyrode's), and diamonds (N=8, unsoaked). Paired two-tailed t-tests were used to determine statistical significance. ns=not significant. All error bars in this figure represent the standard error about the mean. P values: 0.0248 (1 week media vs. 2 week media); 0.7098 (1 week media vs. 1 week Tyrode's); 2.488E-9 (1 week media vs. unsoaked); 0.8314 (2 week media vs. 2 week Tyrode's); 7.460E-7 (2 week media vs. unsoaked); 0.0040 (1 week Tyrode's vs. 2 week Tyrode's); 2.044E-7 (1 week Tyrode's vs. unsoaked); 1.407E-9 (2 week Tyrode's vs. unsoaked). (C) illustrates patch clamp electrophysiology current clamp traces of membrane voltage in DRG neurons illuminated by a 532 nm laser pulse (1 ms duration) at the neuron-PIN-SiNW interface. The NWs were soaked in Tyrode's and media for 2 weeks. These are representative traces of 5 total action potential traces from 3 independent neurons for both 2 week Tyrode's and 2 week media. Including subthreshold depolarizations, a total of 75 traces were collected for the 2 week Tyrode's condition and 83 traces were collected for the 2 week media condition.

To understand how effectively the PIN-SiNWs would be able to perform neuromodulation when not used fresh, PIN-SiNWs were incubated in culture media or Tyrode's buffer for 1- and 2-week time points and used them to trigger APs in primary rat DRG neurons. The minimum laser energy threshold necessary to elicit APs increased from the previously observed 6.44 µJ to an average of 28.33 µJ and 29.58 µJ for the 1-week time point in media and Tyrode's respectively, and 44.30 J and 43.10 µJ for the 2-week time point in media and Tyrode's respectively (FIG. 12). The increased laser energy threshold may be caused by oxidation/hydration induced degradation of both the Si heterojunction and atomic Au activity.

Figure 13:
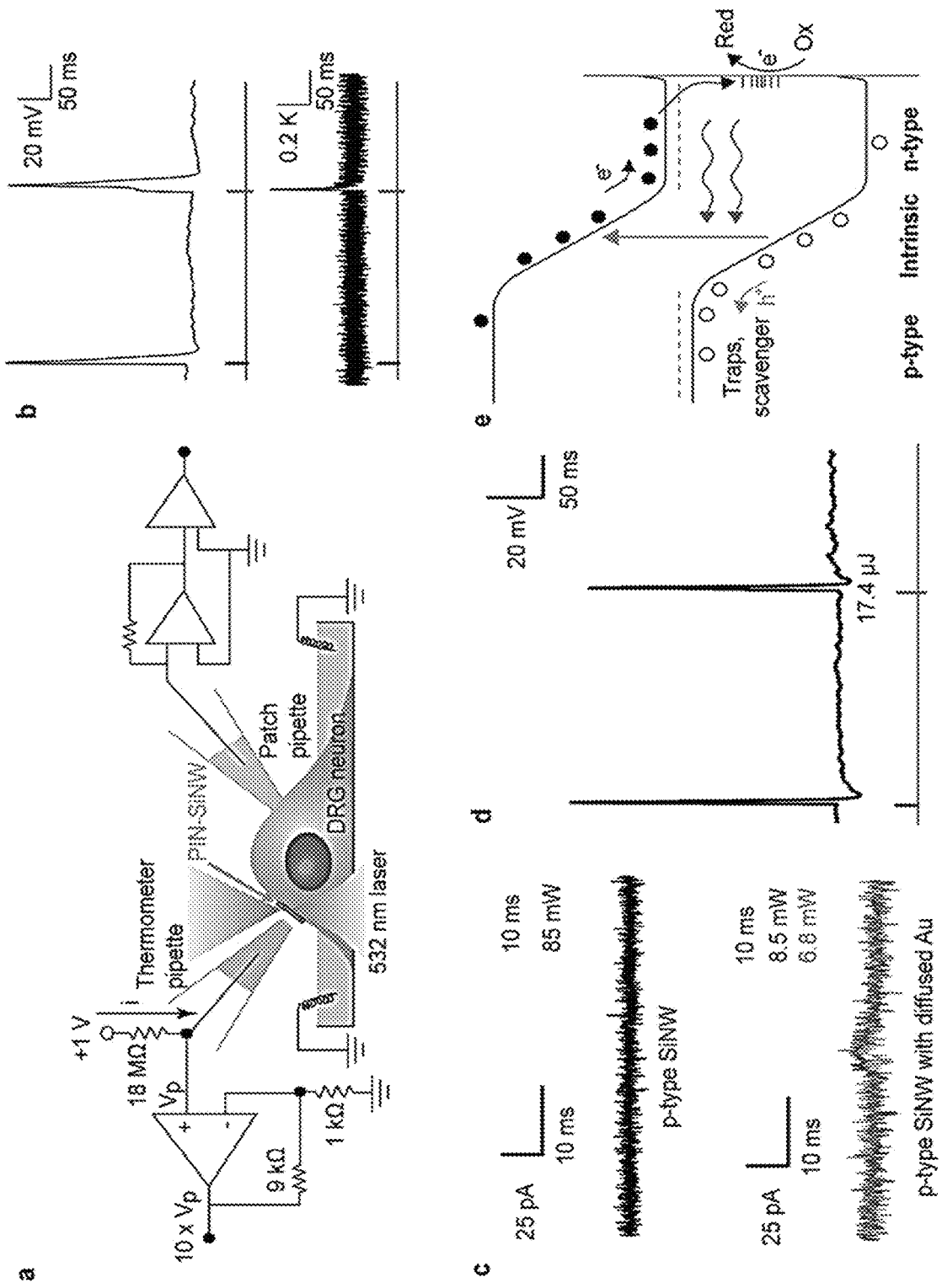
FIG. 13 illustrates that a mechanism of coaxial nanowire photocurrent generation and neuronal modulation is primarily photoelectrochemical, aided by surface atomic Au. (A) shows a schematic of temperature measurement setup for simultaneous measurement of temperature and neuronal APs produced by laser stimulation or injected current through patch amplifier. (B) illustrates a patch clamp electrophysiology current clamp trace of membrane voltage (top) in DRG neuron stimulated by injected current and illuminated by a 532 nm laser pulse at the neuron-PIN-SiNW interface. Corresponding temperature measurement (bottom) taken 2 µm away from neuron/PIN-SiNW interface produced by calibrating the thermometer pipette resistance with temperature changes. This is a representative temperature measurement from one of 18 total traces from 3 independent neurons. (C) provides a photocurrent measurement taken from a single p-type SiNW illuminated with 532 nm laser light for 10 ms at a laser illumination power of 85 mW (top). This is a representative trace from one of a total of 71 traces measured from 4 independent p-type SiNWs. Photocurrent measurement taken from a p-type SiNW with diffused Au for 10 ms at laser illumination powers of 8.5 mW and 6.8 mW. These are representative traces from a total of 52 traces measured from 6 independent p-type SiNWs with diffused Au. (D) illustrates a patch clamp electrophysiology current clamp trace of membrane voltage (top) in DRG neuron stimulated by injected current and illuminated by a 1 ms 17.4 µJ 532 nm laser pulse at the neuron-p-type SiNW with diffused Au interface. This is a representative trace from one of a total of 40 traces measured from 5 independent neurons. (E) provides a band diagram representing the redox reaction that occurs at the interface between the PIN-SiNW and the electrolyte solution. Kinetic barrier for photoelectrochemical reaction is lowered by the presence of atomic Au.
Figure 14:
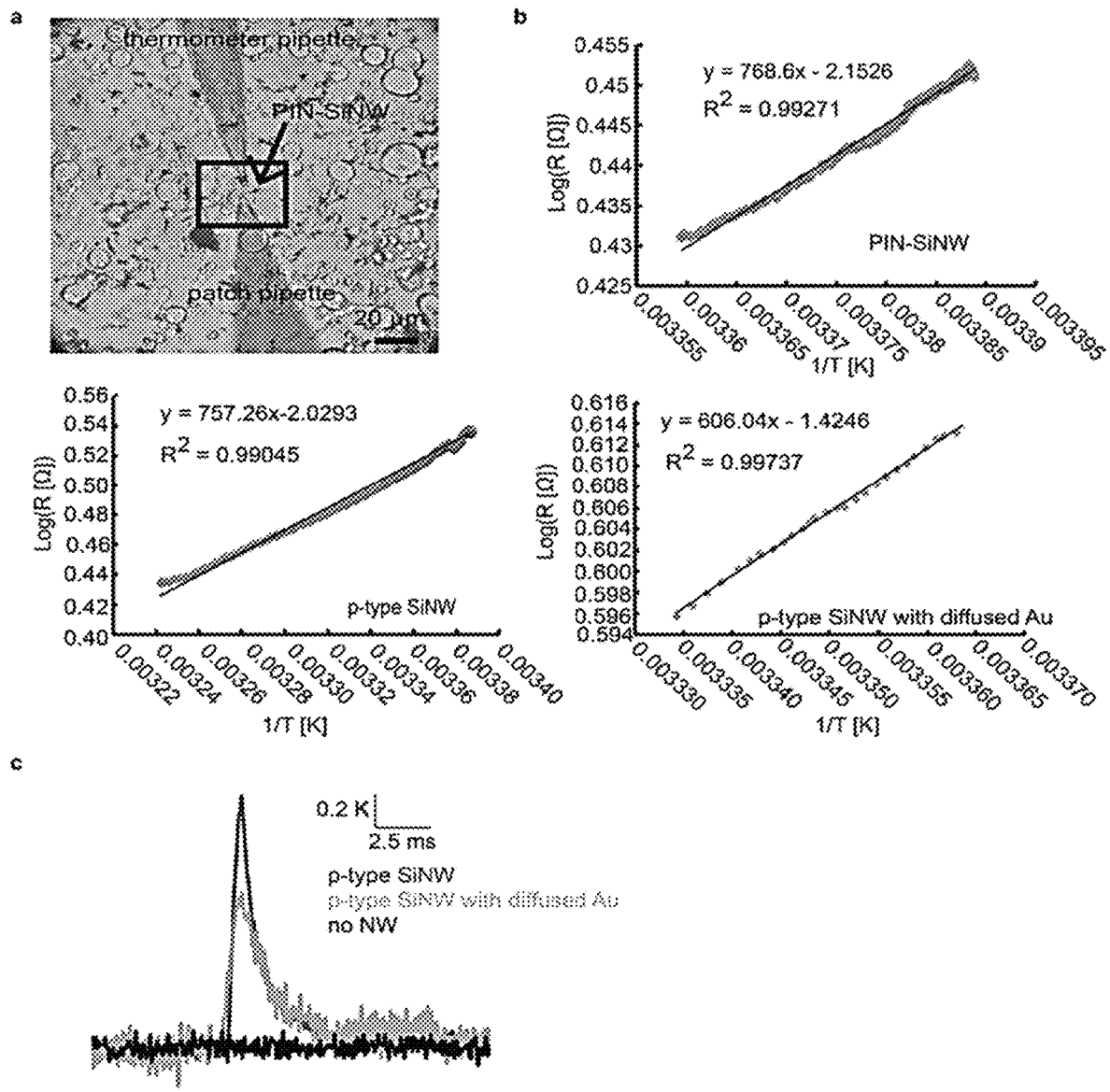
FIG. 14 illustrates that a photothermal effect can be pronounced at higher illumination energy. (A) shows a brightfield image of a neuron during a simultaneous membrane voltage and temperature recording experiment. Thermometer pipette is positioned within ~2 µm of the neuron/PIN-SiNW interface. Neuron is current clamped by a patch pipette from the other side. (B) shows three Calibration curves determined using a linear fit of measured pipette resistances and corresponding bath temperatures demonstrating the relationship between the thermometer pipette resistance and temperature. These curves are used to calculate the temperature change produced as a result of laser stimulation at the neuron-SiNW interface from a measured change in resistance of the thermometer pipette. These are representative calibration curves from one of 3 independent neurons for the PIN-SiNWs, 2 independent neurons for the p-type SiNW with diffused Au, and 2 independent neurons for the p-type SiNW. (C) illustrates a comparison of temperature change produced by a p-type SiNW, a p-type SiNW with diffused Au, and no SiNW upon a 1 ms laser stimulation. The laser energy used for these three measurements were 100 µJ (p-type SiNW), 16.96 µJ (p-type SiNW with diffused Au), and 100 µJ (no NW). When a laser stimulus energy of 100 µJ (i.e., >18 times of the power threshold for PIN-SiNW based stimulation) was applied at the neuron-p-type SiNW interface, only a sub-threshold depolarization was produced and a temperature increase of 1.27 K was measured. At a laser stimulus energy of 16.96 µJ and duration of 1 ms at the Audiffused and neuron-p-type SiNW interface, an AP was produced in the neuron and a temperature increase of 0.72 K was measured. No AP was generated without a NW present. These are representative temperature traces of 27 traces from 2 independent neurons for the ptype SiNW condition, 22 traces from 2 independent neurons for the p-type SiNW with diffused Au condition, and 4 traces from 2 independent neurons for the light only condition.

Probing of the neuromodulation mechanism. Having demonstrated the optical modulation of single primary neuron excitability with PIN-SiNWs, the mechanism of this stimulation was further studied. Previous work has demonstrated that mesoporous silicon materials can elicit APs in neurons via a photothermal effect, the contribution of photothermal current generation to PIN-SiNW-enabled neuromodulation was examined. A calibrated micropipette resistance method was used to measure the temperature change~2 µm away from the neuron-PIN-SiNW interface during laser induced AP generation in the neuron (FIG. 13A, FIG. 14). Laser induced AP generation at a 5.36 µJ laser energy (minimum energy necessary to produce an AP with PIN-SiNWs) resulted in a 0.36 K increase in temperature at the neuron-PIN-SiNW interface (FIG. 13B). In comparison to other photothermally-stimulating materials that produce 2 K temperature increases at similar pipette distances, this temperature increase is minor, suggesting a minor photothermal contribution to the stimulation mechanism described here. No temperature increase was observed in the absence of a SiNW (FIG. 14). Other control experiments further suggest that a photothermal effect is not the primary mechanism here (FIG. 14).

Figure 15:
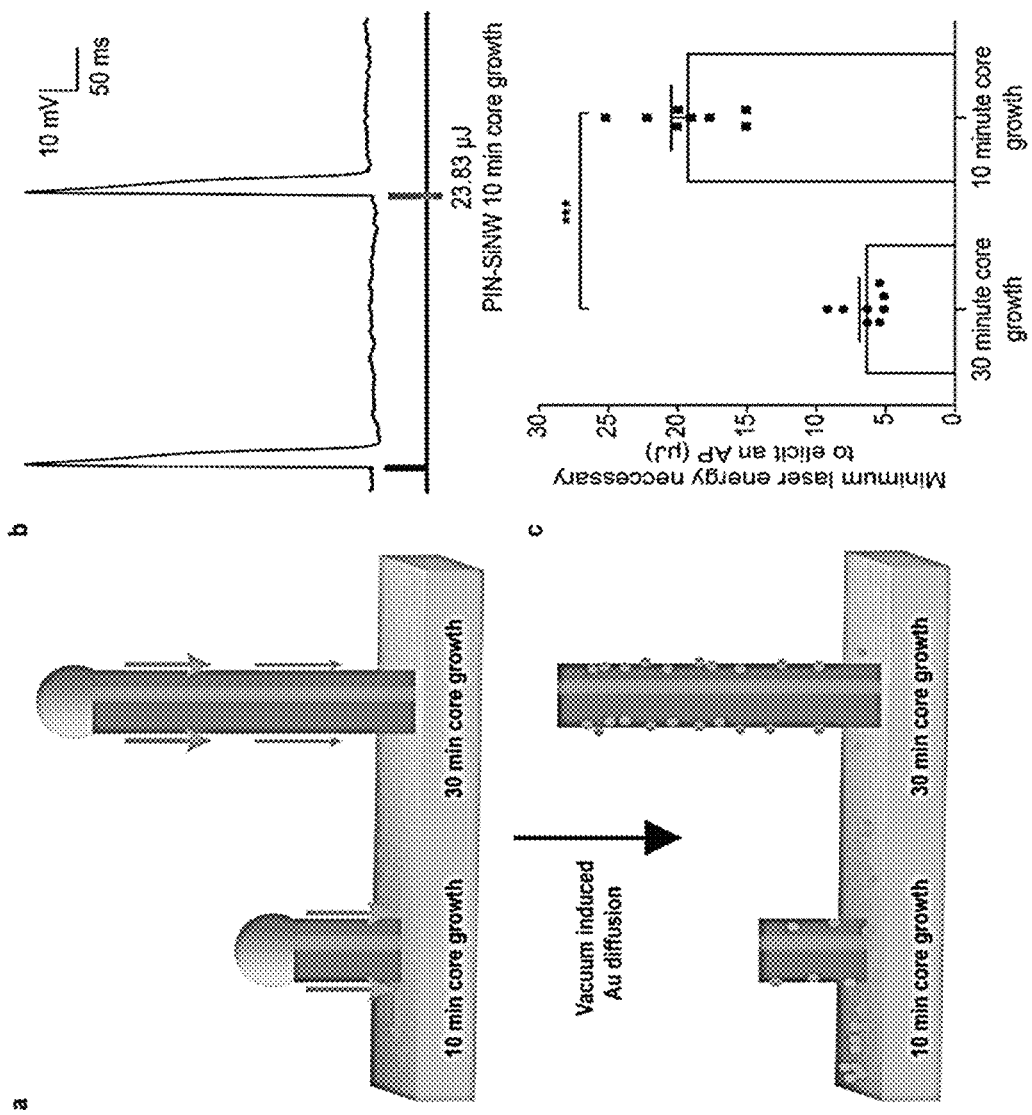
FIG. 15 illustrates that decreasing core growth time decreases the efficiency of neuromodulation. (A) shows a schematic of Au diffusion during 10 min and 30 min core growth. (Top) During vacuum annealing, Au from the catalyst diffuses down the sidewalls of the PIN-SiNW and the growth substrate (also Si); orange arrows represent Au diffusion. (Bottom) After Au diffusion for 30 min in vacuum, for the much shorter NW core (left), much of the Au would have diffused off of the NW onto the growth Si substrate. (B) illustrates a patch clamp electrophysiology current clamp trace of membrane voltage (top) in DRG neuron stimulated by injected current and illuminated by a 1 ms 28.83 µJ 532 nm laser pulse at the neuron-p-type SiNW with diffused Au interface. This is a representative trace from one of 8 action potential traces measured from 6 independent neurons. (C) illustrates a comparison of the minimum 532 nm laser energy necessary to elicit APs in several neurons interfaced with PINSiNWs grown with either a 30 min core (N=6 biological replicates and a total of N=8 technical replicates) or 10 min core (N=6 biological replicates and a total of N=8 technical replicates). Individual data points are indicated with black circles (30 minute growth) and squares (10 minutes growth). A paired two-tailed t-test was used to determine statistical significance. p value: ***, 1.29E-7. Error bars represent the standard error about the mean.

In further delving into the neuro-excitation mechanism, the role of surface atomic gold in the observed photoelectrochemical current generation and neuromodulation was evaluated. Since Au diffusion inherently occurs during PIN-SiNW shell deposition, PIN-SiNWs without diffused Au were unable to be grown. Thus, the atomic Au distribution at the PIN-SiNW surfaces was first reduced by promoting Au diffusion into the Si growth substrate (FIG. 15). It was found that the average minimum laser energy necessary to elicit APs became 19.26 µJ, ~3 times that needed for typical PIN-SiNWs used in this work.

In a second approach, the photoelectrochemical behaviors of pure 200-250 nm p-type SiNWs, and 200-250 nm p-type SiNWs was compared with intentional Au diffusion (FIGS. 13C-D, see Materials and Methods). P-type Si was chosen, instead of n-type Si to serve as controls, as p-type semiconductors in contact with electrolyte solutions experience band bending in such a manner that drives photogenerated electrons towards the semiconductor-electrolyte interface. Thus, light illumination would allow for electron injection from the nanowire into the solution, yielding similar cathodic reaction as what occurs in the case of PIN-SiNWs. Indeed, both p-type and p-type/n-type (n– is the exposed end) diode Si devices have been used for photocathodes in electrochemical cells.

Photocurrents generated by these different nanowires were measured as it was done with the PIN-SiNWs. Currents could not be detected when the laser spot was shone onto a single p-type SiNW (FIG. 13C). However, currents from p-type nanowires with Au catalyst diffused at 750° C. for 30 min after growth were recorded at a laser duration of 10 ms (FIG. 13C). These current peaks were measured to be 28.8 pA and 15.0 pA for laser powers of 8.5 mW and 6.8 mW, respectively (FIG. 13C). Subsequent neuron excitation experiments showed that Au-diffused p-type SiNWs and not p-type SiNWs were able to elicit APs with a minimum laser pulse energy of 17.4 µJ at a 1 ms pulse duration (FIG. 13D). The fact that diffused Au along p-type SiNW enhances photoelectrochemical current generation suggests its catalytic role in the interfacial chemical reaction. This is feasible given Au is more electronegative than Si; therefore, the photogenerated electrons can accumulate near the surface Au sites for cathodic reaction even under physiological condition. The exact chemical species that promote the cathodic reaction is unknown given the heterogenous nature of the culture medium used in the present study. Additionally, the atomic Au covered p-type SiNWs still yield lower amplitudes of currents and require a greater energy threshold to elicit APs in neurons upon light stimulation when compared with those recorded from PIN-SiNWs at similar laser powers and durations (FIGS. 5B-C, FIG. 7, FIG. 13B).

Taken together, these results indicate the combined importance of the diffused Au in promoting the interfacial reaction at the PIN-SiNW surface and charge separation at the diode junction, both enabling photoelectrochemical current generation. More specifically, upon light illumination, holes migrate to the p-type core and electrons to the n-type shell (FIG. 13E). The electrons in the n-type shell are injected through surface state (i.e., atomic Au and other surface defects)-enhanced processes into the electrolyte solution and are able to participate in cathodic reactions (e.g., reduction of protons) (FIG. 13E). The photogenerated holes, however, are swept into a spatially separated region, and consumed by recombination within Si or chemical scavengers at the exposed ends. The anodic reaction is expected to be slower given the exposed p-type surfaces (of the coaxial nanowire) have much smaller surface areas and contain no catalyst, yielding the unipolar photocurrent recording at a timescale relevant to neural excitation. In this way, the PIN-SiNW behaves similarly to a wireless, nanoscale photoelectrochemical cell, with atomic Au to promote the cathodic process, which locally modulates neuronal function (FIG. 13E).

Example 3: Modulating Cellular Activation

Figure 16:
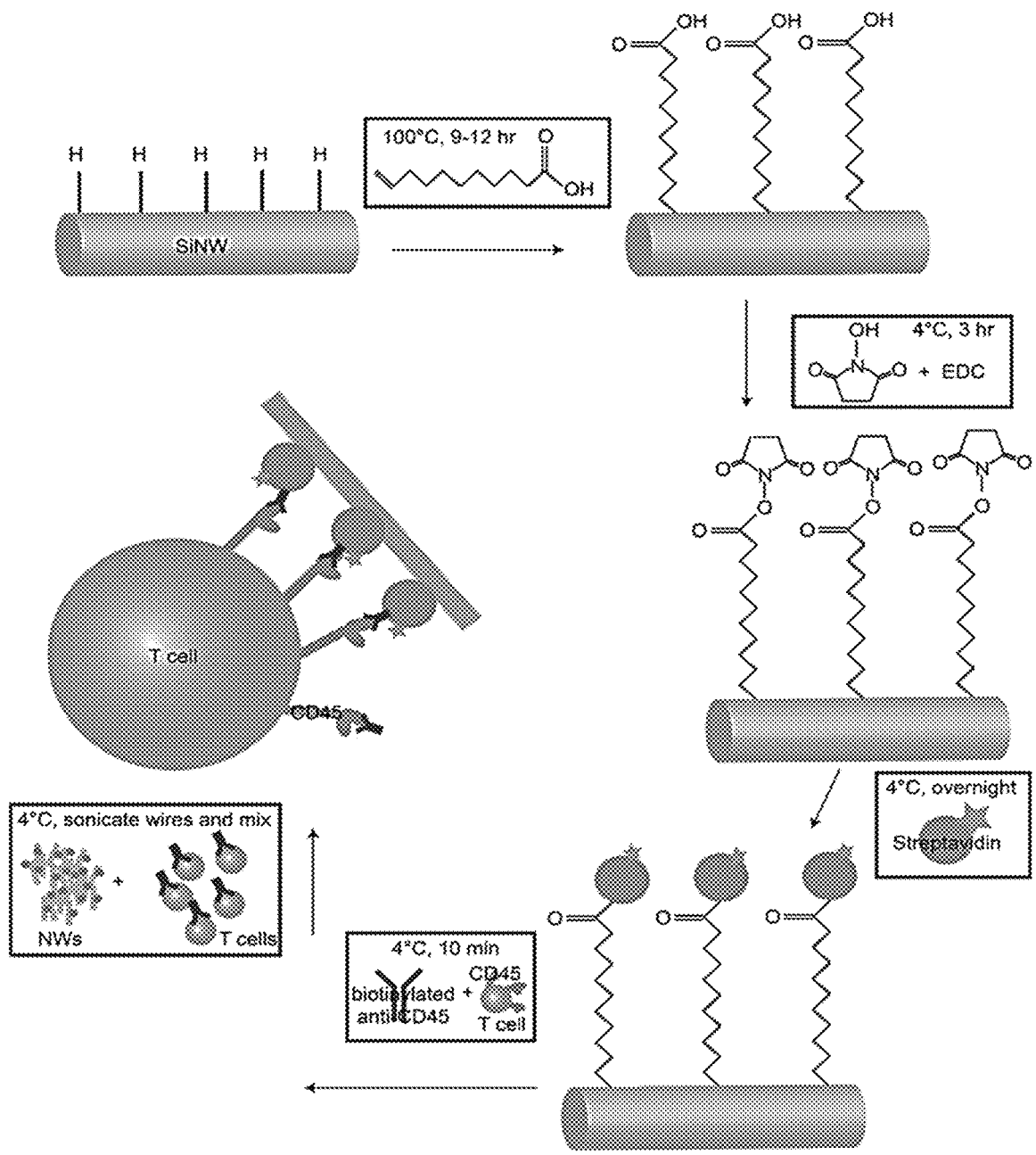
FIG. 16 provides a schematic illustrating the functionalization of a T cell with a PIN silicon nanowire.

First, the preparation of the PIN-SiNWs themselves follows that described in the Materials and Methods above. Next, in the surface functionalization scheme (FIG. 16), the native oxide layer was removed from the PIN-SiNWs on their Si wafer substrate by incubating a nanowire wafer piece in 10% HF for 90 seconds and then rinsing in DI water for 10 seconds. The hydrogen-terminated PIN-SiNWs were then hydrosilylated with undecylenic acid under high temperature conditions. Next, the nanowires were incubate with 1-ethyl-3-(3-dimethylaminopropyl) carbodiimide hydrochloride (EDC), which reacts with the carboxylic acid groups on the surface and forms an active and unstable O-acylisoururea intermediate that can form a dry-stable amine-reactive ester N-hydroxysuccinimide (NHS) intermediate with NHS, which is also included in the reaction. Lastly, the nanowires are reacted with allophycocyanin (APC)-labeled Streptavidin (StrA-APC), which has primary amino groups that can form amide bonds with the original carboxylic acid group from undecylenic acid and displace the NHS intermediate via nucleophilic attack. In order to interface these StrA-APC labeled PIN-SiNWs with T cells, the T cells were then treated with a biotinylated anti-CD45 antibody and mix the T cells with the nanowires. Prior to mixing, the T cells are washed, e.g., twice, to remove free biotinylated anti-CD45 antibodies from the mixture. The relative amount of the StrA-APC labeled PIN-SiNWs may be adjusted depending upon the desired number of StrA-APC labeled PIN-SiNWs per T cell. The advantages of this method are that the nanowires were available to be surface functionalized without the need for an oxide layer on the nanowire (as is often needed in APTES surface modification methods), which can be counterproductive for the efficient production of photocurrents. Moreover, because the nanowire surfaces are functionalized with fluorescently labeled streptavidin, it is very easy to use any antibody for the nanowires to be coupled with. Thus, these nanowires are extremely versatile in terms of the cell types they can target.

Figure 17:
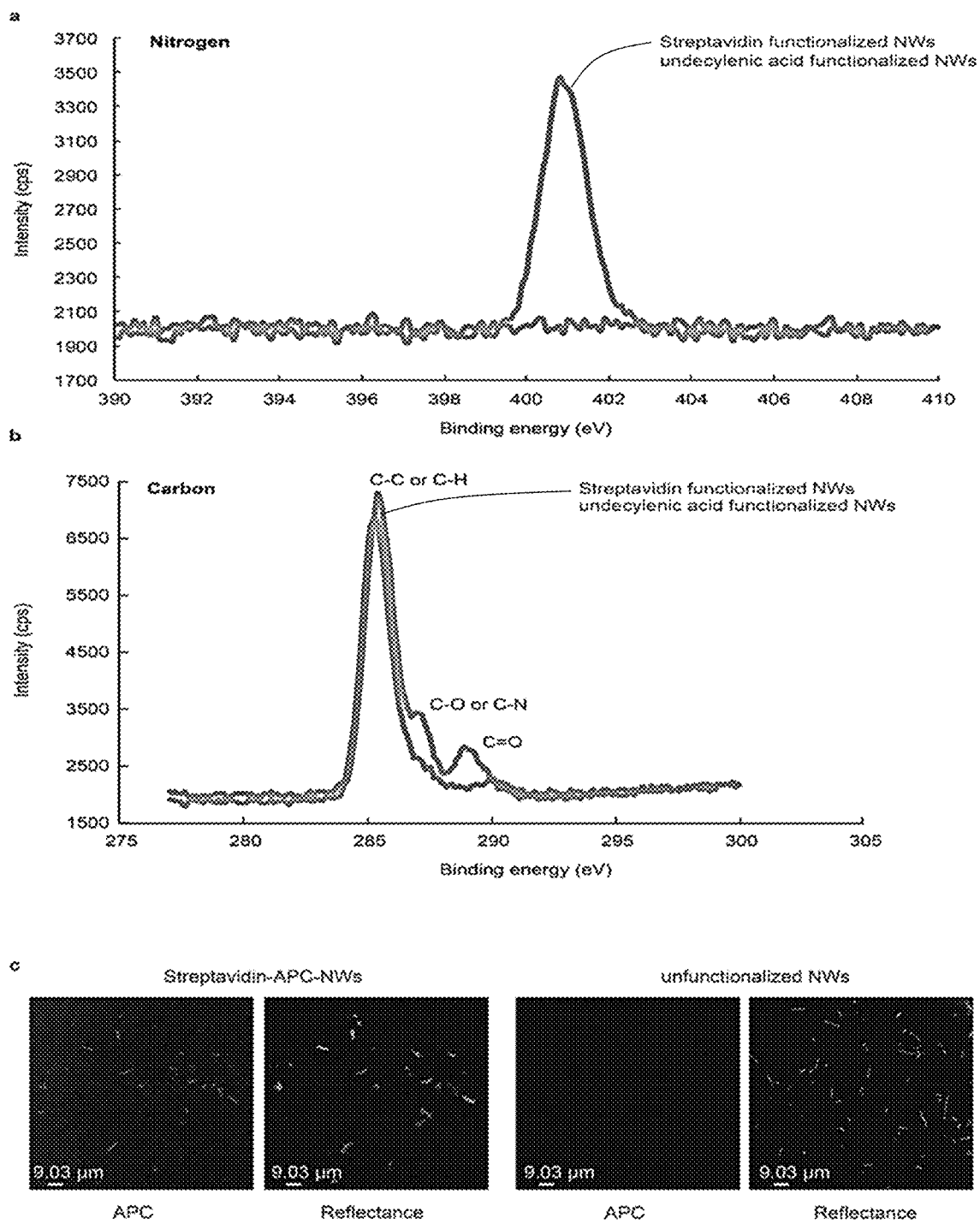
FIG. 17 provides X-ray photoelectron spectroscopy spectra (A), (B); (C) shows confocal microscopy images, all of which demonstrate successful surface labeling of PIN silicon nanowires with fluorescent streptavidin (StrA-APC).

In order to confirm that the surface functionalization scheme was indeed effective, X-ray photoelectron spectroscopy was used to understand the elemental composition of the nanowire surfaces at various stages in the process. It was found that a nitrogen peak at approximately 401 eV, which was absent immediately after hydrosilylation, appeared at the last stage of the functionalization scheme when the nanowires were labeled with StrA-APC (FIG. 17A). Furthermore, when comparing the carbon peaks at these two stages in the process, it was found that all carbon peaks became more pronounced and that a C—O or C—N peak appeared at the StrA-APC stage, consistent with the idea that StrA is a protein and thus would have a more complex carbon profile via XPS (FIG. 17B). Furthermore, upon confocal microscopy imaging of unfunctionalized PIN-SiNWs and StrA-APC labeled PIN-SiNWs, it was found that 100% of the labeled nanowires imaged positively for APC and that 0% of the unlabeled nanowires imaged positively for APC (FIG. 17C).

Figure 18:
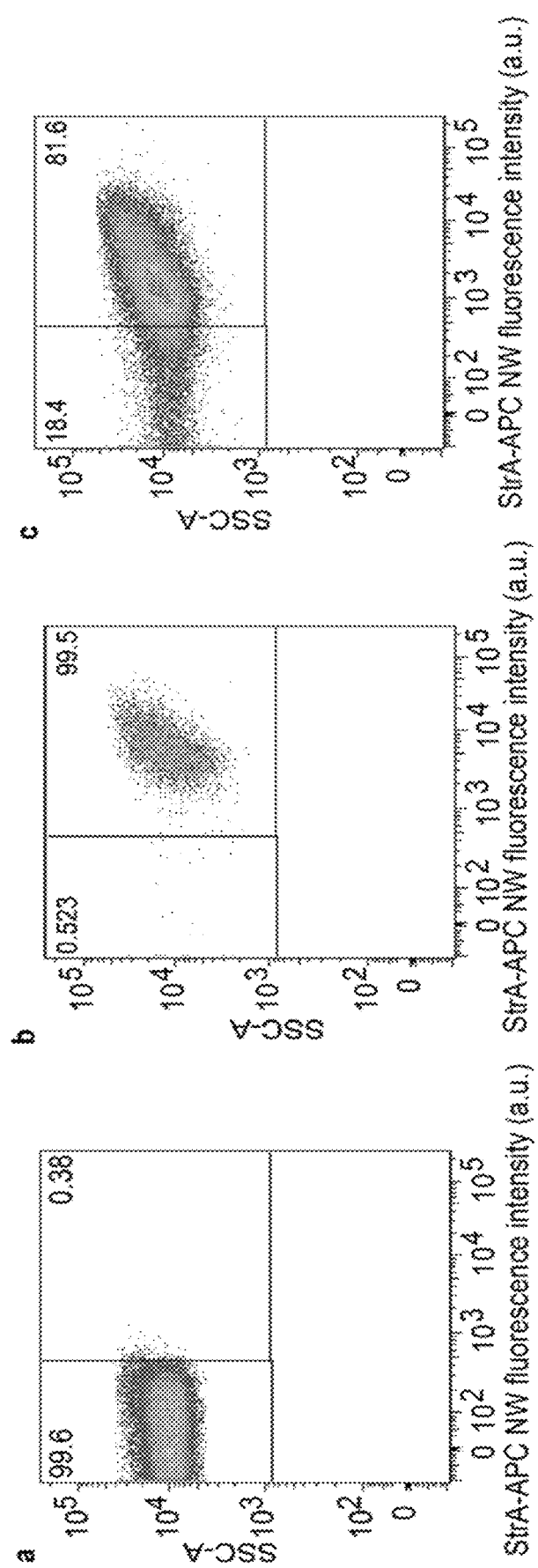
FIG. 18 shows the generation of T cell-PIN silicon nanowire complexes.

Here, it was shown that nanowires which were surface functionalized with APC (fluorophore) labeled streptavidin (StrA-APC PIN-SiNWs) and were incubated with a biotinylated anti-CD45 antibody can bind to T cells. The phosphatase CD45 was chose, as it is excluded from the immune synapse, and so without being bound by a particular theory, it is hypothesized that nanowires binding to T cells through CD45 would have minimal effects on T cell activation. 100% of Jurkat T cells and primary 5 cc7 T cells incubated with unlabeled PIN-SiNWs were APC negative, while 100% of Jurkat T cells and primary 5 cc7 T cells treated with biotinylated anti-CD45 antibody and incubated with StrA-APC PIN-SiNWs were APC positive (FIGS. 18A-B). It was found that the percentage of APC positive cells and spread of this population could vary in any given experiment depending on the cell to nanowire ratio in the sample (FIG. 18C).

Figure 19:
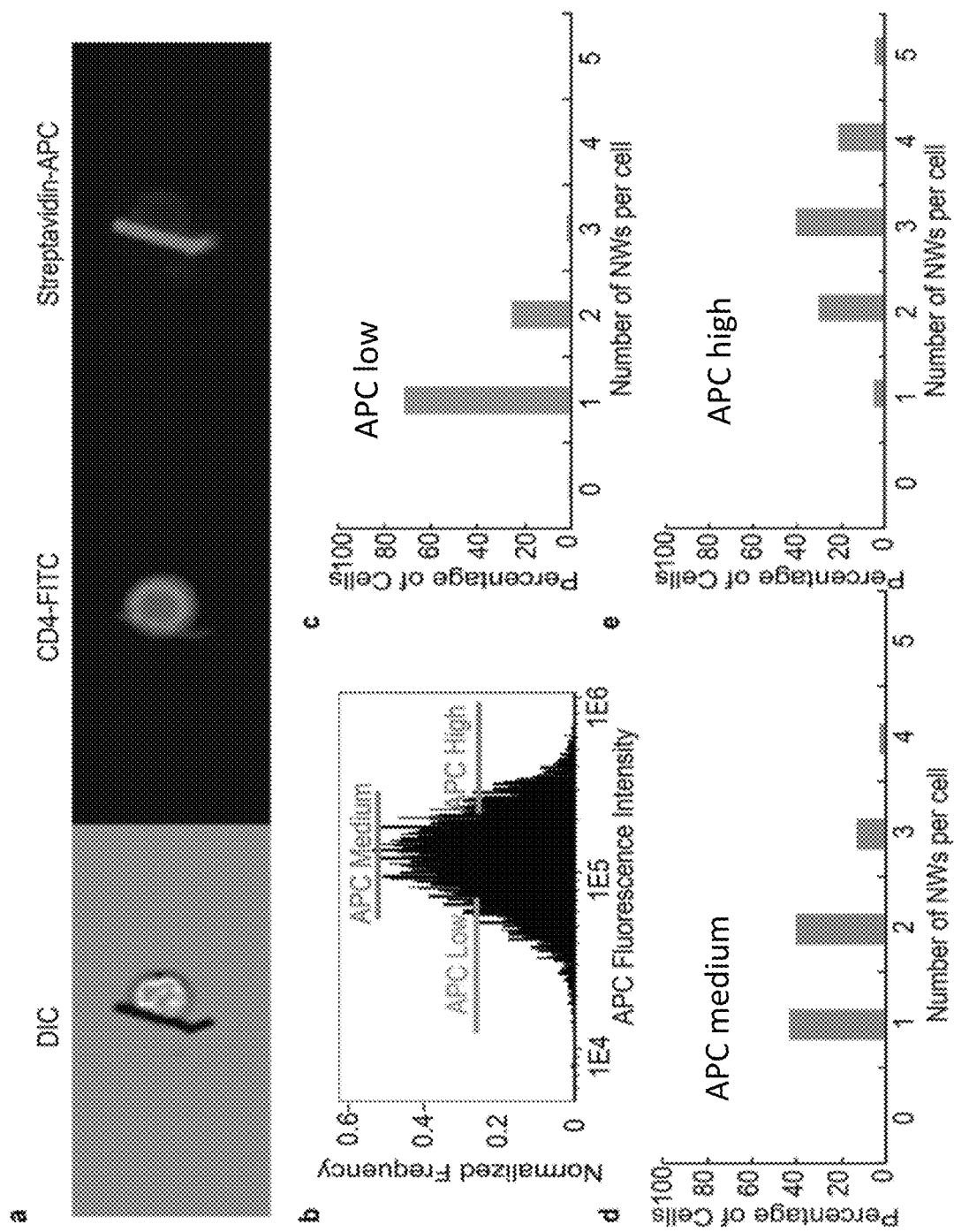
FIG. 19 shows the results of image stream flow cytometry, revealing T cell-PIN silicon nanowire complexes with varying numbers of nanowires for each T cell.

Moreover, ImageStream flow cytometry technology was used to visualize these T cell-nanowire complexes and understand how many PIN-SiNWs were bound to each T cell on average, especially when the spread of the APC was larger. It was found that the nanowires bound to each T cell cound be easily visualized and that there was a APC fluorescence intensity dependent change in the average number of nanowires bound to each cell (FIGS. 19A-E). For the APC high population, it was found that 4.8% of T cells were bound to 1 PIN-SiNW, 29.9% were bound to 2, 40.6% were bound to 3, 20.8% were bound to 4, and 3.9% were bound to 5 (FIGS. 19B-C). In the medium APC population, 43.5% of the T cells were bound to 1 PIN-SiNW, 40.5% were bound to 2, 13% were bound to 3, and 3% were bound to 4 (FIGS. 19B, 19D). In the low APC population, 0.99% of the T cells were not bound to any PIN-SiNWs, 71.2% were bound to 1, 25.6% were bound to 2, 1.48% were bound to 3, and 0.74% were bound to 4 (FIGS. 19B, 19E).

Figure 20:
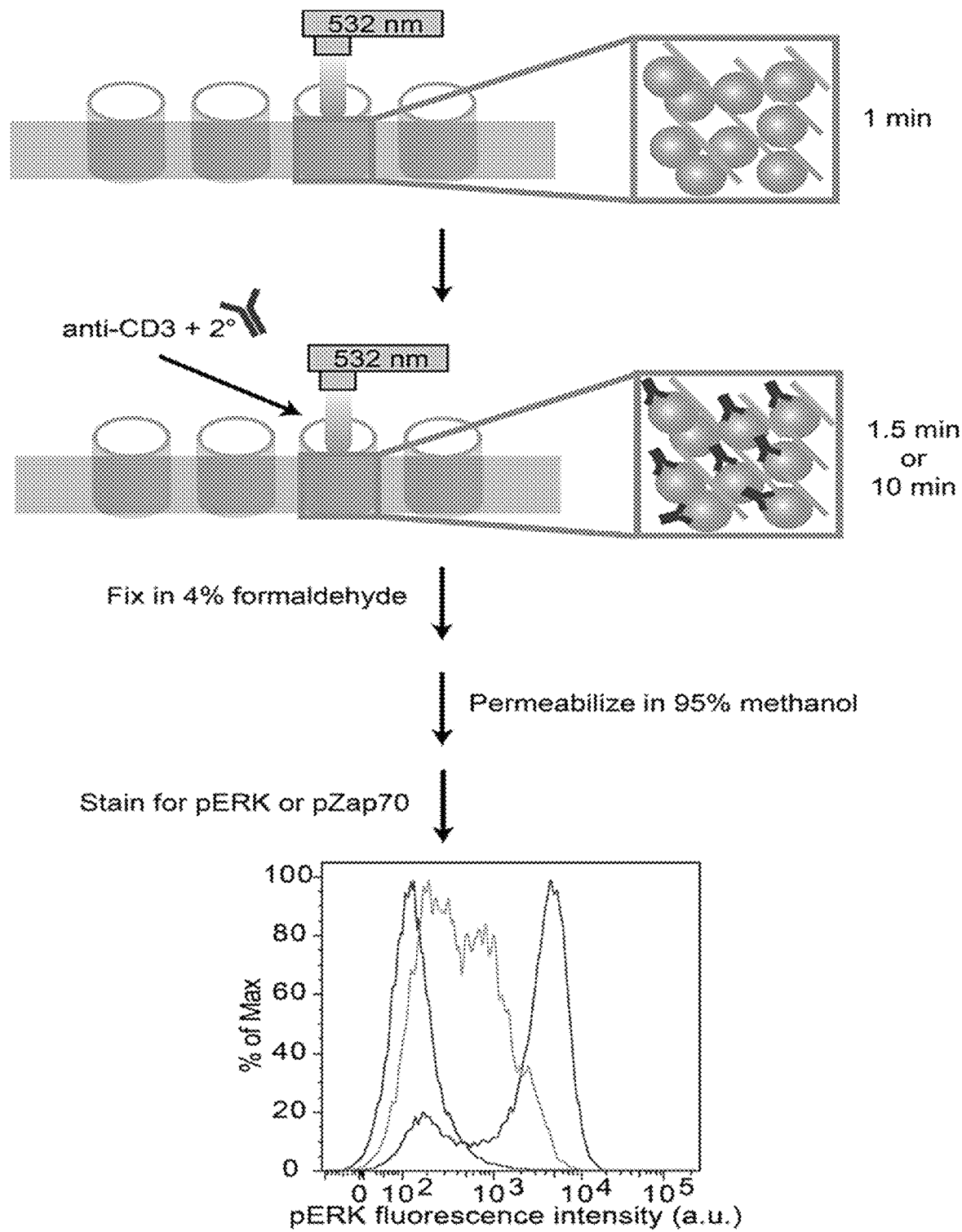
FIG. 20 illustrates the scheme of PIN silicon nanowire-mediated optical depolarization of T cells during T cell activation.

As demonstrated above, the PIN-SiNWs can produce photoelectrochemical currents that can depolarize cell membranes and consequently, so the effects of nanowire-mediated membrane depolarization on T cell activation were examined. A method to optically induce depolarization of populations of T cells complexed with labeled nanowires was used (FIG. 20). 100 µl samples of T cell-nanowire complexes were plated in 96 well plates and used a 532 nm laser to illuminate single wells at a time for 1 minute at 40 mW with a power density of 4.26 mW/mm$^2$ before adding anti-CD3$\delta$ and a secondary antibody to the well to stimulate the TCR (FIG. 20). The 532 nm optical stimulus was then maintained for 10 min or 90 sec in order to capture ERK1/2 phosphorylation or Zap70 phosphorylation events, respectively, via intracellular phosphoflow cytometry.

Figure 21:
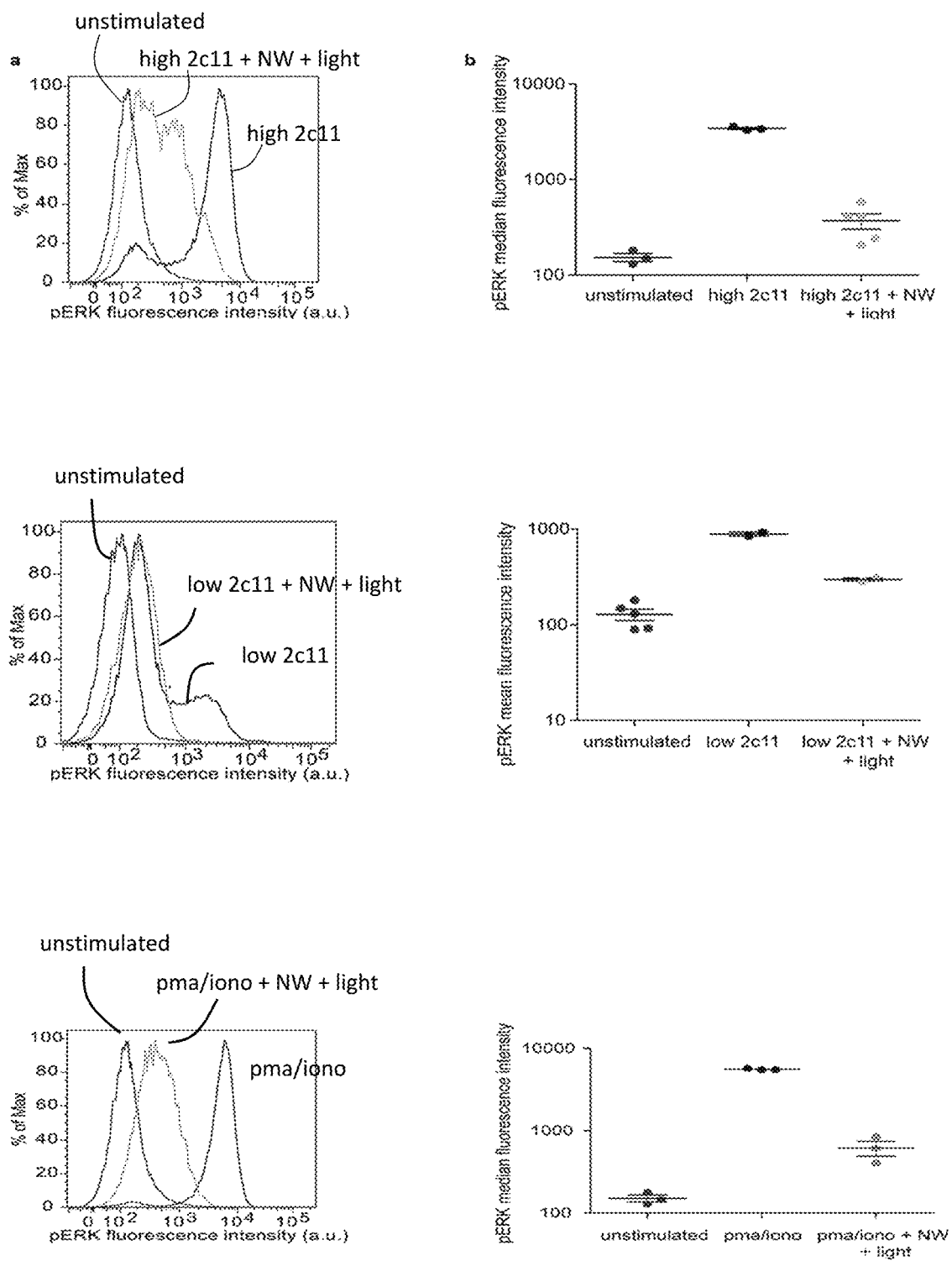
FIG. 21 provides charts demonstrating that TCR activation induced ERK1/2 phosphorylation may be dampened upon PIN silicon nanowire-mediated optical depolarization.

When measuring ERK1/2 phosphorylation in 5 cc7 RAG2−/− mouse splenic T cells that had either been completely unstimulated, stimulated through the TCR with an anti-CD3 antibody (2c11 clone) or TCR stimulated while undergoing optical PIN-SiNW mediated depolarization, it was found that ERK phosphorylation was significantly decreased to near unstimulated levels in the depolarizing condition in both high and low 2c11 concentration conditions (FIGS. 21A-D). In the high 2c11 experiment, the average median fluorescence intensity for unstimulated samples was 153, 3417 for 2c11 stimulated samples, and 370.6 for 2c11 stimulated depolarized samples (FIGS. 21A-B). In the low 2c11 experiment, the average mean fluorescence intensity for unstimulated samples was 128.02, 890.5 for 2c11 stimulated samples, and 298 for 2c11 stimulated depolarized samples (FIGS. 21C-D). In order to further determine whether this effect was completely TCR mediated, T cells were activated using pma and ionomycin, which bypass the TCR to activate PKC theta and induce calcium flux. It was found that PIN-SiNWs similarly abrogate ERK1/2 phosphorylation during pma and ionomycin induced activation (FIGS. 21E-F). In this experiment, the average median fluorescence intensity for unstimulated samples was 153, 5694.7 for 2c11 stimulated samples, and 628 for 2c11 stimulated depolarized samples (FIGS. 21C-D).

Example 4: Photoelectrochemical Behavior of Flexible Silicon Membranes

Materials and Methods

Synthesis of silicon-based materials. Silicon materials (p-type/intrinsic/n-type diode junctions and intrinsic-intrinsic coaxial nanowires) were prepared using a chemical vapor deposition (CVD) method. In a typical synthesis of a p-i-n diode junction, a silicon-on-insulator (SOI) wafer (Ultrasil, USA, device layer, p-type, (100), 0.001-0.005 Ω·cm, 2 µm; buried oxide layer, 1 µm; handle layer, p-type, (100), 1-20 Ω·cm, 650 µm) was used as the substrate for subsequent deposition of intrinsic and n-type layers. The native oxide on the SOI wafer was removed with hydrofluoric acid (HF, 49%, Sigma-Aldrich, USA) right before placing the substrate inside a quartz tube for evacuation. Each of the intrinsic and n-type Si layers was deposited under 650° C. and a chamber pressure of 15 Torr for 20 min. During the intrinsic layer deposition, the flow rates of hydrogen ($H_2$) and silane ($SiH_4$) were set as 60 and 0.3 standard cubic centimeters per minute (sccm), respectively. The n-type layer was deposited with the same flow rates of $H_2$ and $SiH_4$ during the intrinsic layer growth plus a 1.5 sccm flow rate of the dopant gas, phosphine ($PH_3$, 1000 ppm in $H_2$). Measured conductivities of individual layers are ~0.45 Ω·cm for the p-type single crystalline substrate (~2 µm in thickness), ~149 kΩ·cm for the intrinsic polycrystalline layer (~140 nm in thickness), and ~540 Ω·cm for the n-type polycrystalline layer (~190 nm in thickness), respectively.

The nanocrystalline Si nanowire (intrinsic core/intrinsic shell) was synthesized from a two-step process involving an initial growth of a thin intrinsic backbone and a subsequent deposition of a thick intrinsic shell. The core was grown with a gold (Au) nanocluster-catalyzed CVD process where Au colloidal nanoparticles (Ted Pella Inc., USA, 50 nm in diameter) were deposited onto a Si (100) substrate (Nova Electronic Materials, n-type, 0.001-0.005 Ω·cm) as the catalyst. The growth was maintained at 470° C. and 40 Torr for 20 min. The flow rates of $H_2$ and $SiH_4$ were controlled as 60 and 2 sccm, respectively. After the intrinsic nanowire core growth, the $SiH_4$ flow was switched off and the chamber was kept under a $H_2$ atmosphere (60 sccm, 15 Torr) until the temperature ramped up to 600° C. for the subsequent shell deposition. The $H_2$ atmosphere was used to minimize Au diffusion. The intrinsic shell was deposited with flow rates of $H_2$ and $SiH_4$ at 0.3 and 60, respectively, and a chamber pressure of 15 Torr for 40 min.

The metal-decorated Si diode junctions were prepared with an electroless deposition method. In general, the as-synthesized p-i-n diode junctions were dipped into a mixture of metal-containing solutions (chloroauric acid ($HAuCl_4$), potassium tetrachloroplatinate (II) ($K_2PtCl_4$), silver nitrate ($AgNO_3$); 0.01 mM, 0.1 mM, 1 mM) and 1% HF for 3 min at room temperature.

Flexible silicon membrane synthesis. The device fabrication process was divided into two parallel steps including the preparations of both distributed Si meshes and porous polydimethylsiloxane (PDMS, Corning, USA) membranes. The fabrication of distributed Si meshes were performed with a combination of photolithography and etching techniques. In brief, a bilayer of undercut (MicroChem, USA, LOR-3A) and photoresist (MicroChem, USA, SU-8 2005) was spin-coated on the as-synthesized p-i-n diode junction SOI wafer. A mesh structure of SU-8 was patterned with a standard photolithography process consisting of ultraviolet (UV) light exposure (200 mJ/cm$^2$) and developing (MicroChem, USA, SU-8 developer). The as-patterned SU-8 mesh served as an etch mask for the subsequent reactive ion etching (RIE) of Si. The unprotected p-i-n Si layers (~2.3 μm) were removed after 10 min of etching (radiofrequency (RF) power, 100 W; inductive-coupled plasma (ICP) power, 400 W) with a gaseous mixture of tetrafluoromethane (CF$_4$, 45 sccm) and argon (Ar, 5 sccm). The SU-8 protection layer was lift-off by dissolving the undercut LOR-3A layer in Remover-PG (MicroChem, USA). A final wet etching of the oxide layer with 49% HF was performed to release the as-patterned Si diode junction.

The PDMS membrane was prepared using a soft-lithography technique. In general, a SU-8 pillar array (~120 μm in height) was patterned on a Si substrate with the standard photolithography process and served as the soft-lithography mold. A layer of PDMS (precursor:curing agent ratio=10:1) was then spin-coated onto the SU-8 mold and cured at 80° C. overnight. The as-cased PDMS layer was finally released in hexane (Fisher Scientific, USA) to get the holey structure. The distributed Si mesh was then transferred onto the holey PDMS membrane to form the entire device.

Finite element analysis (FEA) of stress distribution. The FEA was performed using COMSOL Multiphysics 5.3 (COMSOL Inc. USA). A 2D plate model in the structural mechanics module was set for the simulation. The von Mises stress distribution was calculated after a point displacement of 500 μm in the z direction at the device center while fixing four edge points.

Electron microscopy. A transmission electron microscope (TEM, JEOL, Japan, JEM-3010) and an aberration-corrected scanning transmission electron microscope (STEM, JEOL, Japan, JEM-ARM200F) were used to image the cross-sectional structures of both the pristine p-i-n Si diode junction and the gold-decorated one. X-ray energy dispersive spectroscopy (XEDS) maps were using the JEM-ARM200F, which was equipped with an Oxford X-Max$^N$ 100TLE windowless SDD X-ray detector (Oxford Instruments, UK). Selected area electron diffraction (SAED) patterns were taken using the JEM-3010. TEM cross-sectional specimen preparations were carried out by controlled tripod polishing followed by liquid-nitrogen-cooled Ar ion millings using a Fischione 1050 TEM mill (Fischione Instruments, USA). A 4-kV ion milling was used to further thin the specimen and a final 0.5 kV milling was performed to remove surface damages. A scanning electron microscope (SEM, Carl Zeiss, Germany, Merlin) was used to image the top view of the gold-decorated Si diode junction, the cross-sectional view of the diode junction, and the flexible device made of the distributed Si mesh and the holey PDMS membrane. Nanocrystalline Si nanowires were sonicated in isopropanol (Sigma-Aldrich, USA) and then dispersed over copper grids (Ted Pella Inc., USA, Lacey Formvar/Carbon, 200 mesh) for side-view imaging using a TEM (JEOL, Japan, JEM-3010). The cross-sections of the nanowires were prepared by ultramicrotomy. In general, Si nanowires were embedded in epoxy resins which were then solidified at 60° C. for 24 h. Thin epoxy sections of ~100 nm were cut using a ultramicrotome (Ultracut E, Reichert-Jung, USA), collected on lacey carbon grids (Ted Pella Inc., USA), and imaged using the same TEM.

X-ray photoelectron spectroscopy (XPS). XPS data were collected using ESCALAB 250 Xi (Thermo Scientific, USA) with a monochromatic Al Kα (hv=1486.6 eV) excitation. The diameter of the X-ray beam was 500 μm. The survey scans were performed with a pass energy of 160 and a step size of 1 eV whereas the high-resolution scans were done with a pass energy of 50 and step size of 0.1 eV. The correction of the XPS spectra for charge accumulation was performed using the Si 2p peak (binding energy=99.4 eV). The Si 2p peaks were fitted using a Shirley background with G/L 30% for Si$^0$ and pure Gaussian for Si$^{4+}$. Peak fitting for the Au 4f signal was determined with a linear background G/L 30%, asymmetric 0.9, and a height factor of 0.75. With these parameters the FWHM range for the gold was from 0.8 eV to 1.25 eV.

Si photo-response measurements. For the photo-response measurements, a standard patch-clamp setup was employed. In particular, an upright microscope (Olympus, Japan, BX61WI) with a 20×/0.5 NA water immersion objective was used to deliver light pulses from a light emitting diode (LED, M530L3, Thorlabs, USA, 530 nm, ~500 μm spot size) or a laser (Laserglow, Canada, 532 nm, diode-pumped solid-state laser, ~5 μm spot size). The light pulses were controlled by transistor-transistor logic (TTL) signals (10 ms) delivered from a digitizer (Molecular Devices, USA, Digidata 1550). Voltage-clamp protocols were done by an Axopatch 200B amplifier (Molecular Devices, USA), controlled by pClamp software (Molecular Devices, USA). Glass pipettes were pulled in a flaming/brown type micropipette puller (Sutter Instrument, USA, P-97) for a final resistance of ~1 MΩ when filled with 1× phosphate buffered saline (PBS, Fisher Scientific, USA) solution. In a typical measurement, a Si material was immersed in the same PBS solution where the pipette tip was positioned in close proximity to the Si surface (~2 μm). The ionic currents across the pipette tip were recorded in the voltage-clamp mode where the holding levels of the pipette were adjusted using the pipette offset knob. The individual quantities of each photo-response, i.e., capacitive, Faradaic, and thermal, were calculated by fitting the plot of the light-induced current amplitude ($\Delta I_{light}$) over the holding level ($I_0$). At a given time point, the slope of the $\Delta I_{light}$–$I_0$ plot represents the photothermal response whereas the intercept of the plot is contributed by the photoelectric responses. Within the photoelectric responses, the capacitive current is defined as the maximal current amplitude after the light onset while the Faradaic current is defined as the current amplitude at the time point of 8.5 ms since illumination starts. The amplitude of the photothermal-induced local temperature increase of the solution was calculated after the calibration of the pipette resistance. After the photo-response measurement, the same micropipette was placed into another dish of pre-heated PBS with an initial temperature of about 50° C. A thermocouple was positioned close to the pipette tip during the temperature measurement. A calibration curve was created, based on the pipette resistance changes in the range between 50° C. and 20° C., which was then used in conjunction with the $\Delta I_{light}$–$I_0$ curve to estimate the local temperature increase.

Mammalian cell cultures: Dorsal root ganglia (DRG) cells were extracted from decapitated P1-P3 Sprague-Dawley rats (Charles River Laboratories, USA) and were placed immediately in ice-cold Dulbecco's modified eagle medium (DMEM/F12, Life Technologies, USA). The ganglia were then transferred to a 2.5 mg/mL trypsin solution (Worthington, USA) in Earle's balanced salt solution (EBSS, Life Technologies, USA) and digested for 20 min in a 37° C. shaker with a speed of 144 rpm. Afterwards, the cells were centrifuged and the supernatant was replaced with EBSS supplemented with 10% fetal bovine serum (FBS) (ATCC, USA). After the mechanical trituration with pipetting, the cell suspension was centrifuged again and the supernatant was replaced with DMEM/F12 containing 5% FBS. Next, cells were seeded onto poly-L-lysine (PLL, Sigma-Aldrich, USA) coated substrates, e.g., glass-bottom Petri dishes, p-i-n diode junction SOI wafers, and allowed 30 min for cell adhesion. Finally, the dishes were filled with DMEM/F12 supplemented with 5% FBS, 100 U/ml penicillin (Sigma-Aldrich, USA), and 100 µg/ml streptomycin (Sigma-Aldrich, USA), and cultured in a 37° C. incubator with 5% carbon dioxide ($CO_2$) until used for experiments.

Human umbilical vein endothelial cells (HUVEC, Life Technologies, USA) and U2OS cells (ATCC, USA) were cultured on glass-bottomed Petri dishes and passaged following standard procedures from the vendors.

In all cell cultures, intrinsic nanocrystalline Si nanowires were introduced and allowed for coculturing for at least 24 hours. Specifically, nanowire suspensions in different cell culture media were prepared by extensively sonicating small pieces of nanowire growth substrates (~2 mm×2 mm) in culture media for 2 min. The as-made nanowire suspensions were added to the cultures in a drug-like fashion (~10 µL of suspension per 1 mL of medium). Before all experiments, cells were washed three times with fresh media.

Immunofluorescence labeling of the DRG culture. DRG and nanowire cocultures were first fixed with 4% paraformaldehyde in PBS (Alfa Aesar, USA, with magnesium and ethylene glycol tetraacetic acid) for 10 min at room temperature. After rinsing in PBS, cells were then permeabilized with 0.1% Triton X-100 in PBS (Sigma Aldrich, USA) for another 10 min at room temperature. Following blocking with 1.5% bovine serum albumin (BSA, Sigma-Aldrich, USA) in PBS for 1 hour, the cells were incubated with primary antibodies (GFAP (GA5) Mouse mAb, 1:300 in 1.5% BSA-PBS for glia; NeuN (D4G40) XP Rabbit mAb, 1:50 in 1.5% BSA-PBS for neuron, Cell Signaling, USA) at room temperature for 1 hour. After washing, secondary antibodies (Goat anti-Mouse IgG (H+L) Superclonal Secondary Antibody, Alexa Fluor 647, 1:150 in 1.5% BSA-PBS for glia; Goat anti-Rabbit IgG (H+L) Secondary Antibody, Alexa Fluor 488, 1:150 in 1.5% BSA-PBS for neuron, Life Technologies, USA) were finally applied. Since NeuN is expressed in the neuronal nucleus, another set of biomarkers, i.e., S-100 for glial cells and Neurofilament for neurons, were stained to test if nanowires were colocalized with neuronal cytoplasm. The staining follows the same procedure as the GFAP/NeuN staining with slight differences in the dilution ratios of the antibodies. In particular, cells after fixation and permeabilization were incubated with primary antibodies (S100 Polyclonal Antibody, 1:100 in 1.5% BSA-PBS for glia, Life Technologies, USA; Neurofilament-H (RMdO 20) Mouse mAb, 1:200 in 1.5% BSA-PBS for neuron, Cell Signaling, USA) at room temperature for 1 hour. After washing, secondary antibodies (Goat anti-Mouse IgG (H+L) Cross-Adsorbed Secondary Antibody, Alexa Fluor 647, 1:200 in 1.5% BSA-PBS for neuron; Goat anti-Rabbit IgG (H+L) Cross-Adsorbed Secondary Antibody, Alexa Fluor 488, 1:200 in 1.5% BSA-PBS for glia, Life Technologies, USA) were finally applied. After washing in PBS, the as-labelled cells were imaged using a confocal laser scanning microscope (Leica, Germany, SP5 II STED-CW) with Si nanowires being imaged simultaneously with the scattered light.

Calcium imaging. Cells, either cocultured with intrinsic nanowires or cultured on p-i-n diode junctions, were stained with 2 µM of Fluo-4 AM (Life Technologies, USA) for 30 min at 37° C. and washed three times with dye-free culture media before imaging. The as-stained cells were imaged using the same Leica SP5 confocal microscope. In a typical experiment, a laser pulse (1 ms, 592 nm) was delivered to the nanowire/cell of interest in the middle of a calcium imaging time series. The cellular fluorescence intensity over time was then analyzed using ImageJ software (National Institutes of Health, USA).

LIVE/DEAD assay. Cells, either cocultured with intrinsic nanowires or cultured on p-i-n diode junctions, were stained with 2 µM of calcein AM (Life Technologies, USA) and 4 UM of ethidium homodimer-1 (Life Technologies, USA) for 30 min at room temperature. The as-stained cells were imaged using the same Leica SP5 confocal microscope. In a typical experiment, a laser pulse (1 ms, 592 nm) was delivered to the nanowire/cell of interest in the middle of an imaging time series. Live cells will stay green throughout the entire sequence while dead cells will be stained red.

Intracellular transport. For the intracellular transport study, a custom-written program in Python was run to automatically track the nanowire and calcium wave-front locations in all 100 frames. To distinguish between different modes of Si nanowire transport, a rolling frame mean squared displacement (MSD) metric was used, where the MSD is the average distance that a particle travels as a function of lag time, given by:

$$\mathrm{MSD} = \left\langle \Delta r^2(\tau) \right\rangle = q\tau^\alpha$$

where $\Delta r$, $\tau$, $q$, and $\alpha$ are the nanowire displacement, lag time, diffusion coefficient and the 'diffusive exponent' respectively. The diffusive exponent, $\alpha$, can be used as a metric of transport properties, distinguishing between Brownian diffusion ($\alpha=1$), restricted diffusion ($\alpha<1$), and active transport ($\alpha>1$) processes. For the plotting, rolling $\alpha$ values were calculated for every 5 frames with a window size of 9.

Live cell microtubule dynamics. In a typical experiment, HUVEC cells with internalized Si nanowires were stained with 200 nM of SiR-tubulin (Cytoskeleton, USA) at 37° C. for 1 hour. 10 µM of verapamil (Cytoskeleton, USA) was also added to inhibit the efflux of the SiR-tubulin. Three times of washing with the dye-free medium was applied before imaging. Under the same Leica SP5 confocal microscope, the Si nanowire of interest was illuminated with a 592 nm laser pulse (1 ms) and the subsequent microtubule dynamics were recorded. The as-recorded videos were processed and analyzed using ImageJ including the analysis of microtubule bounded areas and intercellular conduit lengths over time, and the generation of kymographs.

Electrophysiology and photo-stimulation experiments. All animal protocols used were in accordance to the policies of the University of Chicago and Northwestern University, approved by the Institutional Animal Care and Use Committees (IACUC), and followed the animal welfare guidelines of the Society for Neuroscience and National Institutes of Health.

1) DRG culture on Si diode junctions. Before the experiment, FBS supplemented DMEM/F12 in the culture dish was rinsed three times with the extracellular recording solution (in mM: NaCl 132, KCl 4, $MgCl_2$ 1.2, $CaCl_2$) 1.8, HEPES 10, glucose 5.5; pH 7.4). Desired neurons were patched with a ~2 MΩ pipette, filled with the intracellular pipette solution (in mM: NaCl 10, KCl 150, $MgCl_2$ 4.5, EGTA 9, HEPES 10; pH 7.3). Voltage recordings were made in current-clamp mode using the same setup for the photo-response measurements. Suprathreshold current injections were first delivered to the patched neuron to assess its excitability. Laser pulses (532 nm) with incremental durations were delivered subsequently to excite the cell.

2) Brain slice with Si diode junctions. Wild-type mice (C57BL/6, female and male; Jackson Laboratory, USA) were bred in-house. Mice were 6-9 weeks old at the time of the slice experiments.

a) Slice preparations. Mice were euthanized by anesthetic overdose and decapitation. Brain slices were made in a 4° C. cutting solution (in mM: 110 choline chloride, 11.6 sodium L-ascorbate, 3.1 pyruvic acid, 25 $NaHCO_3$, 25 D-glucose, 2.5 KCl, 7 $MgCl_2$, 0.5 $CaCl_2$), 1.25 $NaH_2PO_4$; aerated with 95% $O_2$/5% $CO_2$) using a vibratome (VT 1200S, Leica, Germany) to make 250 μm thick slices. The slices were transferred to an artificial cerebrospinal fluid (ACSF, composition in mM: 127 NaCl, 25 $NaHCO_3$, 25 D-glucose, 2.5 KCl, 1 $MgCl_2$, 2 $CaCl_2$), 1.25 $NaH_2PO_4$; aerated with 95% $O_2$/5% $CO_2$) and maintained at 34° C. for 30 min. The slices were then returned to room temperature for at least 1 hour prior to the recordings.

b) Electrophysiology. Distributed Si meshes were placed in a recording chamber under an upright microscope (BX51WI; Olympus, Japan), which is equipped with a video camera (Retiga 2000R; QImaging, Canada). Brain slices were then transferred on top of the Si meshes to form contacts. Slices were visualized by bright-field gradient contrast microscopy using an infrared LED (850 nm, M850L2, Thorlabs, USA) as the light source. A low-magnification objective lens (UPlanSApp 4×/NA 0.16, Olympus, Japan) was used to visualize and position the slices. A high-magnification water immersion lens (LUMPlanFLN 60×/NA 1.00, Olympus, Japan) was used to identify neurons for whole-cell recordings.

Borosilicate glass (inner diameter 0.86 mm, outer diameter 1.5 mm with filament, Warner Instruments, USA) was pulled using a P-97 micropipette puller (Sutter Instrument, USA) into patch pipettes with a tip resistance of 2~4 MΩ. Neurons targeted for whole-cell recordings were obtained using micromanipulators (MP-225, ROE-200, MPC-200, Sutter Instrument, USA) and a patch-clamp amplifier (Multiclamp 700B, Axon Instruments, USA). Pipettes containing potassium-based or cesium-based internal solutions were used for voltage-clamp recordings (composition of the internal solution, in mM: 128 potassium or cesium methanesulfonate, 10 HEPES, 10 phosphocreatine, 4 $MgCl_2$, 4 ATP, 0.4 GTP, 3 ascorbate, 1 EGTA, 1 QX-314, and 0.05 Alexa Flour hydrazide, with 4 mg/ml biocytin, at 7.25 pH and 290-295 mOsm). All recordings were made in 34° C. ACSF with the temperature controlled by an in-line feedback-controlled heater (TC 324B, Warner Instruments, USA). Recordings with series resistance>40 MΩ were excluded.

A command potential of −70 mV was applied to isolate excitatory (glutamatergic) post synaptic currents (EPSCs). To test for input to a neuron, blue-laser illuminations (1 ms long pulses, 473 nm, ~2 mW, ~57 μm spot size; MLL-FN473, CNI Laser, China) were delivered onto a nearby spot of the Si mesh.

Multiple trials were sampled at an interstimulus interval of at least 30 s. Recorded currents were amplified, filtered at 4 kHz, and sampled at 40 kHz. Data were acquired using Ephus software and analyzed using routines written in MATLAB (MathWorks, USA).

3) In Vivo Experiments with Distributed Si Meshes.

Wild-type mice (C57BL/6, female and male; Jackson Laboratory, USA) were used, at an age of 6-9 weeks old at the time of the in vivo experiments.

a) Pre-stimulation surgeries. The mouse was deeply anesthetized with ketamine-xylazine (ketamine 80~100 mg/kg, xylazine 5~15 mg/kg, injected intraperitoneally) before the placement of the cranial mounting hardware. A small skin incision was first made over the cerebellum to expose the skull. A stainless-steel set screw (single-ended #8-32, SS8S050, Thorlabs, USA), crimped with a spade terminal (non-insulated, 69145K438, McMaster-Carr, USA) was then affixed with dental cement to the skull. This set screw was later screwed into a tapped hole located at the top of a ½" optical post for the head fixation.

After being head-fixed as described above, craniotomies were made over the motor and somatosensory cortices using a dental drill with large enough openings (~2.5 mm) to allow the attachment of a silicon mesh on the cortex and the passage of a linear probe. The dura was peeled for a full exposure of the cortex, which was important for a good signal transduction at the Si-brain interface. The mouse was then placed in the recording apparatus with the body temperature monitored with a rectal probe and maintained at ~37.0° C. via a feedback-controlled heating pad (FHC, Bowdoin, USA). During the subsequent recordings, ACSF was frequently applied to the exposed brain area to prevent the damage from dehydration. The level of anesthesia was continuously monitored based on whisker movements and paw-pinching/eye-blinking reflexes. Additional anesthetics with 50% of the induction dosage were given when required.

b) Photostimulation apparatus. A customized laser scanning apparatus with a blue laser source (LY473III-100, wavelength 473 nm, maximum power~100 mW, beam diameter~2 mm) mounted on a 3D linear stage was positioned above the mouse head. In the apparatus, the laser beam from the light source goes through an acousto-optic modulator (AOM) and an iris before being deflected by a pair of galvanometer scanners and focused to the Si mesh by a plano-convex spherical lens.

The output laser power was controlled using a customized AOM driver modulated by signal waveforms delivered via a commercial multifunction (analog and digital) interface board (NI USB 6229, National Instruments, USA). A short pulse train was also sent to digitally encode the parameters of the light waveform such as the start point through the digital input port of the electrophysiology data acquisition (DAQ) board. Software tools (LabVIEW, National Instruments, USA) including a graphical user interface (GUI, GenWave) were developed to generate and transfer waveforms to the AOM driver. The system was calibrated using a power meter to determine the relationship between the driver input voltage and the laser scanner output power.

c) Electrophysiology apparatus. Silicon probes of 32-channel linear microelectrode arrays with ~1 MΩ impedances and 50-μm spacings (model A1 32-6 mm-50-177, NeuroNexus, USA) were used for electrophysiological recordings. The probe was fixed to a motorized 4-axis micromanipulator, assembled by mounting a MTSA1 linear translator (Thorlabs, USA) onto a MP285 3-axis manipulator (Sutter Instrument, USA), and positioned under stereoscopic visualizations over a distributed silicon mesh which has been attached to the cortical surface (with the Si layer facing towards the tissue). The probe was tilted by ~30° off the vertical axis for a better collection of the neural signals under the silicon mesh. The probe was then slowly inserted into the cortex at a rate of 2 μm/s controlled by LabVIEW, until it reached a depth of 1600 μm from the pia, with the entry point in the sensorimotor cortex adjacent to the edge of the silicon mesh. Laser pulses with various powers (up to 5 mW, ~216 μm spot size) and durations (up to 100 ms) were delivered onto the Si mesh for the photostimulation of the brain.

Signals were amplified using a RHD2132 amplifier board based on a RHD2132 digital electrophysiology interface chip (Intan Technologies, USA). The filter was set to an analog bandpass of 0.1~7.5 kHz with a digital filter cutoff of 1 Hz. The single channel sample rate was set to 30K SPS.

For hardware control, a RHD2000 USB Interface Board (Intan Technologies, USA) was used for the communication with other digital devices and the streaming of all the neural-signal data from the RHD2000 amplifiers. The USB port of the module was linked with a USB cable to pipe the data stream in to and out of the computer. In this experiment, the digital ports included in the DAQ board were only used for the acquisition of the photostimulation parameters from the AOM controller.

C++/Qt based experimental interface software (Intan Technologies, USA) was used for the amplifier configuration, online visualization, and data logging.

d) Forelimb movement study apparatus. A Chameleon3 USB3 CMOS Mono camera (CM3-U3-13Y3M-CS, FLIR Systems, USA) configured at 640×512 pixels (2×2 binning) was used to record the body movements following the laser stimulations. The video recording was triggered and synchronized by the laser scanning control board with the frame rate of 100 Hz. 50 frames were collected before the start of the stimulation and a total of 100 frames were recorded for a full trial. A fixed focal length lens (35 mm EFL, f/2.0, Navitar, USA) was mounted on the camera for the focusing. The centroids of the mouse claws were tracked in each frame to investigate the forelimb movements following the laser stimulations. The trajectories of the centroids were quantified to illustrate the movements in each trial.

e) Data analyses. The recorded data were stored as raw signals from the amplifiers and filtered by a 60 Hz notch filter. To reduce the contaminations of the probe recording signals due to the strong photovoltaic effect of the Si mesh, a digital high-pass filter (800 Hz cut-off, 2nd-order Butterworth) was used, to shrink the photovoltaic artifact to the first 3 ms post-stimulus window.

The following routines were performed to further analyze the data. First of all, a threshold detector was applied, with the threshold set to the 5 times of the standard deviation (5 SD) to detect the spikes. To mask the photovoltaic effect, spike counts of the first 3 ms window were then replaced by null values. Finally, neural response time stamps were determined for each detected spike and the response waveforms were plotted from −0.67 ms to 1.33 ms with respect to the detected spike time stamp, i.e., 20 points before and 40 points after the spike time stamp with a sampling rate of 30 kHz. The detected waveforms were sorted according to the similarity of the shapes, i.e., peak to valley amplitudes of the responses. All the analysis codes were written in Matlab (Mathworks, USA).

The time stamps of all the spikes from each channel were used to generate the peristimulus time histogram and the heat maps, which represent the instantaneous firing rate, with 1-ms binning. Responses were averaged across all trials in each channel to yield a mean histogram.

Micro computed tomography (microCT) of the Si/brain interface. MicroCT images of gold-decorated Si meshes attached to dead mouse brains were performed on the XCUBE (Molecubes NV., Belgium) by the Integrated Small Animal Imaging Research Resource (iSAIRR) at the University of Chicago. Images were acquired with an x-ray source of 50 kVp and 200 μA in a single frame of 960 projections. Volumetric CT images were reconstructed in a 400×400×400 format with voxel dimensions of 100 μm³. Images were analyzed using AMIRA 5.6 (Thermo Fisher Scientific, USA).

Device-brain peeling adhesion test. Adult C57BL/6 mice (Jackson Laboratory, USA) were sacrificed shortly before the mechanical test. Mouse brains were harvested from dead animals and placed inside PBS solutions prior to the adhesion tests by a tensile test machine (Zwick-Roell, Germany, zwickiLine Z0.5). Briefly, the brain was fixed on a glass slide using a tissue adhesive (Ted Pella, USA, Pelco Pro CA44) and the device was held tightly by a grip. After forming a conformal contact between the device and the brain cortex with an area of ~8 mm×4 mm, a unidirectional tension was applied to peel the device off the brain while the force and the extension were recorded simultaneously. The loading rate was kept constant at 3 mm/min. The adhesion energy per area was calculated by the integration of the force-extension curves divided by the contact areas.

Analysis of the Photo-Response Measurements.

In a typical photo-response measurement, a glass micropipette, with the potential holding at a fixed level ($V_p$), was positioned near a Si material surface immersed in PBS, and a 10-ms long light pulse was delivered to the material in the middle of the trial. Therefore, the recorded current across the pipette tip can be divided into two parts, namely the baseline current $I_0$ at the dark stage and the time-dependent light-generated current $\Delta I_{light}(t)$ at the light stage. During the light illumination period, two parallel processes originated from the Si material can contribute to $\Delta I_{light}(t)$.

The first one is the photoelectric process where the light-generated excessive carriers will accumulate on the Si surface and change the local surface potential. Ions in the nearby medium will be attracted/repelled with respect to this photo-generated potential and create the ionic currents. Since the variation of the surface potential is only a function of the carrier dynamics on the Si surface, the photoelectrically-induced ionic current ($\Delta I_{electric}(t)$) is therefore independent of the holding current level $I_0$.

Another process is related to the photothermal effect of Si where the recombination of light-generated carriers converts part of the input photon energy into the vibrational energy of the Si lattice, which dissipates heat through both Si and the surrounding electrolyte. For the electrolyte with an elevated temperature, mobilities of the ions will increase, resulting in a reduced pipette tip resistance R. Even under a fixed holding potential $V_p$, the current during the light illumination period will change due to the decrease of the pipette resistance. Therefore, the thermally-induced current ($\Delta I_{thermal}(t)$), is strongly related to the holding potential $V_p$ and the baseline current $I_0$, where $V_p=I_0 \times R_0$, $R_0$ is the pipette resistance in dark.

Given the significantly different dependences on the holding current $I_0$ for the electrically-($\Delta I_{electric}(t)$) and thermally-induced currents ($\Delta I_{thermal}(t)$), the total light-generated currents ($\Delta I_{light}(t)=\Delta I_{electric}(t)+\Delta I_{thermal}(t)$) can be potentially decoupled by analyzing current traces recorded at different holding levels.

At a given time point t during the light illumination period, the recorded current, $I_0+\Delta I_{light}(t)$, excluding the photoelectrically-induced current part $\Delta I_{electric}(t)$, and the pipette tip resistance R(t) follow the Ohm's law as long as the holding potential $V_p$ is fixed.

$$V_p = I_0 \times R_0 = (I_0 = \Delta I_{light}(t) \Delta I_{electric}(t)) \times R(t).$$

Rearranging Eq. 1 gives the relationship between the light-induced current $\Delta I_{light}(t)$ and the holding current $I_0$ that $$\Delta I_{light}(t) = \left(\frac{R_0}{R(t)} - 1\right) \times I_0 + \Delta I_{electric}(t).$$

As shown in Eq. 2, the photoelectric effect is explicitly manifested as the intercept of the curve. A photocurrent plot can be generated by plotting the fitted intercept values over time. Two types of photoelectric responses, i.e., capacitive and Faradaic, are further identified based on the dynamics and the amplitude of the currents. Two spiky features at the onset and offset of the light illumination are capacitive currents corresponding to the capacitive charging/discharging processes at the Si/electrolyte interface. A long-lasting current with a lower amplitude is the Faradaic current due to the surface redox reactions.

The photothermal effect, on the other hand, is implicitly embedded in the fitted slope as the pipette resistance is a function of temperature. To calculate the photothermally-induced temperature change of the surrounding medium, a calibration curve of the pipette resistance over temperature is needed, which typically follows an Arrhenius-type relationship that $$\ln R = a \times \frac{1}{T} + c$$

where a and c represent the slope and intercept values.

In conjunction with the slope k(t) from the $\Delta I_{light}$ (f)–$I_0$ plot that $$R(t) = \frac{R_0}{k(t) + 1},$$

the final temperature of the surround medium heated from the photothermal effect is determined only by the slopes of the $\Delta I_{light}(t)$–$I_0$ and the lnR–1/T curves that $$T(t) = \frac{1}{\frac{1}{T_0} - \frac{1}{a}\ln(k(t) + 1)}$$

Notably, since the photothermal effect is a function of the illumination duration, the slope of the $\Delta I_{light}(t)$–$I_0$ plot is also time dependent. The maximal temperature is reached after 10 ms of illumination so $\Delta I_{light,\ 10\ ms}$–$I_0$ plots were used to assess the photothermal responses of various Si materials presented. A temperature over time curve can also be generated using the fitted slope values from each time point.

In summary, the $\Delta I_{light,\ 10\ ms}$–$I_0$ plot method can be applied to virtually all kinds of materials other than just Si to assess their photo-responses, which will fall into the following four categories.

1) In one extreme case where the material has only the photothermal effect without any photoelectric effect, i.e., $\Delta I_{electric}=0$ at all time, Eq. 2 will be reduced to $$\Delta I_{light,10ms} = \left(\frac{R_0}{R_{10ms}} - 1\right) \times I_0$$

The $\Delta I_{light,\ 10\ ms}$–$I_0$ plot will be a slanted line with a zero intercept.

2) In another extreme scenario where the material has only the photoelectric effect without any photothermal effect, i.e., $R_0=R_{10\ ms}$, Eq. 2 can be written as $$\Delta I_{light,\ 10\ ms} = \Delta I_{electric,\ 10\ ms}.$$

The $\Delta I_{light,\ 10\ ms}$–$I_0$ plot will be a horizontal line with a non-zero intercept.

3) If a material does not have any photo-responses, Eq. 2 will be $$\Delta I_{light,\ 10\ ms} = 0.$$

The $\Delta I_{light,\ 10\ ms}$–$I_0$ plot will be a horizontal line with a zero intercept.

4) In any intermediate situations where both the photoelectric and the photothermal effects coexist, the original form of Eq. 2 applies that $$\Delta I_{light,10ms} = \left(\frac{R_0}{R_{10ms}} - 1\right) \times I_0 + \Delta I_{electric,10ms}$$

The $\Delta I_{light,\ 10\ ms}$–$I_0$ plot will be a slanted line with a non-zero intercept.

The Principle of Biology-Guided Biointerface Design

Figure 22:
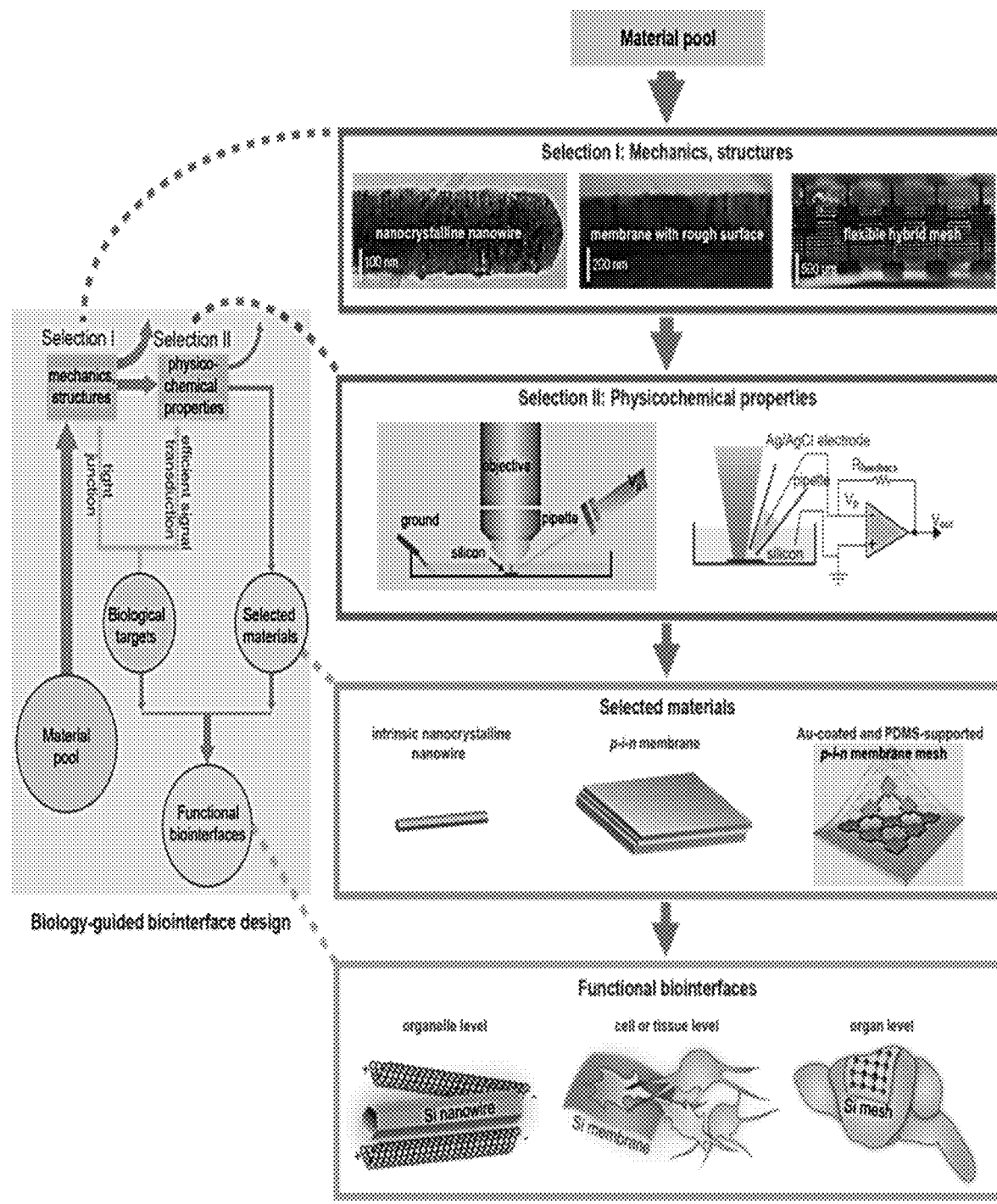
FIG. 22 shows a schematic diagram of the rational design of Si structures for optically-controlled biointerfaces, and a biology-guided design principle that is based on the structures and mechanics (Selection I) and the photo-responses (Selection II) of various Si materials. The Selection I yields nanocrystalline nanowires (for the organelle level interface), membranes with rough surfaces (for the cell and tissue level interface), and flexible and distributed meshes (for the organ level interface) where at least one dimension of the material properties can be tuned to promote tight interfaces. Selection II examines the effects of other orthogonal controls of Si (e.g., size, doping, surface chemistry) for desirable physicochemical processes at the biointerfaces. These two Selections highlight nano-confinement-enabled thermal responses from nanocrystalline nanowires, p-i-n diode junction-enhanced capacitive currents, and metal-enhanced capacitive and Faradaic currents, all in freestanding configurations (Selected materials). In consideration of the materials structures, mechanics, and photo-responses, intrinsic nanocrystalline Si nanowires were the focus for intracellular and the related intercellular probing, and used only the photothermal effect. For single cell or small tissue level inter- and extracellular studies, a light-induced capacitive effect was explored, i.e., a p-i-n Si multilayered membrane was used, where the biological invasiveness from capacitive electrochemical currents are usually minimal. Finally, given that the biological organization at the organ level is very complex, Au-coated Si diode junctions were used for in vivo studies (Functional biointerfaces).

Si-based "bio-tronics" structures with length scales from nanometer to centimeter, which establish intra-, inter- and extracellular biointerfaces, are disclosed. The rationale for development follows this order (FIG. 22). First, a biology-guided Si-based biomaterial design was introduce, which first considers the material structures and mechanics and then the efficient signal transductions at the Si surfaces in saline. Next, three classes of materials were used for establishing biointerfaces across different length scales. Finally, the utility of these new devices was demonstrated by showing light-controlled non-genetic modulations of intracellular calcium dynamics, cytoskeleton-based transport and structures, cellular excitability, neurotransmitter release from brain slices, and brain activities in a mouse model.

Figure 23:
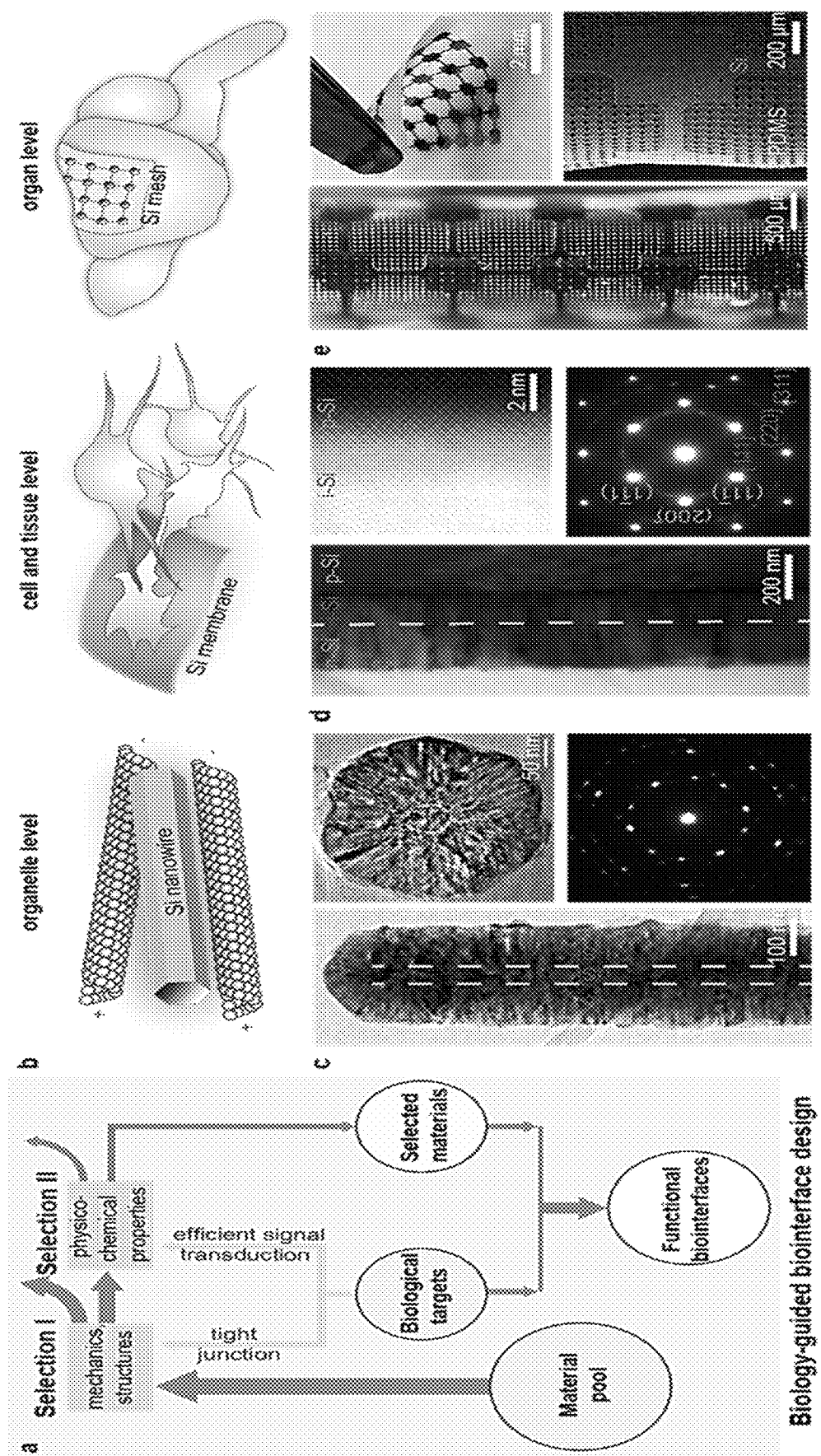
FIG. 23 illustrates Si structures for multiscale biointerfaces. (A) A schematic diagram illustrating the principle of biology-guided biointerface design. The intended biological targets place selection criteria for material structure (I) and function (II), so that the selected materials would display a better chance to establish functional biointerfaces. (B), Silicon-based materials, e.g., nanowires (left), thin membranes (middle), and distributed meshes (right), are chosen after Selection I to form tight interfaces with various biological targets, spanning multiple length scales, e.g., organelles (left), single cells or small tissues (middle), and organs (right). (C) An intrinsic-intrinsic coaxial Si nanowire is synthesized from the deposition of a thick shell over a thin VLS-grown nanowire backbone as shown in a side-view TEM image (left). A cross-sectional TEM image (upper right) shows diameters of ~50 nm and ~270 nm for the core and shell, respectively. A corresponding SAED pattern (lower right) confirms the nanocrystalline structure. Dashed lines highlight the core/shell boundaries. (D) A multilayered p-i-n Si diode junction made by a CVD synthesis of intrinsic and n-type Si layers onto a p-type Si SOI substrate. A cross-sectional TEM image (left) shows the columnar structures of the intrinsic and n-type layers. A low-angle annular dark field scanning TEM (LAADF STEM) image (upper right) and a SAED (zone axis B=[011], lower right) pattern taken at the p-type/intrinsic interface both highlight the single crystalline p-type layer (isolated spots from SAED, periodic atomic columns from STEM) and the nanocrystalline intrinsic layer (concentric rings) from SAED, small crystal domains from STEM). A sharp and oxide free interface is evident from the STEM image with a junction width of <1 nm. Dashed lines mark the intrinsic/n-type (left) and the p-type/intrinsic (upper right) interfaces. (E) A flexible device composed of a stack of a distributed Si mesh and a holey Polydimethylsiloxane (PDMS) membrane. The flexibility is demonstrated by optical (left) and scanning electron (lower right) micrographs and a photograph (upper right) taken from the same device under rolling or bending.

Si displays many size- and doping-dependent physico-chemical processes. To efficiently leverage these processes in the context of biointerfaces, the Si-based materials or devices should be in tight contact (FIG. 23A, Selection I) with their biological counterparts. Such tight interfaces can be established by protein-associated tethering and active motions at the organelle level, by dynamic cellular focal adhesions at the single cell and tissue level, and van der Waals forces at the organ level. To promote these forces, Si materials were focused on nanowire geometries (at the organelle level), membranes with rough surfaces (at the cell and tissue level), and flexible and distributed meshes (at the organ level), where at least one dimension of the material properties can be tuned to promote tight interfaces (FIG. 23B). After the material/device structures are determined, the effects of other orthogonal controls (e.g., size, doping, surface chemistry) to produce the desirable physicochemical processes (FIG. 23B, Selection II) at the biointerfaces were examined. These two-step selections, guided by the need to form tight junctions (Selection I) and efficient signal transductions (Selection II) with the biological targets, would narrow the material options to those that are better suited for the targeted biophysical or biomedical questions.

Selection I for Material Structures

For example, to enable intracellular biointerfaces, Si nanowires were chosen. Additionally, to promote light absorption from single nanowire structures, nanocrystalline Si shells were deposited over a thin, vapor-liquid-solid (VLS) grown Si nanowire backbone (~50 nm in diameter)

(FIG. 23C, left and upper right). Cross-sectional and side-view TEM images reveal that >95% of the total volume is nanocrystalline (FIG. 23C, lower right).

Figure 24:
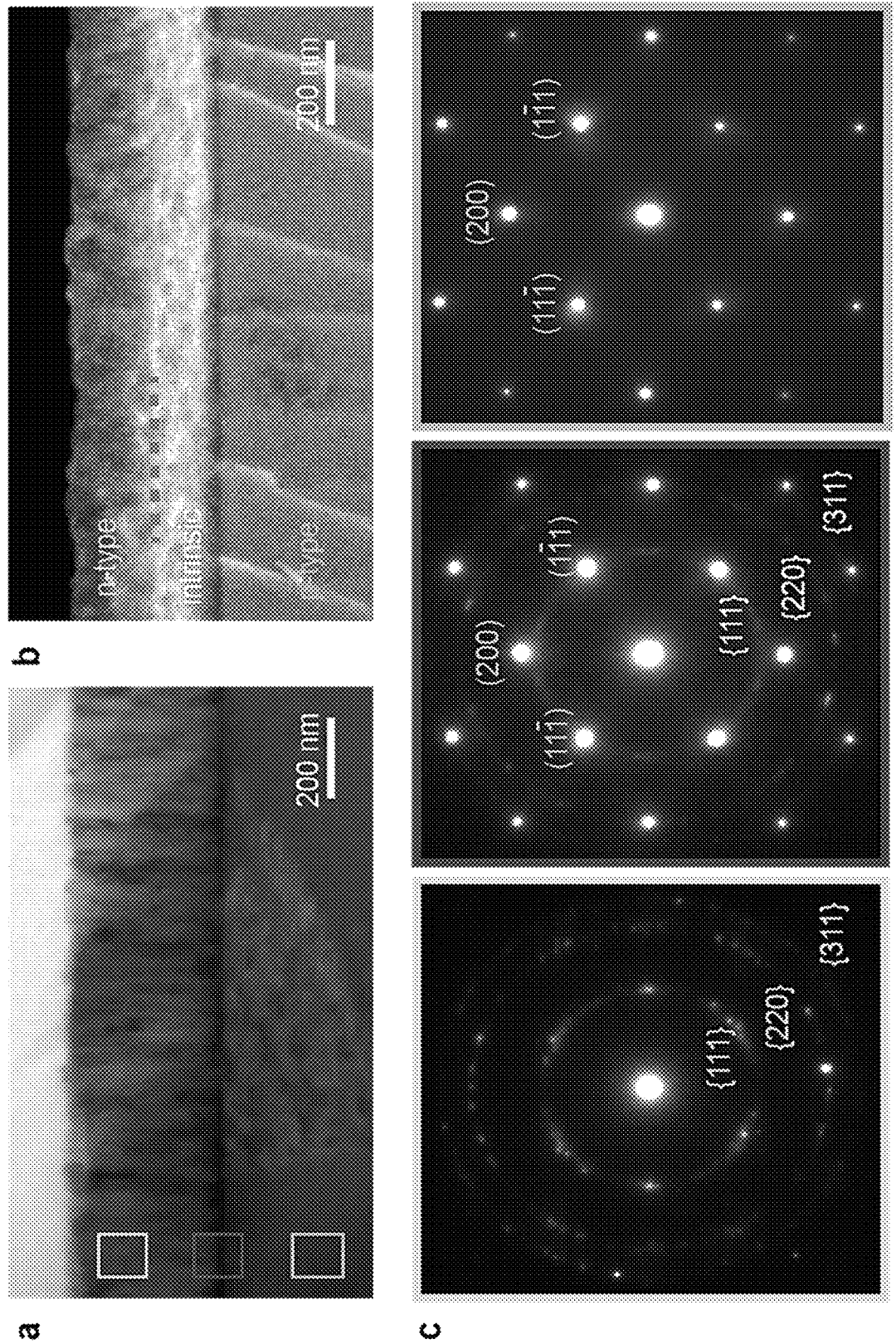
FIG. 24 provides cross-sectional views of the p-i-n Si diode junction. a, A TEM image showing the columnar structure of the intrinsic and n-type layers grown on the p-type substrate. Boxes (n-type Si; p-type/intrinsic interface; p-type Si) denote the regions for SAED in c. (B) A SEM image showing the thicknesses of both the intrinsic (white) and n-type layers. The sample was prepared by the etching of a p-i-n diode junction in a 20% (w/v) potassium hydroxide (KOH) aqueous solution at 60° C. for 10 s. The dashed line highlights the intrinsic/n-type interface. c, SAED patterns taken from the [011] zone axis showing the transition of crystallinity from the [100]-oriented single crystalline p-type substrate (isolated spots with labels) to the nanocrystalline intrinsic (concentric rings with white labels) and n-type (concentric rings with labels) layers with grain boundaries roughly aligned with the direction.
Figure 25:
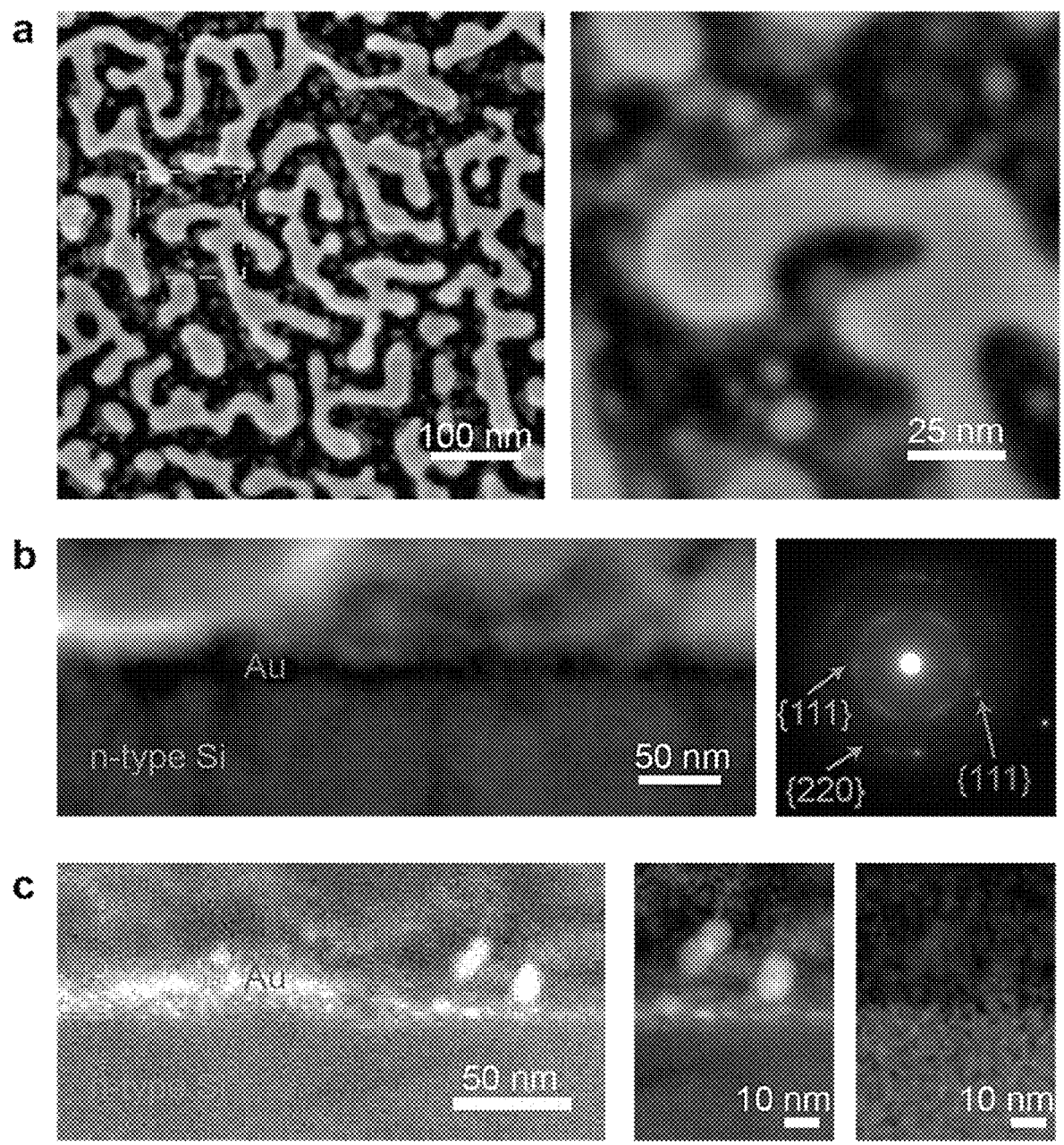
FIG. 25 provides structural characterizations of the gold-decorated p-i-n diode junction. (A) Top-view SEM images showing the interconnected meshes made of gold. The box in the left image highlights the region for a zoom-in view (right), and shows the coexistence of small nanoparticles together with the large meshes. (B) A cross-sectional bright field TEM image (left) taken at the Au—Si interface where Au appears to be dark. A SAED pattern (right) shows the diffraction features from both Si and Au. (C) A high-angle annular dark field (HAADF) STEM image (left) taken at the Au—Si interface where Au has a higher contrast than Si. A zoom-in view (middle) and its corresponding XEDS map (right, Au M series; Si K series) highlights the sharp interface. The existence of small Au nanoparticles right at the interface allows potential charge transfer pathways between Si and Au to promote the photoelectric responses.
Figure 26:
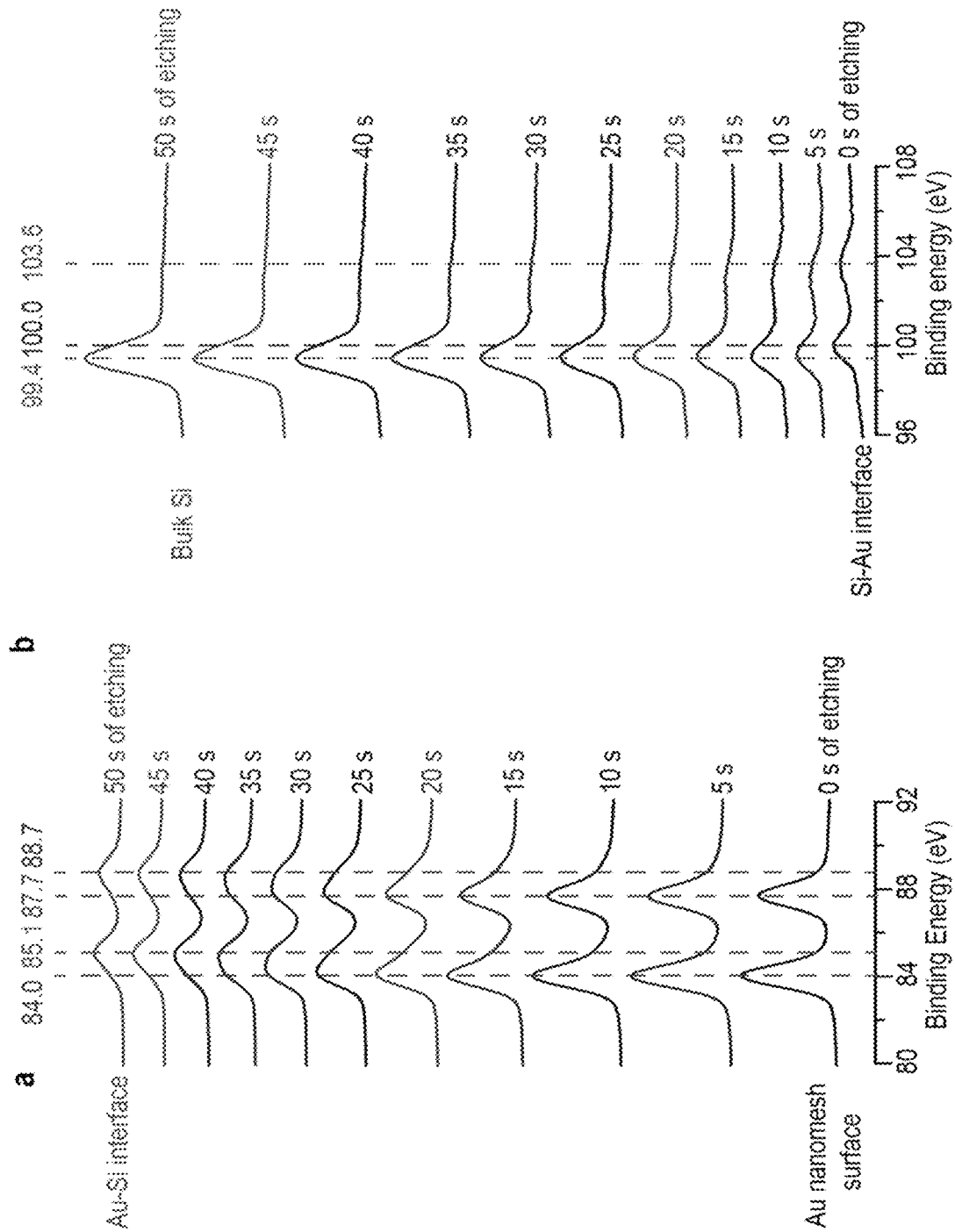
FIG. 26 provides XPS depth profiles suggesting the formation of Au—Si bonds at the interface. (A) XPS spectra of Au taken at different depths from the surface of Au nanoparticles/nanomeshes to the interface between Au and Si. Controlled Ar plasma etchings were employed to provide the depth profiles. The shift of binding energy peaks from metallic Au (84.0 eV of 4f 7/2 and 87.7 eV of 4f 5/2) to intermetallic Au (85.1 eV of 4f 7/2 and 88.7 eV of 4f 5/2) indicates the existence of Au—Si compound at the interface. (B) XPS spectra of Si taken at different depths from the interface between Au and Si to the bulk Si. The facts that the $Si^{4+}$ 2p peak at 103.6 eV diminishes and the $Si^{0}$ 2p peak shifts from 100 eV to 99.4 eV as Si is being etched both suggest the existence of oxidized form of Si at the Au—Si interface.
Figure 27:
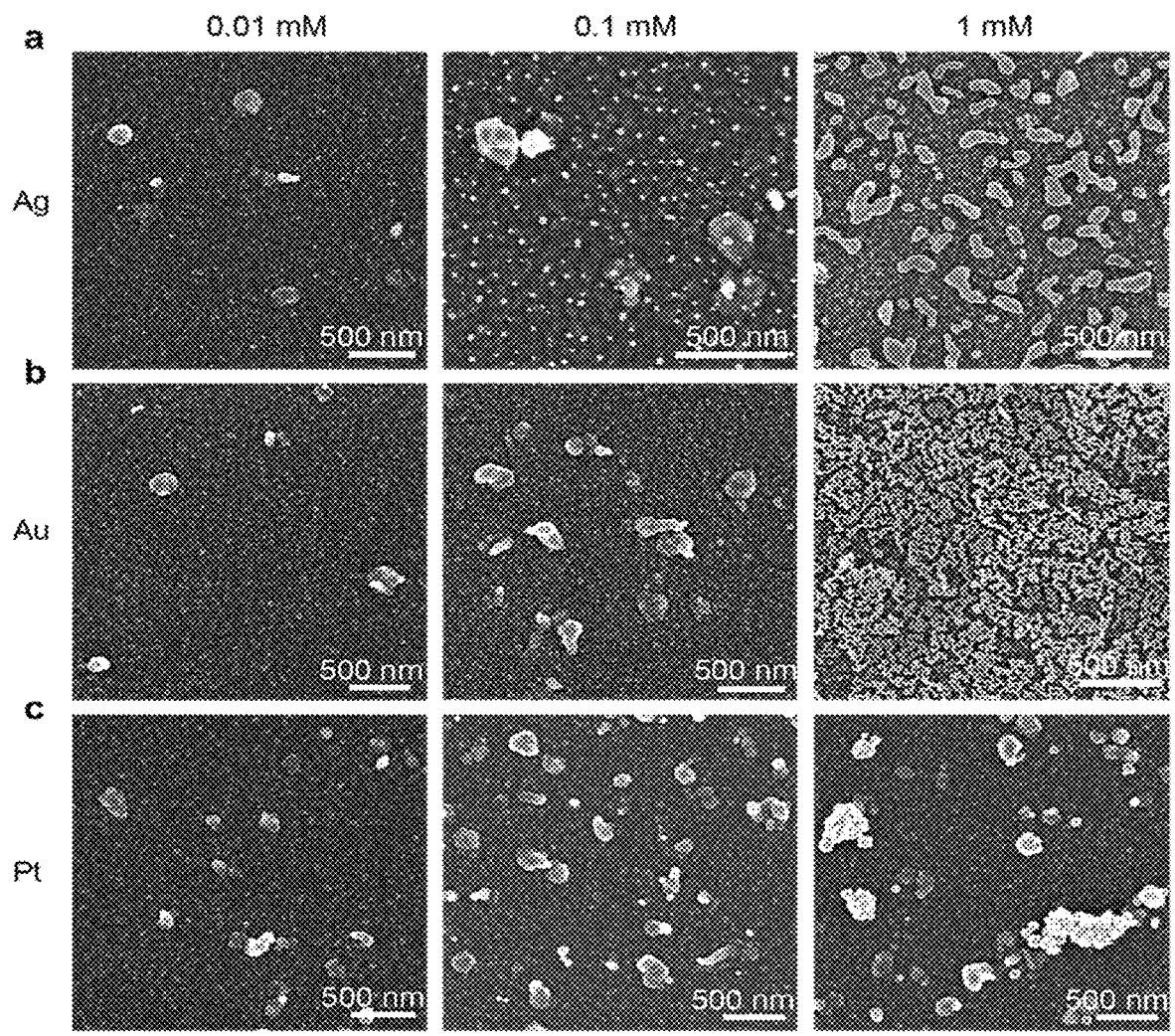
FIG. 27 provides SEM images of various metal-decorated p-i-n junctions (Ag, Au, and Pt) prepared from aqueous precursors of different concentrations (0.01, 0.1, 1 mM). In general, higher concentration of precursors lead to higher surface coverages and/or larger particle sizes.

To build extracellular interfaces with single cells or small tissues, planar Si structures with uniformly doped or dopant modulated configurations were examined to identify the effect of doping. In particular, a p-type/intrinsic/n-type (p-i-n or PIN) Si diode junction was synthesized by chemical vapor deposition (CVD) of intrinsic and n-type Si layers (~140 and ~190 nm in thickness, respectively) over a p-type Si semiconductor-on-insulator (SOI) substrate (p-type Si thickness, ~2 μm) (FIG. 24). Cross-sectional (scanning) transmission electron microscope (TEM) images taken at the interface between the SOI wafer and the as-deposited layers indicate a columnar shell structure with a sharp and oxide-free interface (<1 nm junction width) (FIG. 23D, left and upper right). While the p-type substrate is single crystalline, the i-In-layers are nanocrystalline (FIG. 23D, lower right; FIG. 24), which is reminiscent of the Si nanostructures used for thin film solar cells. The surface of the nanocrystalline layer is rough, which would promote cellular focal adhesions. Beyond doping controls, metal (i.e., gold, silver, and platinum) nanoparticle-covered Si diode junctions were also prepared by electroless deposition in order to expand the repertoire of Si-based biointerfaces (FIG. 25, FIG. 26, FIG. 27).

Figure 28:
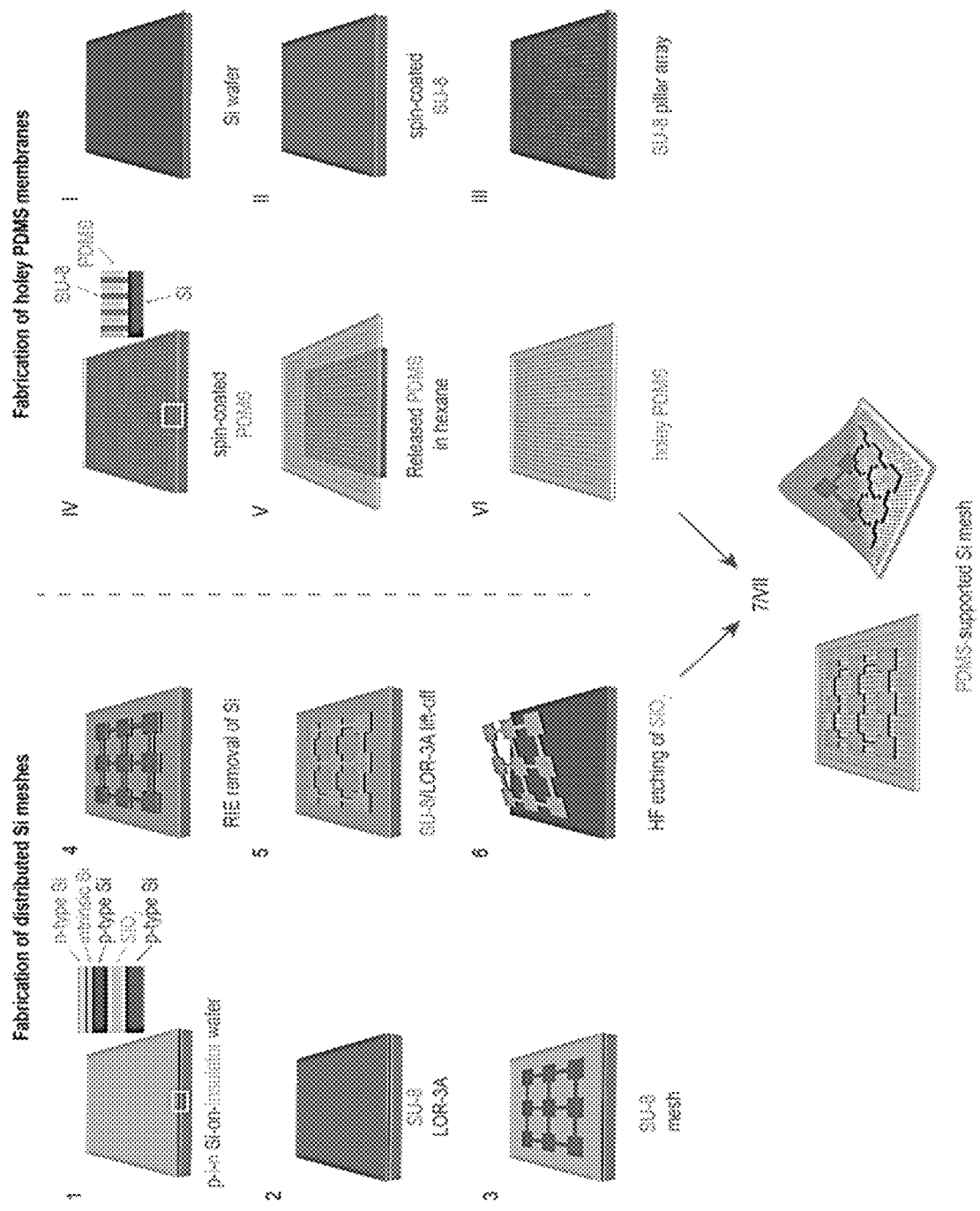
FIG. 28 shows schematic diagrams illustrating the fabrication procedures of the flexible device made of PDMS and Si. (1-6) Fabrication of the distributed Si mesh by a combination of photolithography, reactive ion etching, and wet etching processes. (I-VI) Fabrication of the holey PDMS membrane with the soft lithography technique. (7/VII) Transfer of the Si mesh onto the PDMS membrane for the final device.
Figure 29:
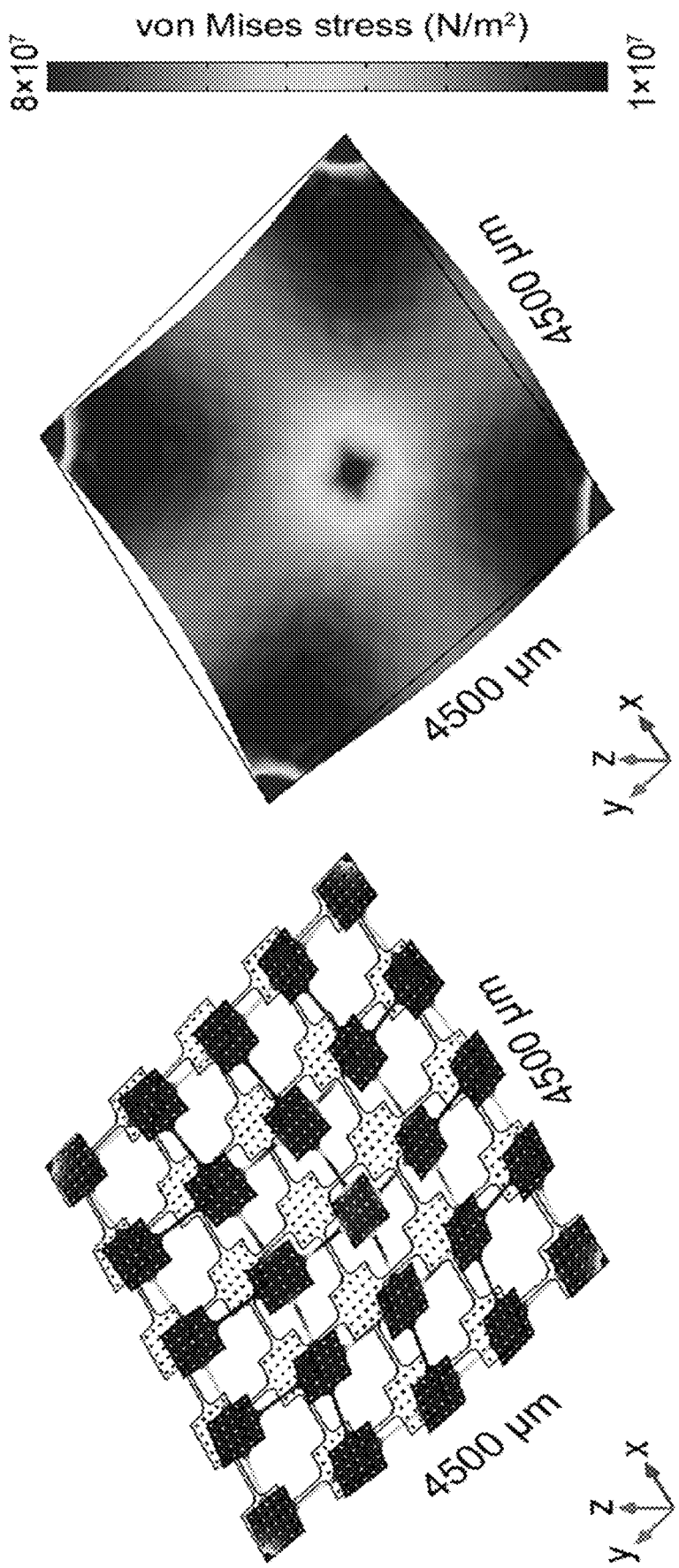
FIG. 29 illustrates a finite element analysis of the von Mises stress distributions in a distributed Si mesh (left) and a solid Si membrane (right) upon indentation. The Si mesh with the holey structure shows a more uniform stress distribution across individual Si pads, suggesting a potentially more consistent optical stimulation performance in different locations. For the solid Si membrane, a large stress variation was observed, suggesting performance heterogeneity. Additionally, the relaxed stress in the distributed mesh suggests a better mechanical stability during the device assembly and operation.

Finally, to create a conformal interface with a soft and curvilinear organ, e.g., a mouse brain cortex, a flexible device made of a distributed mesh of Si membrane (~2.3 μm in thickness) and a porous polydimethylsiloxane (PDMS) substrate (~120 μm in thickness) were prepared (FIG. 23E; FIG. 28). The holey structures in both Si and PDMS can mitigate the stress accumulated across a large device area (FIG. 29), and enhance the device mechanical compliance.

Selection II for Material Functions

Figure 30:
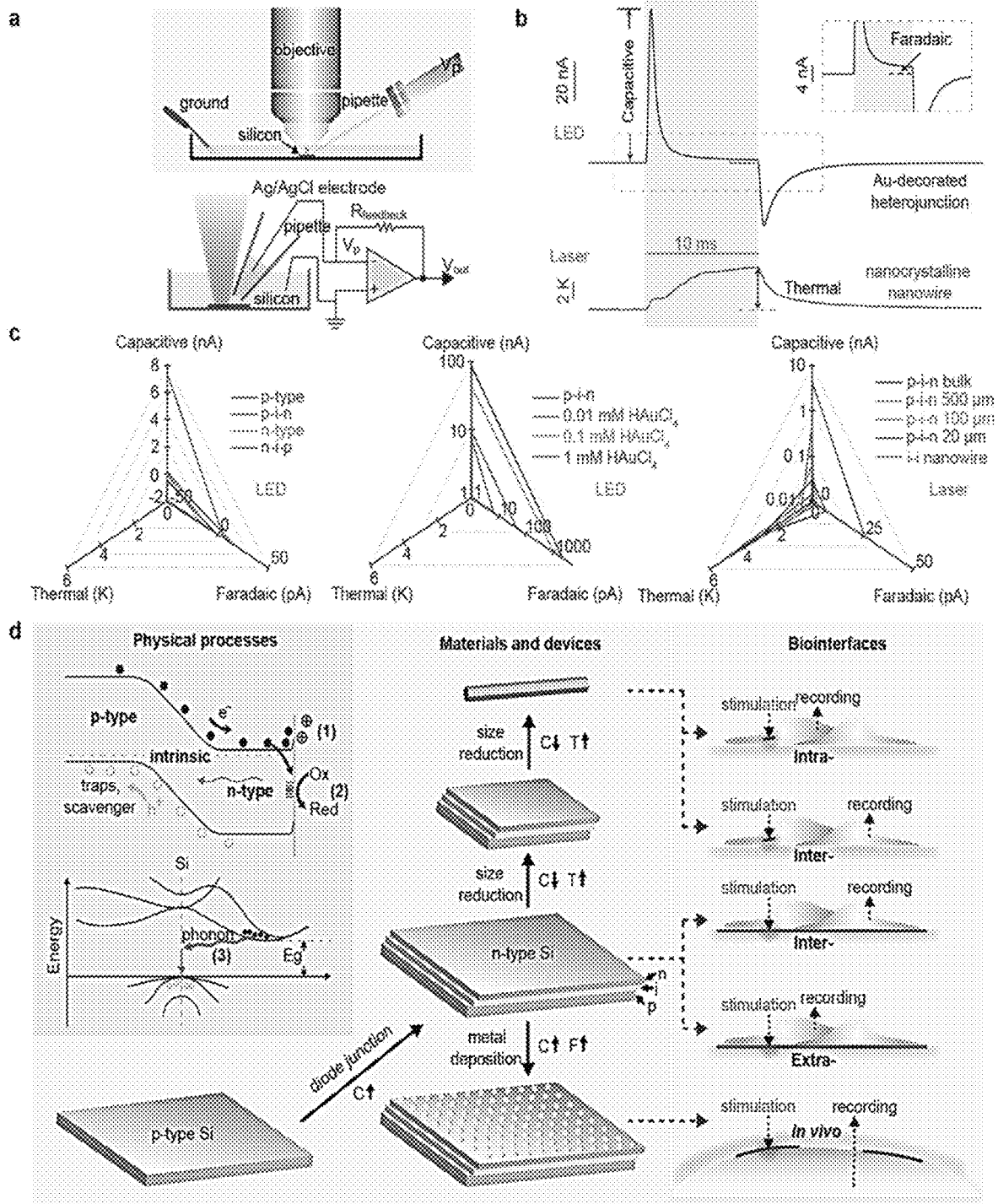
FIG. 30 provides schematic diagrams of the photo-responses of Si materials. (A) Schematic diagrams illustrating the experimental setup for the photo-response measurements from Si structures. Light pulses (530 nm LED or 532 nm laser) are delivered through a water-immersion objective to the Si submerged in a PBS solution. Light-induced currents are recorded at different pipette command potentials ($V_p$) using a voltage-clamp mode, from which capacitive, Faradaic and thermal components can be either directly measured or derived by mathematic fitting. (B) Representative photo-responses of an Au-decorated p-i-n Si diode junction (top, from 1 mM $HAuCl_4$, LED illumination, ~12.05 mW, ~500 μm spot size, ~6 W/cm$^2$) and an i-i nanocrystalline nanowire (bottom, laser illumination, 47.1 mW, ~5 μm spot size, ~240 kW/cm$^2$) showing three major types of the responses, i.e., capacitive (upper), Faradaic (upper inset), and thermal (lower). LED-induced capacitive and Faradaic currents are pronounced in the Au-decorated diode junction. The capacitive current is defined as the maximal current amplitude reached after the light onset while the Faradaic current is defined as the current amplitude at the time point of 8.5 ms since illumination starts. The nanocrystalline nanowire generate significant heating of the surrounding PBS via its photothermal effect under laser illumination. Shaded areas highlight the light illumination periods. The dashed box marks the region for the inset. (C) Quantitative matrices of the three photo-responses, used to evaluate the impact of important materials parameters, e.g., doping (left), surface chemistry (middle), and size (right). Diode junctions (left, p-i-n and n-i-p) show significantly enhanced capacitive currents versus uniformly doped SOI substrates (p-type and n-type). Au-decorated p-i-n diode junctions (middle) promote both capacitive and Faradaic currents. Si structures with smaller dimensions (right) show stronger photothermal responses. (D) A principle for Selection II (FIG. 23A), highlighting the physical origins, the material developing pathways, and the projected biointerfaces. Fundamental processes include the accumulation of ions to balance light-generated excessive carriers near Si surface (1, capacitive, C), the metal-mediated redox reactions (2, Faradaic, F), and the thermalization through phonon emission (3, thermal, T). Considering the size and mechanics match at the biointerfaces (i.e., Selection I, FIG. 23A), these Si structures can be utilized to form optically-controlled intra-(Si nanowires), inter-(Si nanowires and p-i-n diode junctions), and extracellular (pristine and metal-decorated p-i-n diode junctions) biointerfaces.
Figure 31:
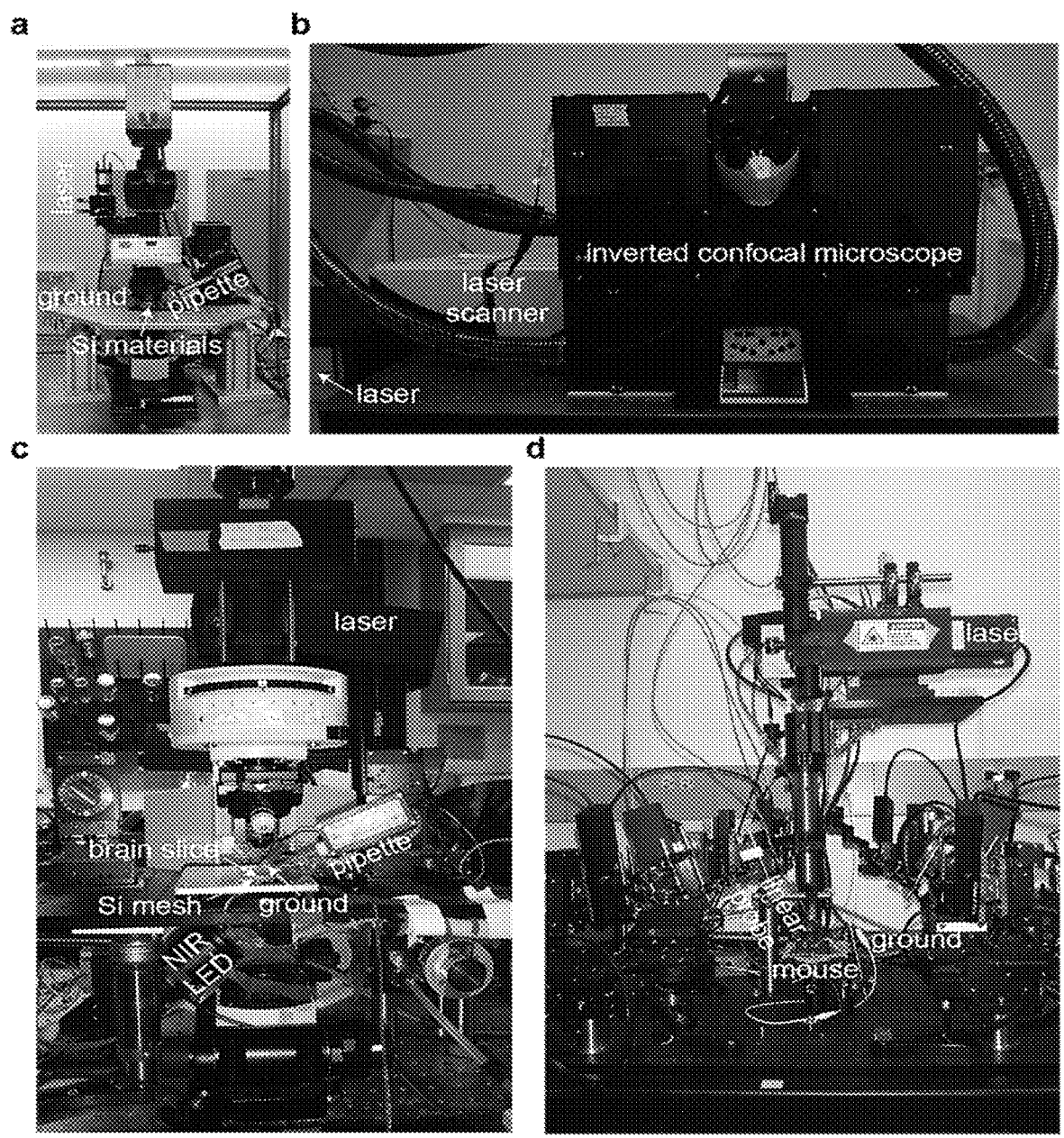
FIG. 31 provides photographs of experimental setups. (A) Photo-response measurements were performed on an upright microscope equipped with a patch-clamp setup and additional light sources of a green laser and a green LED. (B) Intra- and extracellular photostimulation experiments were done using a commercial inverted confocal microscope. The stimulation protocols were conducted in the photo-bleach module. (C) Brain slice photostimulation experiments were conducted on an upright microscope with a patch clamp setup, equipped with near infrared (NIR) illumination for patching and a blue laser for stimulation. (D) In vivo photostimulation was carried out on a custom-built apparatus combining a laser scanning system for photostimulation and an electrophysiological recording system using linear array electrodes.

Given that cellular physiology can be altered with a ~pA level ionic current, a high-precision electrochemical tool, i.e., a patch-clamp setup, was next utilized to investigate the light-induced and biointerface-relevant physicochemical processes (FIG. 23A, Selection II; FIG. 30) that originated from the freestanding Si surfaces. Briefly, different types of Si materials (e.g., nanocrystalline nanowires, and dopant-modulated, surface-treated and size-tuned nano-membranes, as selected from the first step) were immersed into a phosphate-buffered saline solution, and positioned glass micropipette electrodes in close proximity to the Si surfaces (~2 μm) where ionic flows across the pipette tips were measured in the voltage-clamp mode (FIG. 30A, upper; FIG. 31A). Specifically, light pulses (530 nm light-emitting diode (LED) or 532 nm laser, 10 ms) were delivered through a microscope objective to illuminate Si and recorded the ionic current dynamics under different pipette holding potentials (FIG. 30A, lower; Methods).

Using pulsed light illuminations, a universal analysis (Methods, "Analysis of the photo-response measurements") was developed and unambiguously identified and mostly importantly, decoupled two explicit and one implicit element of the photo-responses (FIG. 30B-C). In a representative trial from an Au-decorated p-i-n Si membrane (FIG. 30B, upper), two 'spiky' features under a LED light pulse (~12.05 mW, ~500 μm spot size) with a power density of ~6 W/cm$^2$ were first noticed. The upward (~86 nA, with a transient peak current density at the pipette tip of ~2700 mA/cm$^2$) and downward (~-34 nA, transient current density of ~1100 mA/cm$^2$) components correspond to capacitive charging/discharging processes at the Si/electrolyte interface (FIG. 30D, upper left, 1). The second photo-response element is manifested as a long-lasting current with a lower amplitude (e.g., ~2 nA for the same Au-decorated Si membrane) (FIG. 30B, upper inset), which is indicative of a Faradaic current leading to redox reactions (FIG. 30D, upper left, 2). Metal-free p-i-n Si membranes only display symmetrical capacitive current spikes (FIG. 32), with negligible Faradaic components detected from the local patch-clamp electrode. The last photo-response element is implicit and it corresponds to the local temperature elevation of the solution due to the photothermal effect from Si. In this scenario, the recombination of carriers converts part of the input photon energy into the vibrational energy of the Si lattice (FIG. 30D, lower left, 3), which dissipates heat through both Si and the surrounding electrolyte. Because the glass micropipette resistance is temperature-dependent, the thermal dynamics was determined by fitting the recorded patch-clamp currents at various holding potentials (Methods). For example, a ~5.4 K peak temperature rise from a nanocrystalline Si nanowire upon laser illumination (~47.1 mW, ~5 μm spot size) was recorded at ~240 kW/cm$^2$ for 10 ms (FIG. 30B, lower).

Figure 32:
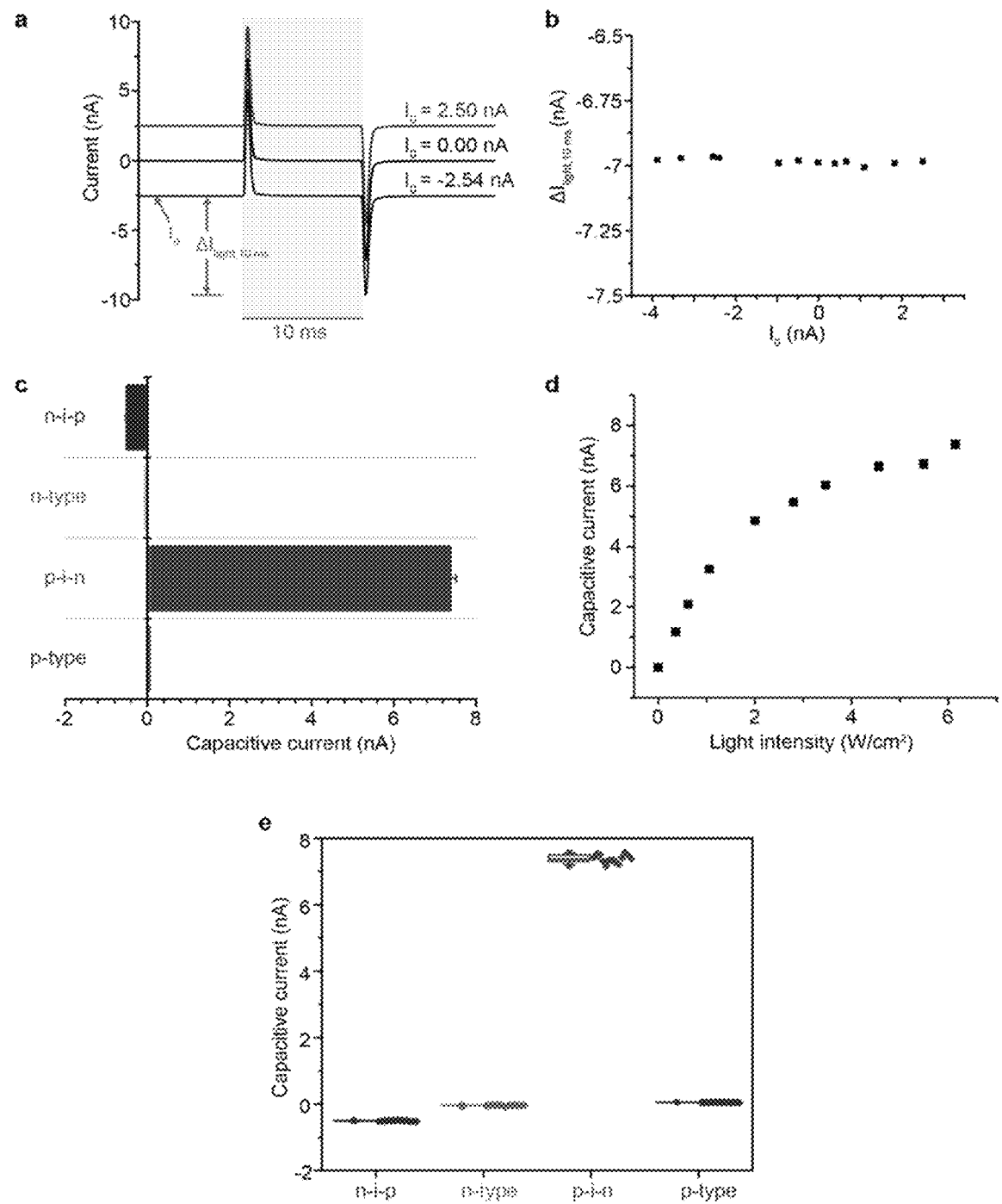
FIG. 32 illustrates photo-responses of dopant modulated Si structures. (A) Representative current traces recorded from a p-i-n diode junction under LED pulses (530 nm, 10 ms, ~12.05 mW, ~500 μm spot size, ~6 W/cm$^2$), showing strong capacitive currents and minimal Faradaic currents. $I_0$ is defined as the baseline holding level before the light illumination. $\Delta I_{light,\ 10\ ms}$ is defined as the maximal relative current amplitude after 10 ms of light illumination with respect to $I_0$. The shaded area marks the light illumination period. (B) The $\Delta I_{light,\ 10\ ms}$–$I_0$ plot shows a negligible slope and a prominent intercept indicating strong photoelectric and weak photothermal responses. (C) Statistical analyses of capacitive currents from different types of Si structures highlight the importance of dopant modulations. Both p-i-n and n-i-p diode junctions show significantly enhanced capacitive currents comparing to uniformly doped p-type and n-type Si. The polarities of the capacitive currents are opposite for Si with reversed doping profiles. Error bars denote standard deviations. (D) The amplitude for the capacitive current of a p-i-n diode junction can be monotonically tuned by the light intensity. Error bars denote standard deviations. (E) Box-and-whisker plots and raw data points of the capacitive currents as shown in (C) Half of the data points are within the boxes, 80% are within the whiskers. Solid and dashed lines represent the medians and means, respectively. Round dots mark the maximum and minimum values. Diamond dots represent the raw data points. n=13 for n-i-p, n=17 for n-type, n=13 for p-i-n, n=16 for p-type.
Figure 33:
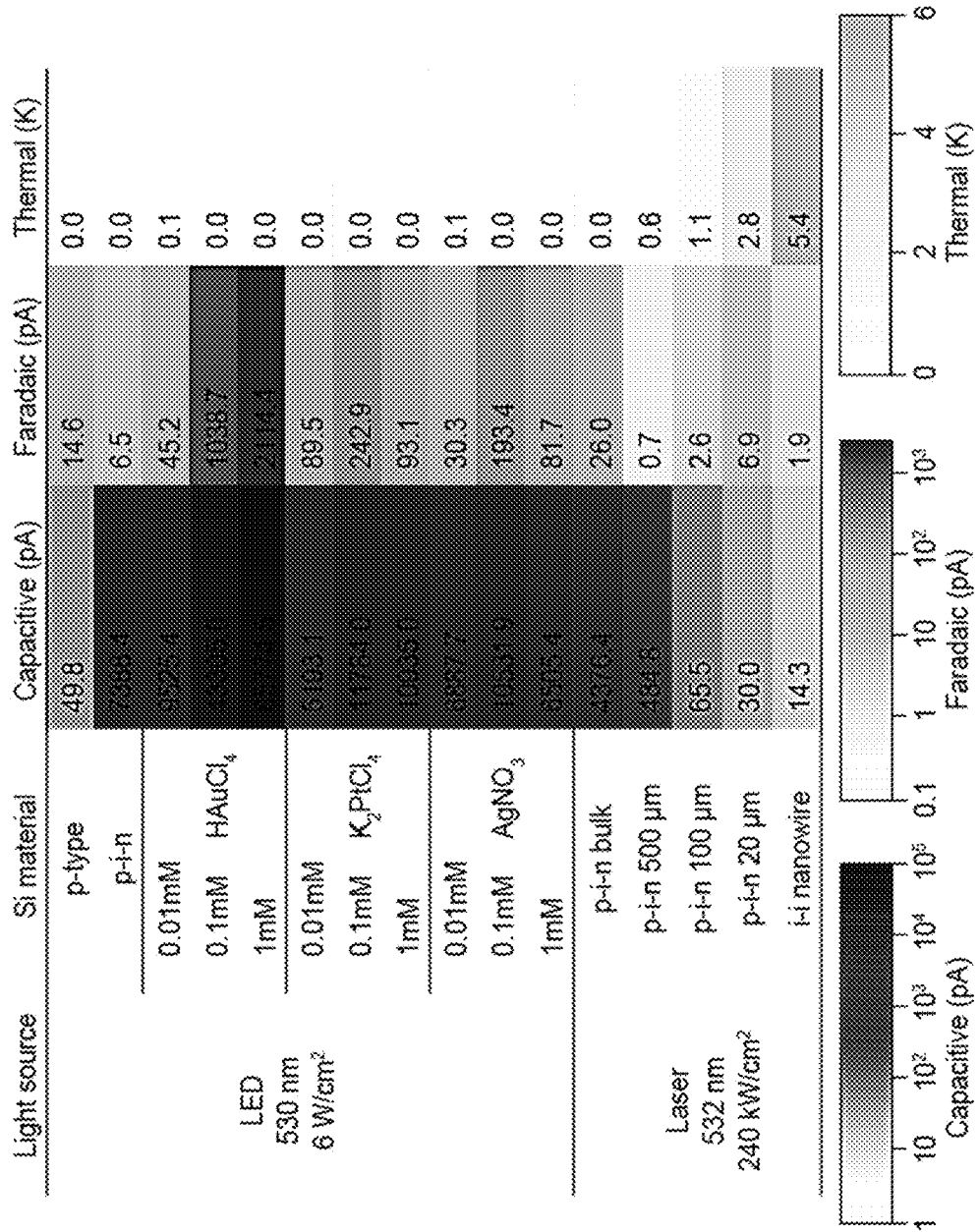
FIG. 33 provides a summary of individual photo-responses from 16 selected Si structures. A p-i-n diode junction promotes the capacitive current over a uniformly doped p-type Si. Metal decorations on the diode junction further enhance the capacitive current, and more importantly, increase the proportion of Faradaic component. Laser illumination on Si materials with smaller dimensions yields stronger photothermal responses. The LED illumination condition: ~12.05 mW, ~500 µm spot size, ~6 W/cm$^2$; the laser illumination condition: ~47.1 mW, ~5 µm spot size, ~240 kW/cm$^2$. Pipette-Si distance~2 µm.
Figure 34:
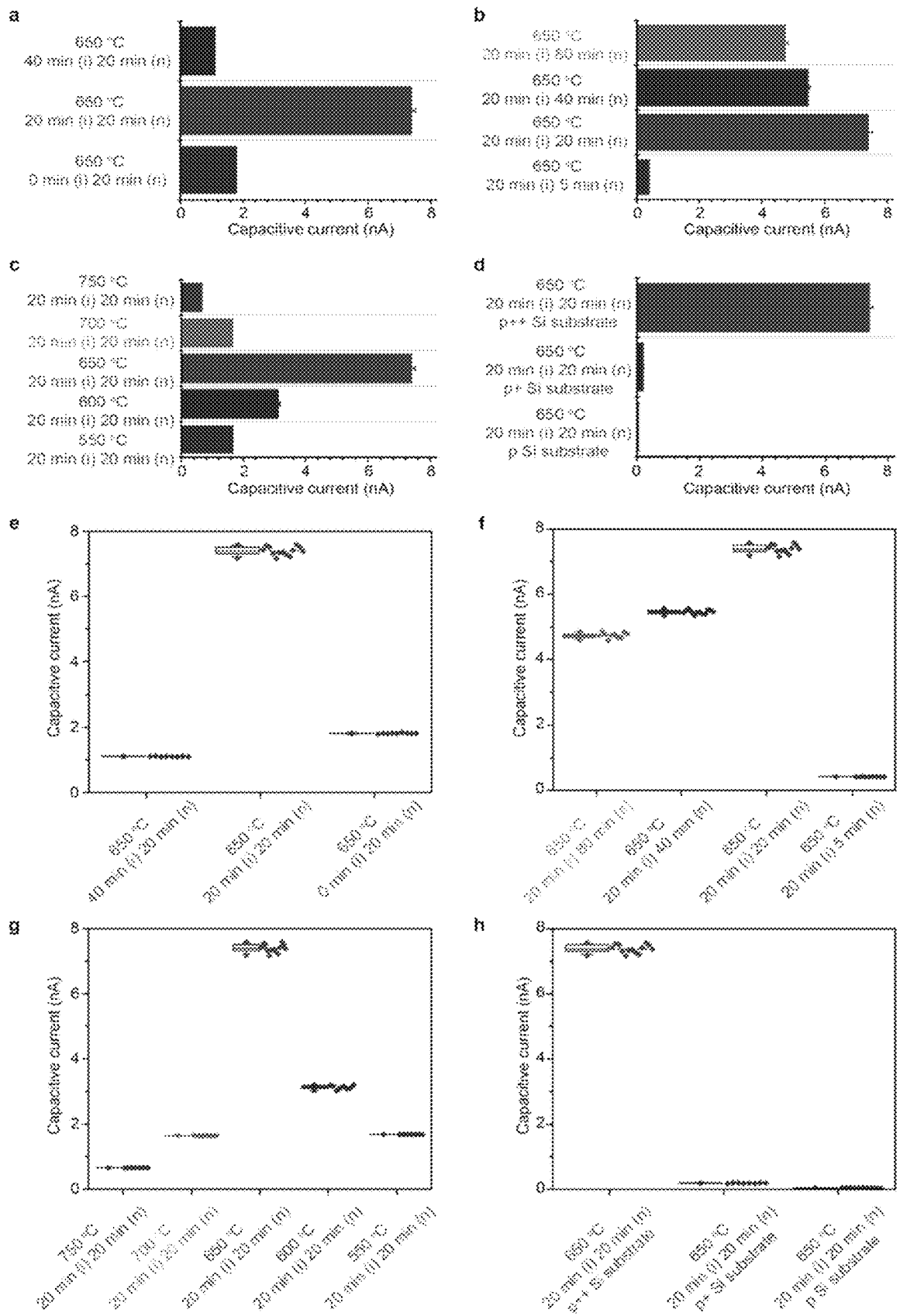
FIG. 34 shows growth condition optimizations of the p-i-n diode junction synthesis. Systematic studies of the intrinsic (A) and the n-type layer (B) deposition time and the growth temperature (C) indicate that an optimal value of the capacitive current can be achieved with a deposition temperature of 650° C. and a duration of 20 min for each of the intrinsic and the n-type layers. (D) A heavily-doped p$^{++}$ Si substrate, rather than p$^+$ or p substrates, yields a higher capacitive current after the formation of a p-i-n diode junction. Error bars denote standard deviations. (E-H) Box-and-whisker plots and raw data points of the capacitive currents as shown in (A-D). Half of the data points are within the boxes, 80% are within the whiskers. Solid and dashed lines represent the medians and means, respectively. Round dots mark the maximum and minimum values. Diamond dots represent the raw data points. In e, n=8 for 650° C. 40 min (i) 20 min (n), n=13 for 650° C. 20 min (i) 20 min (n), n=9 for 650° C. 0 min (i) 20 min (n). In (F), n=10 for 650° C. 20 min (i) 80 min (n), n=12 for 650° C. 20 min (i) 40 min (n), n=13 for 650° C. 20 min (i) 20 min (n), n=9 for 650° C. 20 min (i) 5 min (n). In (G), n=10 for 750° C. 20 min (i) 20 min (n), n=9 for 700° C. 20 min (i) 20 min (n), n=13 for 650° C. 20 min (i) 20 min (n), n=8 for 600° C. 20 min (i) 20 min (n), n=9 for 550° C. 20 min (i) 20 min (n). In (H), n=13 for 650° C. 20 min (i) 20 min (n) p$^{++}$ Si substrate, n=8 for 650° C. 20 min (i) 20 min (n) p$^+$ Si substrate, n=10 for 650° C. 20 min (i) 20 min (n) p Si substrate.

To build quantitative matrices for these three photo-response elements, a library of Si-based materials was screened to evaluate the impact of doping, surface chemistry and size (FIG. 33). The capacitive, Faradaic, and thermal components were extracted from the patch-clamp recordings of 16 representative Si samples (FIG. 33), and projected them onto three axes to decouple any individual contributions (FIG. 30C). The simplest single-crystalline p-type Si SOI substrate (device layer thickness: ~2 μm) was first considered (FIG. 30C, left). A typical experiment (LED illumination, ~12.05 mW, ~500 μm spot size, ~6 W/cm$^2$) shows a small capacitive current of ~50 pA, and a transient peak current density of ~1.6 mA/cm$^2$ at the pipette tip. However, upon deposition of the intrinsic and n-type layers (i.e., forming a p-i-n diode junction) (FIG. 32, FIG. 34), the recorded capacitive current and transient peak current density were boosted to ~7400 pA and ~235 mA/cm$^2$, respectively (FIG. 30C, left; FIG. 32, FIG. 34). This significant enhancement in the capacitive component is likely due to the enhanced light absorption from the nanocrystalline layers and more efficient charge separation by the built-in electric fields across the p-i-n diode junction (FIG. 30D, upper left). The polarity of the capacitive currents (i.e., upward at the onset of light illumination; downward at offset) in both cases stays cathodic, although the dopant types of the electrolyte-interfacing layers are different (p– in p-type SOI device layer, and n– in p-i-n multilayers). This suggests that the primary light-generated carriers accumulated on the Si surfaces are electrons, which are the minority carriers in p-type SOI and the majority carriers in the p-i-n samples, respectively. This observation is similar to the device configurations used in traditional photoelectrochemical devices, i.e., p-type semiconductors in contact with electrolytes would experience the band bending in such a manner that drives photogenerated electrons towards the p-type semiconductor/electrolyte interface, while the built-in electric fields in p-i-n devices sweep photogenerated electrons to the n-type semiconductor/electrolyte interface. With a reversed doping sequence, both the n-type SOI substrate (~-48 pA) and the corresponding n-i-p (~-510 pA) diode junction display the opposite capacitive current polarity (FIG. 30C, left), as expected. Taken together, and consistent with the scenarios in traditional photoelectrochemical cells, the photo-carriers that accumulate at the Si surfaces upon light illumination are minority carriers in uniformly doped cases (i.e., n- or p-type Si) and majority carriers when p-i-n or n-i-p junctions are formed. Finally, in these metal-free samples, the Faradaic and thermal components are negligible e.g., ~7 pA and ~0 K as peak values for p-i-n multilayered sample (FIG. 32, under ~6 W/cm² LED illumination) so the dominant photo-response element in metal-free Si membranes is the capacitive current.

Figure 35:
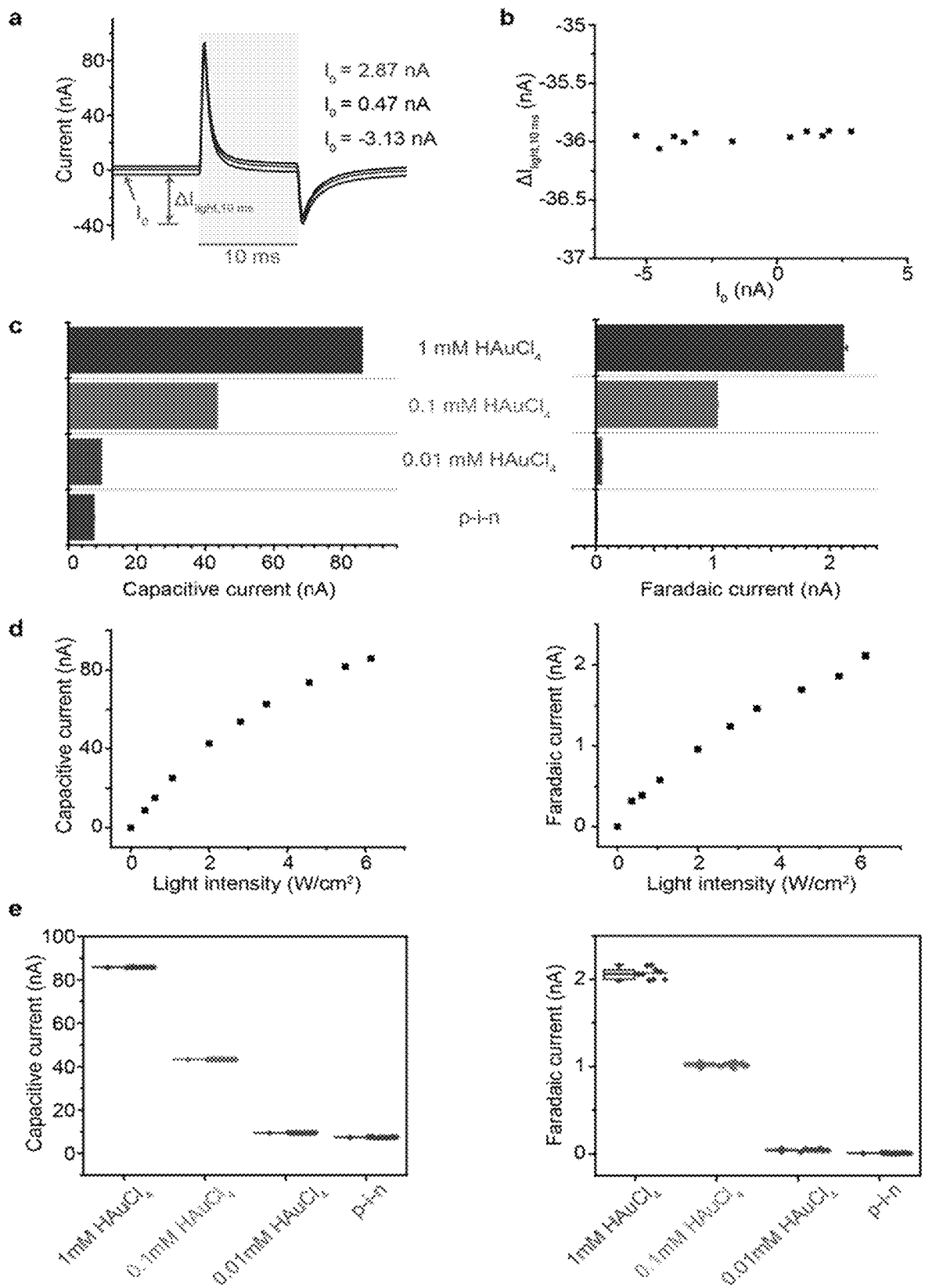
FIG. 35 provides photo-responses of Au-decorated Si structures. (A) Representative current traces recorded from an Au-decorated p-i-n diode junction (from 1 mM HAuCl$_4$) under LED pulsed illuminations (530 nm, 10 ms, ~12.05 mW, ~500 µm spot size, ~6 W/cm$^2$) show strong capacitive and Faradaic currents. $I_0$ is defined as the baseline holding level before the light illumination. $\Delta I_{light,\ 10\ ms}$ is defined as the maximal relative current amplitude after 10 ms of light illumination with respect to $I_0$. The shaded area marks the light illumination period. (B) The $\Delta I_{light,\ 10\ ms}$–$I_0$ plot shows a negligible slope and a prominent intercept indicating strong photoelectric and weak photothermal responses, similar to that from a pristine p-i-n diode junction. (C) Statistical analyses of capacitive (left) and Faradaic currents (right) from p-i-n Si diode junctions with surface Au decorations show that the maximum values of both currents are achieved with Au deposited from 1 mM HAuCl$_4$. Error bars denote standard deviations. (D) The amplitudes for both the capacitive (left) and Faradaic currents (right) of an Au-decorated p-i-n diode junction can be monotonically tuned by the light intensity. Error bars denote standard deviations. (E) Box-and-whisker plots and raw data points of the capacitive and Faradaic currents as shown in (C). Half of the data points are within the boxes, 80% are within the whiskers. Solid and dashed lines represent the medians and means, respectively. Round dots mark the maximum and minimum values. Diamond dots represent the raw data points. n=9 for 1 mM HAuCl$_4$, n=14 for 0.1 mM HAuCl$_4$, n=11 for 0.01 mM HAuCl$_4$, n=13 for p-i-n.
Figure 36:
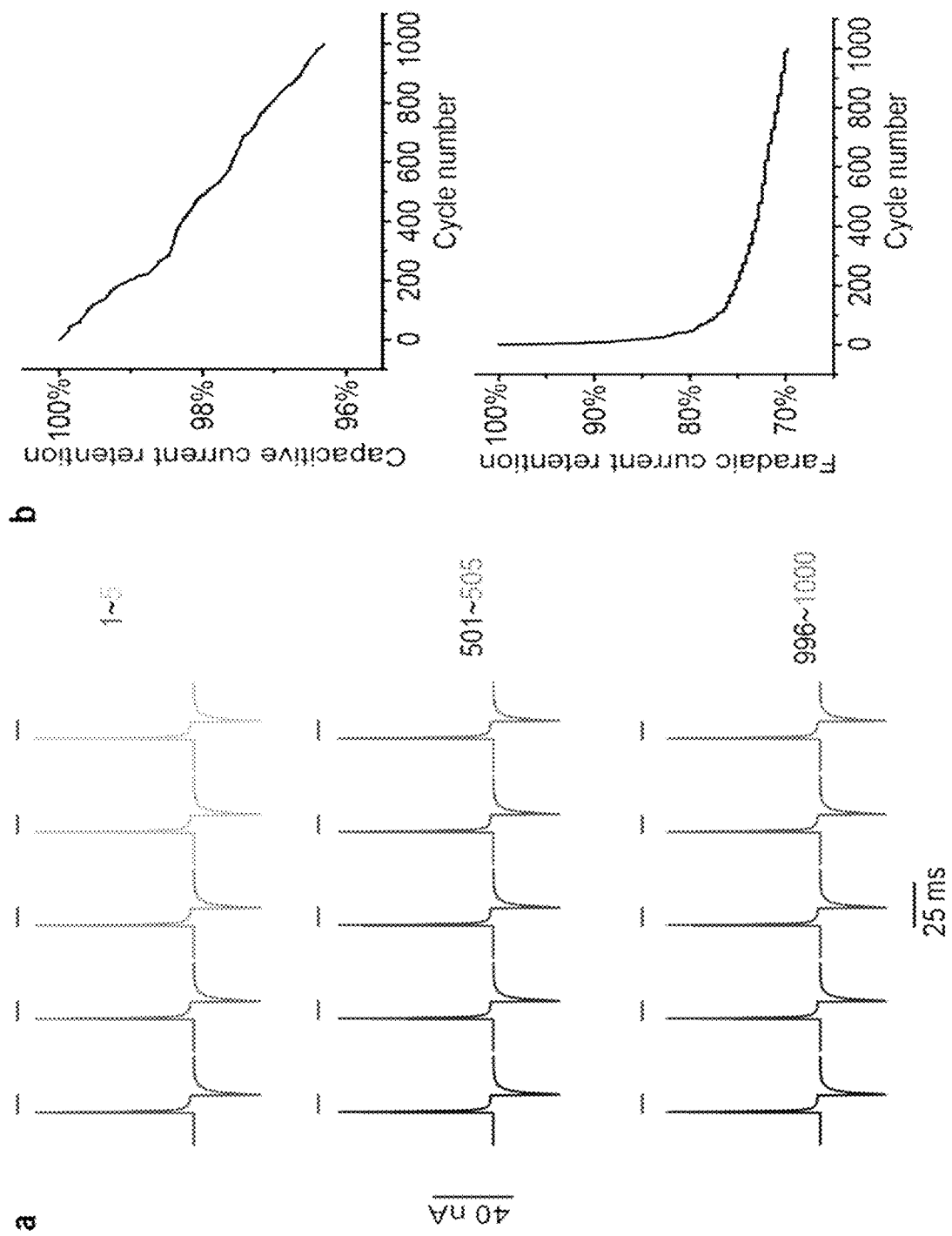
FIG. 36 shows photoelectric responses of Au-decorated diode junctions possess good stabilities. (A) A cyclability test of the same Au-decorated diode junction from 1 mM HAuCl$_4$ with 1000 times of repetitive illuminations (530 nm, 10 ms, ~12.05 mW, ~500 µm spot size, ~6 W/cm$^2$) at a frequency of 2 Hz. Current traces between cycle number 1 and 5, 501 and 505, and 996-1000 are plotted. Bars denote the 10-ms light illumination periods. (B) Both the capacitive and Faradaic currents show high retentions after 1000 cycles. Notably, the capacitive current has an even higher cyclability (~96% retention) versus the Faradaic current (~70% retention), likely benefited from the reversible capacitive charging/discharging processes as oppose to the irreversible surface electrochemical reactions.
Figure 37:
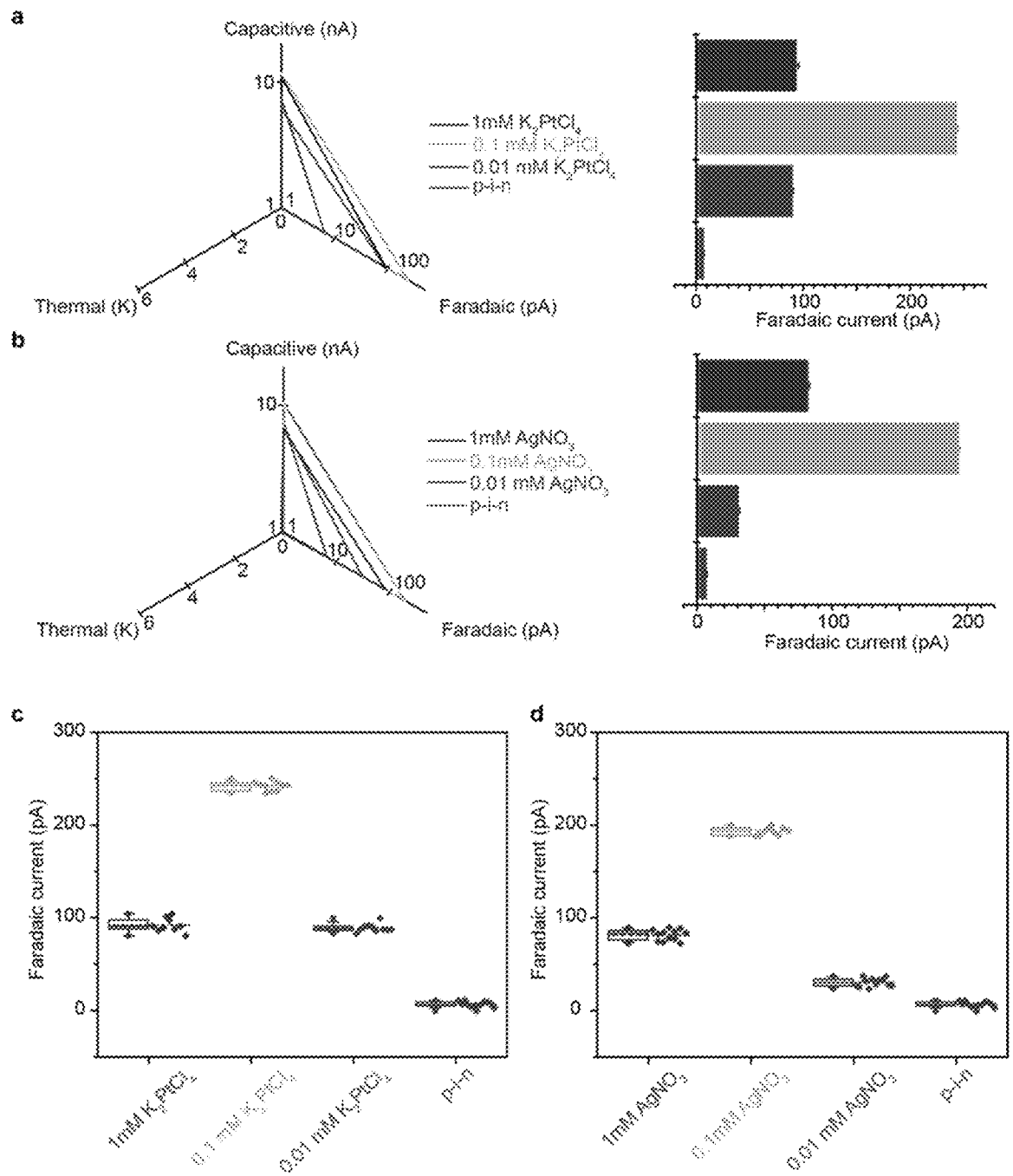
FIG. 37 illustrates metal-enabled promotions of photocurrents in p-i-n diode junctions. Both Pt (A) and Ag (B) can be deposited to enhance the photoelectric responses of the p-i-n diode junction. Maximal Faradaic currents are reached using 0.1 mM of K$_2$PtCl$_4$ or AgNO$_3$ although the enhancements enabled by Pt and Ag are not as pronounced comparing to Au. Error bars denote standard deviations. (C) and (D), Box-and-whisker plots and raw data points of the Faradaic currents as shown in (A) and (B). Half of the data points are within the boxes, 80% are within the whiskers. Solid and dashed lines represent the medians and means, respectively. Round dots mark the maximum and minimum values. Diamond dots represent the raw data points. In (C), n=9 for 1 mM K$_2$PtCl$_4$, n=10 for 0.1 mM K$_2$PtCl$_4$, n=10 for 0.01 mM K$_2$PtCl$_4$, n=13 for p-i-n. In d, n=12 for 1 mM AgNO$_3$, n=9 for 0.1 mM AgNO$_3$, n=12 for 0.01 mM AgNO$_3$, n=13 for p-i-n.

As shown in the Au-decorated p-i-n Si membrane, the Faradaic current can reach ~2 nA (FIG. 30B, upper inset), suggesting a means of charge injection into the solution (FIG. 30D, upper left). Multiple metals were next explored that were commonly exploited catalysts for photoelectrochemistry (e.g., Au, Ag, and Pt) by electroless deposition of nanoparticles onto p-i-n Si surfaces (FIGS. 25-27, 35-37). In all experiments, the introduction of metal species promoted both the capacitive and the Faradaic elements (FIG. 30C, middle; FIG. 35, FIG. 37), with good stabilities over 1000 repetitive illuminations (FIG. 36), likely due to the fact that certain metals can more efficiently collect and solution-inject the photo-generated carriers (as opposed to carrier recombination in bulk Si). Among all the conditions tested, Au prepared by immersion of the p-i-n multilayered membrane in a 1 mM HAuCl₄ solution yielded the highest capacitive (~86 nA) and Faradaic (~2 nA) currents (FIG. 30C, middle). The thermal components under ~6 W/cm² LED illumination were negligible in all metal-decorated Si membranes.

Figure 38:
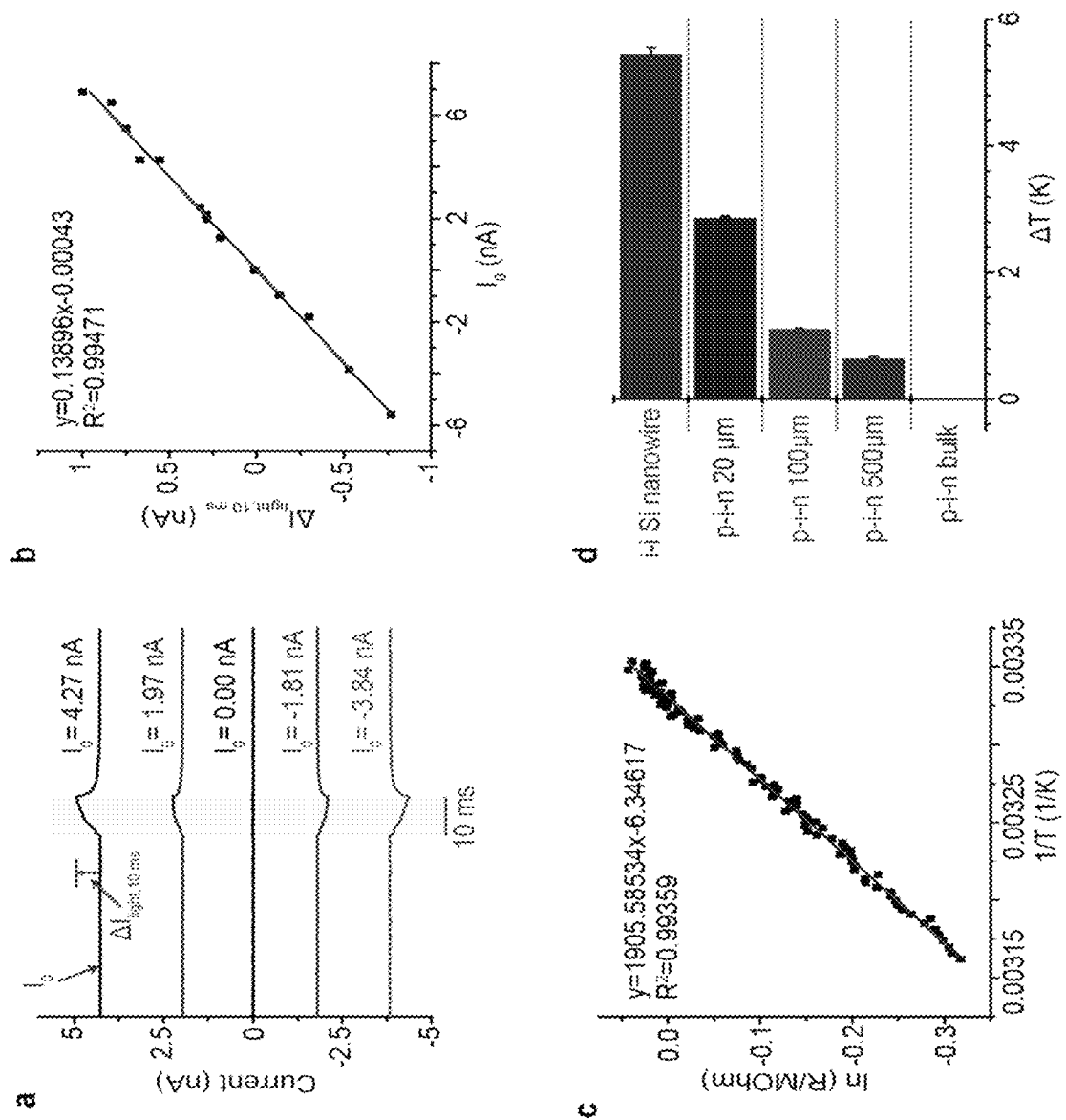
FIG. 38 provides photo-responses of Si structures with different sizes. (A) Representative current traces recorded from an i-i nanocrystalline Si nanowire under laser pulses (532 nm, 10 ms, ~47.1 mW, ~5 µm spot size, ~240 kW/cm$^2$) exhibit a strong dependence on the baseline holding level $I_0$. $\Delta I_{light,\ 10\ ms}$ is defined as the maximal relative current amplitude after 10 ms of light illumination with respect to $I_0$. The shaded area marks the light illumination period. (B) The $\Delta I_{light,\ 10\ ms}$–$I_0$ plot shows a significant slope and a negligible intercept indicating strong photothermal and weak photoelectric responses. (C) The pipette resistance over temperature curve calibrated from the same micropipette used for the photo-response measurements. The temperature increase of the PBS solution caused by the photothermal effect are calculated using both the $\Delta I_{light,\ 10\ ms}$–$I_0$ plot and the T-R calibration curve. Briefly, the resistance of the pipette will decrease after 10 ms of illumination on the Si material due to the photothermal heating of the local PBS solution. The current amplitude during the light illumination will change accordingly following the Ohm's law. The relationship between the pipette resistances after 0 ms ($R_0$) and 10 ms ($R_{10\ ms}$) of illumination can then be linked by $R_{10\ ms}=R_0/(1+k)$, where k is the fitted slope value of the $\Delta I_{light,\ 10\ ms}$–$I_0$. The temperature increase of the solution can then be inferred using the T-R calibration curve. (D) Statistical analyses of the thermal responses of Si structures with different sizes show that the photothermal effect becomes more pronounced with the reduction of the Si dimension. p-i-n diode junctions with different sizes were created by a combination of e-beam lithography and reactive ion etching processes. The temperature increase was calculated by the fitted slope of the $\Delta I_{light,\ 10\ ms} - I_0$. The error bars were included due to the fitting errors of the slopes.

Because single cell or subcellular studies require highly localized interrogation, the laser-induced (~47.1 mW, ~5 μm spot size, ~240 kW/cm²) photo-responses of Si materials with variable lateral dimensions were measured. Decreased electrical/enhanced thermal elements with reduced sizes of p-i-n Si membranes were observed (FIG. 30C, right; FIG. 38). In the case of intrinsic nanocrystalline Si nanowire, the nano-confinement effect led to the highest photothermal response (~5.4 K peak temperature change) with negligible capacitive and Faradaic components (FIG. 30B, lower).

Recommended Materials and Devices for Multiscale Biointerfaces

Figure 39:
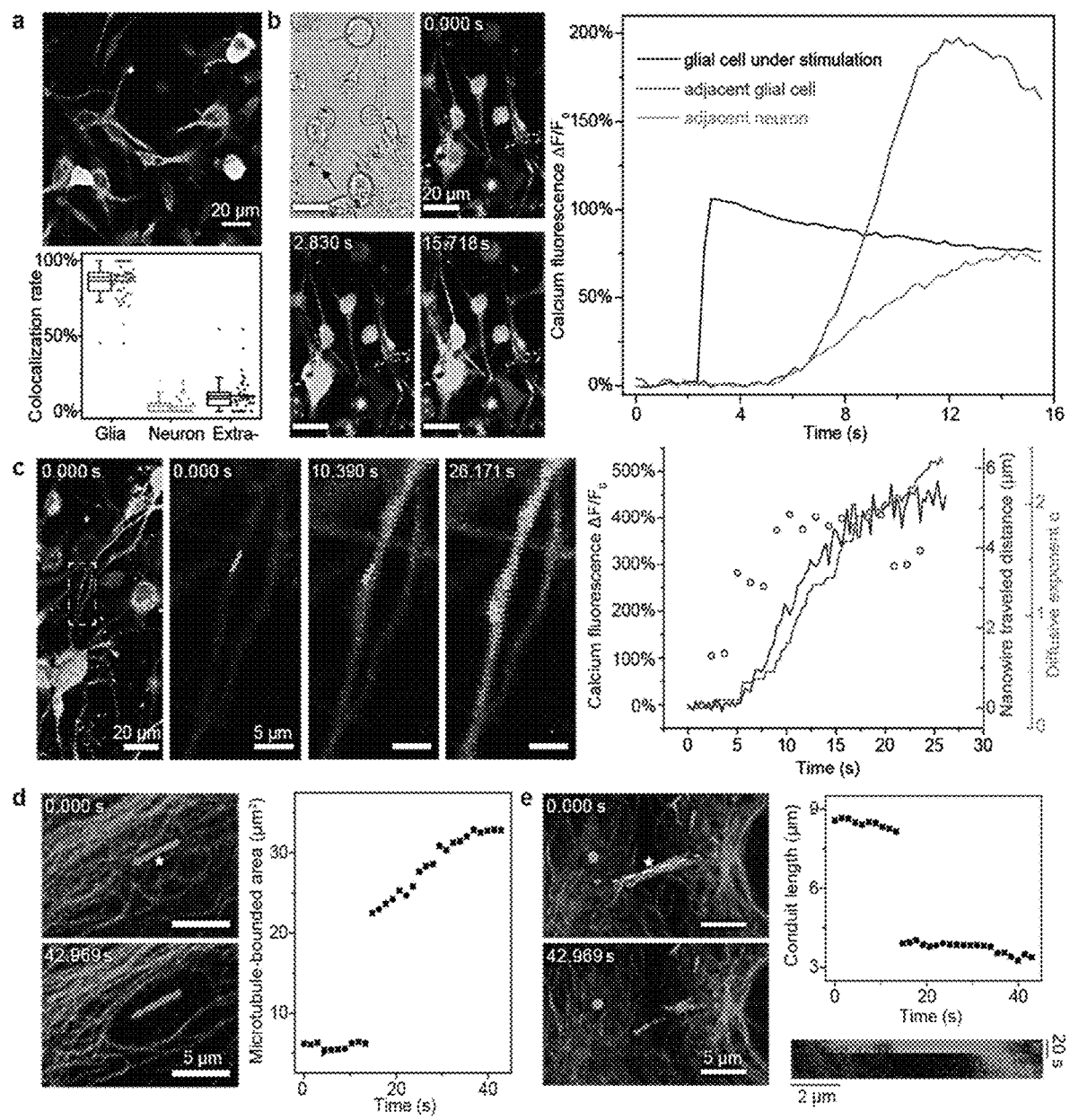
FIG. 39 illustrates Si nanowire-enabled intracellular stimulation interfaces. (A) A confocal microscope image (top) of a DRG-nanowire coculture shows the cell-type-specific overlapping of Si nanowires (neurons; glial cells; Si nanowires). Statistical analysis of the nanowire-cell colocalization rate (bottom) reveals that ~87% of total nanowires overlap with glial cells, ~3% with neurons, and ~10% stay in the extracellular space. Half of the data points are within the boxes, 80% are within the whiskers. Solid and dashed lines represent the medians and means, respectively. Round dots mark the maximum and minimum values. Diamond dots represent the raw data points. n=45. (B) Confocal microscope time series images (upper middle, lower left, and lower middle; calcium; Si nanowires) show that a glial cell with an internalized nanowire can be optically stimulated to trigger intracellular calcium elevation and subsequent intercellular calcium wave propagations to both glial cells and neurons. A differential interference contrast (DIC) image (upper left) highlights the nanowire under stimulation (black arrow) and the morphologies of a neighboring glial cell and a neuron. The laser illumination (592 nm, ~14.4 mW) was on for 1 ms right before the time point of 2.830 s. Quantitative analysis of the fluorescence intensities over time (right) from three regions of interest show calcium dynamics in all cells (black, the glial cell being stimulated; a nearby glial cell; a neighboring neuron). (C) Si nanowires can serve as a dual-role intracellular biophysical tool, i.e., a calcium modulator and a marker for motor protein-microtubule interactions. The location of a nanowire (i.e., a transport marker) in a glial protrusion is tracked while the nearby calcium dynamics is monitored simultaneously, following a remote laser illumination of a different nanowire (i.e., a calcium modulator) to initiate a calcium flux within the network (calcium; Si nanowires; first one from left). The white dashed box marks the region of interest for the transport study. Time series images (second one from left, middle one, second one from right) show a calcium-correlated motion of the Si nanowire. MSD analysis further reveals a mode shift of the nanowire motion from random or restricted diffusions (diffusive exponent, $\alpha \leq 1$) to an active transport ($\alpha \sim 2$). (D) Microtubule networks can be mechanically manipulated by laser illumination (592 nm, 1 ms, ~2.09 mW) of intracellular Si nanowires. Microtubules; Si nanowires. The white star marks the illumination site. (E) Intercellular conduits can also be manipulated (592 nm, 1 ms, ~2.55 mW). Microtubules; Si nanowires. A kymograph (lower right) taken along the white dashed line (upper left) shows the evolution of the conduit length. The white star marks the illumination site.
Figure 40:
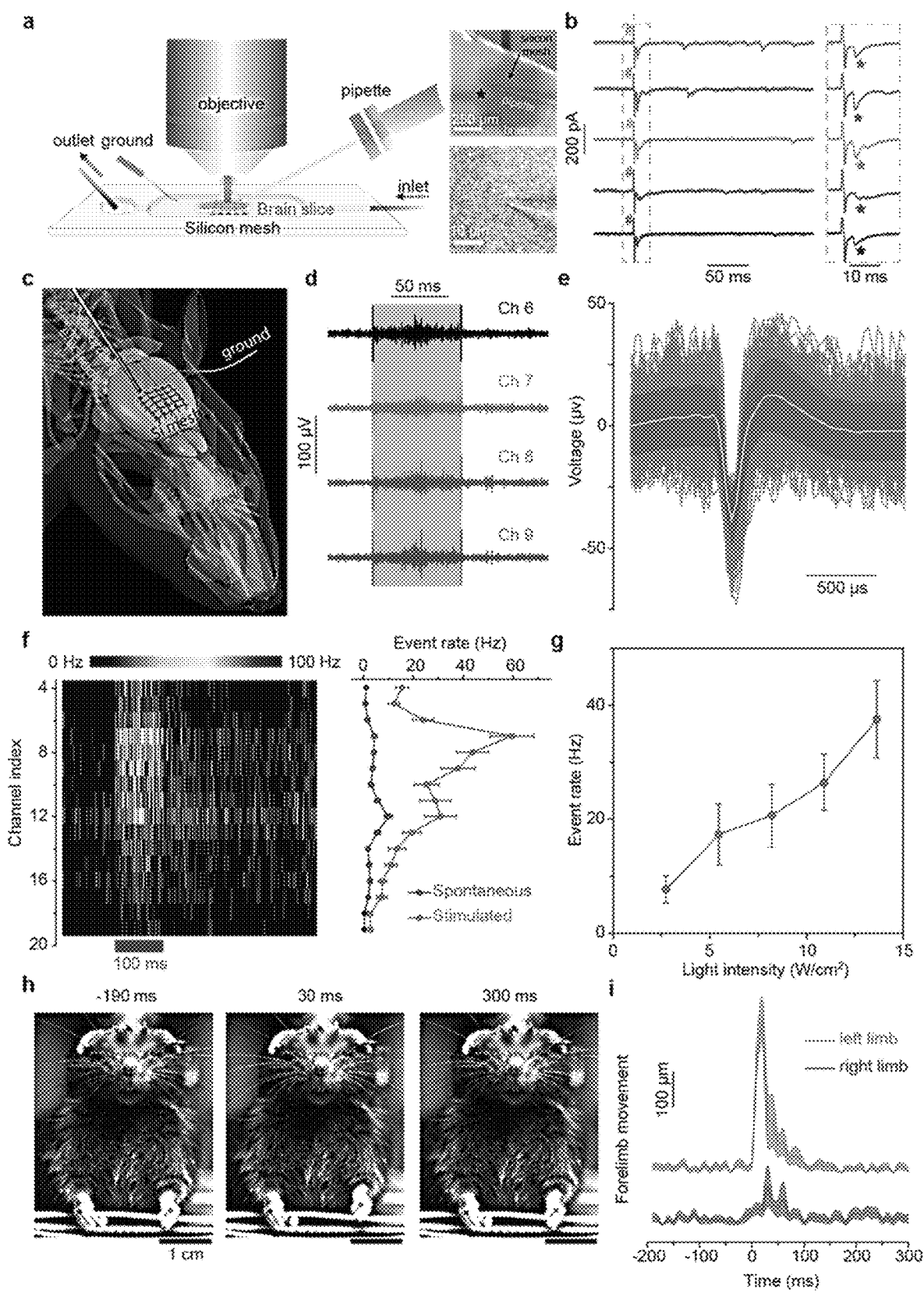
FIG. 40 shows flexible and distributed silicon mesh for optically-controlled extracellular neuromodulation. (A) A schematic diagram of a photostimulation of a brain slice performed in a perfusion chamber (left). A pyramidal neuron in a cortex slice was held at −70 mV in the whole-cell voltage-clamp mode (lower right) while a distributed Si mesh was placed underneath the slice (upper right). Short laser pulses (473 nm, 1 ms, ~2 mW, ~57 μm spot size) were delivered to a spot on the Si mesh (marked by a star) to activate the nearby cells. (B) Example traces from voltage-clamp recordings of the patched pyramidal neuron over 5 trials (left) with 1-ms long laser stimulations. The dashed box marks the time frame for zoom-in views on the right. EPSCs are marked by stars following the illuminations of the Si mesh (right). The shaded area marks the illumination period in each trial. #denotes the photoelectric artifact. (C) A schematic diagram illustrating the in vivo photostimulation test. A linear probe with 32 recording sites is guided into a head-fixed anesthetized mouse brain to sample the evoked neural activities by the illumination of an adjacent silicon mesh. (D) Example traces of raw neural response data from four adjacent channels (Ch 6 to Ch 9) in a single trial of stimulation (473 nm, 100 ms, ~5 mW, ~216 μm spot size) marked by a band. (E) A mean neuron-firing waveform superposed on individual waveforms (black) of both spontaneous and stimulation-evoked activities. The shaded area denotes SD. n=300 with 153 from stimulated and 147 from spontaneous. (F) A heat map of PSTH for channels between 4 and 19 (left). The bar underneath indicates the period of laser stimulation. The mean spontaneous and evoked neural response rates across all trials for the same channels in the PSTH heat map. (G) The evoked neural response rate is positively correlated with the stimulation laser intensity. Error bars represent the s.e.m from 50 trials in channel 9. (H) Snapshots of a forelimb movement study following photo-stimulations. The mouse's left limb moves up and down following the laser illumination (473 nm, 50 ms, ~4 mW, ~216 μm spot size) on a Si mesh attached to the right side of the forelimb primary motor cortex. (I) Time-dependent limb movements show a preferred motion of the left forelimb after the stimulation. The 0 ms time point represents the start of the light pulse. Shaded areas denote s.e.m of the data. n=15.

The physicochemical measurements (FIG. 30; FIG. 23A, Selection II) highlight p-i-n diode junction-enhanced capacitive currents, metal-enhanced capacitive and Faradaic currents, and nano-confinement-enabled thermal responses (FIG. 33; FIG. 30D, middle), all in freestanding configurations. For the present biointerface studies (FIG. 23A, lower right; FIGS. 39-40), most Si materials such as a simple p-type Si membrane or p-i-n Si multilayers with small lateral dimensions (<500 μm), will not be considered given that their photo-response components are small (FIG. 33, with lower color intensity; FIG. 23A, excluded materials from Selection II). The intrinsic nanocrystalline Si nanowires were used for intracellular and the related intercellular probing, and only used the photothermal effect. For single cell or small tissue level inter- and extracellular studies, a light-induced capacitive effect was primarily explored, i.e., a p-i-n Si multilayered membrane were used where the biological invasiveness from capacitive electrochemical currents are usually minimal. Finally, given that the biological organization at the organ level is very complex, the Au-coated Si diode junctions were used for in vivo studies (FIG. 30D, right). Similar to the electrical stimulation of excitable tissues, where both capacitive and Faradaic currents take place at the electrode/electrolyte interface, the Au-coated Si surfaces can deliver similar signals to the biological system for efficient tissue modulations.

Organelle Level Biointerfaces

Figure 41:
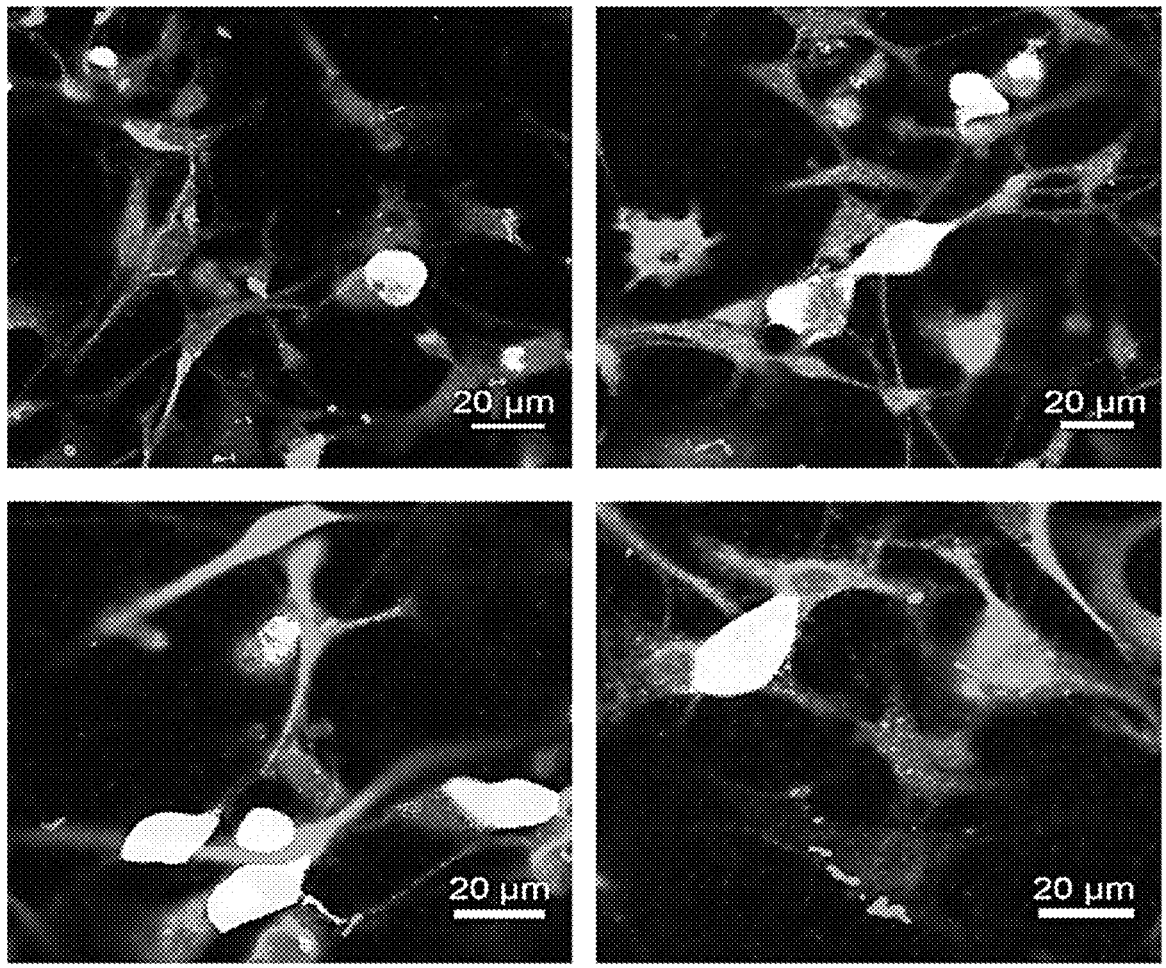
FIG. 41 illustrates nanocrystalline Si nanowires that display cell-type specific overlapping with glial cells. Overlaid confocal microscope images of the DRG-glia system show that nanowires mostly overlap with glial cells (GFAP) versus neurons (NeuN). The fact that the overlapping nanowires exhibit alignment with cellular protrusions and perinucleus clustering rather than random intracellular distributions suggests that nanowires are internalized by the glial cells.
Figure 42:
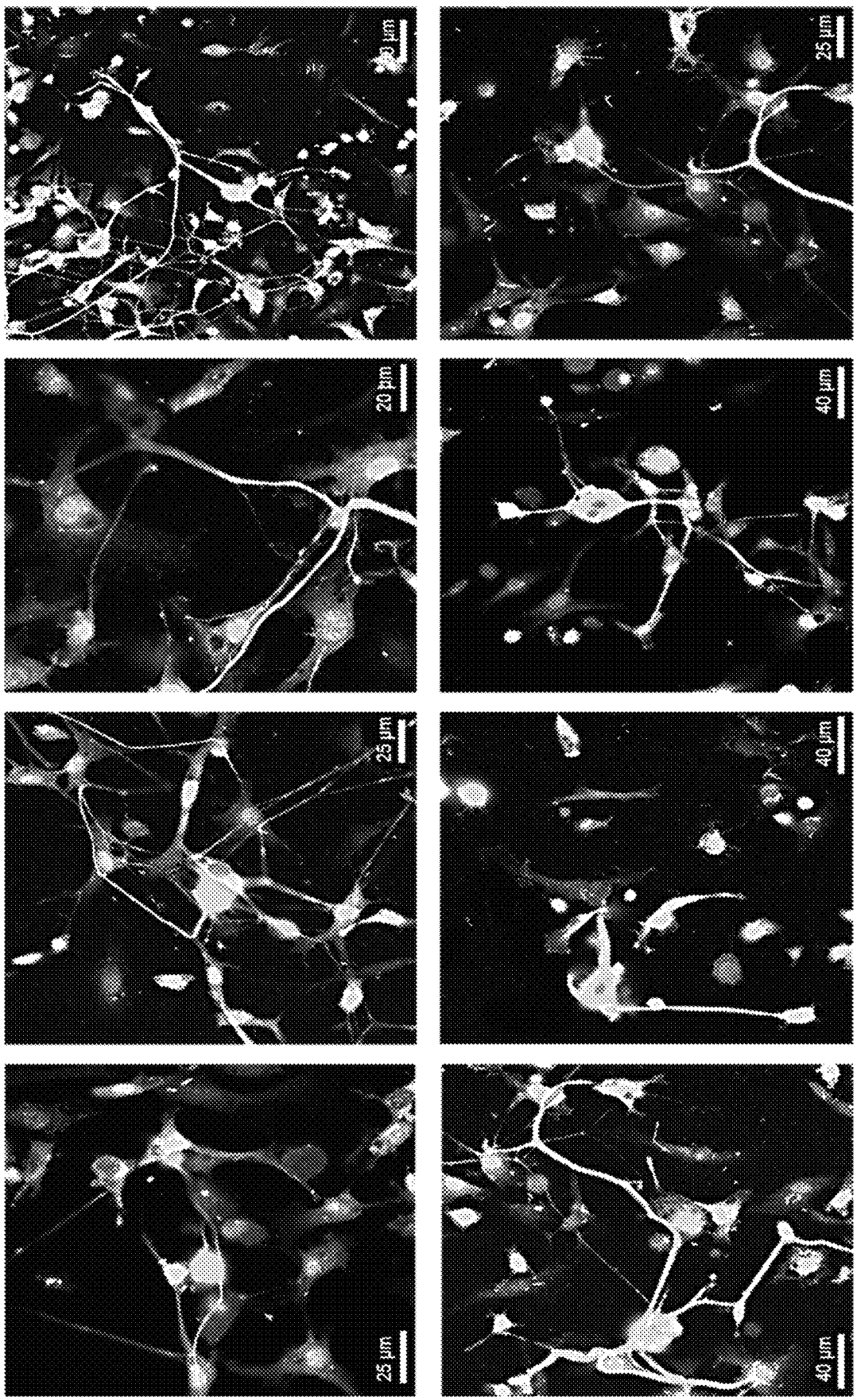
FIG. 42 illustrates nanocrystalline Si nanowires that display cell-type specific overlapping with glial cells. Overlaid confocal microscope images of the DRG-glia system stained with another set of biomarkers confirm that nanowires mostly overlap with glial cells (S-100) versus neurons (Neurofilament). The existence of the naturally occurring neural-glial junctions suggests the potential of realizing remote neuromodulation with glial cell internalized nanowires.
Figure 43:
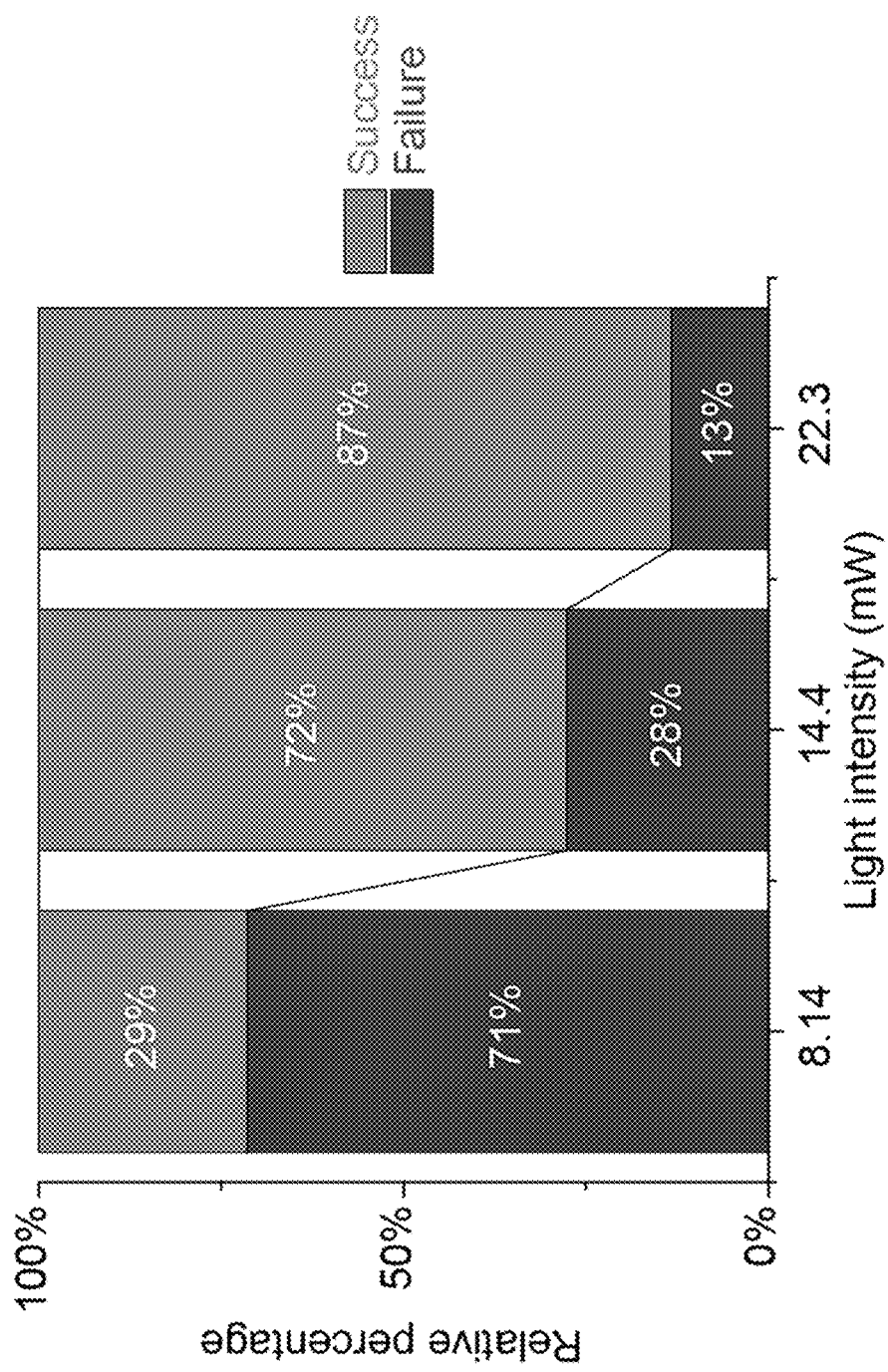
FIG. 43 provides a stacked column plot presenting the relative success/failure rates of the light-controlled calcium modulation experiment using glial cell internalized nanowires (592 nm, 1 ms, ~237 nm spot size). The success rate of eliciting calcium flux increases progressively with higher light. n=14 for 8.14 mW, n=76 for 14.4 mW, n=15 for 22.3 mW, indicating the success rate of intracellular calcium modulation of glial cells may be light intensity dependent.
Figure 44:
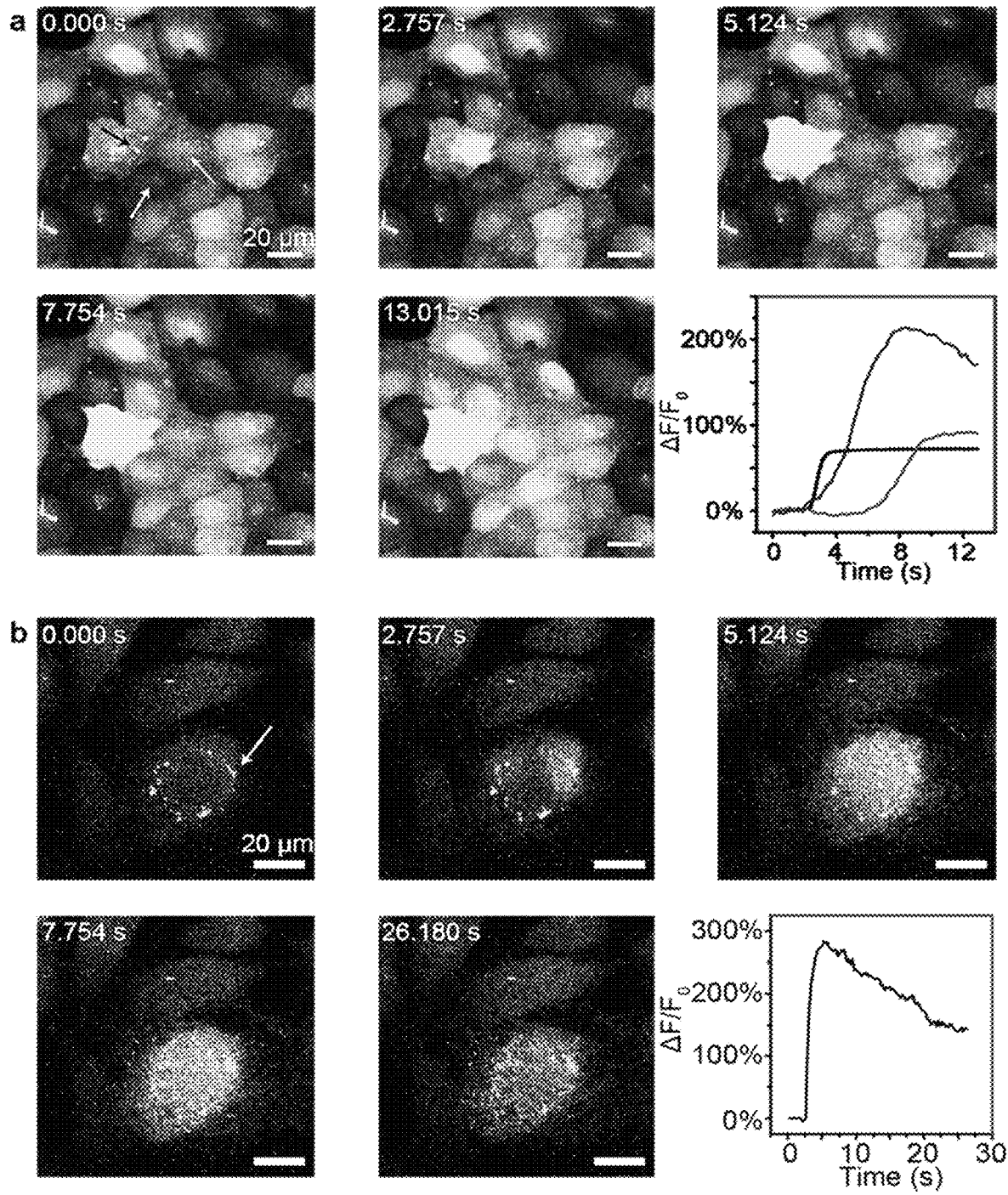
FIG. 44 provides images demonstrating that intracellular stimulation can be extended to multiple cell lines. A cancer cell line, U2OS (A), and an endothelial cell line, HUVEC (B), can both be stimulated intracellularly to elicit the calcium dynamics. Since the intracellular stimulation of calcium largely utilizes the internal calcium storage organelles rather than ion channels on the plasma membranes, this modulation method is general to a broad range of mammalian cells. The stimulation laser (592 nm, ~14.4 mW, ~237 nm spot size) was on for 1 ms right before the time point of 2.757 s. Calcium; Si nanowires. The black arrow marks the nanowire under stimulation, the arrows mark two adjacent cells of interest in (A). The white arrow marks the nanowire under stimulation in (B).
Figure 45:
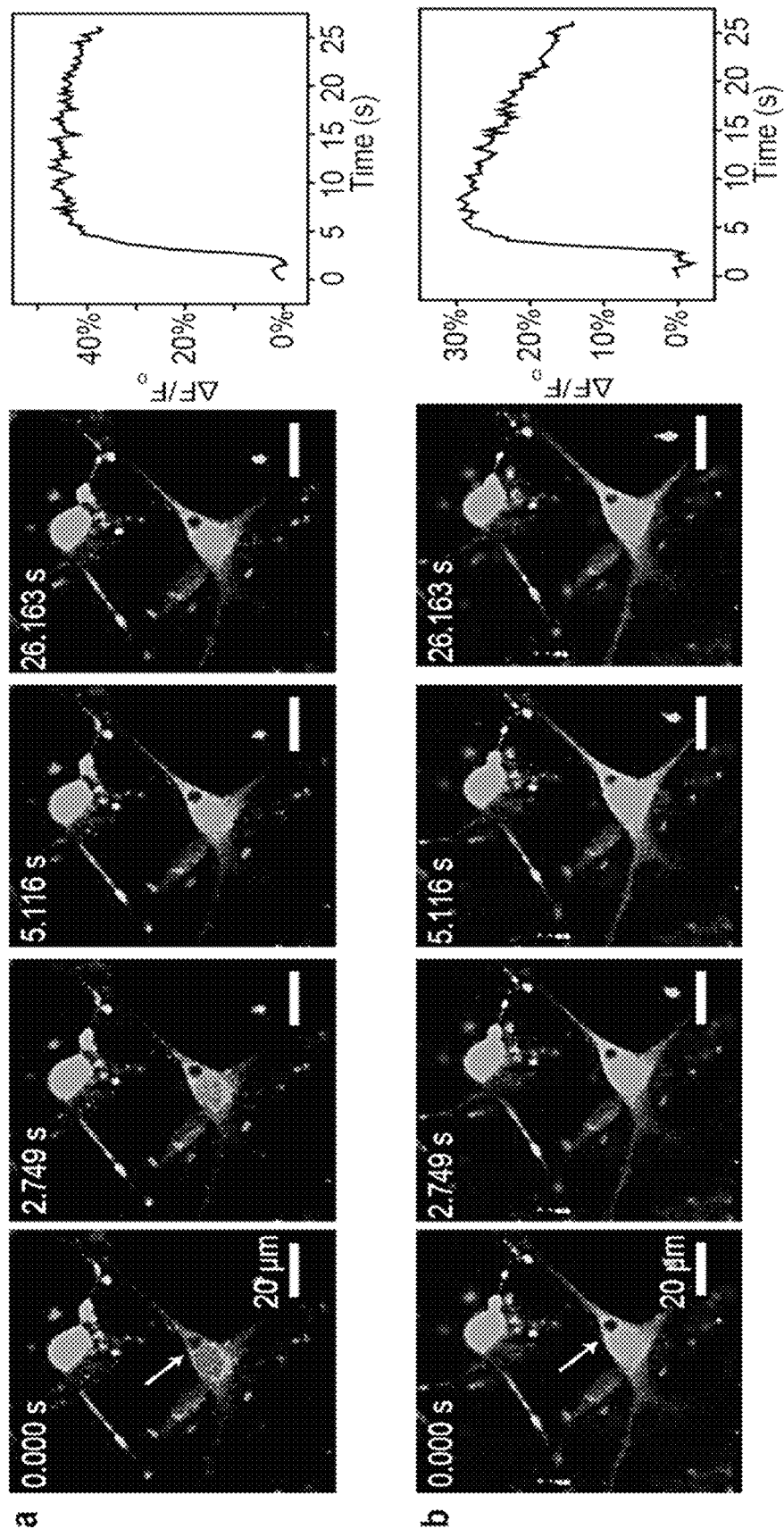
FIG. 45 provides images demonstrating that intracellular stimulation of calcium may be minimally invasive to cells. (A) and (B) The same glial cell with internalized Si nanowires (calcium; Si nanowires) is stimulated repetitively without being damaged. In the second time of stimulation (B), the intracellular calcium concentration can still increase even it is not at its base level. The stimulation laser (592 nm, ~14.4 mW, ~237 nm spot size) was on for 1 ms right before the time point of 2.749 s. White arrows mark the same nanowire under stimulation.
Figure 46:
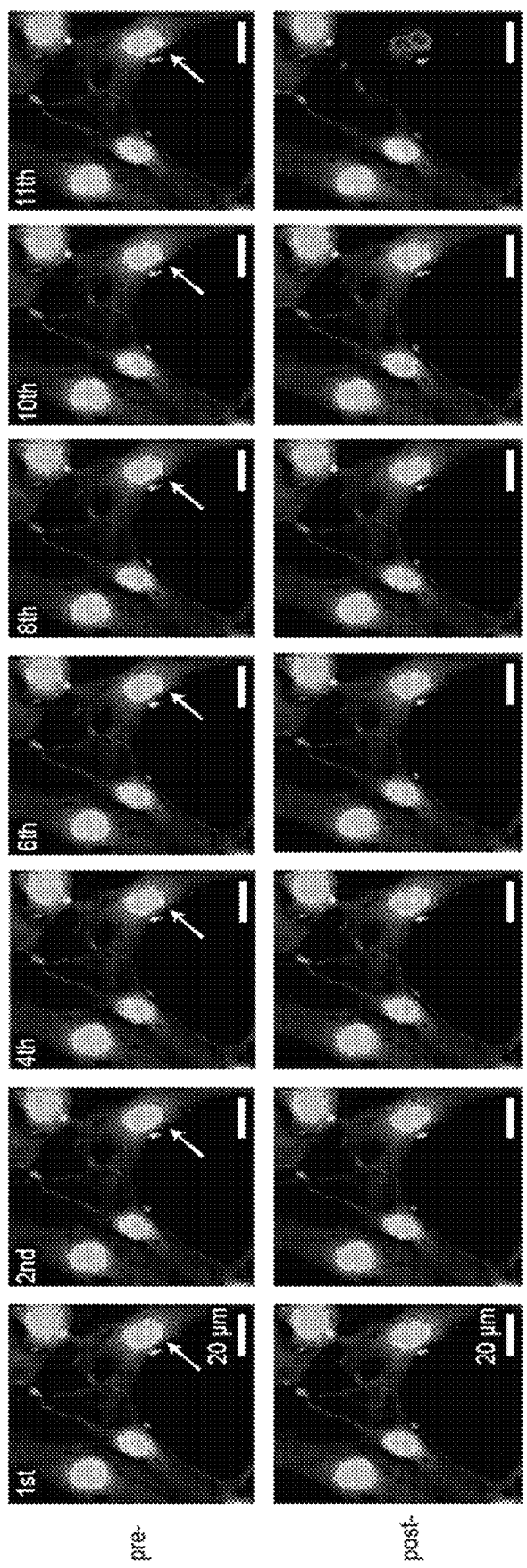
FIG. 46 provides images of minimally invasive intracellular photostimulation of cells. The same glial cell with internalized Si nanowires (calcein; Si nanowires) was stimulated intracellularly for ten consecutive times without being killed. The stimulation condition was ~32.2 mW for 1 ms in the first ten cycles using a 592 nm laser. The cell was killed (ethidium homodimer-1; Si nanowires) after a 1-ms pulse of ~54.1 mW laser was delivered. White arrows mark the laser stimulation sites.
Figure 47:
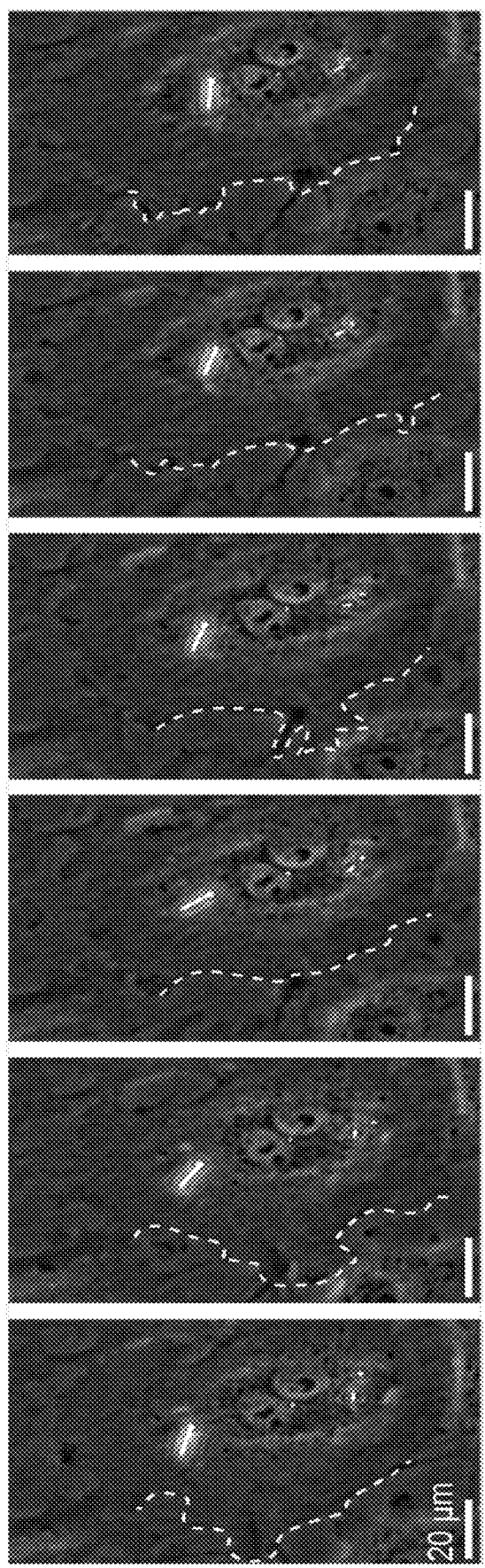
FIG. 47 provides time-lapse phase-contrast image series of a HUVEC cell with internalized nanowires. The cell itself dynamically changed its morphology (marked by dashed lines) and moved constantly over time while the relative orientation and location of the internalized nanowire also underwent rapid movements. This motile biointerface may be further developed to target various intracellular compartments at different stages of the internalization process, or modulate surrounding cells at different locations over time.

Si nanowires for intracellular stimulation biointerfaces were first considered (FIG. 39) because it is an unexplored domain that is beyond the previously studied intracellular sensing or delivery. In a primary culture of neonatal rat dorsal root ganglia (DRG) and associated satellite glia, a cell-type-specific overlapping of nanocrystalline Si nanowires was noticed after ~24 hours of coculturing (by GFAP/NeuN staining in FIG. 39A and FIG. 41; by S-100/Neurofilament staining in FIG. 42). Statistical analysis of the nanowire-cell colocalization revealed that ~87% of total nanowires overlapped with glial cells, ~3% with neurons, and ~10% stayed in the extracellular space (FIG. 39A, lower). Perinucleus clustering, rather than random intracellular distributions, of the colocalized nanowires suggested the internalization of these nanowires. Additionally, the presence of bent nanowires following the contours of a few glial cell membranes implies strong mechanical interactions between cells and nanowires. As suggested by a recent study that label-free nanowires can be internalized through a phagocytosis pathway, the fact that glial cells (versus neurons) do have phagocytic activities supports the observed selective glial internalization. As a result, the control of glial activities with internalized nanocrystalline nanowires as the remotely-controlled stimulators was studied. To this end, an intracellularly-bounded nanowire was illuminated with a laser pulse (592 nm, ~14.4 mW, ~237 nm spot size, 1 ms) in the middle of a time-lapse calcium imaging series (FIG. 39B, FIG. 31B, FIG. 43). Upon light illumination, the glial cell of interest, with the nanowire inside, experiences a fast calcium concentration increase followed by a slow decay. Since the cell is being stimulated intracellularly, the observed calcium dynamics are likely related to the release of calcium from internal storage organelles, e.g., endoplasmic reticulum (ER) and mitochondria, rather than the calcium influx through ion channels at the plasma membrane, and therefore may be extended to other non-excitable cells (FIG. 44). As evidenced by the patch-clamp measurement, nanocrystalline nanowire exhibits a pronounced photothermal effect which results in a transient and localized temperature increase of surrounding cytosol and organelles following the laser pulse. This heating effect can either generate reactive oxygen species (ROS) or transiently depolarize/perforate ER and mitochondrial membranes, all of which can trigger the release of calcium from its reservoir to the cytosol. Nevertheless, the same glial cell calcium dynamics can still be modulated repetitively (FIGS. 45-46), indicating the minimal invasiveness of the intracellular stimulation method. Moreover, not only was it observed the induced intracellular calcium flux from the glia under direct stimulation, but also the intercellular calcium wave propagation to both neighboring glia and DRG cells (FIG. 39B). The selective uptake of nanowires by glia and the existence of glia-glia/glia-neuron communication suggest possible remote cellular modulations through naturally-occurring intercellular junctions. Finally, the cellular and subcellular dynamics can be exploited for motile modulation biointerfaces (FIG. 47).

Figure 48:
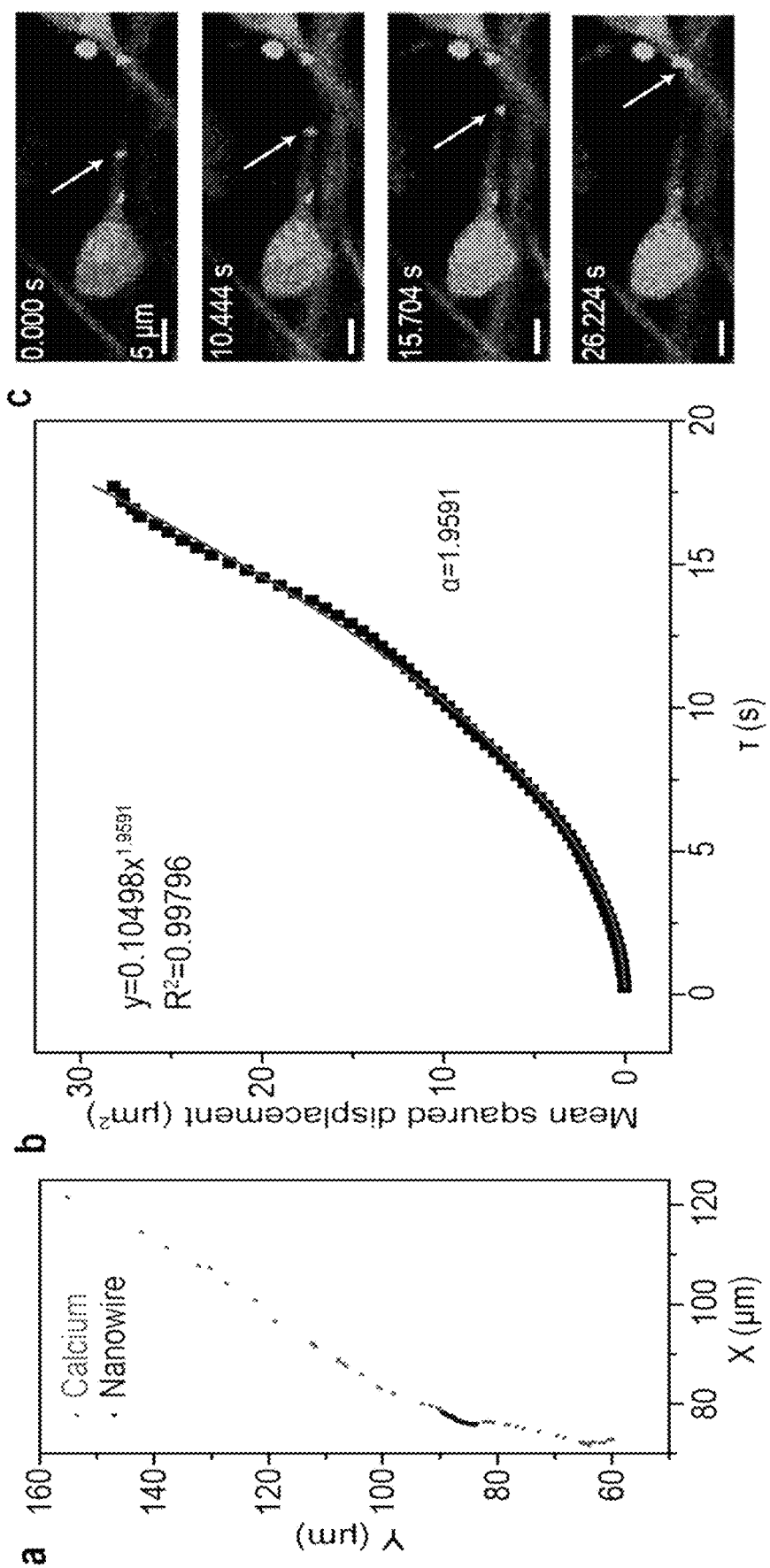
FIG. 48 illustrates correlated motions of calcium wave propagation and nanowire transport. (A) Trajectories of the nanowire movement and the calcium wave-front propagation are overlaid, indicating that the nanowire is transported inside the cell protrusion. (B) Mean-squared displacement analysis of the nanowire motion after the calcium wavefront reaches its original location shows a diffusivity coefficient α~2, suggesting the active transport motion of the nanowire being triggered by the calcium wave. c, An additional image series (calcium; Si nanowires) from a different example, showing the calcium-triggered nanowire transport phenomena. White arrows indicate the nanowire of interest serving as a transport marker.

Because Si nanowires can also display active transport along microtubules, the possibility of using nanocrystalline Si nanowires as a dual-role intracellular biophysical tool was next explored, i.e., a calcium modulator and a marker for motor protein-microtubule interactions. The location of a single nanowire (i.e., a transport marker) was simultaneously tracked in a glial protrusion and monitored the nearby calcium dynamics, following a remote laser illumination of a different nanowire (i.e., a calcium modulator) to initiate a calcium flux within a network (FIG. 39C, first from left). The dynamics of local calcium concentration and the transverse distance of the nanowire, as well as the overlaid time series for both the calcium wave front and the nanowire center (FIG. 39C, first from right), together suggest a calcium-triggered directional transport of intracellular cargo. Additionally, mean-squared displacement (MSD) analysis (Methods) reveals correlated nanowire transport modes with the local calcium dynamics, i.e., from random or restricted diffusions (diffusive exponent, $\alpha \leq 1$) without elevated intracellular calcium, to an active transport (diffusive exponent, $\alpha \sim 2$) after the calcium wave front reached the original nanowire location (FIG. 39C, first from right; FIG. 48). The nanowire transport along the glia protrusion is anterograde, i.e., kinesin-based. The motor protein kinetics are typically enhanced by increased adenosine triphosphate (ATP) activities, which can be triggered by the elevation of intracellular calcium concentration. These results therefore support a mechanism where a cascade of calcium and ATP dynamics is involved for intracellular transport.

Figure 49:
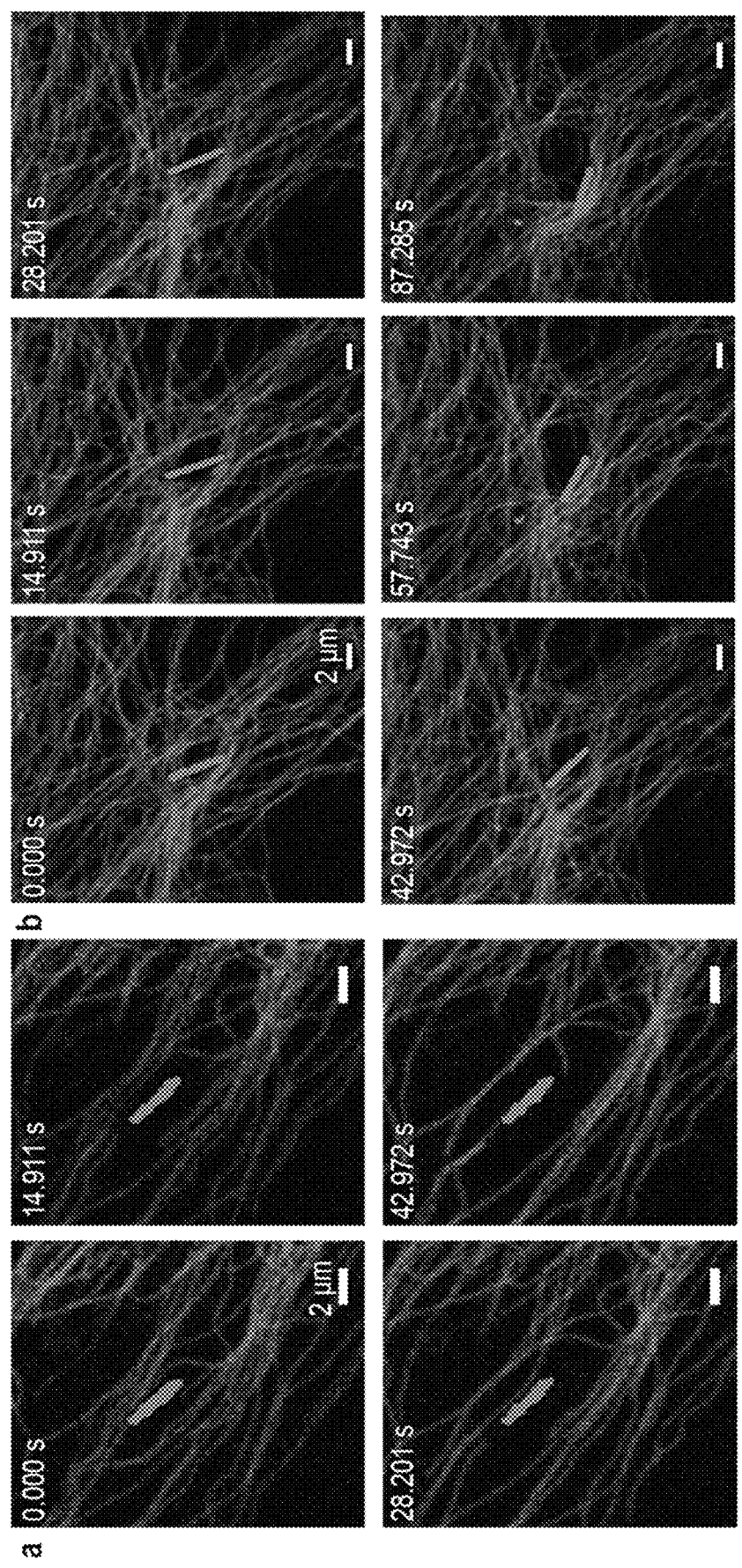
FIG. 49 provides images of microtubule networks being remotely manipulated by intracellular stimulation of Si nanowires. (A) and (B) Two live cell imaging series (microtubules; Si nanowires) showing the repellant of microtubule networks by the laser illuminations (592 nm, ~2.09 mW, ~211 nm spot size) of internalized Si nanowires. The laser pulses were 1 ms long before the time point of 14.911 s. The facts that the nanowires can be moved and get entangled with other microtubules suggest that the cells are alive after the mechanical stimulations.

Besides serving as an intracellular calcium modulator and a transport marker, the photothermal properties of nanocrystalline Si nanowires may be explored to induce a photoacoustic effect for biomechanical manipulation at the subcellular level. To assess this, human umbilical vein endothelial cells (HUVEC), which are active in the phagocytosis of silicon nanowires and have well-studied microtubule networks, were chosen. Nanocrystalline Si nanowires are trapped in the microtubule meshes after coculturing with HUVEC for ~24 hours (FIG. 49). When a laser pulse (592 nm, 1 ms, ~2.09 mW, ~211 nm spot size) was introduced to the nanowire, the surrounding microtubules were rapidly repelled and formed a void space near the nanowire (FIG. 39D; FIG. 49), suggesting a shock-wave generation through a photoacoustic effect. Besides intracellular microtubule networks, Si nanowires can also interface with intercellular conduits, where microtubules form compact bundles. Upon laser illumination of the entangled single nanowire (592 nm, 1 ms, ~2.55 mW, ~211 nm spot size), the bundled microtubules are broken up immediately (FIG. 39E), possibly through a shock-wave-mediated, mechanically-induced microtubule depolymerization. The optically-triggered, and nanowire-enabled mechanical manipulation of cytoskeletal structures may serve as a new tool for the study of intra- and intercellular dynamics where a remote structural manipulation of subcellular structures is desired.

Control experiments without nanowires did not yield any of these intra- or intercellular observations. Moreover, the importance of using silicon nanowires instead of other nanostructures (e.g., Au nanoparticles or nanorods) is due to the following: (1) silicon nanowires can be at least partially exposed in cytosol upon phagocytic cellular entrance, (2) silicon has only a moderate photothermal effect (compared to, e.g., that of Au) (FIGS. 30B-C; FIG. 38) such that the confocal imaging light source itself will not cause heating from the nanostructures, and (3) the high aspect ratio of silicon nanowires enables their axial alignment with respect to the cytoskeletal filaments (FIGS. 39D-E; FIG. 49).

Single Cell and Small Tissue Level Biointerfaces

Figure 50:
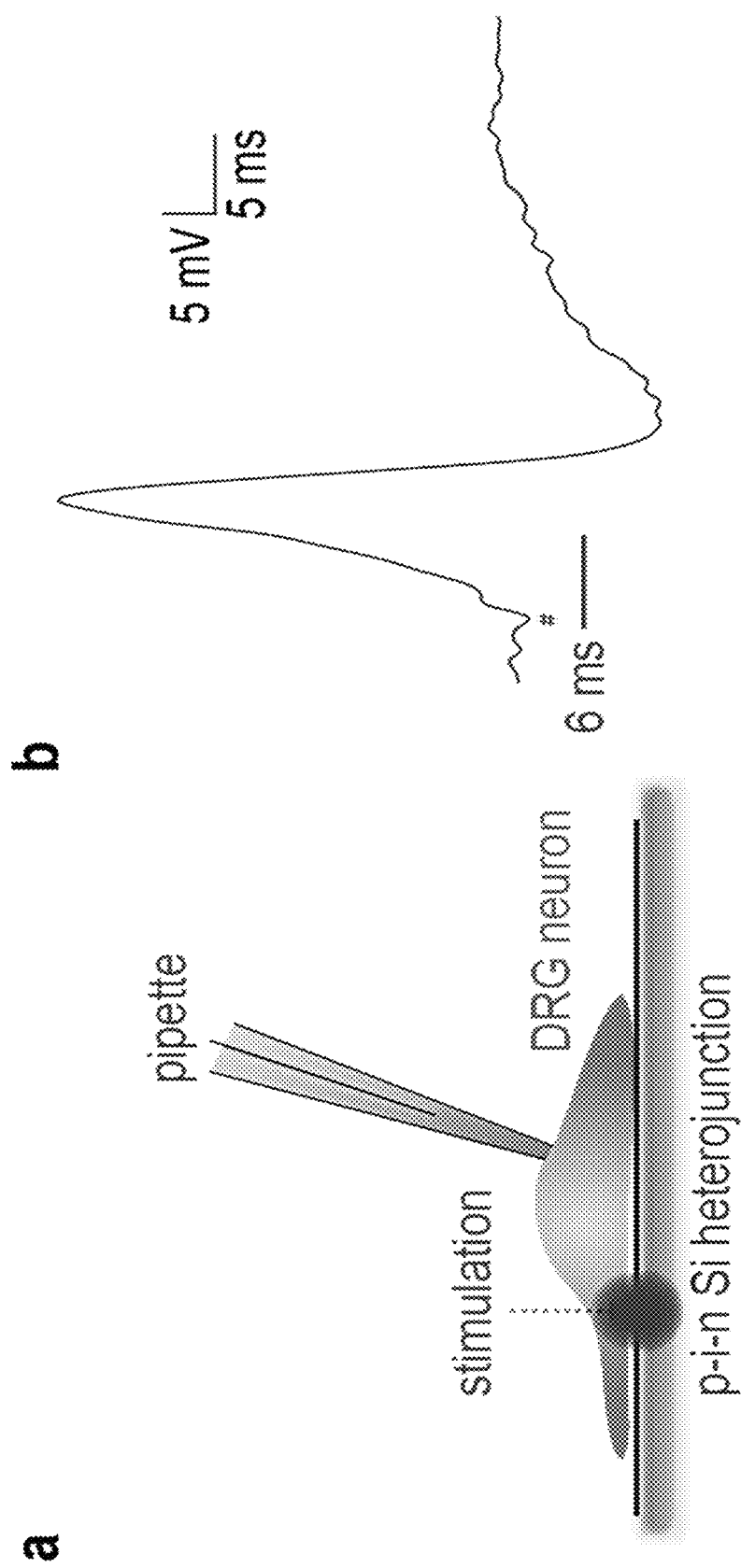
FIG. 50 provides a schematic of optical stimulation of DRG neurons cultured on a p-i-n Si diode junction (A) A schematic illustration of photostimulation of DRG neurons cultured on a Si diode junction substrate. (B) A 6 ms-long laser pulse (532 nm, ~47.1 mW, ~5 μm spot size) can elicit an action potential of the patched neuron. #marks the photoelectric artifact coinciding with the light onset[58,59].
Figure 51:
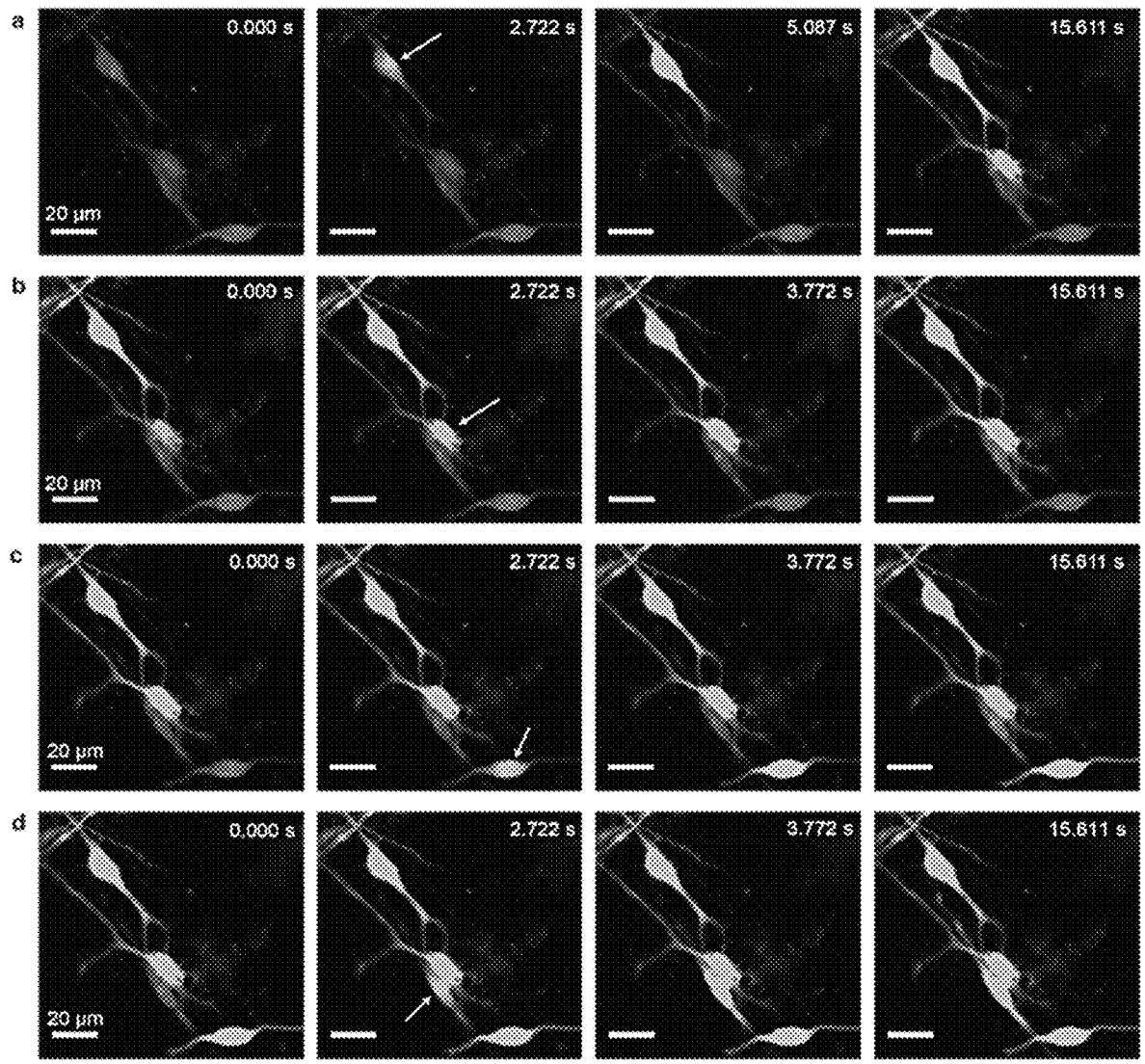
FIG. 51 shows high spatiotemporal-resolution extracellular stimulations of calcium dynamics via p-i-n Si diode junctions. (A-D), Laser illuminations (592 nm, ~14.4 mW) of different cells in a DRG culture (calcium) on a p-i-n Si diode junction, showing stepwise cellular modulation. The illuminations induce localized and fast calcium elevations near the stimulation sites and subsequent calcium wave propagations both intra- and inter-cellularly. Laser stimulations were 1 ms long before the time point of 2.722 s. White arrows mark the laser stimulation sites.
Figure 52:
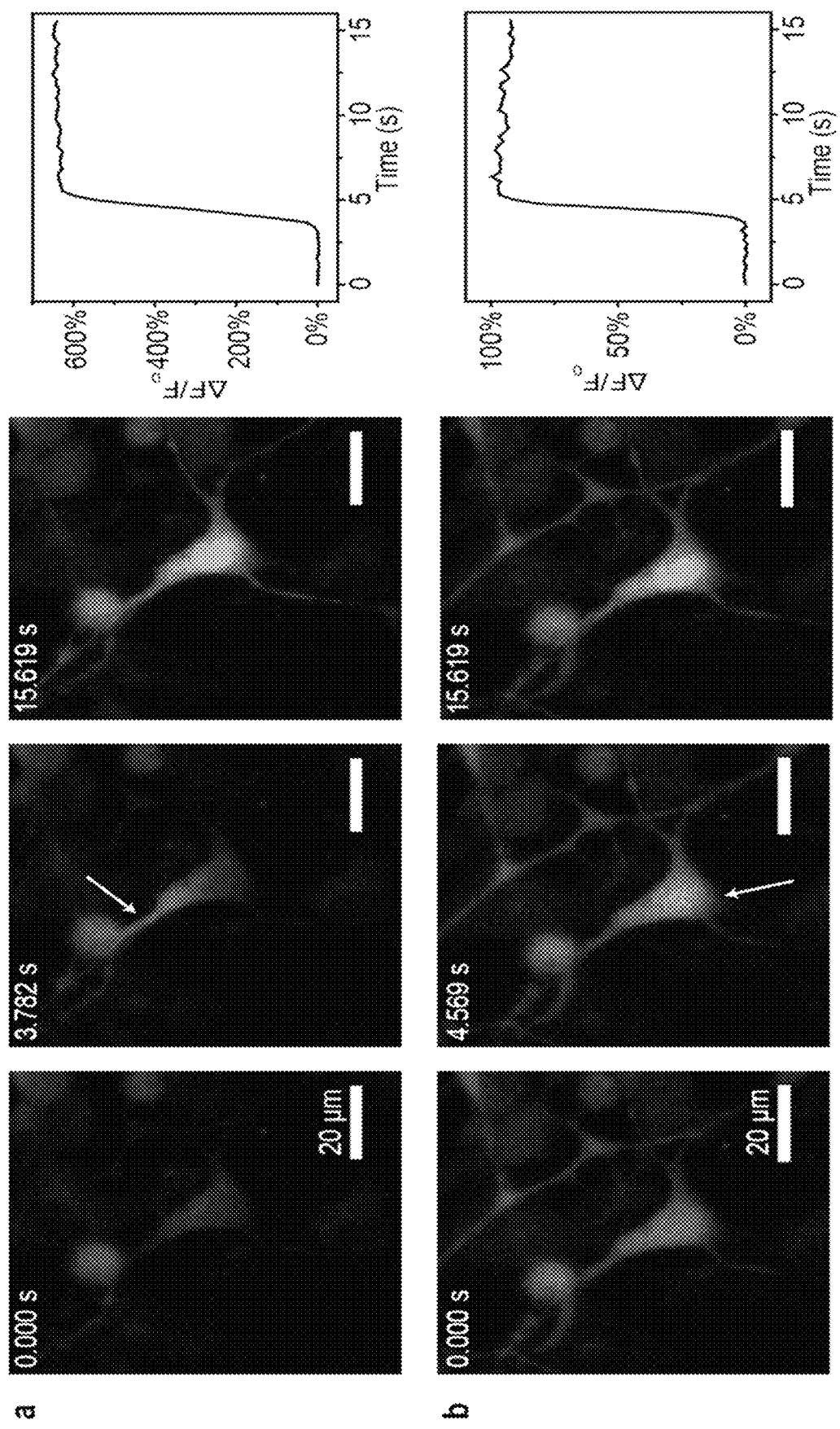
FIG. 52 provides images of minimally invasive extracellular stimulation of calcium in cells. (A) and (B) The same glial cell cultured on a p-i-n Si diode junction (calcium) is stimulated extracellularly in two consecutive series without being damaged. As shown in the first time of stimulation (A), not only the cell body but also the protrusion can be stimulated to induce the cellular calcium dynamics. The stimulation laser (592 nm, ~14.4 mW) was on for 1 ms right before the time point of 3.782 s in each case. White arrows mark the laser stimulation sites.
Figure 53:
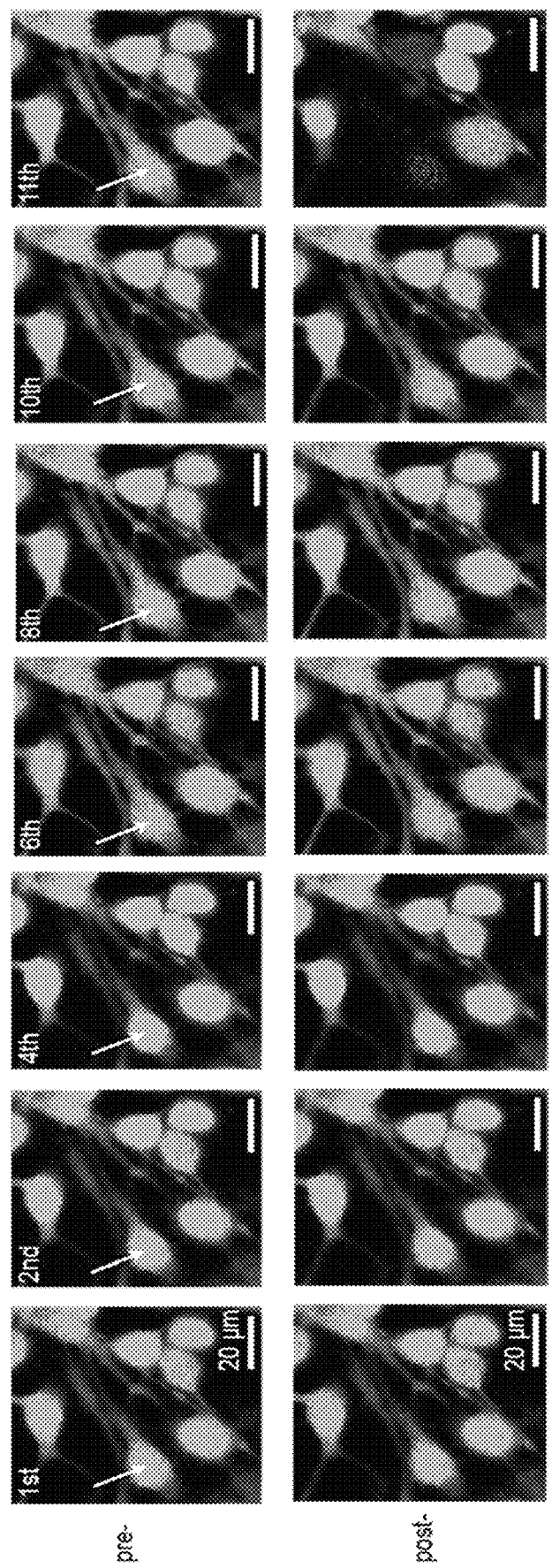
FIG. 53 provides images of minimally invasive extracellular photostimulation of cells. The same glial cell cultured on a p-i-n Si junction (calcein) was stimulated extracellularly for ten consecutive times without being killed. The stimulation condition was ~54.1 mW for 1 ms in the first ten cycles using a 592 nm laser. The cell was killed (ethidium homodimer-1) after a 1-ms pulse of ~79.5 mW laser was delivered. White arrows mark the laser stimulation sites.
Figure 54:
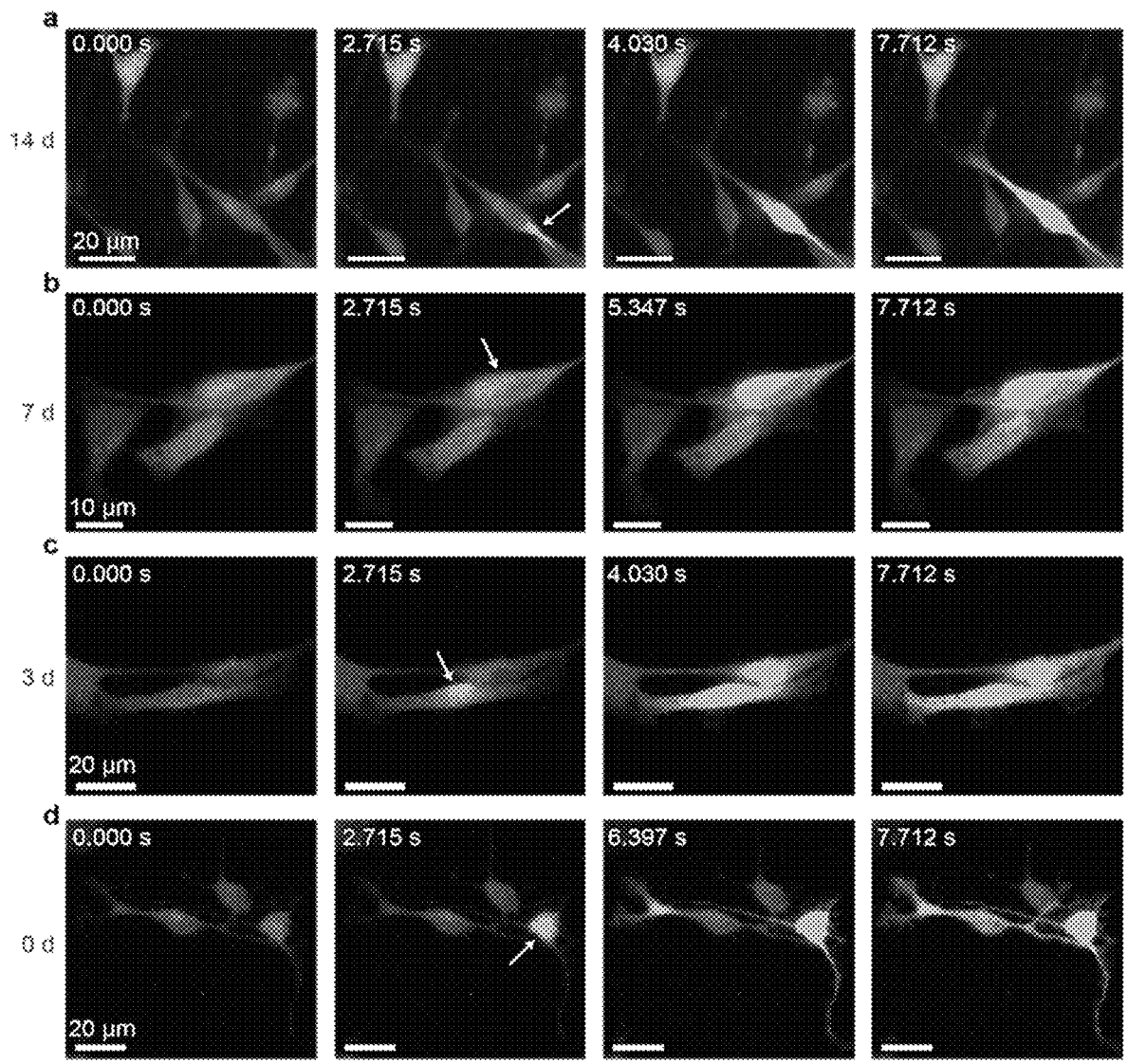
FIG. 54 provides images of extracellular photostimulation of calcium dynamics performed over solution-degraded Si surfaces. Si diode junctions were immersed in PBS solutions under 37° C. for various durations ((A) 14 days; (B) 7 days; (C) 3 days; (D) 0 day) prior to the culture and subsequent photostimulations. The threshold intensity ((A) 42.7 mW; (B) 32.2 mW; (C) 22.3 mW; (D) 14.4 mW) of the laser (592 nm) to elicit calcium dynamics gradually increases for cells cultured on substrates with a longer immersion period. The laser was on for 1 ms right before the time point 2.715 s. White arrows mark the laser stimulation sites.

In addition to the nanowire-enabled intracellular biointerfaces, the possibility of implementing extracellular modulations with larger Si structures was also explored to match the sizes of cultured cellular assemblies and even small tissues. P-i-n Si diode junctions were first tested because their significantly larger light-induced photocurrents (FIGS. 30C-D; FIG. 33) may be readily sensed by cells that are attached directly. Patch clamp and calcium imaging studies show that DRGs cultured on Si diode junctions can be stimulated with focused light pulses (FIGS. 31A-B and FIG. 50) individually or sequentially in a cellular assembly, with a high spatiotemporal resolution and minimal invasiveness (FIGS. 51-53). A pre-immersion of Si substrate in buffer solution for two weeks yielded a two-fold increase in threshold laser intensity (FIG. 54).

An in vitro test was then performed on acute ex vivo brain slices from mouse neocortex interfacing with a distributed p-i-n Si mesh (FIG. 23E) to evaluate the feasibility of the optically-controlled neuromodulation of a small tissue (FIG. 40A, left; FIG. 31C). A whole-cell recording in voltage-clamp mode was made in a cortical pyramidal neuron located in the middle of the 300-μm thick slice while the Si mesh was in contact with the bottom face of the slice (FIG. 40A, lower right). Immediately after flashing a focused laser beam on the Si mesh (473 nm, 1 ms, ~2 mW, ~57 μm spot size) (FIG. 40A, upper right), there were two fast electrical artifacts with opposite polarities (FIG. 40B, marked by #), likely due to the capacitive charging and discharging of the Si/electrolyte/cell interfaces (FIG. 30). Excitatory postsynaptic currents (EPSCs) (FIG. 40B, marked by stars) were then recorded arriving with short latency and low jitter after the photoelectric artifacts. Laser illumination of the Si mesh evoked spikes not in the patched neuron but in one or more presynaptic neurons in the slice, which provided the excitatory synaptic input to the recorded postsynaptic neuron. That the patched cell is not triggered to spike may be due to a combined reason that the cell is far away from the Si under illumination (difference in depth of ~150 μm) and only the immediately neighboring cells may be substantially activated by the localized laser stimulation. The ability to photo-activate presynaptic neurons and detect synaptic inputs with little or no direct activation of the recorded postsynaptic neuron is advantageous for photostimulation mapping of neuronal circuits. The Si mesh in conjunction with focused laser scans thus suggests the potential of this new methodology for ex vivo analysis of brain circuit organization.

Organ Level Biointerfaces

Figure 55:
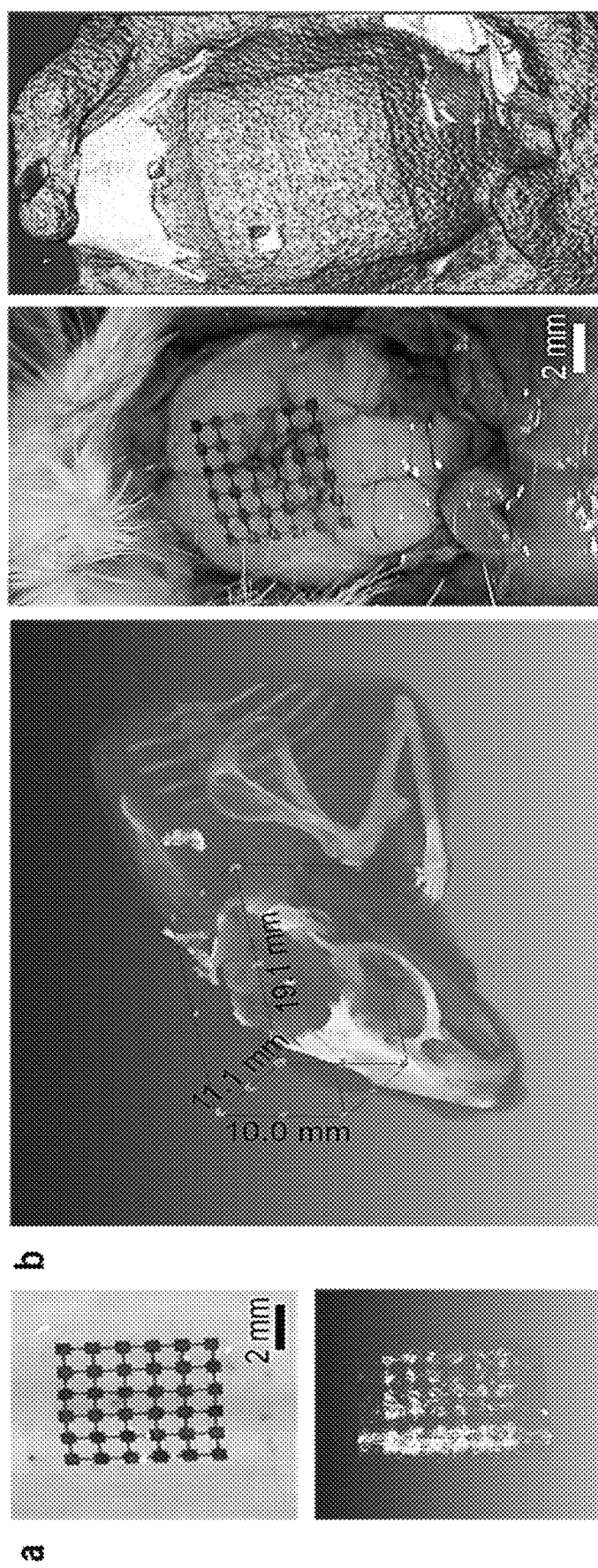
FIG. 55 provides images of a distributed Si mesh forming conformal interfaces with the brain cortex. (A) A photograph (upper) and its corresponding micro-CT image (lower) of a flexible device made of a Si mesh a PDMS layer. The surface decoration with Au also provides additional contrast under x-ray scans. (B) The device can conformally coat the mouse brain cortex as shown both by the photograph (middle) and the CT image (right).
Figure 56:
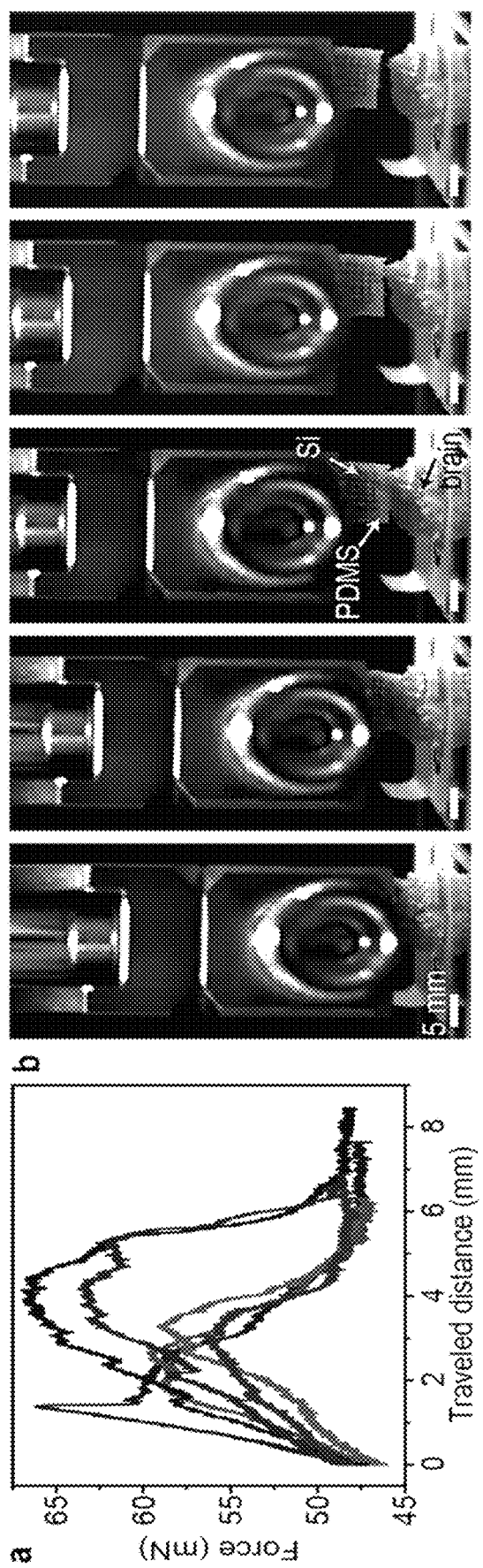
FIG. 56 shows the adhesion of a flexible device made of Si and PDMS to brain tissue. (A) Representative force-extension curves recorded during the peelings of the device from the brain cortex yielding an average adhesion energy of 1.34±0.63 J/m². (B) Snapshots of a typical peeling test showing the adhesion between the device and the brain when detaching.
Figure 57:
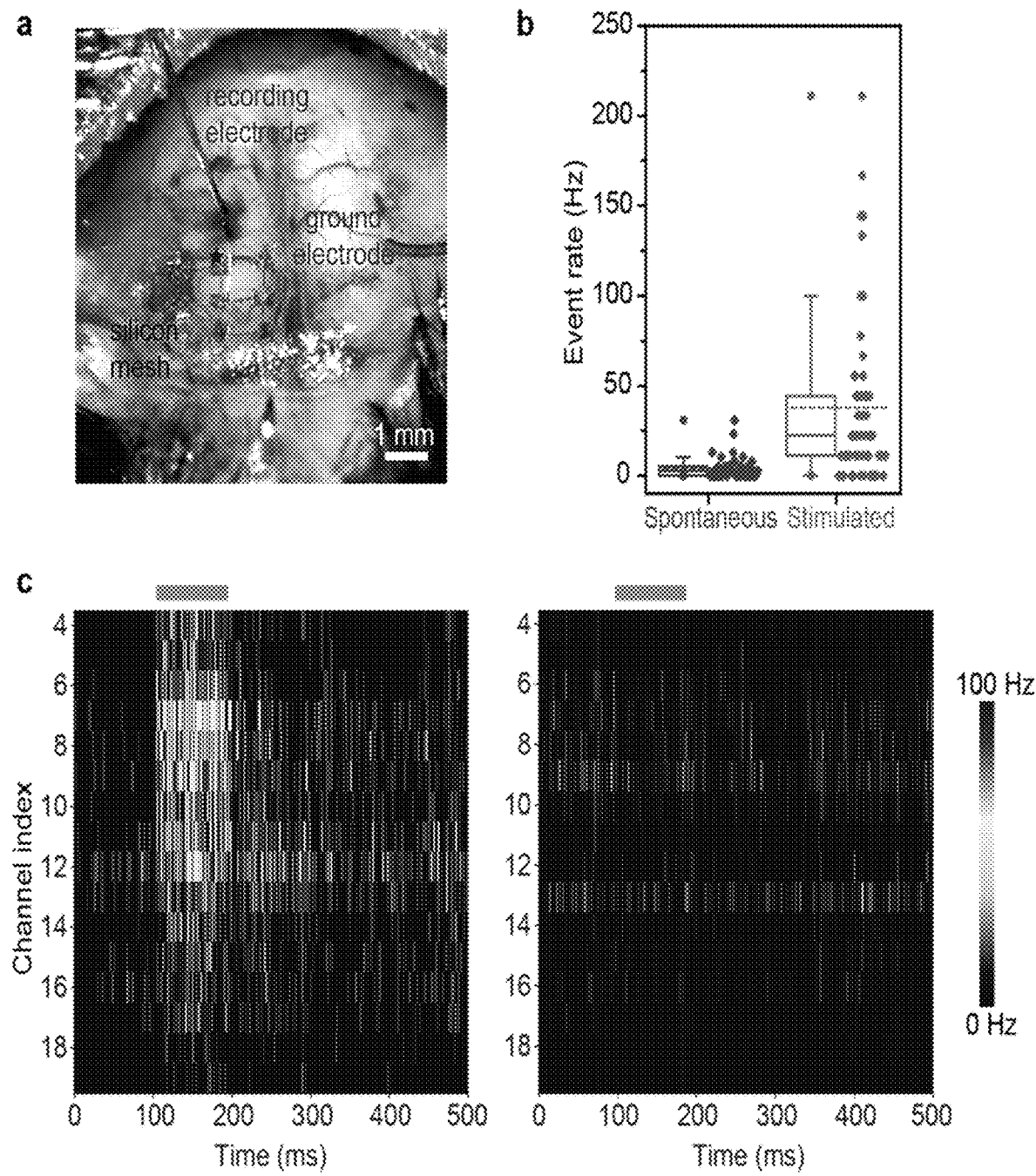
FIG. 57 illustrates recorded brain responses under illumination due to a Si mesh. (A) The experimental paradigm of an in vivo photostimulation test. A linear probe is inserted into the somatosensory cortex with an attached Si mesh in the close proximity. The laser illumination site (473 nm, ~216 μm spot size) is marked by a star. (B) The mean evoked response rate (~37.9 Hz) is significantly different from the spontaneous one (~3.7 Hz). Half of the data points are within the boxes, 80% are within the whiskers. Solid and dashed lines represent the medians and means, respectively. Round dots mark the maximum and minimum values. Diamond dots represent the raw data points. Wilcoxon rank sum test, p=5.5×10⁻⁸. Event rates were calculated from channel 9 with the 5-mW and 100-ms stimulation condition (n=50 trials). (C) Recordings from a control experiment without the Si mesh (right) did not yield significant signals under illumination. Bars mark the illumination periods.
Figure 58:
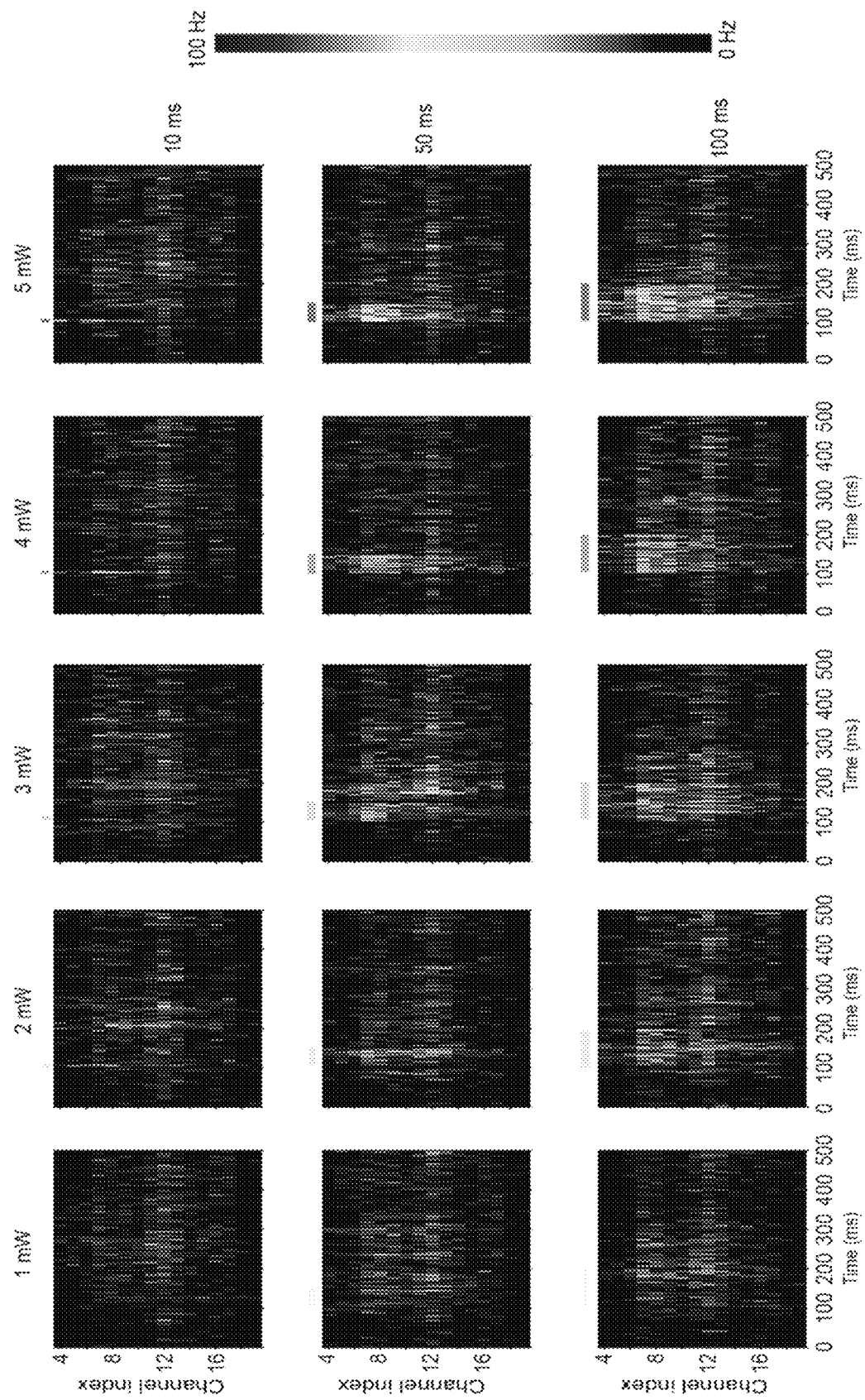
FIG. 58 illustrates a controllable stimulated neural response. Parametric stimulations with varied laser powers and durations (1~5 mW, 10 ms, 50 ms, 100 ms) show a positive correlation between the evoked event rate and the stimulation power, which is essential to the predictive control of the Si mesh as a precise neuromodulator. Bars with different transparencies indicate illumination periods with different laser powers.
Figure 59:
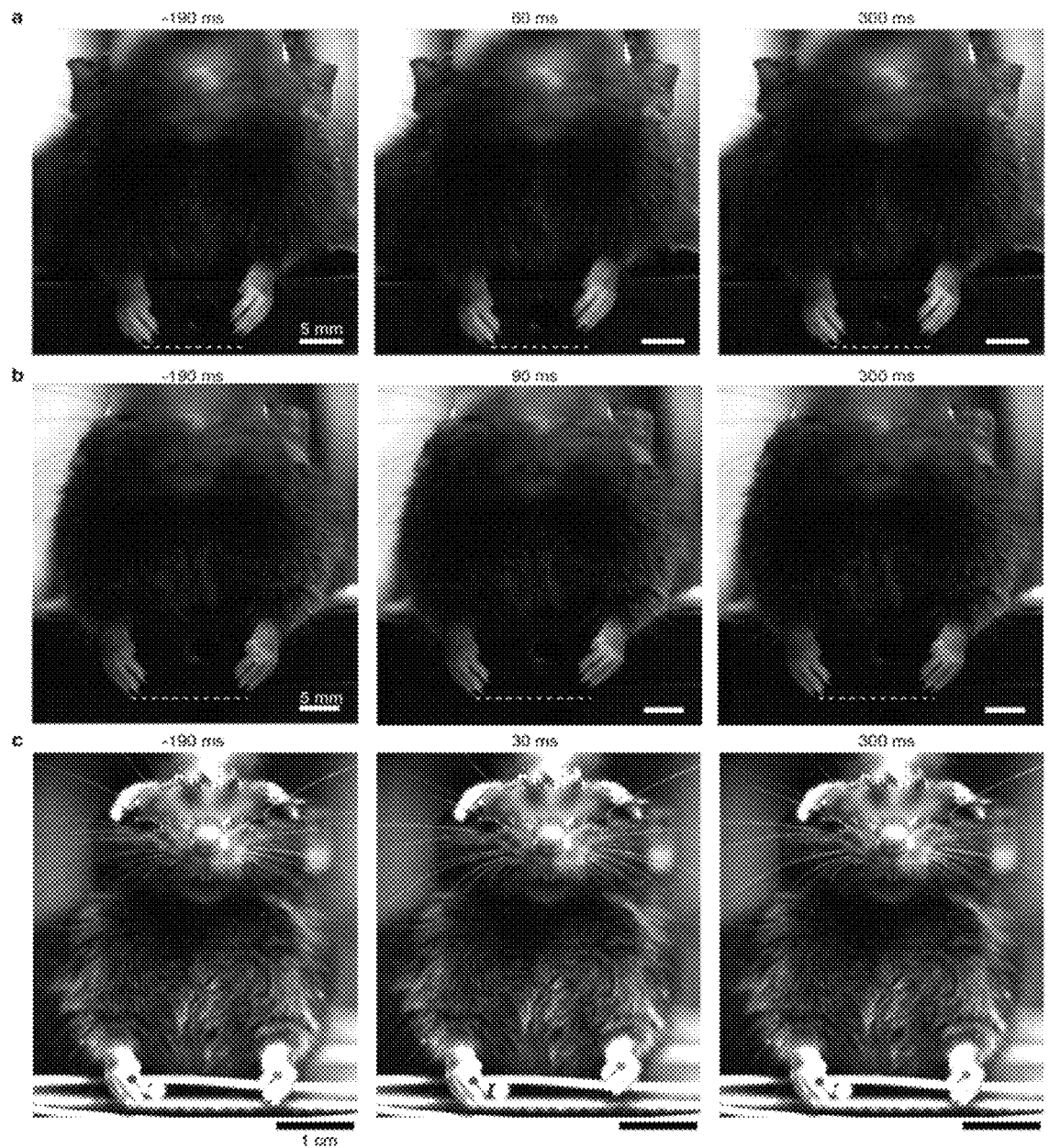
FIG. 59 provides images of mouse forelimb movement triggered by photostimulation of the Si mesh. More examples showing the preferred left forelimb movements following the laser illuminations (50 ms, ~5 mW for a; 100 ms, ~4 mW for b; 50 ms, ~4 mW for c, 473 nm, ~216 μm spot size) of Si meshes attached to the right side of the forelimb primary motor cortex. The 0 ms time point denotes the light onset. White dashed lines in a and b were drawn to highlight the longitudinal movements of the left forelimbs.
Figure 60:
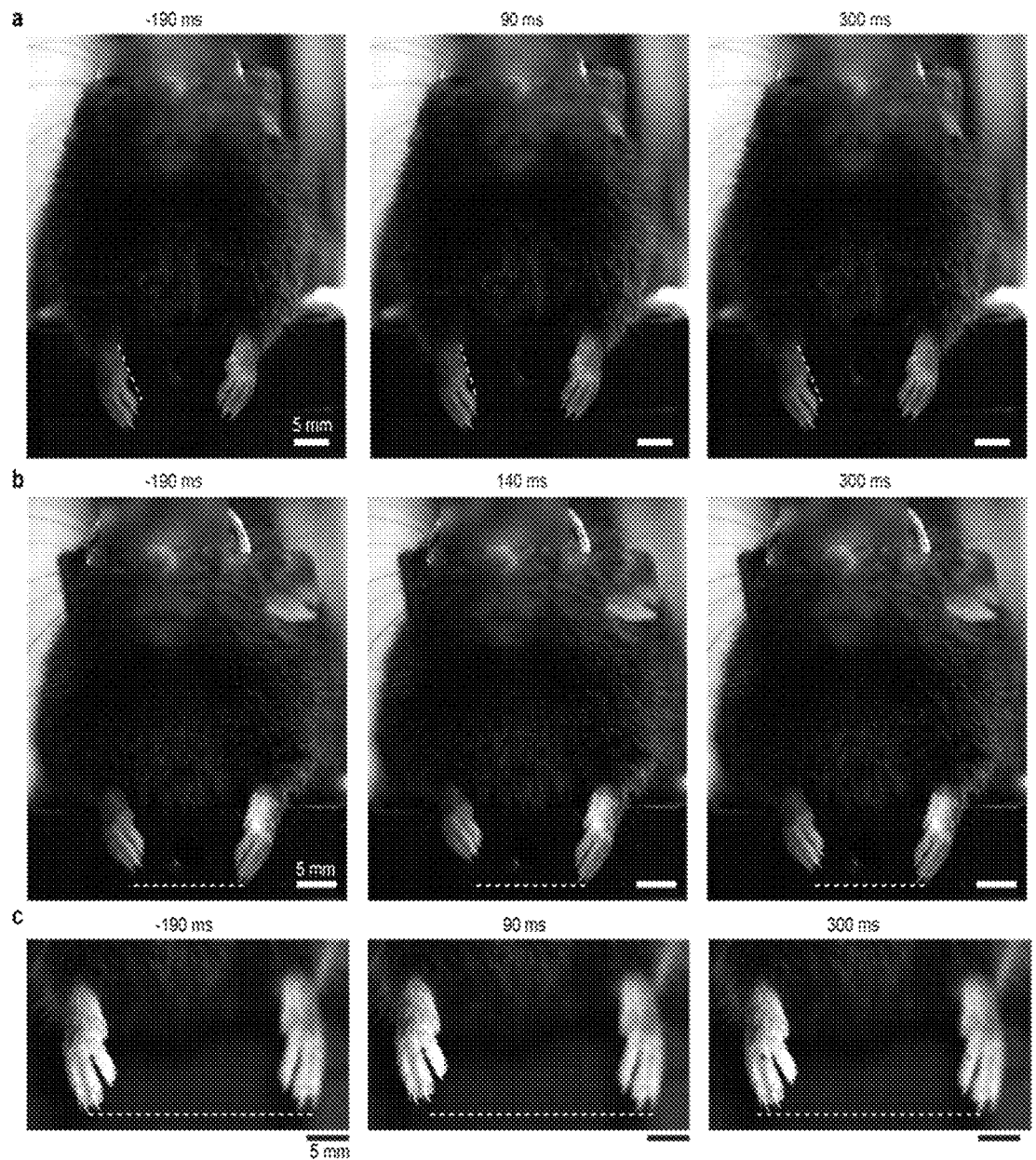
FIG. 60 Photostimulation of the forelimb motor cortex triggers the contra side forelimb preferred movement. The right forelimb movements can be triggered by the laser illuminations (50 ms, ~1 mW for a; 50 ms, ~5 mW for b; 100 ms, ~5 mW for c, 473 nm, ~216 μm spot size) of Si meshes attached to the left side of the forelimb primary motor cortex. See Supplementary Videos 3 and 4 for more details. The 0 ms time point denotes the light onset. The right forelimb in a underwent a lateral movements after the stimulation as indicated by the changes of the dashed line orientations. White dashed lines in b and c were drawn to highlight the longitudinal movements of the right forelimbs.
Figure 61:
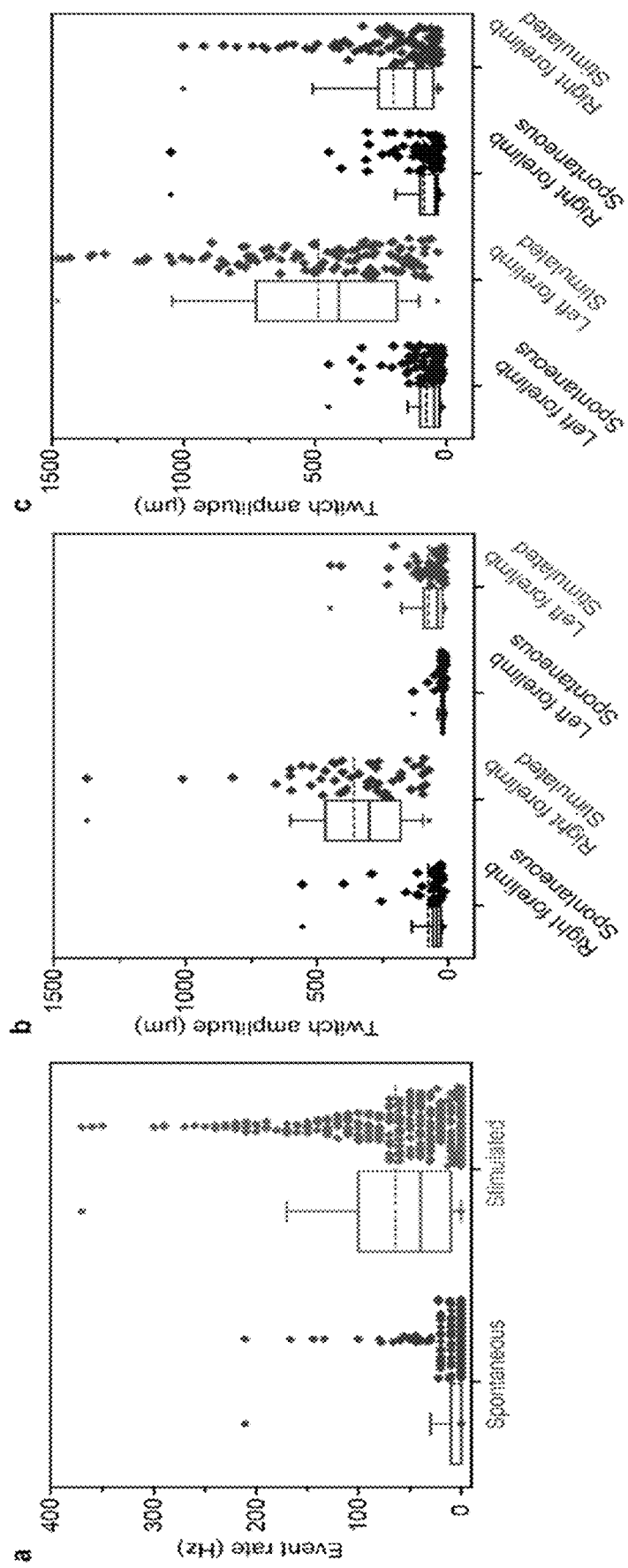
FIG. 61 provides quantitative comparisons of brain activities and forelimb movements before and after photostimulations. (A) The mean spontaneous response rate (~9.4 Hz) is significantly smaller from the evoked one (~64.3 Hz). Paired t-test, $p=3.8\times10^{-34}$. Event rates were calculated from the 5-mW and 100-ms stimulation condition. n=371 trials from three different mice. (B) and (C), Photostimulations of Si meshes attached to the primary motor cortex ((B) left cortex; (C) right cortex) evoked movements of contralateral forelimbs ((B) right forelimb; (C) left forelimb) with significantly higher twitch amplitudes than the ipsilateral ones ((B) left forelimb; (C) right forelimb). n=50 trials from four mice in (B) n=119 trials from five mice in c. Half of the data points are within the boxes, 80% are within the whiskers. Solid and dashed lines represent the medians and means, respectively. Round dots mark the maximum and minimum values. Diamond dots represent the raw data points.

Finally, an Au-decorated and Si mesh-based flexible membrane was interfaced with a mouse brain to control the brain activities, e.g., the ability to sense, interpret, and act upon the environment. The bilayer device layout, consisting of the Au-decorated Si mesh and the holey PDMS membrane (FIG. 23E), allows the device's conformal attachment to the brain cortex (FIG. 55) with sufficient adhesion (FIG. 56). An Au decorated surface was chosen due to its large capacitive and Faradic current components. The in vivo photostimulation experiment was performed using an extracellular linear array to record neural activities following laser illuminations (473 nm, ~5 mW, 100 ms, ~216 μm spot size) of the silicon mesh attached to the somatosensory cortex of an intact mouse brain (FIG. 40C; FIG. 31D and FIG. 57). In individual trials of the test, enhanced neural activities were evident during the illumination period—with significant photoelectric artifacts at the light onsets and offsets (FIG. 40D). The detected spike-like events using criteria of a high pass filter of 800 Hz and a threshold of 5 times the noise level standard deviation (SD) exhibit waveforms typical of natural extracellular electrophysiological recordings (FIG. 40E). Peristimulus time histograms (PSTH) from 16 channels (FIG. 40F) (with the depths between 200 μm and 900 μm below the pia) clearly show the illumination-triggered neural responses, in the upper and middle layers of the sensorimotor cortex. Statistical analyses further revealed that the evoked responses have a significantly higher rate than the spontaneous ones (FIG. 57). In addition, stronger short-latency activity was observed in more superficial neurons, which were closer to the silicon mesh and thus may be more easily activated. Over time, activity spreads to deeper layers (FIG. 40F), consistent with the propagation of signals through the local and long-range cortical circuits, similar to patterns observed with optogenetic photostimulation. Moreover, parametric stimulations show a colligative behavior in that the activated neural response rate is correlated with the stimulation power (FIG. 40G; FIG. 58), which is essential to the predictive control of the Si mesh as a precise neuromodulator. Finally, based on the electrophysiology studies, the Si mesh-enabled photostimulations of the brain cortex was tested to determine if it can trigger movements of anesthetized mice. When a Si mesh attached to the right side of the forelimb primary motor cortex was illuminated, the contralateral left forelimb of the mouse showed a large, rapid up-and-down (flexion-extension) movement shortly after the stimulation (FIG. 40H and FIG. 40I; FIG. 59) The video of the movement is also provided as Supplementary Video 1 and Supplementary Video 2, both available from Supplementary Information for Jiang et al., Nature Biomedical Engineering 2:508-521 (2018), available at http://doi.org/10. 1038/s41551-018-0230-1. Conversely, photostimulation of the left forelimb motor cortex evoked movements of the contralateral right forelimb (FIG. 60; Supplementary Videos 3 and 4, both available from Supplementary Information for Jiang et al. provided above). In some cases, small ipsilateral forelimb movements were also evoked (FIG. 40H-I), possibly reflecting activation of uncrossed (ipsilateral) corticospinal projections and/or interhemispheric (callosal) circuits. Overall, the observations of cortically evoked movements are consistent with the functional organization of the forelimb motor control system (FIG. 61).

Example 5: Optical Training of Cardiomyocytes and Isolated Hearts with Silicon Mesh A freestanding SiNW mesh was used in optical training of cultured neonatal rat cardiomyocytes as well as adult rat hearts ex vivo to beat at a target frequency (FIG. 23A). An uninformed search approach was used for generating a large set of transient, localized and effective input signals (e.g., Sn(r, l, t)) to trigger a single integrated cardiac response (i.e. ∫S·dt), enabled by (1) a fast-moving illumination via either a lateral laser scanning or the mechanical motion of a beating heart (Level 1, serial process, FIG. 23B), and (2) a high density array of SiNWs that can not only generate light-induced physicochemical outputs but also exhibit waveguiding behavior for light intensity modulation (Level 2, parallel process, FIG. 23B). Integrating these modalities (i.e. ∫S·dt) allows for the training approach to mimic physiological stimuli, by spatially engaging whole cells with massive number of optical inputs during a short period of time (FIG. 23A). The training method consists of identifying a pre-stimulus frequency via calcium imaging, optically training cells using a scanning laser stimulus with programmed on/off cycles, and tracking a post-stimulus frequency as feedback for subsequent training until the target cells or tissue beats at the target frequency (FIG. 23B). This method can avoid potential issue of missing optimal conditions (e.g., Sn(r, l, t) or Sm(r', l', t+dt) or their combinations) for cellular modulation, and it does not require any pre-knowledge about the exact biointerfaces.

Figure 62:
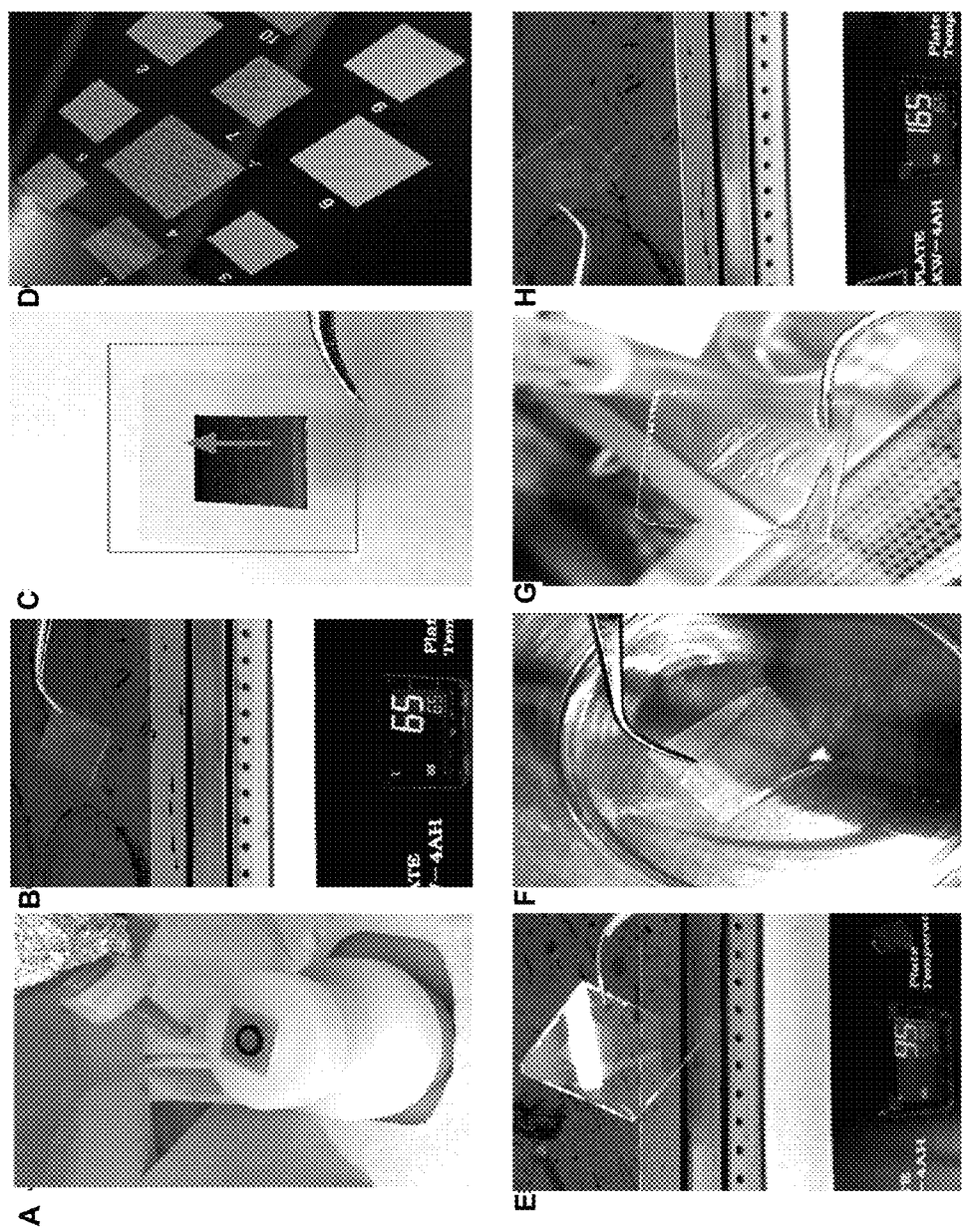
FIG. 62 illustrates SU-8-PIN Mesh Synthesis. SU-8 grid structure is fabricated via photolithography. (A) SU-8 2005 precursor is spun onto a glass slide at 2500 rpm for 5 seconds and 3500 rpm for 55 seconds to form a 5 μm thick SU-8 layer on the glass slide. (B) SU-8 precursor is heated to 65° C. for 180 sec and then 95° C. for 180 sec. (C) After this pre-bake step, SiNWs are integrated via mechanical translation from the original growth wafer onto the surface of the SU-8. Orange box denotes glass slide with SU-8 and SiNW growth wafer (SiNWs face glass slide). Wafer is translated across SU-8 surface in the direction of arrow, and SiNWs break off growth substrate and become embedded in SU-8 surface. (D) Samples are patterned via a chrome photolithography mask and hard contact lithography with a UV light exposure dose of 175 mJ. (E) After exposure, samples are baked again at 65° C. for 180 sec and 95° C. for 180 sec for the post-bake step to crosslink SU-8. (F, G) Samples are developed in SU-8 developer for 30 seconds and rinsed in IPA for 15 seconds and dried under $N_2$. (H) Finally a post-bake step is performed at 165° C. for 20 minutes.
Figure 63:
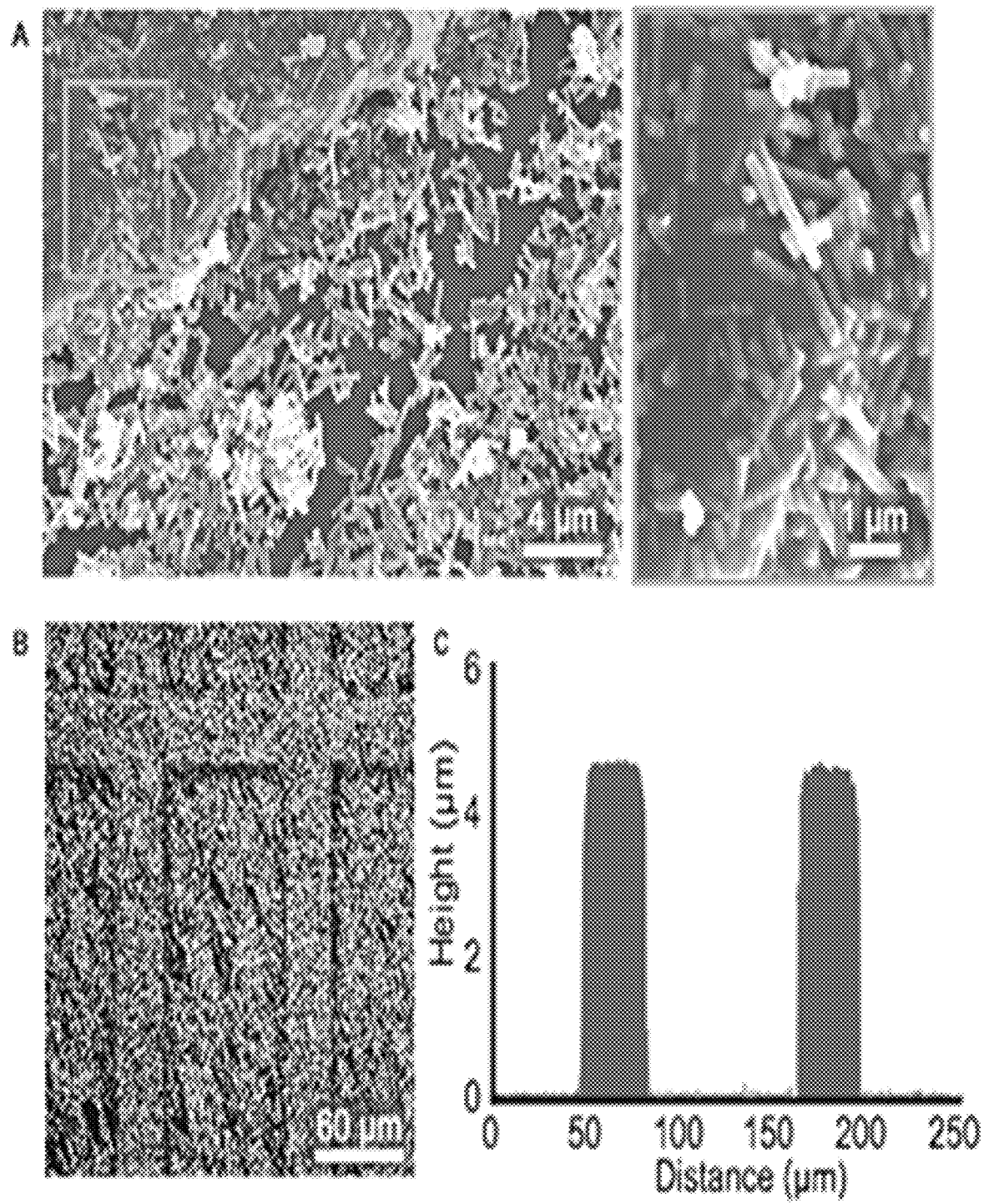
FIG. 63 illustrates SU-8-PIN Mesh Properties. (A) SEM image of high-density PIN-SiNW mesh integrated into a SU-8 grid support. Zoomed in SEM image of SiNWs integrated into the surface of the SU-8 polymer. (B,C) Laser scanning confocal microscopy images show two different NW density and corresponding height profile showing 5 μm height of SU-8-PIN mesh reconstructed from laser scanning confocal 3D data.
Figure 64:
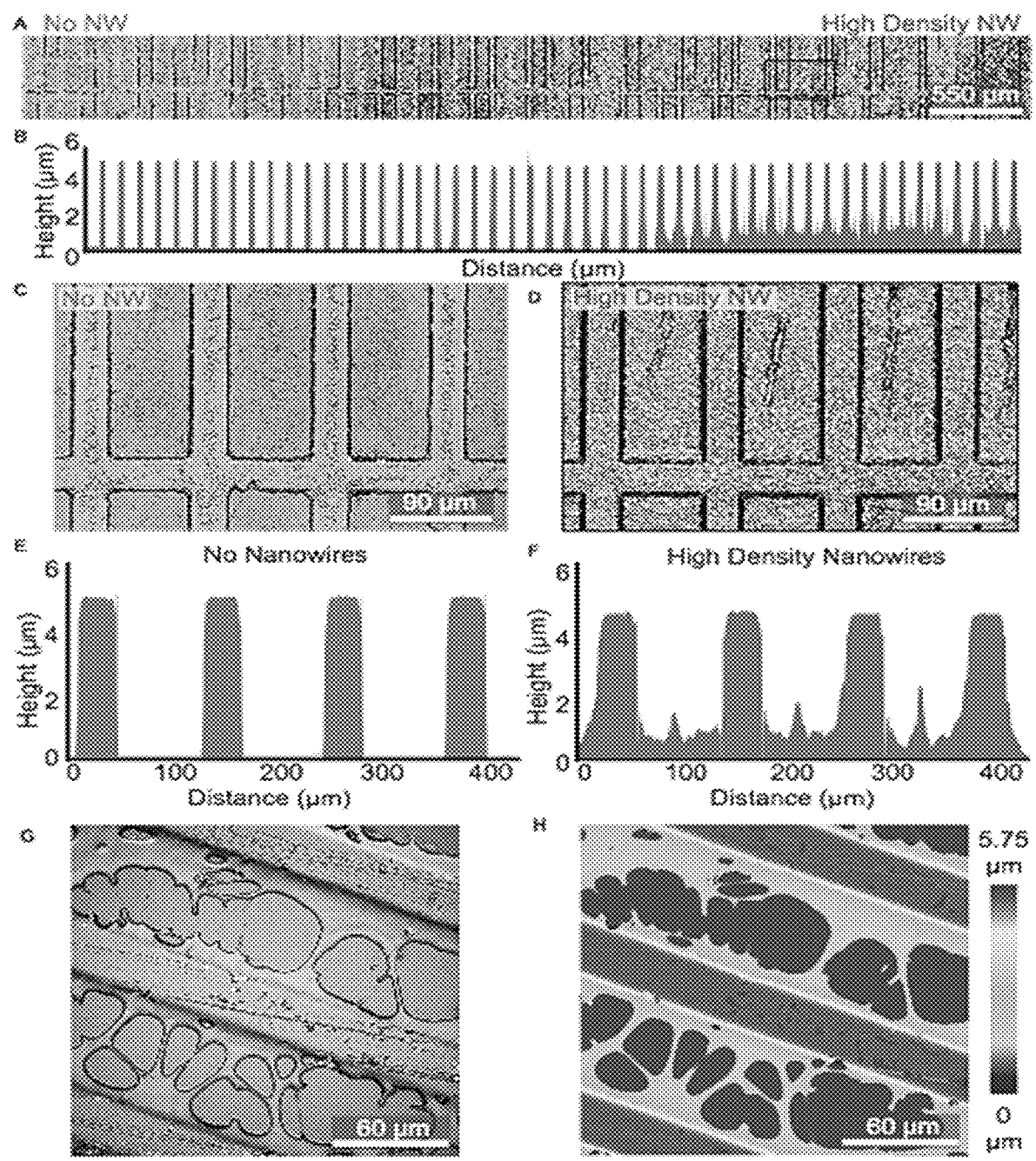
FIG. 64 illustrates waveguiding effects of SiNW in SU-8 synthesis. (A) Laser scanning confocal image of SU-8 mesh with very high photolithography UV exposure dose, 400 mJ, fabricated with SiNWs only present in the right half. (B) Height profiles the SU-8 mesh in (A). Height profiles are reconstructed from laser scanning confocal 3D data displaying SU-8 in the mesh gaps in the presence of SiNWs and no SU-8 in the gaps in the absence of SiNWs. These are representative traces of 4 different meshes. (C, D) Zoomed in laser scanning confocal images of SU-8 mesh from (A) in the presence of nanowires (black box inset from (A)) and in the absence of nanowires (box inset from (A)). (E,F) Height profiles reconstructed from laser scanning confocal 3D data of SU-8 mesh regions displayed in (C) and (D), respectively. (G) Laser scanning confocal image of SU-8-PIN mesh. (H) 3D map displaying height profiles of image in (G). This sample was exposed to a high dose of UV light energy (400 mJ) and contains a low density of nanowires.
Figure 65:
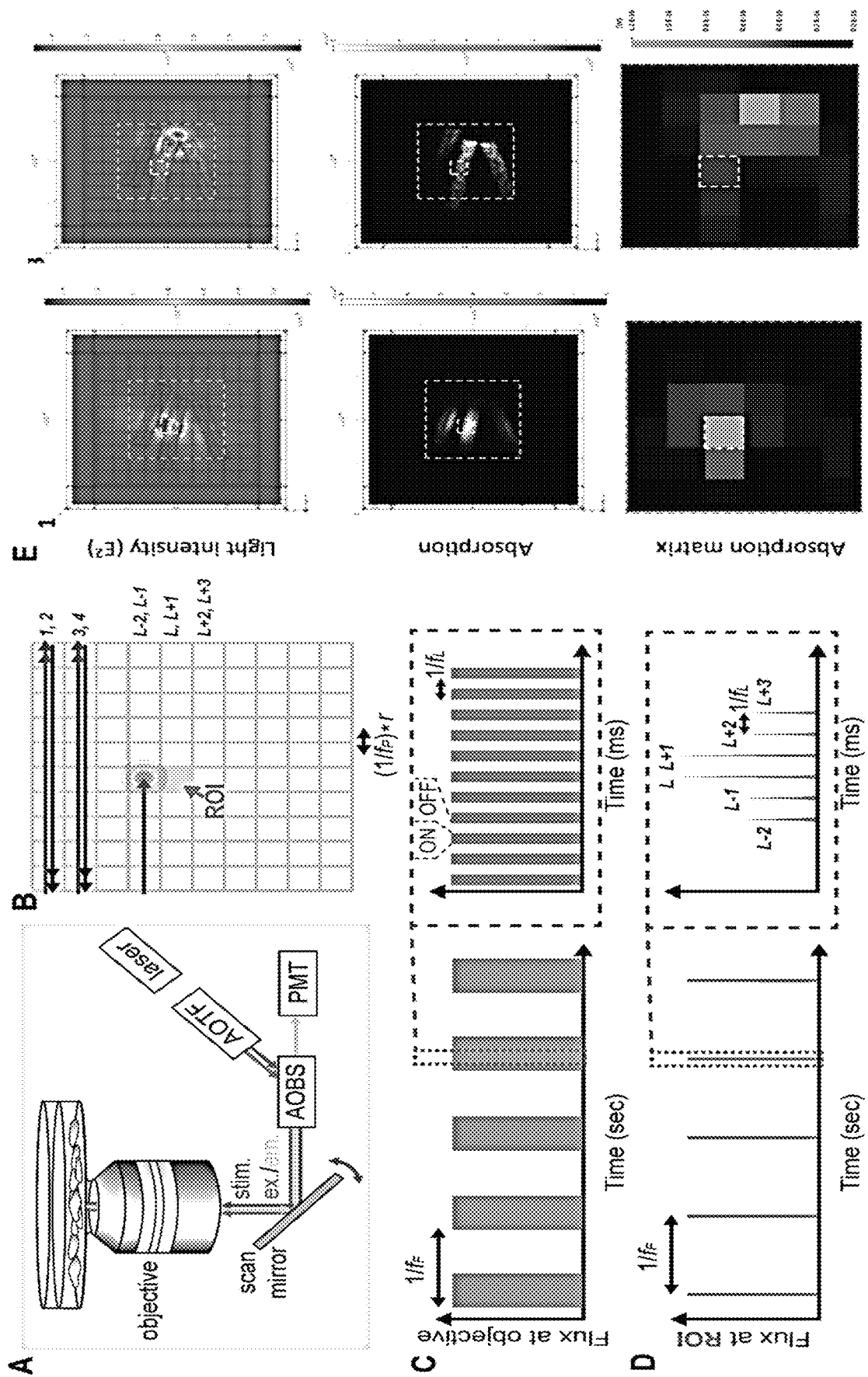
FIG. 65 provides schematics and images of the optical training of cardiomyocytes using a polymer-silicon mesh.

The composite mesh was fabricated using SU-8 as the polymer support component, and coaxial p-type/intrinsic/n-type silicon nanowires (PIN-SiNWs), previously shown to produce photoelectrochemical currents and elicit action potentials in single neurons, as the semiconductor modulation component (FIG. 63). With mechanical transfer and subsequent photolithography (FIG. 1C), a high-density mesh of PIN-SiNWs was integrated onto an SU-8 grid (FIG. 23D, FIGS. 62-63). The resultant composite contains a high density PIN-SiNW network that spans across the 86×424 µm window regions in the SU-8 grid (FIG. 23D, FIGS. 63-64). Using confocal microscopy, thin filaments of SU-8 polymerized were identified beneath the SiNWs in the window regions (FIG. 23E), which could not have been formed by direct exposure to UV light during photolithography, as the window regions are blocked by the mask (FIG. 23C, FIG. 65). Moreover, in the absence of SiNWs, no evidence of these thin SU-8 filaments was observed (FIG. 64), suggesting that the mechanically transferred SiNWs can form a self-aligned optical guide for SU-8 polymerization (FIG. 23C, lower). Simulations performed suggest that SiNWs exhibit wave guiding behavior during the lithography process that results in UV light leakage into the window regions of the SU-8 grid, thus allowing for aligned SU-8 polymerization to produce mechanical support for the high density SiNWs (FIG. 23F).

With this polymer-silicon mesh, an uninformed search-based optical training method was designed for cultured cardiomycytes (FIG. 65A). This approach pairs confocal laser scanning (i.e. the serial search for locations, FIG. 23B) with PIN-SiNW-enabled waveguiding (i.e. the parallel search for intensities; FIG. 23B) to produce a combinatorial collection of transient illumination conditions with variable locations and intensities over whole cell areas. First, a diffraction-limited 0.6 µW 516 nm laser spot was scanned over a region of interest, at a 1.024 MHz pixel rate (fP) and 1 kHz line-scan rate (fL) with 2 scans/line (FIGS. 65A-B). This 1.024 MHz frequency is much faster than the frequency range for targeted cardiomyocyte contractions or the frame rate (~0.5-3 Hz, fF), allowing for cellular integration of multiple tiny stimuli that yields one response event (i.e. a single cardiomyocyte beat measured as a single calcium spike). After the full area of interest is scanned, a programmed off-time (i.e., without light illumination) occurs (FIG. 65C). The desired output frequency (fF) is achieved via cycles of defined on- and off-time periods (FIG. 65C). Each pixel (e.g., the orange square in FIG. 65B) experiences six times of direct incident fluxes per frame, given the diffraction-limited spot size is slightly larger than that of the pixel and the 2 scans/line used in the present study (FIG. 65D). Second, in parallel with the scanning modality (i.e. serial search), simulations showed that the PIN-SiNWs allow for light propagation into surrounding hypothetical pixels (FIG. 65E). The exact configuration of the SiNWs around the illumination spot determines the distribution of absorbed energy at nearby pixels that are contain both a cell and SiNW(s) (FIG. 65E). The simultaneously generated variations in absorbed energies constitutes the parallel search pathway. The energy variation at each pixel is related to the change of stimulatory strengths, which depends on both the laser spot location and the SiNW configurations. Taken together, the combination of the scanning operation (i.e., serial search) and the SiNW network (i.e., parallel search) efficiently utilizes the laser stimulus, by drastically increasing the variations in stimulation position and intensity while keeping the total input radiant low.

Figure 66:
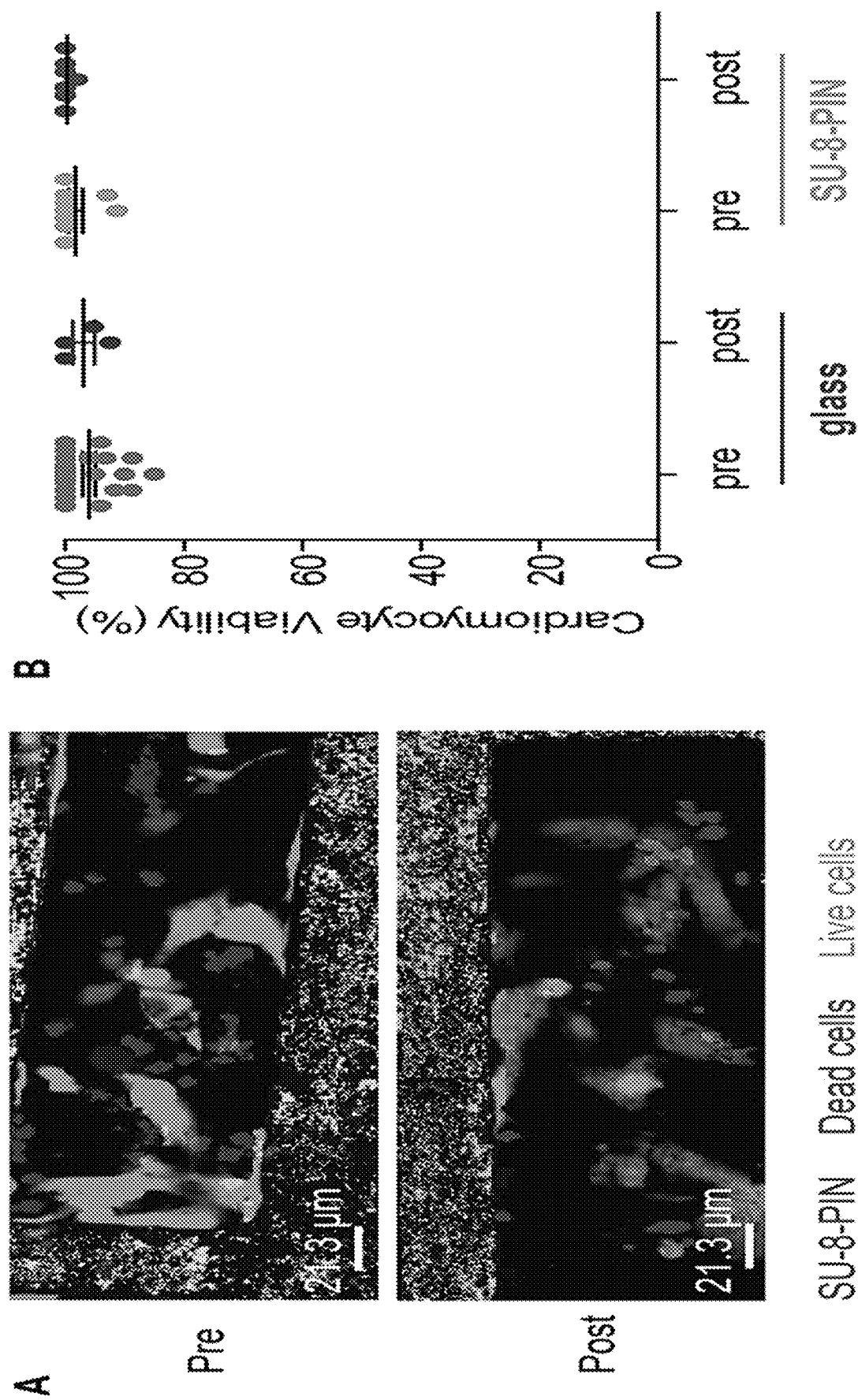
FIG. 66 provides a viability assay demonstrating that optical training of cells cultured on SU-8-PIN mesh does not induce cytotoxicity. (A) Live/Dead staining of cardiomyocytes and cardiac fibroblasts cultured on fibronectin coated SU-8-PIN meshes before optical training (top) and after optical training (bottom). Live cells, dead cells, and the SU-8-PIN mesh are shown. (B) Percentage of live cardiomyocytes cultured on glass and the SU-8-PIN mesh before and after optical training (lighter dots and darker dots, respectively). Only cardiomyocytes were counted (not fibroblasts) and cardiomyocytes were distinguished from fibroblasts by cell morphology. Each point represents the percent viability from one image taken from a total of 4 different glass samples and 3 different SU-8-PIN meshes. Percent viability was calculated from 21, 4, 9, and 7 images for glass pre training and post training, and SU-8-PIN pre training and post training, respectively.
Figure 67:
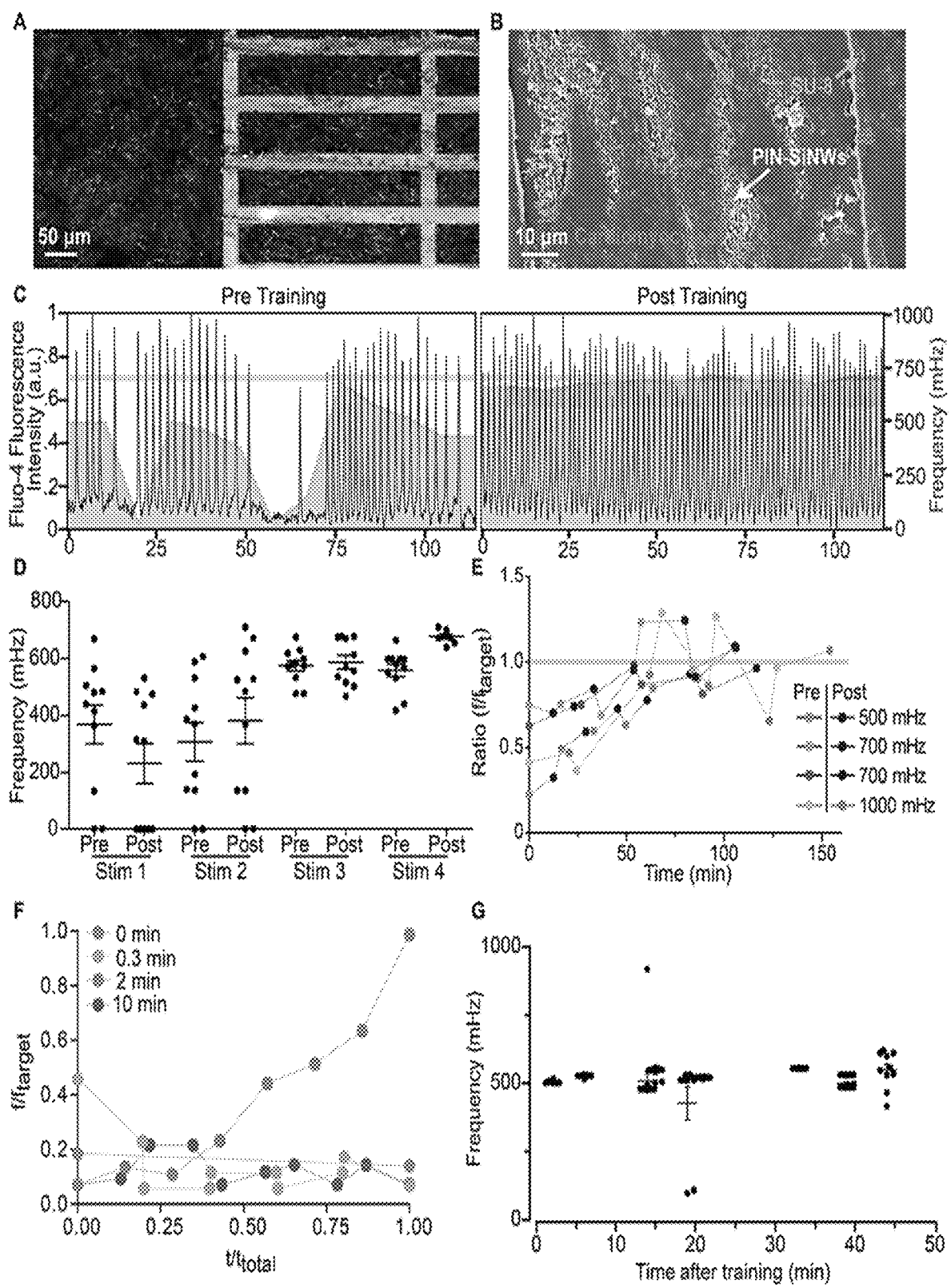
FIG. 67 illustrates the use of an uninformed search method to train cardiomyocytes on fibronectin coated composite meshes to beat at a target beating frequency.

Use of this uninformed search method was next demonstrated to train cardiomyocytes to beat at a target beating frequency. Neonatal rat ventricular cardiomyocytes were cultured on fibronectin coated composite meshes, and confirmed the substrate biocompatibility via a live/dead viability assay (FIG. 66). Immunofluorescence images demonstrated that the cells in contact with the mesh aligned with the long axis of the SU-8 grid structure, and were well connected via gap junctions (FIG. 67A). Scanning electron microscopy imaging confirmed intimate interactions between the cardiomyocytes and the PIN-SiNWs in the window region of the SU-8 grid (FIG. 67B).

Figure 68:
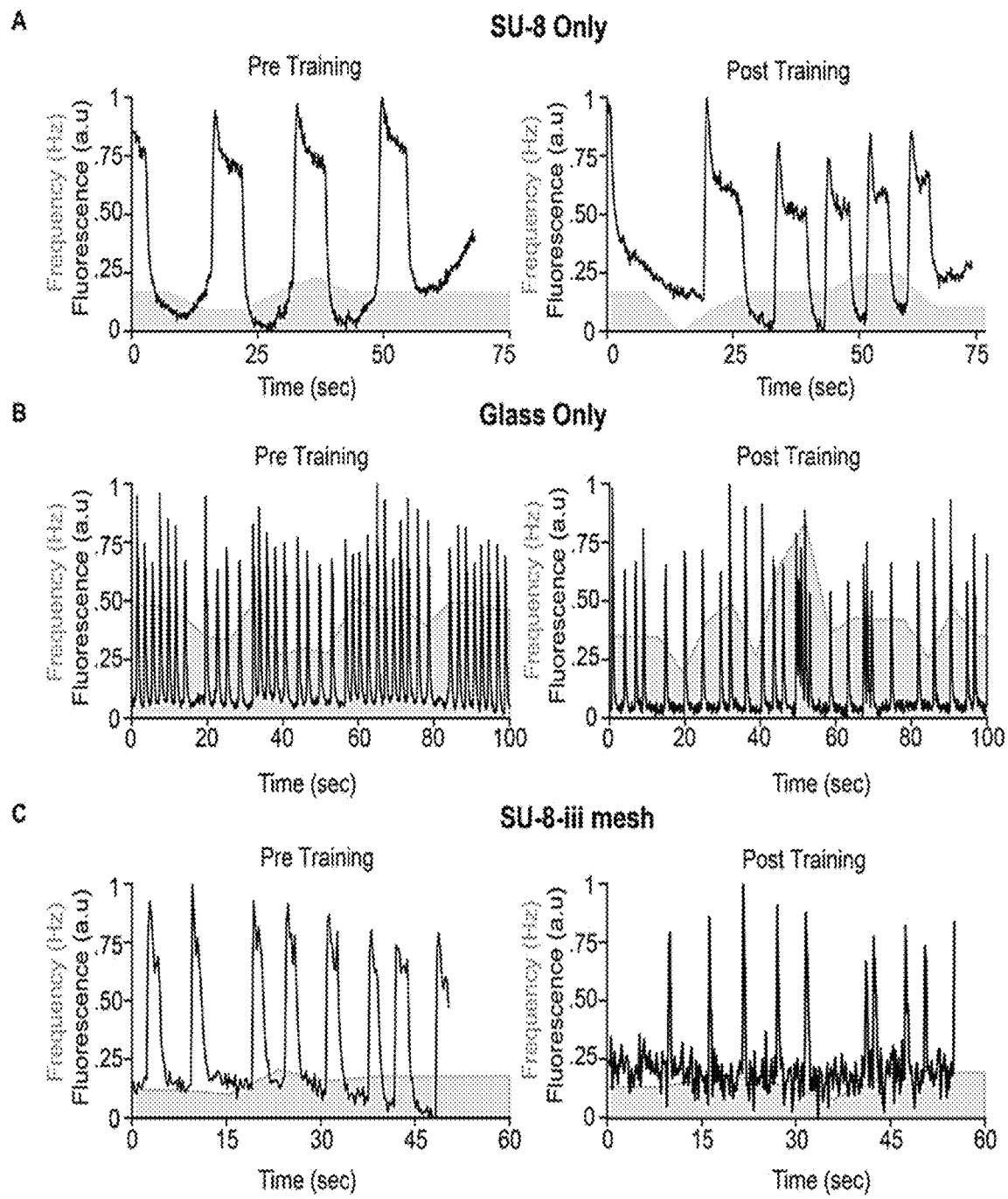
FIG. 68 illustrates optical stimulation of cardiomyocytes on SU-8 grids, glass, and SU-8-iii meshes, which may not result in training. (A-C) Fluo-4 calcium imaging traces (black traces) depicting pre training and post training beating patterns for a single cell from groups of cardiomyocytes that were trained to beat at 700 mHz for 75 min of total stimulation time on fibronectin-coated (A) SU-8 grid (19 cells), (B) glass (15 cells), or (C) SU-8-iii mesh (7 cells). A running average of frequencies every 18 seconds were plotted behind the black traces to show how consistently the cell was beating before and after the training (mountain plot). These are representative traces from 3 different experiments for each condition.
Figure 69:
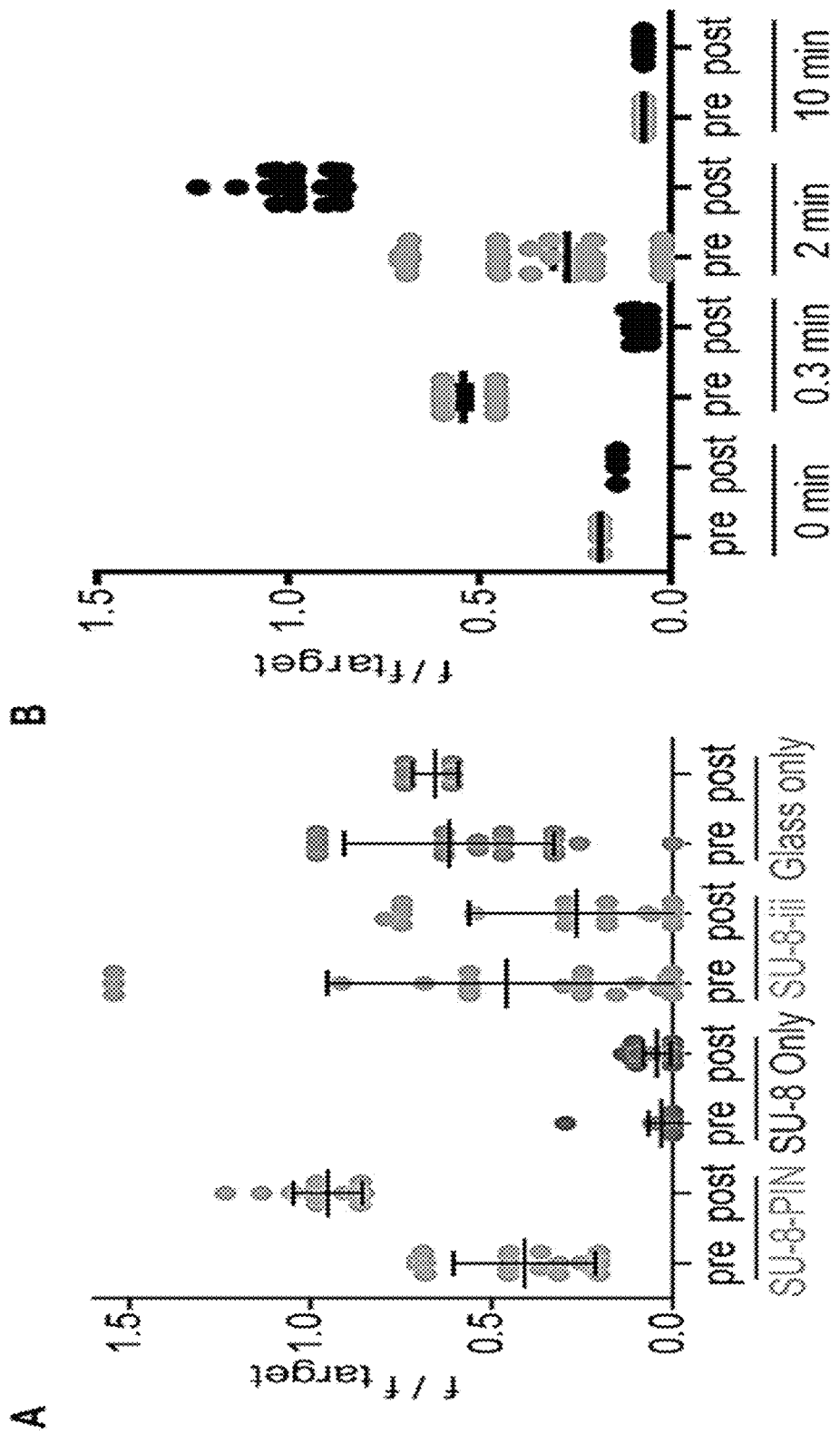
FIG. 69 provides a comparison of optical stimulation of cardiomyocytes on various substrates and with various stimulation break times. (A) Comparison of optical training efficacy of cardiomyocytes cultured on fibronectin-coated SU-8-PIN meshes, SU-8 grids, SU-8-iii meshes, or glass. Efficacy was determined by plotting the ratio of the beating frequency of individual cells (N=29 for SU-8-PIN pre and post; N=77 for SU-8 pre and post; N=23 for SU-8-iii pre and post; N=25 for glass pre and post) to the target beating frequency before and after optical training (pre and post, respectively). These values were taken from 4 separate stimulation experiments for the SU-8-PIN condition in which cells were paced to 500, 700, or 1000 mHz, 3 for SU-8 condition that were all paced to 700 mHz, 3 for SU-8-iii condition that were all paced to 700 mHz, and 2 for the glass condition that were paced to 700 or 476 mHz. Points with the same values are sometimes overlaid. (B) Comparison of optical training efficacy of cardiomyocytes cultured on fibronectin-coated SU-8-PIN meshes with different break times between training periods (0 min, 0.3 min, 2 min, 10 min). Efficacy was determined by plotting the ratio of the beating frequency of individual cells (N=4 for 0 min pre and post; N=16 for 0.3 min pre and post; N=45 for 2 min pre and post; N=8 for 10 min pre and post) to the target beating frequency before and after optical training (pre and post, respectively). These values were taken from 1 stimulation experiment for the 0 min condition in which cells were paced to 700 mHz, 2 for the 0.3 min condition that were paced to 700 mHz or 2.42 Hz, 5 for the 2 min condition that were paced to 500, 700, or 1000 mHz, and 1 for the 10 min condition that were paced to 700 mHz. Points with the same values are sometimes overlaid.

In order to characterize the cellular response to optical training, calcium imaging was used to infer the beating frequency of the cells before and after each optical stimulation period, which were separated by 2 min break times. A group of eleven cardiomyocytes was trained to beat at 700 mHz and demonstrated that prior to stimulation for a total of 97.9 min, they displayed an incoherent beating pattern with frequencies ranging from 0 to 669 mHz, as shown by calcium imaging traces of a representative cell (FIG. 67C). After an optical training for a total of 97.9 min (four optical training periods), this cell beat consistently at ~700 mHz for another 107.8 sec (FIG. 67C). When plotting the average beating frequencies of this cell in 18 second intervals (calculated as moving averages over each 107.8 second pre and post stimulation period), it was observed that the spread of the frequencies decreased with more optical training and that the frequencies measured trended towards the target frequency of 700 mHz (FIG. 67D). It was also found that the post stimulus frequency is not always the same as the pre stimulus frequency for the next training session, indicating that the 2 min break time between training sessions can allow for cells to adjust into their stimulation-induced beating state (FIG. 67D). The estimated laser radiant exposure is ~1.3 mJ/cm$^2$ per targeted cardiac action potential, which is much lower than that used in fixed-point modulation of neuronal activities with the same material (e.g., ~30 J/cm$^2$) and is at least 3 times smaller than those obtained from other non-genetic cardiac modulation materials. It was further demonstrated these trends in several batches of cardiomyocytes that were trained to beat at 500, 700, or 1000 mHz, indicating that this training approach can be used for cardiomyocytes with different baseline frequencies. However, the path to the target frequency can vary based upon the group of cells being stimulated due to natural physiological variation in cellular behavior as well as nanowire density in a given mesh (FIG. 67E). Control samples that were cultured on either glass, gridded SU-8 alone, or SU-8 grid meshes with intrinsic Si core-shell nanowires (SU8-iii-SiNW) did not display training behavior to a target frequency (FIGS. 68-69). Additionally, although fixed-spot stimulation can temporarily train cardiomycotes, it required orders of magnitude higher radiant exposure (>50 J/cm$^2$) and caused significant cytotoxicity, as opposed to negligible cytotoxicity in uninformed search-based training where low power and fast scanning laser illumination is used (FIG. 69).

The 'memory' behavior of the cardiomyocytes was further characterized by altering the time intervals between stimulation periods. It was found that break times between stimuli of 0 min, 0.3 min, and 10 min, did not result in effective training, but that the 2 min break time was optimal (FIG. 67F, FIG. 69). Without being bound by a particular theory, it is hypothesized that these very short or very long break times either do not give the cardiomyocytes enough time to adapt to the stimuli they are receiving or are so long that they lose the effect of training, respectively. Thus, break times in the 2 min time range seem to be the most effective in the training approach (FIG. 69). To understand the strength of memory effect observed in the cardiomyocytes, evaluation of cardiomyocyte beating long after the end of the optical training period was examined. In a group of cardiomyocytes that were trained to beat at 500 mHz, the cells in and in close proximity (within ~300 μm radius) to the stimulated region maintained their trained 500 mHz beating frequency for 40 min after the last optical stimulus and at 45 min exhibited a slightly larger spread of frequencies (FIG. 67G). Any outlier cells that were not beating at approximately 500 mHz likely represent cells that were not as electrically connected to the trained cells (FIG. 67G). These results demonstrate that the present training approach is effective in inducing synchronization of cardiomyocyte beating to a target frequency and a cellular memory of the learned beating frequency after the optical stimulus is removed. This 'memory' effect can be advantageous in comparison to other approaches, such as optogenetics and IR optical stimulation, which mainly operate by modulating target cells only when the light stimulus is present.

Figure 70:
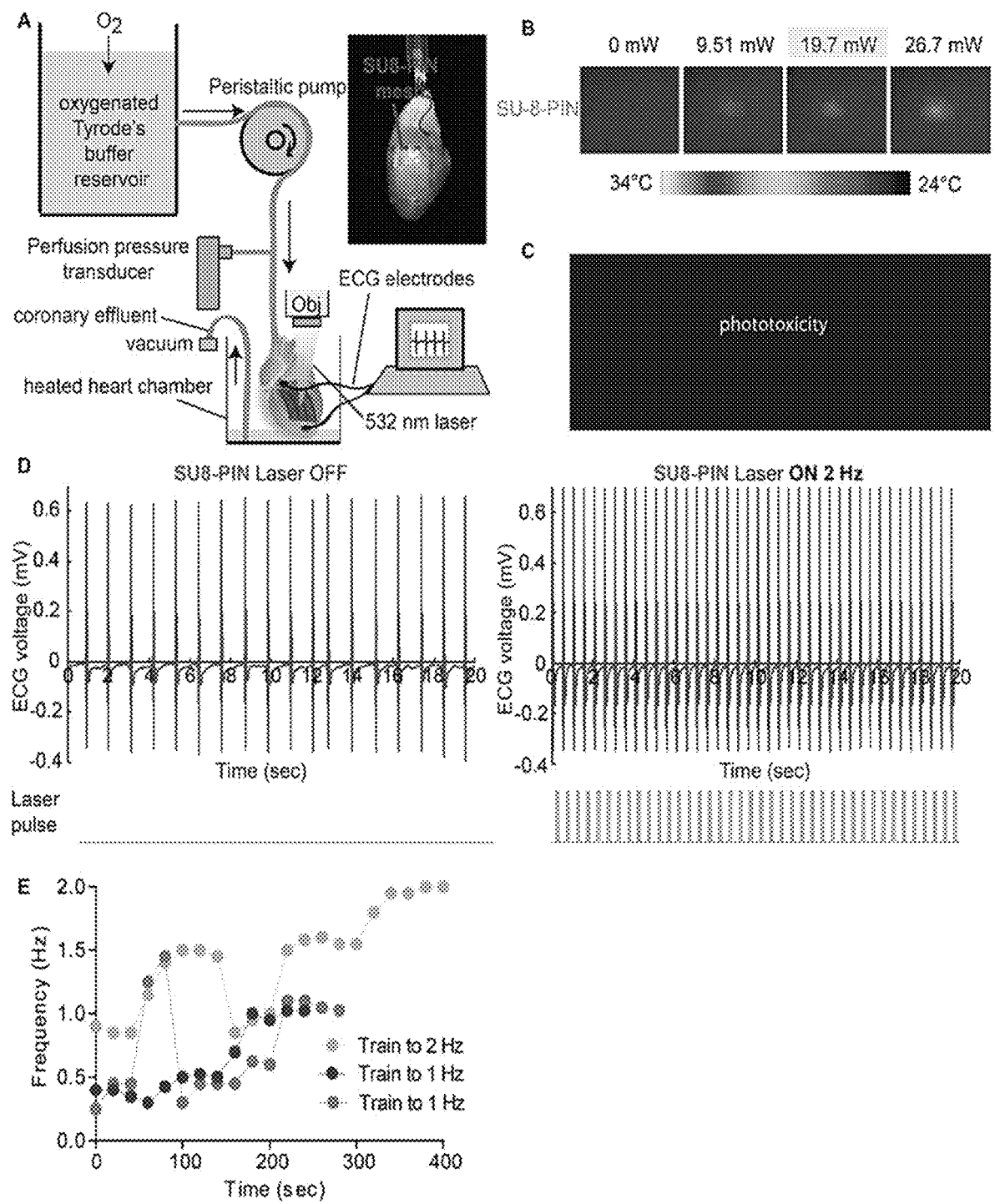
FIG. 70 illustrates a cardiomyocyte training approach in adult rat hearts ex vivo using a Langendorff setup.
Figure 71:
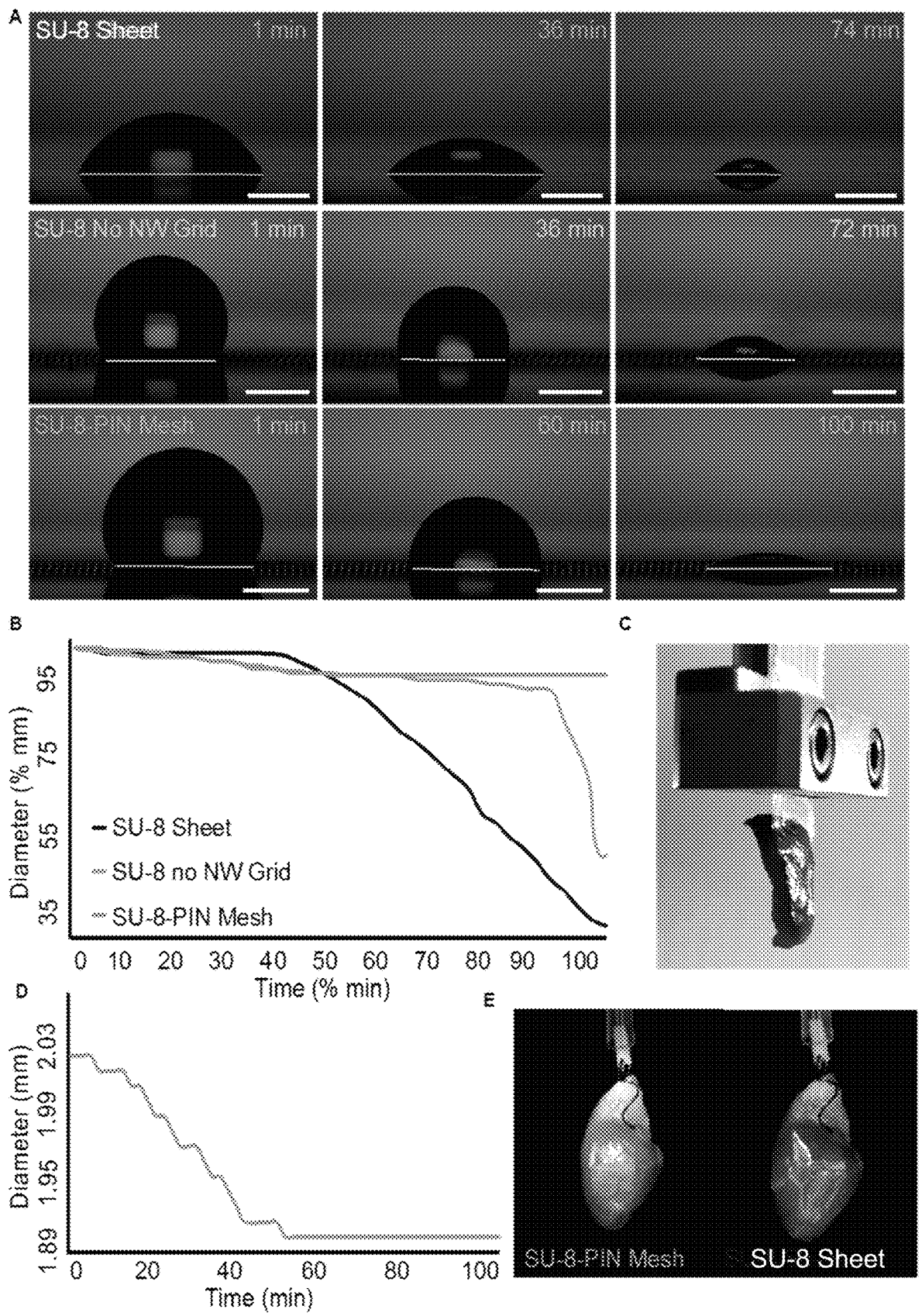
FIG. 71 illustrates sutureless tissue adhesion achieved through water adhesion to mesh structure. (A) Droplet drying of 2-3 µL droplets of DI water on SU-8 sheet, SU-8 grid and SU-8-PIN mesh. Droplets on both the SU-8 grid and SU-8-PIN mesh structures have a contact angle of ~120°. These are representative images of N=4 samples for each type of SU-8 structure. Lines mark drop diameter. Scale bars are 1 mm. (B) Droplet diameter during the drying process was plotted for a SU-8 sheet, SU-8 mesh, and SU-8-PIN mesh as a function of time. Drop diameter and time are scaled by plotting the ratio of diameter/max diameter for each sample and time/max time for each sample. These are representative traces of N=4 samples for each type of SU-8 structure. (C) Tissue slice supported by SU-8 mesh structure solely via water adhesion. Wet tissue was brought into contact with SU-8 mesh and was supported by mesh for 20 minutes. (D) Droplet diameter drying was plotted as a function of time for SU-8-PIN mesh, displaying stepwise nature of droplet diameter change during drying due to the grid structure, which cannot be seen when plotting as percent diameter in (B). (E) SU-8-PIN mesh and SU-8 sheet wrapped around adult rat resulting from water adhesion. SU-8-PIN mesh fully.
Figure 72:
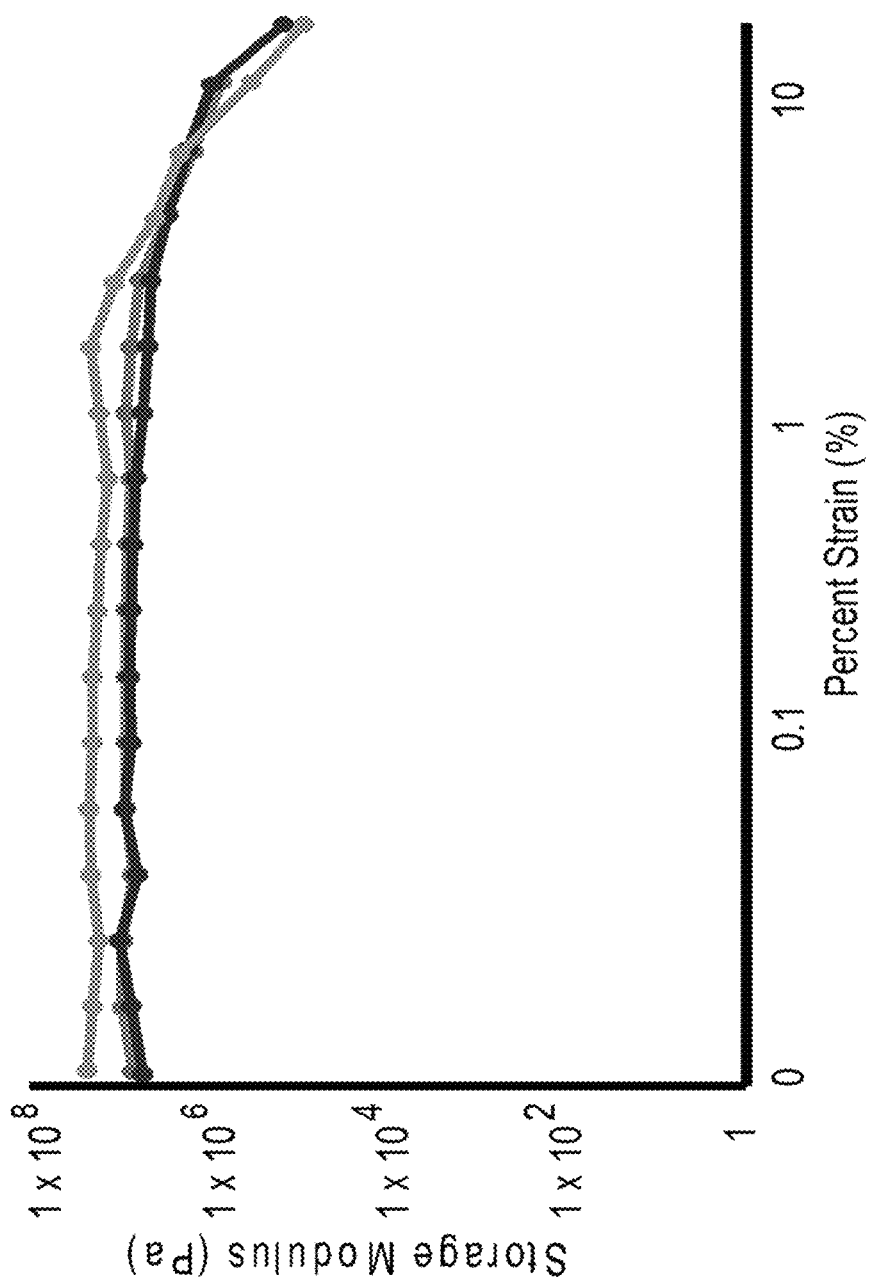
FIG. 72 illustrates dynamic mechanical analysis tests of mesh stability under cyclic strain. Dynamic mechanical analysis tensile test of the SU-8-PIN mesh stretched at a frequency of 100 mHz of over a range of 0.009% to 14.8% strain. Graph displays 3 representative traces showing modulus up to between 9%-14% strain after which significant tears begin to form. SU-8-PIN mesh (6 samples) was stable up to an average of 9.1% strain as compared to SU-8 sheet (4 samples) which was stable only up to 2.3% strain before significant tearing occurred.
Figure 73:
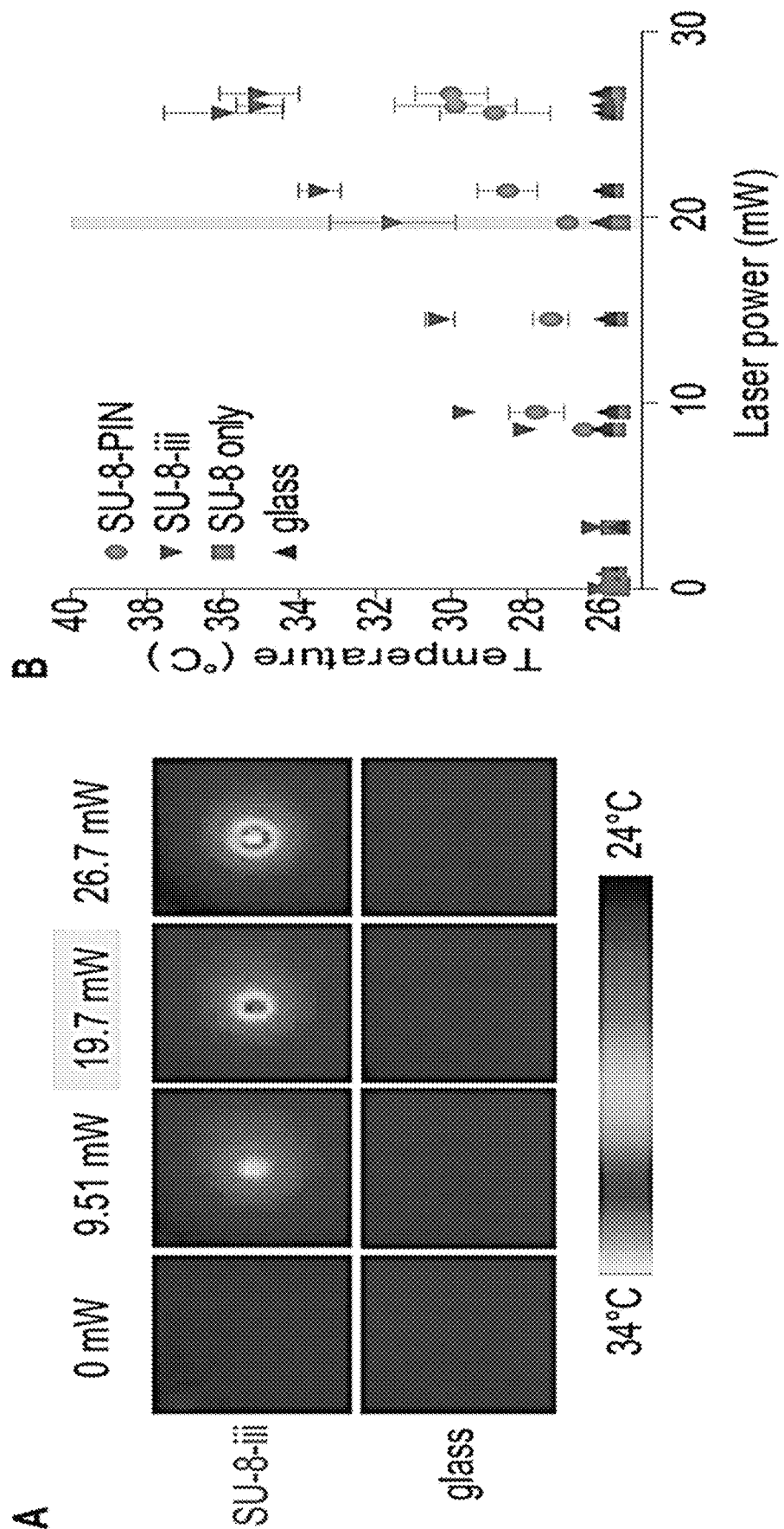
FIG. 73 shows temperature increases caused by laser stimulation of a SU-8-PIN mesh and a SU-8-iii mesh. (A) IR camera images of the SU-8-iii mesh or glass alone being exposed to 532 nm laser light focused through a 5× objective at various powers. The laser power used for ex vivo heart training is highlighted. (B) Maximum temperatures were plotted for 3 SU-8-PIN meshes, 3 SU-8-iii meshes, 3 SU-8 only grids, and 3 glass alone that were illuminated with 532 nm laser light at various powers. The bar represents the power that was used for ex vivo heart training.

The present cardiomyocyte training approach was then tested in adult rat hearts ex vivo using a Langendorff setup (FIG. 70A). The pericardia of the hearts were removed in the left ventricle and an SU8-SiNW mesh was placed onto the exposed myocardium (FIG. 70A). The mesh conformably wraps around and adheres to the wet curved surface of the myocardial tissue via capillary action without the need for sutures or tissue adhesive (FIG. 70A). Contact angle experiments indicated that this observed tissue adhesion occurs as a result of the presence of the SU-8 microstructure and SiNWs in the mesh (FIG. 71). Dynamic mechanical analysis tests confirmed the durability of the mesh during repeated cyclic stretching, indicating that the mesh would be able to withstand the mechanical beating motion of the heart (FIG. 72). A 532 nm laser (19.7 mW) was focused through a 5× objective onto the SU8-SiNW mesh on the heart, and was set to pulse at the target training frequency via a waveform generator. The frequency of the beating heart was recorded via ECG electrodes that were placed on the apex and aorta of the heart. The fast variation in the laser spot location and size due to the contractile motion of the heart yields an analogous situation (i.e., a large collection of variations in light illumination intensity and location within a short time period) to the aforementioned scanning laser stimulus. However, in this case, the 'scanning' motion occurs in the z-axis rather than the x and y axes, causing fluctuations in optical stimulus intensities hitting the heart (FIG. 70A). Using an infrared camera, the maximum temperature increase caused by constant laser illumination of the mesh was assessed at 19.7 mW (FIG. 70B). A stabilized 1.1° C. increase in temperature was found when PIN-SiNW mesh was used (FIG. 70B), which was much less in comparison to the 5.4° C. increase for intrinsic SiNW (i.e., iii-SiNW) mesh (FIG. 73) and suggest that the photoelectrochemical mechanism in the PIN-SiNW system is prominent. Moreover, when assessing phototoxicity in hearts that had been exposed to the pulsed light stimulus for 30 min using propidium iodide (FIG. 70C), it was found that SU-8-PIN mesh with 3.5 Hz pulsed 532 nm light had an average of 35 dead cells per mm$^2$ as compared to 33 dead cells per mm$^2$ in a control with no light exposure for 30 minutes. As a positive control for the dye, a heart to 8 W of 3.5 Hz pulsed infrared laser light was exposed for 10 seconds and induced visible tissue death with 62 dead cells per mm$^2$ in a tissue slice. These results indicate that optical stimulation of the SU-8-SiNW mesh produces very little heat and does not induce significant phototoxicity in adult rat hearts.

Figure 74:
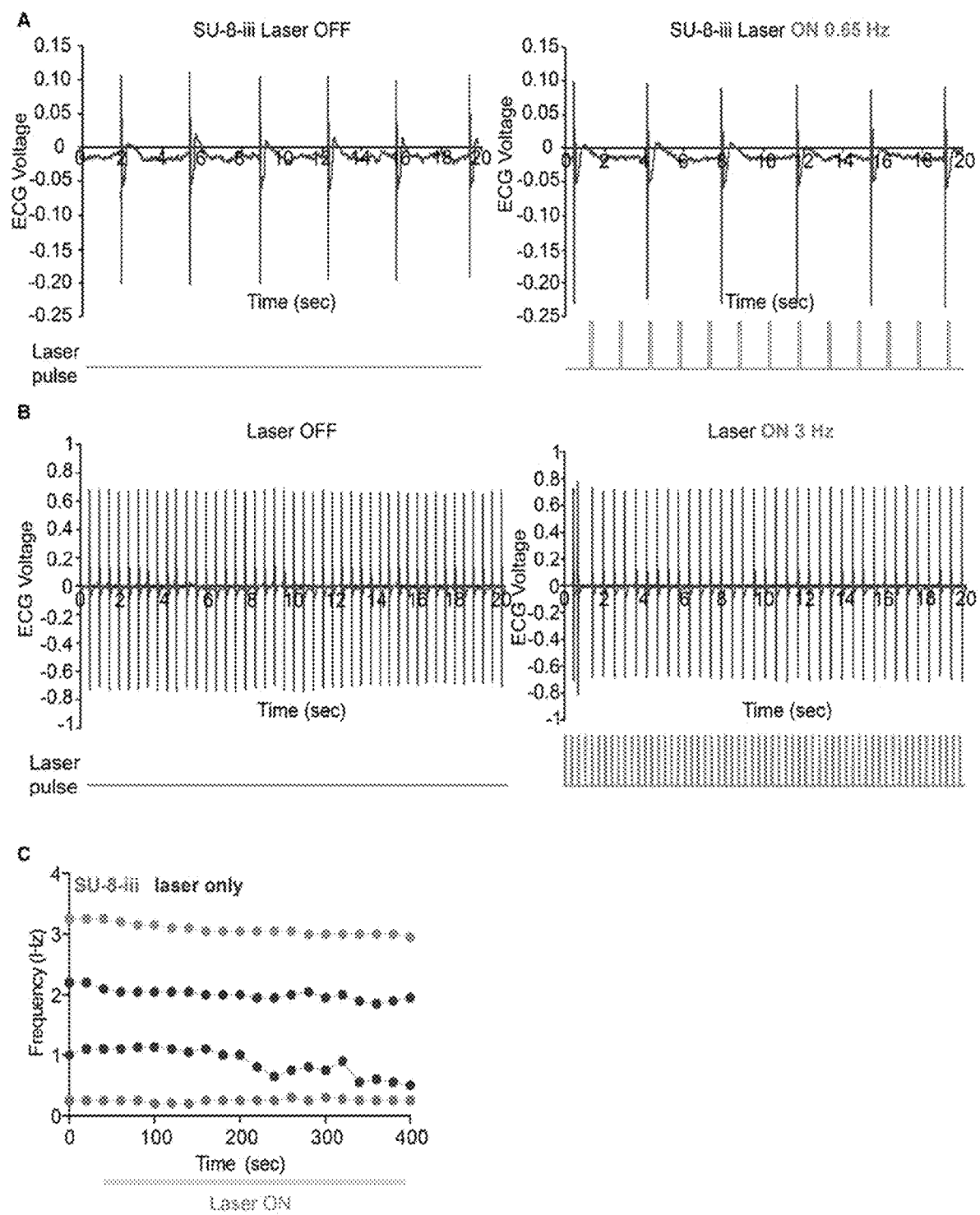
FIG. 74 illustrates optical training of adult rat hearts ex vivo using SU-8-iii meshes and light (A) Electrocardiogram recordings from an adult heart with an SU-8-iii mesh beating at 0.3 Hz prior to being exposed to 532 nm laser light pulses (left) and during exposure to 532 nm laser light pulses at 0.65 Hz on the SU-8-PIN mesh (right). Light pulses are indicated under the ECG traces. These are representative traces of N=2 different hearts and N=3 different experiments. (B) Electrocardiogram recordings from an adult heart without any mesh beating at 2 Hz prior to being exposed to 532 nm laser light pulses (left) and during exposure to 532 nm laser light pulses at 3 Hz on the SU-8-PIN mesh (right). Light pulses are indicated under the ECG traces. These are representative traces of N=6 different hearts and N=6 different experiments (C) Beating frequencies of four adult hearts with SU-8-iii meshes or without any mesh 40 seconds prior to being exposed to 532 nm laser light (first 2 points of each trace) and during exposure to 532 nm laser light (all other points in the traces). Connections between dots do not represent real data and are just a way to visualize the trend.

Finally, the efficacy of training hearts through optical stimulation over SU-8-SiNW mesh-covered hearts was assessed. Training of a heart that is beating at a baseline of 0.9 Hz was demonstrated to beat at 2 Hz after 4.7 min of 532 nm pulsed light exposure (FIG. 70D). The training of this heart resulted in a consistent 2 Hz beating pattern although it did not deterministically line up with light pulses (FIG. 70D). When training hearts using SU-8-SiNW meshes to beat at various target frequencies, it was found that the path to the target frequency was characterized not by a steady increase in frequency over time, but a series of slight rises and falls in frequency that end in the target frequency over the span of 2.3 to 4.7 min of light exposure and remain at that target frequency for at least 1.3 min (FIG. 70E). Intrinsic SiNW meshes or light alone, was not successful in training to the target frequency within a 6.7 min span of time, and instead either an unchanged beating frequency or a gradual slight decline in frequency was observed over time (FIG. 74). These results demonstrate an easily implemented optical training method for hearts ex vivo, where constant mechanical motion of the contracting heart enables the uninformed search for variable illumination intensities and locations.

A flexible polymer-silicon mesh and an uninformed search-based optical training approach were developed. These together mimicked the spatiotemporal multisite inputs in naturally occurring cellular signaling (FIG. 23A). This training approach is characterized by fast variation of both the optical stimulation intensity and position. It requires a radiant exposure (per targeted action potential) that, while still larger than that of optogenetic approaches, is lowest among existing non-genetic cardiac modulation methods. This biomimetic approach was used to optically train both cultured cardiomyocytes and intact hearts to beat at target frequencies, allowing for groups of cardiomyocytes to synchronize and maintain their beating frequency at the target level long after the optical stimulus is removed. The findings have implications for both fundamental multi-cell bioelectric studies as well as photo-responsive cardiac therapeutics in the clinic.

Various aspects of the disclosure are further exemplified by the non-limiting embodiments recited in the claims below. In each case, features of multiple claims can be combined in any fashion not inconsistent with the specification and not logically inconsistent.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method for modulating activity of a cell, the method comprising:
    contacting a membrane of the cell with a silicon nanostructure to form a structure-cell membrane interface, the silicon nanostructure comprising a p-type/intrinsic/n-type (PIN) coaxial Si nanowire or a PIN Si diode junction, wherein the silicon nanostructure further comprises gold, silver, or platinum on a surface of the silicon nanostructure, wherein the silicon nanostructure is distributed on or within a flexible substrate comprising one or more polymers, and wherein the flexible substrate includes a mesh; and
    exposing the interface to light so as to depolarize the cell membrane thereby increasing a threshold for activation of the cell, wherein the cell is capable of being activated by light, and wherein the cell is a neuron or an immune cell.

2. The method according to claim 1, wherein the structure-cell interface is a direct interface between the silicon nanostructure and the cell membrane;
    and/or wherein the contacting is without penetrating the cell membrane;
    and/or wherein the exposing is for a time ranging from 0.5 ms to 15 ms;
    and/or wherein the light is provided at an excitation wavelength ranging from 400 to 900 nm;
    and/or wherein the light is provided at a power in a range of 1 mW to 1 W.

3. The method of claim 1, wherein the cell is an immune cell selected from T cells, B cells, basophils, neutrophils, Natural Killer cells, mast cells, eisonophils, and macrophages and/or a T cell selected from regulatory T cells and CD4+ T cells.

4. The method of claim 1, wherein the silicon nanostructure further comprises a targeting moiety for targeting the cell, wherein the targeting moiety comprises a member of a binding pair.

5. The method of claim 4, wherein the binding pair is selected from antibody-antigen, and receptor-ligand.

6. The method of claim 1, wherein the silicon nanostructure is suspended in a pharmaceutically acceptable solution or gel.

7. The method of claim 6, wherein the solution or a gel has an average concentration of silicon nanostructures in a range of 10,000 to 10,000,000 nanostructures/mL.

8. The method of claim 1, wherein the silicon nanostructure is distributed on the flexible substrate at a surface average density ranging from 10,000 to 1,000,000 nanostructures/mm$^2$.

9. The method of claim 1, wherein the one or more polymers is selected from a photoresist polymer, a biocompatible polymer, a biodegradable polymer, an extracellular matrix protein, and a combination thereof.

10. The method of claim 1, wherein the one or more polymers comprises SU-8 photoresist or polydimethylsiloxane.

11. The method of claim 8, wherein the flexible substrate has an open porosity of at least about 30%.

12. The method according to claim 1, wherein the flexible substrate comprises a polydimethylsiloxane (PDMS) membrane and the mesh comprises SU-8.

* * * * *